(12) United States Patent
Skjaerbaek et al.

(10) Patent No.: US 7,576,078 B2
(45) Date of Patent: Aug. 18, 2009

(54) TETRAHYDROQUINOLINE ANALOGUES AS MUSCARINIC AGONISTS

(75) Inventors: Niels Skjaerbaek, Vedbaek (DK); Kristian Norup Koch, Copenhagen (DE); Bo Lennart Mikael Friberg, Vellinge (SE); Bo-Ragnar Tolf, Malmö (SE)

(73) Assignee: Acadia Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 11/417,865

(22) Filed: May 3, 2006

(65) Prior Publication Data

US 2006/0199813 A1 Sep. 7, 2006

Related U.S. Application Data

(63) Continuation of application No. 10/329,455, filed on Dec. 23, 2002.

(60) Provisional application No. 60/344,722, filed on Dec. 28, 2001.

(51) Int. Cl.
*A61P 25/00* (2006.01)
*A61K 31/54* (2006.01)
*C07D 279/16* (2006.01)

(52) U.S. Cl. .................. 514/224.2; 544/51; 544/52

(58) Field of Classification Search .............. 514/224.2; 544/51, 52
See application file for complete search history.

(56) References Cited

U.S. PATENT DOCUMENTS

| 3,324,137 | A | 6/1967 | Zenitz ................. 260/292 |
| 3,365,457 | A | 1/1968 | Zenitz ................. 260/292 |
| 5,707,798 | A | 1/1998 | Brann ...................... 435/6 |
| 5,770,734 | A | 6/1998 | Sabb ...................... 544/363 |
| 5,786,367 | A | 7/1998 | Oshiro et al. ............. 514/312 |
| 2004/0067931 | A1 | 4/2004 | Kelly et al. ........... 514/210.21 |
| 2005/0130961 | A1 | 6/2005 | Davis et al. | |

FOREIGN PATENT DOCUMENTS

| EP | 0 541 263 A1 | 5/1993 |
| EP | 0 577 325 A1 | 1/1994 |
| EP | 0 584 487 | 3/1994 |
| EP | 0 934 932 A1 | 8/1999 |
| EP | 1 260 512 A1 | 11/2002 |
| WO | WO 99 50247 A | 10/1999 |
| WO | WO 01 27104 A | 4/2001 |
| WO | WO 01/49679 A1 | 7/2001 |
| WO | WO 01 83472 A | 11/2001 |
| WO | WO 03/057672 A2 | 7/2003 |

OTHER PUBLICATIONS

Messer W., The Utility of Muscarinic Agonists in the Treatment of Alzheimer's Disease, Journal of Molecular Neuroscience, vol. 19, pp. 187-193, 2002.*

International Search Report for PCT Application No. PCT/US02/41617 mailed Aug. 25, 2003.
International Search Report and Written Opinion from International Application No. PCT/US2005/045313 dated May 23, 2006.
Bodick et al., Effects of xanomeline, a selective muscarinic receptor agonist, on cognitive function and behavioral symptoms in Alzheimer disease, Arch. Neurol. 54:465-473 (1997).
Bond et al., Physiological effects of inverse agonists in transgenic mice with myocardial overexpression of the β-adrenoceptor, Nature 374:272 (1995).
Brauner-Osborne, et al. Pharmacology of muscarinic acetylcholine receptor subtypes (m1-m5): high throughput assays in mammalian cells, Eur. J. Pharmacol. 295:93-102 (1996).
Bymaster et al., Unexpected antipsychotic-like activity with the muscarinic receptor ligand (5R, 6R)6-(3-propylthio-1,2,5-thiadiazol-4-yl)-1-azabicyclo[3.2.1]octane, Eur. J. Pharmacol. 356:109-119 (1998).
Bymaster et al., Potential role of muscarinic receptors in schizophrenia, Life Sci. 64:527-534 (1999).
Felder et al., Therapeutic opportunities for muscarinic receptors in the central nervous system, J. Med. Chem. 43:4333-4353 (2000).
Friedman et al., Pharmacologic strategies for augmenting cognitive performance in schizophrenia, Biol. Psychiatry 45:1-16 (1999).
Mokrosz et al., 5-HT1A and 5HT2A receptor affinity and functional profiles of some N-[3-(4-aryl-1-piperazinyl)propyl] derivatives of indolin-2(1H)-one, quinolin-2(1H)-one and Isoquinolin-1(2H)-one, Pharmazie, 52, 6:423-428 (1997).
Pace et al., A mutant α subunit Gi2 induces neoplastic transformation of Rat-1 cells, Proc. Natl. Acad. Sci. USA 88:7031-35 (1991).
Rowley et al., Current and novel approaches to the drug treatment of schizophrenia, J. Med. Chem. 44:477-501 (2001).
Sauerberg et al., Muscarinic agonists with antiphsychotic-like activity: structure-activity relationships of 1,2,5-Thiadiazole analogues with functional dopamine antagonist activity, J. Med. Chem. 41:4378-4384 (1998).
Shannon et al., Xanomeline: a novel muscarinic receptor agonist with functional selectivity for m1 receptors, J. Pharmacol. Exp. Ther. 269:271-281 (1994).
Shannon et al., Muscarinic receptor agonists, like dopamine receptor antagonist antipsychotics, inhibit conditioned avoidance response in rats, J. Pharmacol. Exp. Ther. 290:901-907 (1999).
Shannon et al., Xanomeline, an M1/M4 preferring muscarinic cholinergic receptor agonist, produces antipsychotic-like activity in rats and mice, Schizophrenia Res. 42:249-259 (2000).
Spalding T.A., Trotter C., Skjaerbaek N., Messier T.L., Currier E.A., Burstein E.S., Li D., Hacksell U., Brann M.R, Discovery of an ectopic activation site on the M1 muscarinic receptor, Mol. Pharmacol. 61(6):1297-302 (2002).
Vallar et al., Altered Gs and adenylate cyclase activity in human GH-secreting pituitary adenomas, Nature 330:556-58 (1987).

* cited by examiner

*Primary Examiner*—Brenda L Coleman
(74) *Attorney, Agent, or Firm*—Knobbe, Martens, Olson & Bear LLP

(57) ABSTRACT

The present invention relates to tetrahydroquinoline compounds as muscarinic receptor agonists; compositions comprising the same; methods of inhibiting an activity of a muscarinic receptor with said compounds; methods of treating a disease condition associated with a muscarinic receptor using said compounds; and methods for identifying a subject suitable for treatment using said compounds.

20 Claims, No Drawings

TETRAHYDROQUINOLINE ANALOGUES AS MUSCARINIC AGONISTS

RELATED APPLICATIONS

The present application is a continuation of U.S. application Ser. No. 10/329,455, filed Dec. 23, 2002, by Skjaerbaek et al., entitled "TETRAHYDROISOQUINOLINE ANALOGUES AS MUSCARINIC AGONISTS," which in turn claims priority to U.S. Provisional Application Ser. No. 60/344,722, filed Dec. 28, 2001, by Skjaerbaek, entitled "TETRAHYDROISOQUINOLINE ANALOGUES AS MUSCARINIC AGONISTS," both of which are incorporated by reference herein in their entirety, including any drawings.

FIELD OF THE INVENTION

The present invention relates to compounds that affect cholinergic receptors, especially muscarinic receptors. The present invention provides compounds that are agonists of cholinergic receptors including muscarinic receptors, especially the $M_1$ and $M_4$ subtype of muscarinic receptors. The invention also provides methods of using the provided compounds for modulating conditions associated with cholinergic receptors, especially for treating or alleviating disease conditions associated with muscarinic receptors, such as the $M_1$ and/or $M_4$ receptor subtypes.

BACKGROUND

Muscarinic cholinergic receptors mediate the actions of the neurotransmitter acetylcholine in the central and peripheral nervous systems. Muscarinic receptors play a critical role in the central nervous system mediating higher cognitive functions, as well as in the peripheral parasympathetic nervous system where they mediate cardiac, respiratory, digestive, and endocrine and exocrine responses. Five distinct muscarinic receptor subtypes have been identified, $M_1$-$M_5$. The muscarinic $M_1$ receptor subtype is predominantly expressed in the cerebral cortex and is believed to be involved in the control of higher cognitive functions; the $M_2$ receptor is the predominant subtype found in heart and is involved in the control of heart rate; the $M_3$ receptor is widely expressed in many peripheral tissues and is believed to be involved in gastrointestinal and urinary tract stimulation as well as sweating and salivation; the $M_4$ receptor is present in brain and may be involved in locomotion; the $M_5$, receptor is present in the brain where its role is at present poorly defined. $M_1$ and $M_4$ have been particularly associated with the dopaminergic system.

Conditions associated with cognitive impairment, such as Alzheimer's disease, are accompanied by a reduction of acetylcholine content in the brain. This is believed to be the result of degeneration of cholinergic neurons of the basal forebrain, which widely innervate multiple areas of the brain, including the association cortices and hippocampus, that are critically involved in higher processes.

Efforts to increase acetylcholine levels have focused on increasing levels of choline, the precursor for acetylcholine synthesis, and on blocking acetylcholineesterase (AChE), the enzyme that metabolizes acetylcholine. Attempts to augment central cholinergic function through the administration of choline or phosphatidylcholine have not been successful. ACHE inhibitors have shown therapeutic efficacy, but have been found to have frequent cholinergic side effects due to peripheral acetylcholine stimulation, including abdominal cramps, nausea, vomiting, and diarrhoea. These gastrointestinal side effects have been observed in about a third of the patients treated. In addition, some AChE inhibitors, such as tacrine, have also been found to cause significant hepatotoxicity with elevated liver transaminases observed in about 30% of patients. The adverse effects of AChE inhibitors have severely limited their clinical utility.

The dopamine hypothesis of schizophrenia suggests that increased dopamine neurotransmission underlies the positive symptoms of the disease and is supported by the evidence that dopamine receptor blockade is effective in ameliorating such psychotic symptoms. Further, drugs that enhance dopamine neurotransmission in the brain cause psychotic-like episodes in man and exacerbate psychotic symptoms in schizophrenic patients. In animal studies, drugs that increase dopamine neurotransmission cause behavioural effects such as increased locomotion, climbing and deficits in prepulse inhibition. Known antipsychotics and dopamine receptor antagonists can block these behavioural effects. Unfortunately, dopamine receptor antagonists also cause severe extrapyramidal side effects in patients as predicted by induction of catalepsy in animal models. These extrapyramidal side effects include tremor, bradykinesia, akithesias, and tardive dyskinesias.

Due in part to these observations, the discovery of agents with $M_1$ receptor agonist activity has been sought after for the treatment of dementia. However, existing agents lack specificity in their actions at the various muscarinic receptor subtypes. Known $M_1$ muscarinic agonists such as arecoline have also been found to be weak agonists of $M_2$ as well as $M_3$ receptor subtypes and are ineffective in the treatment of cognitive impairment, due in large part to their dose-limiting $M_2$ and $M_3$ receptor mediated side effects.

Xanomeline (Shannon et al., *J. Pharmacol. Exp. Ther.* 1994, 269, 271; Shannon et al., *Schizophrenia Res.* 2000, 42, 249) is an $M_1$/$M_4$ preferring muscarinic receptor agonist with little or no affinity for dopamine receptors despite inhibiting A10 but not A9 dopamine cells. The thiadiazole derivative PTAC has been reported (Shannon et al., *European Journal of Pharmacology,* 1998, 356, 109) to have partial agonist effect at muscarinic $M_2$ and $M_4$ receptors and antagonist effect at muscarinic $M_1$, $M_3$, and $M_5$ receptors as well as exhibiting functional dopamine antagonism.

Recently, muscarinic agonists including xanomeline have been shown to be active in animal models with similar profiles to known antipsychotic drugs, but without causing catalepsy (Bymaster et al., *Eur. J. Pharmacol.* 1998, 356, 109, Bymaster et al., *Life Sci.* 1999, 64, 527, Shannon et al., *J. Pharmacol. Exp. Ther.* 1999, 290, 901, Shannon et al., *Schizophrenia Res.* 2000, 42, 249). Further, xanomeline was shown to reduce psychotic behavioural symptoms such as delusions, suspiciousness, vocal outbursts, and hallucinations in Alzheimer's disease patients (Bodick et al., *Arch. Neurol.* 1997, 54, 465), however treatment induced side effects that severely limit the clinical utility of this compound.

Analogues of 1,2,5-thiadiazole have been reported (Sauerberg et al., *J. Med. Chem.* 1998, 41, 4378) to have high affinity and selectivity for central muscarinic receptors as well as exhibiting functional dopamine antagonism despite lack of affinity for dopamine receptors.

The present investigators have, in part, focussed their efforts on the development of molecules that simultaneously reduced the positive symptoms and improved the negative symptoms and the cognitive impairments associated with schizophrenia as a novel treatment of mental disorders. It is the intent of the present investigators to demonstrate that muscarinic $M_1$ and/or $M_4$ agonists with combined $D_2$ antagonist activity may possess superior antipsychotic efficacy without the side effects associated with high dose $D_2$ antagonism alone. The $D_2$ antagonist properties of some of the compounds of the present invention may contribute to a reduction in the positive symptoms of this disease.

Based on distribution of $M_1$ and $M_4$ receptors in the cerebral cortex and hippocampus (the areas involved in higher order cognitive functions), the $M_1$ and/or $M_4$ agonist properties of these compounds may reduce the cognitive dulling and perhaps ameliorate other negative symptoms associated with schizophrenia. (Friedman, Biol. *Psychiatry*, 1999, 45, 1; Rowley, *J. Med. Chem.* 2001, 44, 477; Felder, *J. Med. Chem.* 2000, 43, 4333). This unique combination of central nervous system activities in one molecule is unprecedented and may lead to the development of an entirely new class of antipsychotic drugs, ones with the superior clinical properties without the limiting side-effect profile.

U.S. Pat. Nos. 3,324,137 and . 3,365,457 describe N-[indolyl-lower-alkanoyl]-1,5-iminocycloalkanes and iminocycloalkanes not encompassed by the invention.

EP 0 584 487 describes 4,5-dihydo-4-oxo-pyrroles with linked to piperazine rings not encompassed by the invention.

Mokrosz et al (*Pharmazie*, 52, 1997, 6, p 423) describes N[3-(4-aryl)-1-piperazinyl)propyl] derivatives of indolin-2(1H)-one, quinolin-2-(1H)-one and isoquinolin-1-(2H)-one, which are not encompassed by the invention.

SUMMARY OF THE INVENTION

The invention provides novel compounds of formula I, as well as salts and isomers thereof

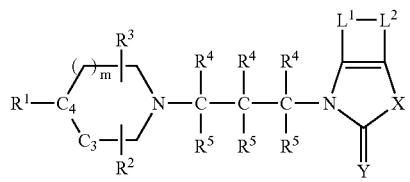

I wherein $R^1$ is a monoradical selected from the group consisting of optionally substituted $C_{1-6}$-alkyl, optionally substituted $C_{2-6}$-alkylidene, optionally substituted $C_{2-6}$-alkenyl, optionally substituted $C_{2-6}$-alkynyl, optionally substituted O—$C_{1-6}$-alkyl, optionally substituted O—$C_{2-6}$-alkenyl, optionally substituted O—$C_{2-6}$-alkynyl; optionally substituted S—$C_{1-6}$-alkyl, optionally substituted S—$C_{2-6}$-alkenyl, optionally substituted S—$C_{2-6}$-alkynyl;

m is 0, 1 or 2;

$C_3$-$C_4$ is $CH_2$—CH or CH=C or $C_4$ is CH and $C_3$ is absent;

$R^2$ and $R^3$ are independently selected from the group consisting of hydrogen, optionally substituted $C_{1-6}$ alkyl, optionally substituted O—$C_{1-6}$ alkyl, halogen, hydroxy or selected such that $R^2$ and $R^3$ together form a ring system;

each $R^4$ and $R^5$ is independently selected from the group consisting of hydrogen, halogen, hydroxy, optionally substituted $C_{1-6}$-alkyl, optionally substituted O—$C_{1-6}$alkyl, optionally substituted aryl-$C_{1-6}$ alkyl, and optionally substituted arylheteroalkyl;

$L^1$ and $L^2$ are biradicals independently selected from the group consisting of —C($R^6$)=C($R^7$), —C($R^6$)=N—, —N=C($R^6$)—, —S—, —NH— and —O—; wherein only one of $L^1$ and $L^2$ may be selected from the group consisting of —S—, —NH— and —O—;

Y is selected from the group consisting of O, S, and $H_2$;

X is a biradical selected from the group consisting of —C($R^6$)($R^7$)—C($R^6$)($R^7$)—, —C($R^6$)=C($R^7$)—, —O—C($R^6$)($R^7$)—, C($R^6$)($R^7$)—O—, —S—C($R^6$)($R^7$)—, —C($R^6$)($R^7$)—S—, —N($R^N$)—C($R^6$)($R^7$)—, —C($R^6$)($R^7$)—N($R^N$)—, —C($R^6$)($R^7$)—C($R^6$)($R^7$)—C($R^6$)($R^7$)—, —O—C($R^6$)($R^7$)—C($R^6$)($R^7$)—, S—C($R^6$)($R^7$)—C($R^6$)($R^7$)—, N($R^N$)—C($R^6$)($R^7$)—C($R^6$)($R^7$)—, —C($R^6$)($R^7$)—C($R^6$)($R^7$)—O—, —C($R^6$)($R^7$)—C($R^6$)($R^7$)—S—, —C($R^6$)($R^7$)—C($R^6$)($R^7$)—N($R^N$)—, —C($R^6$)($R^7$)—C($R^6$)=C($R^7$)—, and —C($R^6$)=C($R^7$)—C($R^6$)($R^7$), wherein $R^6$ and $R^7$ are independently selected from the group consisting of hydrogen, halogen, hydroxy, nitro, cyano, $NR^NR^N$, $N(R^N)$—C(O)N($R^N$), optionally substituted $C_{1-6}$-alkyl, $C_{2-6}$-alkenyl, $C_{2-6}$-alkynyl, optionally substituted O—$C_{1-6}$-alkyl, optionally substituted O-aryl, optionally substituted O—$C_{2-6}$-alkenyl, optionally substituted O—$C_{2-6}$-alkynyl wherein $R^N$ is selected from the group consisting of hydrogen, and optionally substituted $C_{1-6}$-alkyl.

The invention further provides compositions comprising
i) one or more compounds of formula I, and;
ii) at least one pharmaceutically acceptable excipient or carrier.

The invention also provides methods of treating a disease in a mammal, such as a human, wherein modulation of the activity of a cholinergic receptor is associated with a physiologically beneficial response in said disease of said mammal. In one embodiment, a method includes administering an effective amount of a compound of formula I.

Thus, the invention provides methods of treating or preventing or alleviating one or more symptoms associated with a disorder in a mammal, such as a human, said disorder associated with a muscarinic receptor, for example, the $M_1$ muscarinic receptor subtype. In one embodiment, a method includes the administration of an effective amount of the compound of formula I, a pharmaceutically acceptable salt thereof, a stereoisomer thereof, or a pharmaceutical composition comprising either entity. Particular disorders treatable by a method of the invention include, for example, Alzheimer's disease, Parkinson's disease, schizophrenia, Huntington's chorea, Friederich's ataxia, Gilles de la Tourette's Syndrome, Down Syndrome, Pick disease, dementia, clinical depression, age-related cognitive decline, cognitive impairment, forgetfulness, confusion, memory loss, attentional deficits, deficits in visual perception, depression, pain, sleep disorders, psychosis, sudden infant death syndrome, increased intraocular pressure and glaucoma.

The invention additionally provides a method of treating a mental disorder wherein the physiologically beneficial response is due to modulation in terms of $M_1$ agonism; $M_1$ and $M_4$ agonism; both $M_1$ agonism and $D_2$ antagonism; or $M_1$ and $M_4$ agonism and $D_2$ antagonism.

The invention additionally provides the use of a compound of formula I, a pharmaceutically acceptable salt thereof, a stereoisomer thereof, or a pharmaceutical composition comprising either entity, for the preparation of a medicament for the treatment of diseases or disorders associated with a cholinergic receptor or ligand thereof.

The invention therefore provides methods for the preparation of a medicament for the treatment of diseases or disorders selected from the group consisting of Alzheimer's disease, Parkinson's disease, schizophrenia, Huntington's chorea, Friederich's ataxia, Gilles de la Tourette's Syndrome, Down Syndrome, Pick disease, dementia, clinical depression, age-related cognitive decline, cognitive impairment, forgetfulness, confusion, memory loss, attentional deficits, deficits in visual perception, depression, pain, sleep disorders, psychosis, sudden infant death syndrome, increased intraocular pressure and glaucoma.

The invention further provides methods of increasing an activity of a cholinergic receptor. In one embodiment, a method includes contacting the cholinergic receptor or a system containing the cholinergic receptor with an effective amount of at least one compound of formula I to increase an activity of the cholinergic receptor.

The invention provides kits including one or more compounds of the invention, and instructions for practicing a method of the invention. In one embodiment, instructions are for treating or preventing or alleviating one or more symptoms associated with a disorder in a mammal, such as a human, said disorder associated with a muscarinic receptor, for example, the $M_1$ muscarinic receptor subtype. In another embodiment, instructions are for increasing cholinergic receptor activity or activating cholinergic receptors.

DESCRIPTION OF THE INVENTION

For the purpose of the current disclosure, the following definitions shall in their entireties be used to define technical terms.

The term "agonist" is defined as a compound that increases the activity of a receptor when it contacts the receptor.

The term "antagonist" is defined as a compound that competes with an agonist or inverse agonist for binding to a receptor, thereby inhibiting or blocking the action of an agonist or inverse agonist on the receptor. However, an antagonist (also known as a "neutral" antagonist) has no effect on constitutive receptor activity.

The term "inverse agonist" is defined as a compound that decreases the basal activity of a receptor (i.e., signaling mediated by the receptor). Such compounds are also known as negative antagonists. An inverse agonist is a ligand for a receptor that causes the receptor to adopt an inactive state relative to a basal state occurring in the absence of any ligand. Thus, while an antagonist can inhibit the activity of an agonist, an inverse agonist is a ligand that can alter the conformation of the receptor in the absence of an agonist. The concept of an inverse agonist has been explored by Bond et al. in *Nature* 374:272 (1995). More specifically, Bond et al. have proposed that unliganded $\beta_2$-adrenoceptor exists in an equilibrium between an inactive conformation and a spontaneously active conformation. Agonists are proposed to stabilize the receptor in an active conformation. Conversely, inverse agonists are believed to stabilize an inactive receptor conformation. Thus, while an antagonist manifests its activity by virtue of inhibiting an agonist, an inverse agonist can additionally manifest its activity in the absence of an agonist by inhibiting the spontaneous conversion of an unliganded receptor to an active conformation.

The "$M_1$-receptor" is defined as a receptor having an activity corresponding to the activity of the m1 muscarinic receptor subtype characterized through molecular cloning and pharmacology.

The term "subject" refers to an animal, for example a mammal, such as a human, who is the object of treatment, observation or experiment.

The term "selective" is defined as a property of a compound whereby an amount of the compound sufficient to effect a desired response from a particular receptor type, subtype, class or subclass causes a substantially smaller or no effect upon the activity of other receptor types.

The $EC_{50}$ for an agonist is intended to denote the concentration of a compound needed to achieve 50% of a maximal response seen in an in vitro assay such as R-SAT. For inverse agonists, EC50 is intended to denote the concentration of a compound needed to achieve 50% inhibition of an R-SAT response from basal, no compound, levels.

As used herein, the term "coadministration" of pharmacologically active compounds refers to the delivery of two or more separate chemical entities, whether in vitro or in vivo. Coadministration refers to the simultaneous delivery of separate agents; to the simultaneous delivery of a mixture of agents; as well as to the delivery of one agent followed by delivery of a second agent or additional agents. In all cases, agents that are coadministered are intended to work in conjunction with each other.

In the present context, the term "$C_{1-6}$-alkyl" means a linear or branched saturated hydrocarbon chain wherein the longest chain has from one to six carbon atoms, such as methyl, ethyl, n-propyl, isopropyl, n-butyl, isobutyl, sec-butyl, tert-butyl, pentyl, isopentyl, neopentyl, and hexyl.

In the present context, the term "$C_{2-8}$-alkenyl" means a linear or branched hydrocarbon group having from two to eight carbon atoms and containing one or more double bonds. Illustrative examples of $C_{2-8}$-alkenyl groups include allyl, homo-allyl, vinyl, crotyl, butenyl, pentenyl, hexenyl, heptenyl and octenyl. Illustrative examples of $C_{2-8}$-alkenyl groups with more than one double bond include butadienyl, pentadienyl, hexadienyl, heptadienyl, heptatrienyl and octatrienyl groups as well as branched forms of these. The position of the unsaturation (the double bond) may be at any position along the carbon chain.

In the present context the term "$C_{2-8}$-alkynyl" means a linear or branched hydrocarbon group containing from two to eight carbon atoms and containing one or more triple bonds. Illustrative examples of $C_{2-8}$-alkynyl groups include ethynyl, propynyl, butynyl, pentynyl, hexynyl, heptynyl and octynyl groups as well as branched forms of these. The position of unsaturation (the triple bond) may be at any position along the carbon chain. More than one bond may be unsaturated such that the "$C_{2-8}$-alkynyl" is a di-yne or enedi-yne as is known to the person skilled in the art.

In the present context, the term "$C_{3-8}$-cycloalkyl" includes three-, four-, five-, six-, seven-, and eight-membered rings comprising carbon atoms only, whereas the term "heterocyclyl" means three-, four-, five-, six- seven-, and eight-membered rings wherein carbon atoms together with from 1 to 3 heteroatoms constitute said ring. The heteroatoms of such heterocyclyl groups are independently selected from oxygen, sulphur, and nitrogen.

The term "Heterocyclyl" groups may further contain one or more carbonyl or thiocarbonyl functionalities, so as to make the definition include oxo-systems and thio-systems such as lactams, lactones, cyclic imides, cyclic thioimides, cyclic carbamates, and the like.

$C_{3-8}$-cycloalkyl and heterocyclyl rings may optionally contain one or more unsaturated bonds situated in such a way, however, that an aromatic π-electron system does not arise.

Heterocyclyl rings may optionally also be fused to aryl rings, such that the definition includes bicyclic structures. Examples of such fused heterocyclyl groups share one bond with an optionally substituted benzene ring. Examples of benzo-fused heterocyclyl groups include, but are not limited to, benzimidazolidinone, tetrahydroquinoline, and methylenedioxybenzene ring structures.

Illustrative examples of "$C_{3-8}$-cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, cycloheptene, 1,2-cycloheptadiene, 1,3-cycloheptadiene, 1,4-cycloheptadiene and 1,3,5 cycloheptatriene.

Illustrative examples of "heterocyclyls" are the heterocycles tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, thiazoline, thiazolidine, 1,3-oxathiolane, Binding to the heterocycle may be at the position of a heteroatom or via a carbon atom of the heterocycle, or, for benzo-fused derivatives, via a carbon of the benzenoid ring.

In the present context the term "aryl" means a carbocyclic aromatic ring or ring system. Moreover, the term "aryl" includes fused ring systems wherein at least two aryl rings, or at least one aryl and at least one $C_{3-8}$-cycloalkyl share at least one chemical bond. Illustrative examples of "aryl" rings include optionally substituted phenyl, naphthalenyl, phenanthrenyl, anthracenyl, tetralinyl, fluorenyl, indenyl, and indanyl. An example of an aryl group is phenyl. The term "aryl" relates to aromatic, typically benzenoid groups connected via one of the ring-forming carbon atoms, and optionally carrying one or more substituents selected from halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. As stated, aryl groups may be phenyl, and, most suitably, substituted phenyl groups, carrying one or two, same or different, of the substituents listed above. One pattern of substitution is para and/or meta. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 3-cyanophenyl, 4-cyanophenyl, dimethylphenyl, naphthyl, hydroxynaphthyl, hydroxymethylphenyl, trifluoromethylphenyl, alkoxyphenyl.

In the present context the term "aryl($C_{1-6}$-alkyl)" means a carbocyclic aromatic ring as defined above connected via a $C_{1-6}$-alkyl group.

The term arylheteroalkyl should be interpreted as an aryl group, as defined above, connected, as a substituent, via a $C_{1-6}$-alkyl tether which, additionally, contains, in the chain, at least one atom selected from the group consisting of oxygen, sulfur, and nitrogen.

In the present context, the term "heteroaryl" means a heterocyclic aromatic group where one or more carbon atoms in an aromatic ring have been replaced with one or more heteroatoms selected from the group comprising nitrogen, sulphur, phosphorous and oxygen.

Furthermore, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one $C_{3-8}$-cycloalkyl ring share at least one chemical bond.

The term "heteroaryl" is understood to relate to aromatic, $C_{2-6}$ cyclic groups further containing one O or S atom or up to four N atoms, or a combination of one O or S atom with up to two N atoms, and their substituted as well as benzo- and pyrido-fused derivatives, typically connected via one of the ring-forming carbon atoms. Heteroaryl groups may carry one or more substituents, selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. Particular heteroaryl groups are five- and six-membered aromatic heterocyclic systems carrying 0, 1, or 2 substituents, which may be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, and tetrazole, as well as furazan, 1,2,3-oxadiazole, 1,2,3-thiadiazole, 1,2,4-thiadiazole, triazole, benzotriazole, quionoline, isoquinoline, pyridazine, pyrimidine, purine, pyrazine, pteridine, pyrrole, phenoxazole, oxazole, isoxazole, oxadiazole, benzopyrazole, indazole, quinolizine, cinnoline, phthalazine, quinazoline, and quinoxaline. The most typical substituents are halo, hydroxy, cyano, O—$C_{1-6}$-alkyl, $C_{1-6}$-alkyl, hydroxy-$C_{1-6}$-alkyl, amino-$C_{1-6}$-alkyl.

When used herein, the term "O—$C_{1-6}$-alkyl" means $C_{1-6}$-alkyloxy, or alkoxy, such as methoxy, ethoxy, n-propoxy, isopropoxy, n-butoxy, isobutoxy, sec-butoxy, tert-butoxy, pentyloxy, isopentyloxy, neopentyloxy and hexyloxy The term "halogen" includes fluorine, chlorine, bromine and iodine.

When used herein, the term "optionally substituted" means that the group in question may be substituted one or several times, such as 1 to 5 times, 1 to 3 times, or 1 to 2 times, with one or more groups selected from $C_{1-6}$-alkyl, $C_{1-6}$-alkoxy, oxo (which may be represented in the tautomeric enol form), carboxyl, amino, hydroxy (which when present in an enol system may be represented in the tautomeric keto form), nitro, alkylsulfonyl, alkylsulfenyl, alkylsulfinyl, $C_{1-6}$-alkoxycarbonyl, $C_{1-6}$-alkylcarbonyl, formyl, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkanoyloxy, $C_{1-6}$-alkylsulphonyloxy, dihalogen-$C_{1-6}$-alkyl, trihalogen-$C_{1-6}$-alkyl, and halo. In general, the above substituents may be susceptible to further optional substitution The term "salt" means pharmaceutically acceptable acid addition salts obtainable by treating the base form of a functional group, such as an amine, with appropriate acids such as inorganic acids, for example hydrohalic acids; typically hydrochloric, hydrobromic, hydrofluoric, or hydroiodic acid; sulfuric acid; nitric acid; phosphoric acid and the like; or organic acids, for example acetic, propionic, hydroacetic, 2-hydroxypropanoic acid, 2-oxopropanoic acid, ethandioic, propanedioic, butanedioic, (Z)-2-butenedioic, (E)-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic acid, cyclohexanesulfamic, 2-hydoxybenzoic, 4-amino-2-hydroxybenzoic, and other acids known to the skilled practitioner.

The method of the invention relates to the modulation of a cholinergic receptor. Typically, said cholinergic receptor is a muscarinic receptor; one example of a cholinergic receptor is a muscarinic receptor of $M_1$-receptor subtype. As can be seen from the Examples, in suitable embodiments, the cholinergic receptor may be either or both the muscarinic $M_1$-receptor and the muscarinic $M_4$-receptor subtypes. The physiologically beneficial response in the method of the invention is typically associated with the specific activation of the $M_1$-receptor subtype over the $M_2$- or $M_3$-receptor subtype, or the specific activation of the $M_1$- and $M_4$-receptor subtypes over the $M_2$- or $M_3$-receptor subtype. Moreover, a physiologically beneficial response in a method of the invention is typically associated with the agonistic activity of the compound of formula I or IA. Thus, in one embodiment, the compound of formula I or IA is a muscarinic agonist, such as an $M_1$ agonist or an $M_1$ and $M_4$ agonist.

A further aspect of the invention relates to a method of increasing the activity of a cholinergic receptor. In one embodiment, a method includes contacting a cholinergic receptor or a system containing a cholinergic receptor with an effective amount of at least one compound of formula I or IA, as defined supra.

A related aspect of the invention is directed to a method of treating or preventing or alleviating one or more symptoms associated with a disorder in a mammal, such as a human. In one embodiment, a method includes the administration of an effective amount of a compound of formula I or IA, said disorder associated with a muscarinic receptor, for example, $M_1$ muscarinic receptor subtype.

The disorders associated with the $M_1$ muscarinic receptor subtype are typically mental disorders. Suitable mental disorders which can be treated by the method of the invention may be selected from the group comprising of cognitive impairment, forgetfulness, confusion, memory loss, attentional deficits, deficits in visual perception, depression, pain, sleep disorders, psychosis, and increased intraocular pressure.

Disorders associated with the $M_1$ muscarinic receptor subtype need not be a mental disorder. For instance, increased intraocular pressure is associated with the $M_1$ muscarinic receptor subtype. Disorders to which the method of the invention are directed therefore include non-mental disorders.

Disorders to which the method of the invention are directed may be further selected from the group comprising neurodegenerative diseases, Alzheimer's disease, Parkinson's disease, schizophrenia, Huntington's chorea, Friederich's ataxia, Gilles de la Tourette's Syndrome, Down Syndrome, Pick disease, dementia, clinical depression, age-related cognitive decline, attention-deficit disorder, sudden infant death syndrome, and glaucoma.

As stated, the compounds of the invention have high selectivity and affinity for the muscarinic $M_1$ receptor subtypes. As can be seen from the Examples, the compounds also have high affinity for one or both of the $M_1$ and $M_4$ receptor subtypes, selectively over other receptors such as the $M_2$, $M_3$ and $M_5$ receptor subtypes. The compounds of the invention typically act, at least in part, as an $M_1$ agonist or as $M_1$ and $M_4$ agonist.

The compounds of the invention also have an affinity for the dopamine $D_2$ receptor. As discussed supra in connection with the dopamine hypothesis in relation to schizophrenia, compounds which act as both muscarinic agonists and dopamine antagonists may be keys to adequately treat many mental disorders. Thus, the invention is also directed to methods of treating mental disorders, using compounds of the invention, said compounds acting as a $D_2$ antagonist or $D_2$ inverse agonist as well as a muscarinic agonist, particularly an $M_1$ agonist or as $M_1$ and $M_4$ agonist. Thus, the method of the invention may be such that the disease in a mental disorder and the physiologically beneficial response to due to modulation in terms of $M_1$ agonism; $M_1$ and $M_4$ agonism; both $M_1$ agonism and $D_2$ antagonism; or $M_1$ and $M_4$ agonism and $D_2$ antagonism.

In one aspect of the invention, the compounds of the invention are anti-psychotic agents, said anti-psychotic activity due to the compounds of the invention acting as $M_1$ agonist; or as $M_1$ and $M_4$ agonists; or acting as an both $M_1$ agonists and $D_2$ antagonist; or as $M_1$ and $M_4$ agonists and $D_2$ antagonists.

Another aspect of the invention relates to the use of a compound of formula IA, or a pharmaceutically acceptable salt thereof, or a pharmaceutical composition comprising either entity, for the preparation of a medicament for the treatment of diseases or disorders associated with a cholinergic receptor or ligand thereof. The medicament may be for the treatment of diseases associated with the receptors as discussed supra and for disorders as discussed supra. A related aspect of the invention is directed to a pharmaceutical composition comprising an effective amount of a compound of formula I, as defined supra, or pharmaceutically acceptable salts thereof, a stereoisomer thereof, or a pharmaceutical composition comprising either entity, together with pharmaceutically acceptable carriers or excipients.

The invention provides novel compounds of formula I, as well as salts and isomers thereof

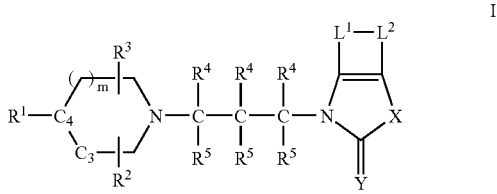

wherein $R^1$ is a monoradical selected from the group consisting of optionally substituted $C_{1-6}$-alkyl, optionally substituted $C_{2-6}$-alkylidene, optionally substituted $C_{2-6}$-alkenyl, optionally substituted $C_{2-6}$-alkynyl, optionally substituted O—$C_{1-6}$-alkyl, optionally substituted O—$C_{2-6}$-alkenyl, optionally substituted O—$C_{2-6}$-alkynyl; optionally substituted S—$C_{1-6}$-alkyl, optionally substituted S—$C_{2-6}$-alkenyl, optionally substituted S—$C_{2-6}$-alkynyl;

m is 0, 1 or 2;

$C_3$-$C_4$ is $CH_2$—CH or CH=C or $C_4$ is CH and $C_3$ is absent;

$R^2$ and $R^3$ are independently selected from the group consisting of hydrogen, optionally substituted $C_{1-6}$ alkyl, optionally substituted O—$C_{1-6}$ alkyl, halogen, hydroxy or selected such that $R^2$ and $R^3$ together form a ring system;

each $R^4$ and $R^5$ is independently selected from the group consisting of hydrogen, halogen, hydroxy, optionally substituted $C_{1-6}$-alkyl, $OC_{1-6}$alkyl, aryl-$C_{1-6}$alkyl, and arylheteroalkyl;

$L^1$ and $L^2$ are biradicals independently selected from the group consisting of —C($R^6$)=C($R^7$), —C($R^6$)=N—, —N=C($R^6$)—, —S—, —NH— and —O—; wherein only one of $L^1$ and $L^2$ may be selected from the group consisting of —S—, —NH— and —O—;

Y is selected from the group consisting of O, S, and $H_2$;

X is a biradical selected from the group consisting of —C($R^6$)($R^7$)—C($R^6$)($R^7$)—, —C($R^6$)=C($R^7$)—, —O—C($R^6$)($R^7$)—, C($R^6$)($R^7$)—O—, —S—C($R^6$)($R^7$)—, —C($R^6$)($R^7$)—S—, —N($R^N$)—C($R^6$)($R^7$)—, —C($R^6$)($R^7$)—N($R^N$)—, —C($R^6$)($R^7$)—C($R^6$)($R^7$)—C($R^6$)($R^7$)—, —O—C($R^6$)($R^7$)—C($R^6$)($R^7$)—, S—C($R^6$)($R^7$)—C($R^6$)($R^7$)—, N($R^N$)—C($R^6$)($R^7$)—C($R^6$)($R^7$)—, —C($R^6$)($R^7$)—C($R^6$) ($R^7$)—O, —C($R^6$)($R^7$)—C($R^6$)($R^7$)—S, C($R^6$)($R^7$)—C($R^6$) ($R^7$)—N($R^N$)—, —C($R^6$)($R^7$)—C($R^6$)=C($R^7$)—, and —C($R^6$)C($R^7$)—C($R^6$)($R^7$), wherein $R^6$ and $R^7$ are independently selected from the group consisting of hydrogen, halogen, hydroxy, nitro, cyano, $NR^N R^N$, $N(R^N)—C(O)N(R^N)$, optionally substituted $C_{1-6}$-alkyl, $C_{2-6}$-alkenyl, $C_{2-6}$-alkynyl, optionally substituted $O—C_{1-6}$-alkyl, optionally substituted O-aryl, optionally substituted $O—C_{2-6}$-alkenyl, optionally substituted $O—C_{2-6}$-alkynyl wherein $R^N$ is selected from the group consisting of hydrogen, and optionally substituted $C_{1-6}$-alkyl.

The present investigators have found that the compounds of the invention have a high affinity and specificity for the $M_1$ muscarinic receptor. The compounds of the invention may be of use in an array of conditions associated with the modulation of the $M_1$ muscarinic receptor subtype.

Typically, the compounds of formula I are such that $R^1$ is selected from the group consisting of optionally substituted $C_{1-6}$-alkyl, optionally substituted $C_{1-6}$-alkylidene, optionally substituted $C_{2-6}$-alkenyl, optionally substituted $C_{2-6}$-alkynyl, optionally substituted $O—C_{1-6}$-alkyl, and optionally substituted $O—C_{2-6}$-alkenyl. $R^1$ can be selected from the group consisting of optionally substituted $C_{1-6}$-alkyl, optionally substituted $C_{1-6}$-alkylidene, optionally substituted $C_{2-6}$-alkenyl, optionally substituted $O—C_{1-6}$-alkyl. $R^1$ can typically be selected from the group consisting of optionally substituted $C_{1-6}$-alkyl, optionally substituted $C_{1-6}$-alkylidene, and optionally substituted $O—C_{1-6}$-alkyl. Most typically, $R^1$ is selected from the group consisting of optionally substituted $C_4$-alkyl, optionally substituted $C_5$-alkyl, optionally substituted $C_4$-alkylidene, and optionally substituted $O—C_{1-6}$-alkyl. In a preferred embodiment, $R^1$ may be unsubstituted $C_4$-alkyl, unsubstituted $C_5$-alkyl, or unsubstituted $O—C_3$-alkyl, e.g. n-butyl, n-pentyl, or n-propyloxy.

In a particular embodiment of the invention, the compounds of formula I are such that $R^1$ is an optionally substituted $C_{1-6}$-alkyl, selected from the group consisting of unsubstituted $C_{1-6}$-alkyl, and $C_{1-6}$-alkoxyalkyl. The $C_{1-6}$-alkoxyalkyl may be $C_{1-3}$-alkoxy$C_{1-3}$alkyl. Typically, the $C_{1-6}$-alkoxyalkyl is selected from methoxypropyl, ethoxyethyl, propyloxymethyl, and methoxyethyl.

In one embodiment of the invention, the compounds of formula I are piperidines, bicyclic piperidines, 3-4-unsaturated piperidines or bicyclic 3-4-unsaturated piperidines. Within this embodiment, the $C_3$-$C_4$ bond may be a single bond to form either a piperidine ring or a bicylic piperidine. Alternatively, piperidine may be 3-4 unsaturated. That is to say that $C_3$-$C_4$ may be a double bond ($C_3$=$C_4$) so as to form either a 3-4-unsaturated piperidine or bicyclic 3-4-unsaturated piperidine.

In another embodiment of the invention, m is 0 and $C_3$ is absent while $C_4$ is CH, so as to result in an azetidine ring. Bicyclic analogues of azetidine are also included.

In an alternative embodiment, m is 0 so as to result in a pyrrolidine ring or a 3-pyrroline, when C3-C4 is a single bond or a double bond, respectively. Bicyclic analogues of pyrrolidine ring or a 3-pyrroline are further included. In a further suitable embodiment, m is 2 so as to form a 7-membered ring. In a particular embodiment, m is 1.

In one embodiment, $R^2$ and $R^3$ together form a bicyclic ring system such that

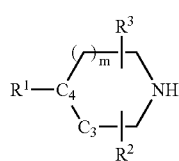

is selected from the group consisting of

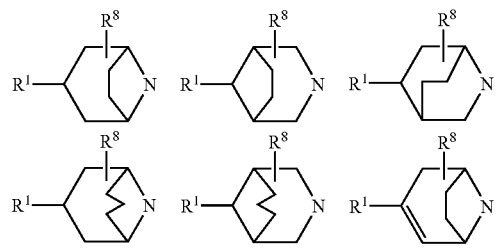

wherein $R^8$ is present 0, 1, or 2 times and is independently selected from the group consisting of optionally substituted $C_{1-6}$ alkyl, optionally substituted $O—C_{1-6}$ alkyl, halogen, hydroxy.

Within such an embodiment, $R^2$ and $R^3$ may preferably be selected such that $R^2$ and $R^3$ together form a ring system such that

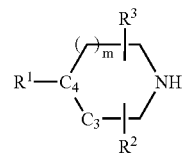

is selected from the group comprising

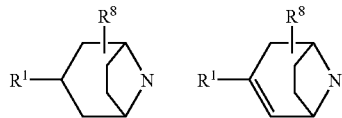

In a more preferred embodiment, the substituents $R^2$ and $R^3$ are selected so that the bicyclic ring is 3-substituted 8-azabicyclo[3.2.1]octane.

However, in a particular embodiment, $R^2$ and $R^3$ are independently selected from the group consisting of hydrogen, optionally substituted $C_{1-6}$ alkyl, optionally substituted $O—C_{1-6}$ alkyl, halogen and hydroxy.

Thus, in a combination of embodiments of compounds of formula I, $C_3$-$C_4$ is a single bond, $R^2$ and $R^3$ are independently selected from the group consisting of hydrogen, optionally substituted $C_{1-6}$ alkyl, optionally substituted $O—C_{1-6}$ alkyl, halogen and hydroxy, and m is 1. Suitably, $R^2$ and $R^3$ are hydrogen.

In a further combination, m can be 0, $C_3$ can be absent, and $C_4$ can be CH such that

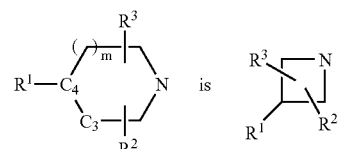

In a further combination of embodiments, $C_3$-$C_4$ and m are so as to form a piperidine ring, for example, wherein $R^2$ and $R^3$ are hydrogen. In additional embodiments, $C_3$-$C_4$ and m are so as to form a piperidine ring, $R^2$ and $R^3$ are hydrogen, and $R^1$ an unsubstituted $C_4$-alkyl, an unsubstituted $C_5$-alkyl, or an $O$—$C_3$-alkyl, such as butyl, pentyl, or propyloxy.

Thus, in one embodiment

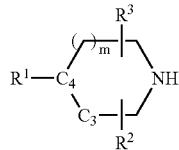

is a 4-butyl piperidine.

In another embodiment

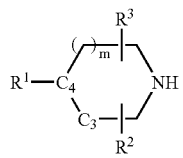

is 4-butyl piperidine.

In one embodiment of the invention, $C_3$-$C_4$ and m are such as to form an azetidine ring, $R^2$ and $R^3$ are hydrogen, and $R^1$ is selected from unsubstitued $C_4$-alkyl, unsubstituted $C_5$-alkyl, and $O$—$C_3$-alkyl. Thus, in one embodiment

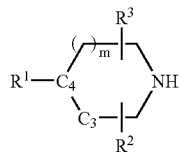

is a 4-butylazetidine.

In one aspect of the invention a 3-carbon tether is linking the two nitrogen atoms of the two ring systems of the compounds of formula I. The present investigators have found that this optionally substituted propylene spacer unit provides for compounds with highly efficacious binding capacity to the cholinergic receptors. More specifically, the compounds of the invention show agonistic properties at cholinergic receptors, especially muscarinic receptors.

In one embodiment, the tether

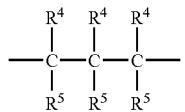

is unsubstituted, meaning that all of $R^4$ and $R^5$ are hydrogen.

In another embodiment one of the substituents $R^4$ is selected from the group consisting of $C_{1-6}$-alkyl, $O$—$C_{1-6}$-alkyl, and halogen, while the other two of the substituents $R^4$ are hydrogen.

In a combination of embodiments one of the substituents $R^4$ is selected from the group consisting of $C_{1-6}$-alkyl, $O$—$C_{1-6}$-alkyl, and halogen, while the other two of the substituents $R^4$ are hydrogen, and all of $R^5$ are hydrogen.

In a preferred embodiment one of the substituents $R^4$ is selected from the group consisting of methyl, methoxy, ethyl, and fluoro while the remaining $R^4$ and $R^5$ are all hydrogen.

Typically, when one of the substituents $R^4$ is $C_{1-6}$-alkyl, $O$—$C_{1-6}$-alkyl, or halogen, the tether is a 2-substituted-1,3-propylene group.

In a further suitable embodiment, the tether is a 2,2-disubstituted-1,3-propylene group, in which one of $R^4$ and one of $R^5$ are typically $C_{1-6}$-alkyl or fluoro.

Certain embodiments of the invention, wherein the propylene tether carries one or more substituents possess a stereogenic atom in the propylene tether. As set forth in the Examples, such chiral compounds may be preferred either in racemic or enantiomerically enriched form. Pure enantiomers and racemates are both included in the invention.

X may be a 1-, 2-, or 3-atom linear unit such that, together with the atoms in the ring comprising X, a 5-, 6- or 7-membered ring is formed. As stated, X, within the ring, is a biradical selected from the group consisting of —$C(R^6)(R^7)$—$C(R^6)(R^7)$—, —$C(R^6)$=$C(R^7)$—, —$O$—$C(R^6)(R^7)$—, $C(R^6)(R^7)$—$O$—, —$S$—$C(R^6)(R^7)$—, —$C(R^6)(R^7)$—$S$—, —$N(R^N)$—$C(R^6)(R^7)$—, —$C(R^6)(R^7)$—$N(R^N)$—, —$C(R^6)(R^7)$—$C(R^6)(R^7)$—$C(R^6)(R^7)$—, —$O$—$C(R^6)(R^7)$—$C(R^6)(R^7)$—, $S$—$C(R^6)(R^7)$—$C(R^6)(R^7)$—, $N(R^N)$—$C(R^6)(R^7)$—$C(R^6)(R^7)$—, —$C(R^6)(R^8)$—$C(R^6)(R^7)$—$O$, —$C(R^6)(R^7)$—$C(R^6)(R^7)$—$S$, —$C(R^6)(R^7)$ $C(R^6)(R^7)$—$N(R^N)$—, —$C(R^6)(R^7)$—$CH$=$CH$— and —$CH$=$CH$—$C(R^6)(R^7)$.

In a preferred embodiment X is selected from the group consisting of —$C(R^6)(R^7)$—$C(R^6)(R^7)$—, —$C(R^6)$=$C(R^7)$—, —$O$—$C(R^6)(R^7)$—, $C(R^6)(R^8)$—$O$—, —$S$—$C(R^6)(R^7)$—, —$C(R^6)(R^7)$—$S$—, —$N(R^N)$—$C(R^6)(R^7)$—, —$C(R^6)(R^7)$—$N(R^N)$—.

In a more preferred embodiment X is selected from the group consisting of —$C(R^6)(R^7)$—$C(R^6)(R^7)$—, —$O$—$C(R^6)(R^7)$—, $C(R^6)(R^8)$—$O$—, and —$C(R^6)$=$C(R^7)$—.

$R^6$ and $R^7$ are optional substituents of the ring system. An array of substituents is anticipated by the present investigators and are known to the person skilled in the art. The substituents $R^6$ and $R^7$ may independently be selected from the group consisting of hydrogen, halogen, hydroxy, nitro, cyano, $NR^NR^N$, $N(R^N)$—$C(O)N(R^N)$, optionally substituted $C_{1-6}$-alkyl, $C_{2-6}$-alkenyl, $C_{2-6}$-alkynyl, optionally substituted $O$—$C_{1-6}$-alkyl, optionally substituted $O$-aryl, optionally substituted $O$—$C_{2-6}$-alkenyl, optionally substituted $O$—$C_{2-6}$-alkynyl.

Suitably, when the substituents $R^6$ and $R^7$ occur within the definition of X, they are typically selected from hydrogen, halogen, hydroxy and $C_{1-6}$-alkyl. More typically, $R^6$ and $R^7$, when consituting part of the definition of X, are both hydrogen.

In one embodiment, Y is selected from the group consisting of O, S and $H_2$.

In a preferred embodiment, Y is O.

As stated, $L^1$ and $L^2$ are biradicals independently selected from the group consisting of —$C(R^7)$=$C(R^8)$, —$C(R^7)$=$N$—, —$N$=$C(R^7)$—, —$S$—, —$NH$— and —$O$—; wherein only one of $L^1$ and $L^2$ may be selected from the group consisting of —$S$— and —$O$—. Typically, $L^1$ and $L^2$ are such that

is an aromatic or heteroaromatic ring. In one embodiment, $L^1$ and $L^2$ are independently selected from the group consisting of —C($R^6$)=C($R^7$)—, —C($R^6$)=N—, —N=C($R^7$)—, and —S—; wherein only one of $L^1$ and $L^2$ is —S—. In another embodiment, at least one of $L^1$ and $L^2$ is C($R^6$)=C($R^7$). In yet another embodiment, $L^1$ and $L^2$ are so as to form a 6-membered ring. In still another embodiment, both of $L^1$ and $L^2$ are —C($R^6$)=C($R^7$)—.

Suitably, when the substituents $R^6$ and $R^7$ occur within the definition of

they are typically selected from hydrogen, halogen, hydroxy, $C_{1-6}$-alkyl and O—$C_{1-6}$alkyl.

Preferably, when the substituents $R^6$ and $R^7$ occur within the definition of

they are selected from hydrogen, fluoro, chloro, methyl, and methoxy.

Thus, in a combination of embodiments, the compounds of the invention are of formula Ia

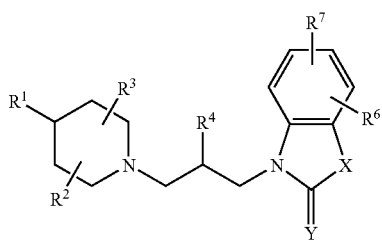

wherein $R^1$ is selected from the group consisting of optionally substituted $C_{1-6}$-alkyl, optionally subtituted $C_{1-6}$-alkylidene, optionally substituted $C_{2-6}$-alkenyl, optionally substituted $C_{2-6}$-alkynyl, optionally substituted O—$C_{1-6}$-alkyl, optionally substituted O—$C_{2-6}$-alkenyl; and $R^2$, $R^3$, $R^4$, X, Y, $R^6$, and $R^7$ are as defined supra.

In another combination of embodiments, the compounds of the invention are of formula Ia, wherein X is selected from the group consisting of —C($R^6$)($R^7$)—C($R^6$)($R^7$)—, —C($R^6$)=C($R^7$)—, —O—C($R^6$)($R^7$)—, C($R^6$)($R^8$)—O—, —S—C($R^6$)($R^7$)—, —C($R^6$)($R^7$)—S—, —N($R^N$)—($R^6$)($R^7$)—, —C($R^6$)($R^7$)—N($R^N$)—, wherein $R^6$ and $R^7$ are suitably hydrogen.

In a further combination of embodiments, the compounds of the invention are of formula Ia, wherein Y is O.

In yet another combination of embodiments, the compounds of the invention are of formula Ia, wherein $R^4$ is selected from hydrogen, $C_{1-6}$-alkyl, O—$C_{1-6}$-alkyl, and halogen.

In a further combination of embodiments, the compounds of the invention are of formula Ia, wherein $R^6$ and $R^7$ are selected from hydrogen, halogen, hydroxy, $C_{1-6}$-alkyl and O—$C_{1-6}$-alkyl.

In another combination of embodiments, the compounds of the invention are of formula Ia, wherein the optionally substituted $C_{1-6}$-alkyl is selected from the list comprising unsubstituted $C_{1-6}$-alkyl, and $C_{1-6}$-alkoxyalkyl, and wherein Y is selected from the group consisting of O and $H_2$, and wherein X is selected from the group consisting of —C($R^6$)($R^7$)—C($R^6$)($R^7$)—, —C($R^6$)=C($R^7$)—, —O—C($R^6$)($R^7$)—, —C($R^6$)($R^7$)—O—, —S—C($R^6$)($R^7$)—, —C($R^6$)($R^7$)—S—, and wherein $L^1$ and $L^2$ are independently selected from the group consisting of —C($R^6$)=C($R^7$)—, —C($R^6$)=N—, and —N=C($R^7$)—, and wherein $R^4$ selected from the group consisting of hydrogen, halogen, hydroxy, optionally substituted $C_{1-6}$-alkyl, and optionally substituted O—$C_{1-6}$alkyl.

In a further combination of embodiments, the compounds of the invention are optionally substituted 1-[3-(4-alkylpiperidin-1-yl)propyl]-1,2,3,4-tetrahydroquinolines, optionally substituted 1-[3-(4-alkylpiperidin-1-yl)propyl]-3,4-dihydro-1H-quinolin-2-ones, optionally substituted 1-[3-(4-alkylpiperidin-1-yl)propyl]-1H-quinolin-2-ones, optionally substituted 4-[3-(4-alkylpiperidin-1-yl)propyl]-4H-benzo[1,4]oxazin-3-ones, optionally substituted 4-[3-(4-alkylpiperidin-1-yl)propyl]-4H-benzo[1,4]thiazin-3-ones; optionally substituted 1-[3-(3-alkyl-8-azabicyclo[3.2.1]oct-8-yl)propyl]-1,2,3,4-tetrahydroquinolines; optionally substituted 1-[3-(3-alkyl-8-azabicyclo[3.2.1]oct-8-yl)propyl]-3,4-dihydro-1H-quinolin-2-ones, optionally substituted 1-[3-(3-alkyl-8-azabicyclo[3.2.1]oct-8-yl)propyl]-1H-quinolin-2-ones optionally substituted 4-[3-(3-alkyl-8-azabicyclo[3.2.1]oct-8-yl)propyl]-4H-benzo[1,4]oxazin-3-ones; optionally substituted 4-[3-(3-alkyl-8-azabicyclo[3.2.1]oct-8-yl)propyl]-4H-benzo[1,4]thiazin-3-ones; optionally substituted 1-[3-(3-alkylazetidin-1-yl)propyl]-3,4-dihydro-1H-quinolin-2-ones, optionally substituted 1-[3-(3-alkylazetidin-1-yl)propyl]-1H-quinolin-2-ones, optionally substituted 1-[3-(3-alkylazetidin-1-yl)propyl]-1,2,3,4-tetrahydroquinolines; optionally substituted 4-[3-(3-alkylazetidin-1-yl)propyl]-4H-benzo[1,4]oxazin-3-ones; optionally substituted 4-[3-(3-alkylazetidin-1-yl)propyl]-4H-benzo[1,4]thiazin-3-ones.

Suitable embodiments of the compounds of the invention may be selected from the group consisting of 1-[3-(4-Butyl-piperidin-1-yl)-propyl]-1,2,3,4-tetrahydro-quinoline; 1-[3-(4-Butyl-piperidin-1-yl)-propyl]-2-methyl-1,2,3,4-tetrahydro-quinoline; 1-[3-(4-Butyl-piperidin-1-yl)propyl]-6-methyl-1,2,3,4-tetrahydro-quinoline; 1-[3-(4-Butyl-piperidin-1-yl)-propyl]-8-methyl-1,2,3,4-tetrahydro-quinoline; 1-[3-(4-Butyl-piperidin-1-yl)-propyl]-7-fluoro-2-methyl-1,2,3,4-tetrahydro-quinoline; 1-[3-(4-Butyl-piperidin-1-yl)-propyl]-7-trifluoromethyl-1,2,3,4-tetrahydro-quinoline; 1-[3-(4-Butyl-piperidin-1-yl)-propyl]-3,4-dihydro-1H-quinolin-2-one; 1-[3-(4-Butyl-piperidin-1-yl)-propyl]-6-methoxy-3,4-dihydro-1H-quinolin-2-one; 4-[3-(4-Butyl-piperidin-1-yl)propyl]-4H-benzo[1,4]thiazin-3-one; 4-[3-(4-Butyl-piperidin-1-yl)-propyl]-4H-benzo[1,4]oxazin-3-one; 4-[3-(4-Butyl-piperidin-1-yl)-propyl]-6-methyl-4H-benzo[1,4]oxazin-3-one; 6-Acetyl-4-[3-(4-butyl-piperidin-1-yl)-propyl]-4H-benzo[1,4]oxazin-3-one; 4-[3-(4-Butyl-piperidin-1-yl)-propyl]-6-methyl-3,4-dihydro-2H-benzo[1,4]oxazine; and 4-[3-(4-Butyl-piperidin-1-yl)- propyl]-6-ethyl-3,4-dihydro-2H-benzo[1,4]oxazine; (R)-4-[3-(4-Butylpiperidin-1-yl)-2-methylpropyl]-4H-benzo[1,4]thiazin-3-one; (R)-4-[2-Methyl-3-(4-propoxypiperidin-1-yl)propyl]-4H-benzo[1,4]thiazin-3-one; (R)-4-[3-(4-Butylidene-piperidin-1-yl)-2-methyl-propyl]-4H-benzo[1,4]thiazin-3-one; (R)-4-[3-(3-Butyl-8-aza-bicyclo[3.2.1]oct-8-yl)-2-methyl-propyl]-4H-benzo[1,4]thiazin-3-one; (R)-4-[2-Methyl-3-(3-pentyl-8-aza-bicyclo[3.2.1]oct-8-yl)propyl]-4H-benzo[1,4]thiazin-3-one; 4-[3-(4-Butylpiperidin-1-yl)propyl]-6,8-dichloro-7-methyl-4H-benzo[1,4]oxazin-3-one; 4-[3-(4-Butyl-piperidin-1-yl)propyl]-6,8-dimethyl-4H-benzo[1,4]oxazin-3-one (81MF2237F); 6-tert-Butyl-4-[3-(4-butyl-piperidin-1-yl)propyl]-4H-benzo[1,4]oxazin-3-one; 4-[3-(4-Butylpiperidin-1-yl)propyl]-5-methyl-4H-benzo[1,4]oxazin-3-one; 4-[3-(4-Butylpiperidin-1-yl)propyl]-7-methyl-4H-benzo[1,4]oxazin-3-one; 4-[3-(4-Butylpiperidin-1-yl)propyl]-6-chloro-7-nitro-4H-benzo[1,4]oxazin-3-one; 4-[3-(4-Butylpiperidin-1-yl)propyl]-7-chloro-4H-benzo[1,4]oxazin-3-one; 4-[3-(4-Butylpiperidin-1-yl)propyl]-6-fluoro-4H-benzo[1,4]oxazin-3-one; 4-[3-(4-Butylpiperidin-1-yl)propyl]-7,8-difluoro-4H-benzo[1,4]oxazin-3-one; 4-[3-(4-Butylpiperidin-1-yl)propyl]-4H-pyrido[4,3-b][1,4]thiazin-3-one; 4-[3-(4-Propoxypiperidin-1-yl)propyl]-4H-benzo[1,4]thiazin-3-one; 4-[3-(4-Propoxypiperidin-1-yl)propyl]-4H-benzo[1,4]oxazin-3-one; 4-[3-(4-Butylpiperidin-1-yl)propyl]-7-fluoro-4H-benzo[1,4]oxazin-3-one; 4-[3-(4-Butylidenepiperidin-1-yl)propyl]-4H-benzo[1,4]thiazin-3-one; 4-[3-(4-Butylidenepiperidin-1-yl)propyl]-4H-benzo[1,4]oxazin-3-one; 4-[3-(3-Butylidene-8-aza-bicyclo[3.2.1]oct-8-yl)propyl]-4H-benzo[1,4]oxazin-3-one; 4-[3-(4-Butylpiperidin-1-yl)propyl]-6-methoxy-4H-benzo[1,4]oxazin-3-one; 4-[3-(4-Butylpiperidin-1-yl)propyl]-6,8-dichloro-7-ethyl-4H-benzo[1,4]oxazin-3-one; 4-[3-(4-Butylpiperidin-1-yl)propyl]-8-fluoro-4H-benzo[1,4]oxazin-3-one; 6-Bromo-4-[3-(4-butylpiperidin-1-yl)propyl]-8-fluoro-4H-benzo[1,4]oxazin-3-one; 4-[3-(4-Butylpiperidin-1-yl)propyl]-8-isopropyl-4H-benzo[1,4]oxazin-3-one; (R,S)-4-[3-(4-Butylpiperidin-1-yl)-2-hydroxy-propyl]-6-methyl-4H-benzo[1,4]oxazin-3-one; (R,S)-4-[3-(4-Butylpiperidin-1-yl)-2-hydroxypropyl]-4H-benzo[1,4]oxazin-3-one; (−)-4-[3-(4-Butylpiperidin-1-yl)-2-hydroxypropyl]-4H-benzo[1,4]oxazin-3-one; (R,S)-4-[3-(4-Butylpiperidin)-2-methoxypropyl]-4H-benzo[1,4]oxazin-3-one; (R,S)-4-[2-Hydroxy-3-(3-pentylbicyclo[3.2.1]oct-8-yl)-propyl]-4H-benzo[1,4]oxazin-3-one; 4-[2-(4-Butylpiperidin-1-ylmethyl)allyl]-4H-benzo[1,4]oxazin-3-one; (R,S)-4-[3-(4-Butylpiperidin-1-yl)-2-fluoropropyl]-4H-benzo[1,4]oxazin-3-one; (S)-4-[3-(4-Butyl-piperidin-1-yl)-2-methyl-propyl]-4H-benzo[1,4]oxazin-3-one; (R)-4-[3-(4-Butylpiperidin-1-yl)-2-methylpropyl]-4H-benzo[1,4]oxazin-3-one; (R)-4-[2-Methyl-3-(4-propoxypiperidin-1-yl)-propyl]-4H-benzo[1,4]oxazin-3-one; (R)-4-[3-(4-Butylidenepiperidin-1-yl)-2-methylpropyl]-4H-benzo[1,4]oxazin-3-one; (R)-4-[3-(3-Butyl-8-aza-bicyclo[3.2.1]oct-8-yl)-2-methylpropyl]-4H-benzo[1,4]oxazin-3-one; (R)-4-[2-Methyl-3-(3-pentyl-8-azabicyclo[3.2.1]oct-8-yl)propyl]-4H-benzo[1,4]oxazin-3-one; (R)-6-Fluoro-4-[2-methyl-3-(4-propoxy-piperidin-1-yl)-propyl]-4H-benzo[1,4]oxazin-3-one; (R)-4-[3-(4-Butylidenepiperidin-1-yl)-2-methyl-propyl]-6-fluoro-4H-benzo[1,4]oxazin-3-one; (R)-4-[3-(4-Butylpiperidin-1-yl)-2-methylpropyl]-6-fluoro-4H-benzo[1,4]oxazin-3-one; (R)-4-[3-(3-Butyl-8-azabicyclo[3.2.1]oct-8-yl)-2-methylpropyl]-6-fluoro-4H-benzo[1,4]oxazin-3-one; (R)-6-Fluoro-4-[2-methyl-3-(3-pentyl-8-azabicyclo[3.2.1]oct-8-yl)-propyl]-4H-benzo[1,4]oxazin-3-one; (R)-4-[3-(4-Butylpiperidin-1-yl)2-methylpropyl]-7-Fluoro-4H-benzo[1,4]oxazin-3-one; (R)-7-Fluoro-4-[2-methyl-3-(4-propoxypiperidin-1-yl)propyl]-4H-benzo[1,4]oxazin-3-one; (R)-4-[3-(4-Butylidenepiperidin-1-yl)-2-methylpropyl]-7-fluoro-4H-benzo[1,4]oxazin-3-one; (R)-4-[3-(3-Butyl-8-azabicyclo[3.2.1]oct-8-yl)-2-methylpropyl]-7-fluoro-4H-benzo[1,4]oxazin-3-one; (R)-7-Fluoro-4-[2-methyl-3-(3-pentyl-8-azabicyclo[3.2.1]oct-8-yl)-propyl]-4H-benzo[1,4]oxazin-3-one; (R)-4-[3-(4-Butylpiperidin-1-yl)-2-methyl-propyl]-6-methoxy-4H-benzo[1,4]oxazin-3-one; (R)-4-[3-(4-Butylidenepiperidin-1-yl)-2-methylpropyl]-6-methoxy-4H-benzo[1,4]oxazin-3-one; (R)-4-[3-(3-Butyl-8-azabicyclo[3.2.1]oct-8-yl)-2-methylpropyl]-6-methoxy-4H-benzo[1,4]oxazin-3-one; (R)-6-Methoxy-4-[2-methyl-3-(3-pentyl-8-aza-bicyclo[3.2.1]oct-8-yl)propyl]-4H-benzo[1,4]oxazin-3-one; (R)-6-Methoxy-4-[2-methyl-3-(4-propoxypiperidin-1-yl)propyl]-4H-benzo[1,4]oxazin-3-one; (R)-6-Methyl-4-[2-methyl-3-(4-propoxypiperidin-1-ylpropyl]-4H-benzo[1,4]oxazin-3-one; (R)-4-[3-(4-Butylidenepiperidin-1-yl)-2-methylpropyl]-6-methyl-4H-benzo[1,4]oxazin-3-one; (R)-4-[3-(4-Butylpiperidin-1-yl)-2-methylpropyl]-6-methyl-4H-benzo[1,4]oxazin-3-one; (R)-4-[3-(3-Butyl-8-azabicyclo[3.2.1]oct-8-yl)-2-methylpropyl]-6-methyl-4H-benzo[1,4]oxazin-3-one; (R)-4-[3-(3-Pentyl-8-azabicyclo[3.2.1]oct-8-yl)-2-methylpropyl]-6-methyl-4H-benzo[1,4]oxazin-3-one; 1-[3-(4-Propoxypiperidin-1-yl)propyl]-3,4-dihydro-1H-quinolin-2-one; 1-[3-(4-Butylpiperidin-1-yl)propyl]-6-fluoro-3,4-dihydro-1H-quinolin-2-one; 6-Fluoro-1-[3-(4-propoxypiperidin-1-yl)propyl]-3,4-dihydro-1H-quinolin-2-one; (R,S)-1-[3-(4-Butylpiperidin-1-yl)-2-methylpropyl]-6-fluoro-3,4-dihydro-1H-quinolin-2-one; (R,S)-6-Fluoro-1-[3-(4-propoxypiperidin-1-yl)-2-methylpropyl]-3,4-dihydro-1H-quinolin-2-one; 1-[3-(4-Butylpiperidin-1-yl)propyl]-6-chloro-3,4-dihydro-1H-quinolin-2-one; 1-[3-(4-Butylpiperidin-1-yl)propyl]-6-methyl-3,4-dihydro-1H-quinolin-2-one; 6-Methyl-1-[3-(4-propoxypiperidin-1-yl)propyl]-3,4-dihydro-1H-quinolin-2-one; 1-[3-(4-Butylpiperidin-1-yl)propyl]-7-fluoro-3,4-dihydro-1H-quinolin-2-one; 1-[3-(4-Butylpiperidin-1-yl)propyl]-5-methyl-3,4-dihydro-1H-quinolin-2-one; 1-[3-(4-Butylpiperidin-1-yl)propyl]-7-methyl-3,4-dihydro-1H-quinolin-2-one; 1-[3-(4-Butylpiperidin-1-yl)propyl]-7-fluoro-6-methyl-3,4-dihydro-1H-quinolin-2-one; 1-[3-(4-Butylpiperidin-1-yl)propyl]-6,7-difluoro-3,4-dihydro-1H-quinolin-2-one; 6,7-Difluoro-1-[3-(4-propoxypiperidin-1-yl)propyl]-3,4-dihydro-1H-quinolin-2-one; (R,S)-1-[3-(4-Butylpiperidin-1-yl)-2-methylpropyl]-6,7-difluoro-3,4-dihydro-1H-quinolin-2-one; (R,S)-6,7-Difluoro-1-[3-(4-propoxypiperidin-1-yl)-2-methylpropyl]-3,4-dihydro-1H-quinolin-2-one; 1-[3-(4-Butylpiperidin-1-yl)propyl]-6-fluoro-7-methyl-3,4-dihydro-1H-quinolin-2-one; 6-Fluoro-7-methyl-1-[3-(4-propoxypiperidin-1-yl)propyl]-3,4-dihydro-1H-quinolin-2-one; (R,S)-1-[3-(4-Butylpiperidin-1-yl)-2-methylpropyl]-6-fluoro-7-methyl-3,4-dihydro-1H-quinolin-2-one; (R,S)-6-Fluoro-7-methyl-1-[2-methyl-3-(4-propoxypiperidin-1-yl)-propyl]-3,4-dihydro-1H-quinolin-2-one; 1-[3-(4-Butyl-piperidin-1-yl)propyl]-6-fluoro-5-methyl-3,4-dihydro-1H-quinolin-2-one; 6-Fluoro-5-methyl-1-[3-(4-propoxypiperidin-1-yl)propyl]-3,4-dihydro-1H-quinolin-2-one; (R)-1-[3-(4-Butylpiperidin-1-yl)-2-methylpropyl]-3,4-dihydro-1H-quinolin-2-one; (R)-1-[2-Methyl-3-(4-propoxypiperidin-1-yl)propyl]-3,4-dihydro-1H-quinolin-2-one; (R)-1-[3-(4-Butylidenepiperidin-1-yl)-2-methylpropyl]-3,4-dihydro-1H-quinolin-2-one; (R)-1-[3-(3-Butyl-8-azabicyclo[3.2.1]oct-8-yl)-2-methylpropyl]-3,4-dihydro-1H-quinolin-2-one; (R)-1-[2-Methyl-3-(3-pentyl-8-azabicyclo[3.2.1]oct-8-yl)propyl]-3,4-dihydro-1H-quinolin- 2-one; 1-[3-(4-Butylpiperidin-1-yl)propyl]-1H-quinolin-2-one; 1-[3-(4-Propoxypiperidin-1-yl)propyl]-1H-quinolin-2-one; 1-[3-(4-Butylpiperidin-1-yl)propyl]-6-fluoro-1H-quinolin-2-one; 1-[3-(4-Butylpiperidin-1-yl)propyl]-6-methyl-1H-quinolin-2-one; 1-[3-(4-Butylpiperidin-1-yl)propyl]-7-fluoro-1H-quinolin-2-one; 1-[3-(4-Butylpiperidin-1-yl)propyl]-6-methoxy-1H-quinolin-2-one; 1-[3-(4-Butylpiperidin-1-yl)propyl]-6-chloro-1H-quinolin-2-one; 1-[3-(4-Butylpiperidin-1-yl)propyl]-5-methyl-1H-quinolin-2-one; 1-[3-(4-Butyl-piperidin-1-yl)propyl]-7-methyl-1H-quinolin-2-one; (R)-1-[3-(4-Butylpiperidin-1-yl)-2-methylpropyl]-1H-quinolin-2-one; (R)-1-[2-Methyl-3-(4-propoxypiperidin-1-yl)propyl]-1H-quinolin-2-one; 1-[3-(4-Allyloxypiperidin-1-yl)propyl]-1H-quinolin-2-one; (R,S)-4-[3-(4-Butylpiperidin-1-yl)-2-methylpropyl]-6-methyl-4H-benzo[1.4]oxazin-3-one; (R,S)-4-[2-Methyl-3-(4-propoxypiperidin-1-yl)propyl]-6-methyl-4H-benzo[1.4]oxazin-3-one; (R,S)-4-[3-(4-Butylidenepiperidin-1-yl)-2-methylpropyl]-6-methyl-4H-benzo[1.4]oxazin-3-one; (R,S)-4-[3-(3-Butyl-8-azabicyclo[3.2.1]oct-8-yl)-2-methylpropyl]-6-methyl-4H-benzo[1.4]oxazin-3-one; (R,S)-4-[2-Methyl-3-(3-pentyl-8-azabicyclo[3.2.1]oct-8-yl)propyl]-6-methyl-4H-benzo[1.4]oxazin-3-one; (R,S)-4-[3-(4-Butylpiperidin-1-yl)-2-methylpropyl]-6-fluoro-4H-benzo[1.4]oxazin-3-one; (R,S)-6-Fluoro-4-[2-methyl-3-(4-propoxypiperidin-1-yl)propyl]-4H-benzo[1.4]oxazin-3-one; (R,S)-4-[3-(4-Butylidenepiperidin-1-yl)-2-methylpropyl]-6-fluoro-4H-benzo[1.4]oxazin-3-one; (R,S)-4-[3-(3-Butyl-8-azabicyclo[3.2.1]oct-8-yl)-2-methylpropyl]-6-fluoro-4H-benzo[1.4]oxazin-3-one; (R,S)-6-Fluoro-4-[2-methyl-3-(3-pentyl-8-azabicyclo[3.2.1]oct-8-yl)propyl]-4H-benzo[1.4]oxazin-3-one; (R,S)-4-[3-(4-Butylpiperidin-1-yl)-2-methylpropyl]-7-fluoro-4H-benzo[1.4]oxazin-3-one; (R,S)-7-Fluoro-4-[2-methyl-3-(4-propoxypiperidin-1-yl)propyl]-4H-benzo[1.4]oxazin-3-one; (R,S)-4-[3-(4-Butylidenepiperidin-1-yl)-2-methylpropyl]-7-fluoro-4H-benzo[1.4]oxazin-3-one; (R,S)-4-[3-(3-Butyl-8-azabicyclo[3.2.1]oct-8-yl)-2-methylpropyl]-7-fluoro-4H-benzo[1.4]oxazin-3-one; (R,S)-7-Fluoro-4-[2-methyl-3-(3-pentyl-8-azabicyclo[3.2.1]oct-8-yl)propyl]-4H-benzo[1.4]oxazin-3-one; (R,S)-3-[3-(4-Butylpiperidin-1-yl)-2-methylpropyl]-3H-benzothiazol-2-one; (R,S)-4-[2-Methyl-3-(4-propoxypiperidin-1-yl)propyl]-3H-benzothiazol-2-one; (R,S)-4-[3-(4-Butylidenepiperidin-1-yl)-2-methylpropyl]-3H-benzothiazol-2-one; (R,S)-3-[3-(3-Butyl-8-azabicyclo[3.2.1]oct-8-yl)-2-methylpropyl]-3H-benzothiazol-2-one; (R,S)-3-[2-Methyl-3-(3-pentyl-8-azabicyclo[3.2.1]oct-8-yl)propyl]-3H-benzothiazol-2-one; (R,S)-4-[3-(4-Butylpiperidin-1-yl)-2-methylpropyl]-4H-benzo[1,4]oxazin-3-one; (R,S)-4-[2-Methyl-3-(4-propoxypiperidin-1-yl)propyl]-4H-benzo[1,4]oxazin-3-one; (R,S)-4-[3-(4-Butylidenepiperidin-1-yl)-2-methylpropyl]-4H-benzo[1,4]oxazin-3-one; (R,S)-4-[3-(3-Butyl-8-azabicyclo[3.2.1]oct-8-yl)-2-methylpropyl]-4H-benzo[1,4]oxazin-3-one; (R,S)-4-[2-Methyl-3-(3-pentyl-8-azabicyclo[3.2.1]oct-8-yl)propyl]-4H-benzo[1,4]oxazin-3-one; (R,S)-4-[3-(4-Butylpiperidin-1-yl)-2-methylpropyl]-4H-benzo[1,4]thiazin-3-one; (R,S)-1-[2-Methyl-3-(4-propoxypiperidin-1-yl)propyl]-4H-benzo[1,4]thiazin-3-one; (R,S)-4-[3-(4-Butylidenepiperidin-1-yl)-2-methylpropyl]-4H-benzo[1,4]thiazin-3-one; (R,S)-4-[3-(3-Butyl-8-azabicyclo[3.2.1]oct-8-yl)-2-methylpropyl]-4H-benzo[1,4]thiazin-3-one; (R,S)-4-[2-Methyl-3-(3-pentyl-8-azabicyclo[3.2.1]oct-8-yl)propyl]-4H-benzo[1,4]thiazin-3-one; (R,S)-1-[3-(4-Butylpiperidin-1-yl)-2-methylpropyl]-3,4-dihydro-1H-quinolin-2-one; (R,S)-1-[2-Methyl-3-(4-propoxypiperidin-1-yl)propyl]-3,4-dihydro-1H-quinolin-2-one; (R,S)-1-[3-(4-Butylidenepiperidin-1-yl)-2-methylpropyl]-3,4-dihydro-1H-quinolin-2-one; (R,S)-1-[3-(3-Butyl-8-azabicyclo[3.2.1]oct-8-yl)-2-methylpropyl]-3,4-dihydro-1H-quinolin-2-one; (R,S)-1-[2-Methyl-3-(3-pentyl-8-azabicyclo[3.2.1]oct-8-yl)propyl]-3,4-dihydro-1H-quinolin-2-one; (R,S)-4-[3-(4-Butylpiperidin-1-yl)-2-methylpropyl]-6-methoxy-4H-benzo[1,4]oxazin-3-one; (R,S)-4-[2-Methyl-3-(4-propoxypiperidin-1-yl)-6-methoxy]-4H-benzo[1,4]oxazin-3-one; (R,S)-4-[3-(4-Butylidenepiperidin-1-yl)-2-methylpropyl]-6-methoxy-4H-benzo[1,4]oxazin-3-one; (R,S)-4-[3-(3-Butyl-8-azabicyclo[3.2.1]oct-8-yl)-2-methylpropyl]-6-methoxy-4H-benzo[1,4]oxazin-3-one; (R,S)-1-[2-Methyl-3-(3-pentyl-8-azabicyclo[3.2.1]oct-8-yl)propyl]-6-methoxy-4H-benzo[1,4]oxazin-3-one; (R,S)-4-[3-(4-Butylpiperidin-1-yl)-2-methylpropyl]-6,7-difluoro-4H-benzo[1,4]oxazin-3-one; (R,S)-6,7-Difluoro-4-[2-methyl-3-(3-pentyl-8-azabicyclo[3.2.1]oct-8-yl)propyl]-4H-benzo[1,4]oxazin-3-one; (R,S)-4-[3-(3-Butoxy-8-azabicyclo[3.2.1]oct-8-yl)-2-methylpropyl]-6-fluoro-4H-benzo[1,4]oxazin-3-one; (R,S)-6-Fluoro-4-{3-[3-(2-methoxyethyl)-8-azabicyclo[3.2.1]oct-8-yl]-2-methylpropyl}-4H-benzo[1,4]oxazin-3-one, (R,S)-4-[3-(3-Butylazetidin-1-yl)-2-methylpropyl]-6-fluoro-4H-benzo[1,4]oxazin-3-one; (R,S)-6-Fluoro-4-[2-methyl-3-(3-propoxyazetidin-1-yl)propyl]-4H-benzo[1,4]oxazin-3-one; (R,S)-4-[3-(3-Butylazetidin-1-yl)-2-methoxypropyl]-6-fluoro-4H-benzo[1,4]oxazin-3-one; 4-[3-(4-Butyl-3-fluoropiperidin-1-yl)-2-methylpropyl]-6-fluoro-4H-benzo[1,4]oxazin-3-one.

The compounds of the invention have the ability to increase cholinergic receptor activity or activate cholinergic receptors. Cholinergic receptor activity includes signaling activity or any other activity that is directly or indirectly related to cholinergic signalling or activation. The cholinergic receptors include muscarinic receptors, especially the m1 or m4 subtype of muscarinic receptors. The muscarinic receptor can be, for example, in the central nervous system, peripheral nervous system, gastrointestinal system, heart, endocrine glands, or lungs. The muscarinic receptor can be a wild-type, truncated, mutated, or modified cholinergic receptor.

Kits comprising the compounds of the present invention, and instructions for practicing a method of the invention, for example, increasing cholinergic receptor activity or activating cholinergic receptors, are also provided.

The system containing the cholinergic receptor may, for example, be a subject such as a mammal, non-human primate or a human. The system may also be an in vivo or in vitro experimental model, such as a cell culture model system that expresses a cholinergic receptor, a cell-free extract thereof that contains a cholinergic receptor, or a purified receptor. Non-limiting examples of such systems are tissue culture cells expressing the receptor, or extracts or lysates thereof.

Cells that may be used in a method of the invention include any cell capable of mediating signal transduction via cholinergic receptors, such as the m1 muscarinic receptor, either via endogenous expression of receptor (certain types of neuronal cells lines, for example, natively express the m1 receptor), or such as following introduction of an exogenous gene into the cell, for example, by transfection of cells with plasmids containing the receptor gene. Such cells are typically mammalian cells (or other eukaryotic cells, such as insect cells or Xenopus oocytes), because cells of lower life forms generally lack the appropriate signal transduction pathways for the present purpose. Specific non-limiting examples of suitable cells include: the mouse fibroblast cell line NIH 3T3 (ATCC CRL 1658), which responds to transfected m1 receptors by increased growth; RAT 1 cells (Pace et al., *Proc. Natl. Acad. Sci. USA* 88:7031-35 (1991)); and pituitary cells (Vallar et al.,

*Nature* 330:556-58 (1987)). Other useful mammalian cells include but are not limited to HEK 293 cells, CHO cells and COS cells.

The compounds of the present invention also have the ability to reduce intraocular pressure and therefore can be used in the treatment of such diseases associated with intraocular pressure, e.g., glaucoma. Glaucoma is a disease in which an abnormality is observed in the circulation-control mechanism of the aqueous humor filling up the anterior chamber, i.e., the space formed between the cornea and the lens. This leads to an increase in the volume of the aqueous humor and an increase in intraocular pressure, consequently leading to visual field defects and even to loss of eyesight due to the compulsion and contraction of the papillae of the optic nerve.

Accordingly, the invention also provides methods of treating a disease in a mammal, such as a human, wherein modulation of the activity of a cholinergic receptor is associated with a physiologically beneficial response in said disease of said mammal. In one embodiment, a method includes administering an effective amount of a compound of formula I, as defined supra, to achieve a physiologically beneficial response. Typically, the cholinergic receptor is a muscarinic receptor, more typically the cholinergic receptor is a muscarinic $M_1$-receptor subtype. Alternatively, the cholinergic receptor is the muscarinic $M_4$-receptor subtype.

The invention further provides methods of treating or preventing or alleviating the symptoms associated with a disorder in a mammal, such as a human. In one embodiment, a method includes the administration of an effective amount of the compound of formula I, said disorder associated with a muscarinic receptor, such as the $M_1$ muscarinic receptor subtype, to treat or prevent or alleviate one or more symptoms associated with the disorder.

The physiologically beneficial response is typically associated with the selective modulation of the muscarinic $M_1$-receptor subtype in relation to the muscarinic $M_2$- or $M_3$-receptor subtypes. In one embodiment, the compound in the method of the invention is a muscarinic agonist.

The disease or disorder treated by the compounds of the invention is typically a mental disorder and the physiologically beneficial response is due to modulation in terms of $M_1$ agonism; $M_1$ and $M_4$ agonism; both $M_1$ agonism and $D_2$ antagonism; or $M_1$ and $M_4$ agonism and $D_2$ antagonism.

A further and related aspect of the invention relates to methods of increasing an activity of a cholinergic receptor. In one embodiment, a method includes contacting the cholinergic receptor or a system containing the cholinergic receptor with an effective amount of at least one compound as defined supra to increase an activity of a cholinergic receptor.

As can be ascertained from the above discussion, the compounds of the invention are intended, at least in part, for use as pharmaceutical medicaments. Thus, the invention provides compositions comprising i) one or more compounds of formula I, as defined supra; and ii) at least one pharmaceutically acceptable excipient or carrier. As the invention relates to the use of a compound of formula I, as defined supra, the invention also provides a compound of formula I, a pharmaceutically acceptable salt thereof, a stereoisomer thereof, or a pharmaceutical composition comprising either entity, for the preparation of a medicament for the treatment of diseases or disorders associated with a cholinergic receptor or ligand thereof.

The invention thus relates, in part, to a method of treating or preventing or alleviating one or more symptoms associated with a disorder in a mammal, such as a human. In one embodiment, a method includes the administration of an effective amount of the compound of formula I, said disorder associated with a muscarinic receptor, such as the $M_1$ muscarinic receptor subtype, to prevent or alleviate one or more symptoms. Disorders include those selected from the group consisting of cognitive impairment, forgetfulness, confusion, memory loss, attentional deficits, deficits in visual perception, depression, pain, sleep disorders, psychosis, and increased intraocular pressure. Disorders also include those selected from the group consisting of neurodegenerative diseases, Alzheimer's disease, Parkinson's disease, schizophrenia, Huntington's chorea, Friederich's ataxia, Gilles de la Tourette's Syndrome, Downs Syndrome, Pick disease, dementia, clinical depression, age-related cognitive decline, attention-deficit disorder, sudden infant death syndrome, and glaucoma. Consequently, the invention further relates to a use of a compound of formula I, a pharmaceutically acceptable salt thereof, a stereoisomer thereof, or a pharmaceutical composition comprising either entity, for the preparation of a medicament for the treatment of diseases or disorders including those selected from the group consisting of Alzheimer's disease, Parkinson's disease, schizophrenia, Huntington's chorea, Friederich's ataxia, Gilles de la Tourette's Syndrome, Down Syndrome, Pick disease, dementia, clinical depression, age-related cognitive decline, cognitive impairment, forgetfulness, confusion, memory loss, attentional deficits, deficits in visual perception, depression, pain, sleep disorders, psychosis, sudden infant death syndrome, increased intraocular pressure and glaucoma.

Compounds according to the invention may be used alone at appropriate dosages defined by routine testing in order to obtain optimal pharmacological effect on a muscarinic receptor, in particular the muscarinic $M_1$ or $M_4$ receptor subtype, while minimizing any potential toxic or otherwise unwanted effects. In addition, co-administration or sequential administration of other agents that improve the effect of the compound may, in some cases, be desirable.

The pharmacological properties and selectivity of the compounds of the invention for specific muscarinic receptor subtypes may be demonstrated by a number of different assay methods using, for example, recombinant receptor subtypes, the human receptors as available, e.g., conventional second messenger or binding assays. A particularly convenient functional assay system is the receptor selection and amplification assay (R-SAT assay) in U.S. Pat. No. 5,707,798, which describes a method of screening for bioactive compounds by utilizing the ability of cells transfected with receptor DNA, e.g., coding for the different muscarinic subtypes, to amplify in the presence of a ligand of the receptor. Cell amplification is detected as increased levels of a marker also expressed by the cells.

The invention is disclosed in further detail in the following examples.

EXAMPLES

Example 1

Synthetic Chemistry

General Analytical LC-MS Procedures

Procedure 1:

Spectra were obtained using a HP1100 LC/MSD-instrument. A set-up with a binary pump, auto sampler, column oven, diode array detector, and electro spray ionisation interface was used. A reversed phase column (C18 Luna 3μ, 75×4.6 mm ID) with a guard column cartridge system was used. The mobile phase was MeCN/8 mM aqueous ammonium acetate. A 15-minute gradient program was used, starting at 70% MeCN over 12 minutes to 95% MeCN, over 1 minute to 70% MeCN, hold for 2 minutes. The flow rate was 0.6 ml/min.

Procedure 2:

Spectra were obtained using a Waters LC/ZMD-instrument. A set-up with a 600 gradient pump, 2700 sample manager, 996 diode array detector, and electro spray ionisation interface was used. A reversed phase column (C18 X-Terra 5µ, 50×4.6 mm ID) with a guard column cartridge system was used. The mobile phase was MeCN/10 mM aqueous ammonium acetate. A 14-minute gradient program was used; starting at 30% MeCN, over 10 minutes to 95% MeCN, hold for 2 minutes, over 0.5 minutes to 30% MeCN, hold for 4.5 minutes. The flow rate was 1 ml/min.

General Preparative LC-MS Procedures

Procedure 1:

Preparative purification was performed on a Waters auto purification system (600 pumps, 2700 sample manager, 996 PDA detector, ZMD mass spectrometer).

The columns used were YMC C18 J'sphere ODS H80. Buffer A was 0.15% TFA in water, buffer B was 0.15% TFA in MeCN/water 95/5. The columns were operated at 17 ml/min. Following an initial hold of 2.5 min at 30% buffer B, compounds were separated using a gradient af 30-100% buffer B in 8.5 min. A dual column set-up with two pumps was used to equilibrate one column, while running on the other.

Procedure 2:

Preparative purification was performed on Waters Delta 4000 preparative system, Water 2487 dual absorbance detector, and Waters Fraction collector II. The column used was a Luna 15 µm C18, 250×21.2 mm. The following mobile phases were used: $H_2O$/MeCN ammonium acetate buffer (25 nM) or $H_2O$/MeCN TFA buffer (25 nM).

Heating with microwave irradiation was performed with a Smith Creator single-mode cavity (Personal Chemistry AB, Uppsala, Sweden) producing continuous irradiation at 2.45 GHz. The microwave-assisted reactions were performed in caped Smith process vials with a magnetic stirring bar. To secure sufficient irradiation absorption the liquid sample volume was ≧0.5 mL.

Cation exchange CC was performed with Varian BOND ELUT (mega BE-SCX, 1 g, 6 ml) columns. After applying the compound to the column, it was first washed with MeOH (2 column volumes) and thereafter the desired compound was eluted applying 2 column volumes of an $NH_4OH$ (25% $NH_3$ in $H_2O$)/MeOH mixture (1:9).

(R,S)-1-(4-Butylpiperidin-1-yl)-3-chloropropan-2-ol (101IS93-1)

A 4 mL vial was charged with 4-butylpiperidine (0.29 g, 2.0 mmol) and epichlorohydrin (0.190 g, 2.1 mmol) and was shaken at rt for 4 h. The resulting thick oil was purified by flash chromatography ($SiO_2$; $CH_2Cl_2$/acetone/MeOH 85/10/5) to yield the title compound as an oil (0.31 g, 64%). $^1$H NMR (CDCl$_3$) δ 3.95-3.85 (m, 1H), 3.60-3.48 (m, 1H), 2.97-2.88 (m, 1H), 2.82-2.72 (m, 1H), 2.46-2.35 (m, 1H), 2.30-2.20 (m, 1H), 1.98-1.88 (m, 1H), 1.70-1.58 (m, 2H), 1.35-1.08 (m, 9H), 0.88 (t, J=6.8 Hz, 3H); $^{13}$C NMR (CDCl$_3$) δ 66.7, 61.5, 55.9, 53.1, 47.4, 36.4, 35.8, 32.9, 32.6, 29.2, 23.1, 14.3.

(R,S)-4-Butyl-1-(3-chloro-2-fluoropropyl)piperidine (101IS93-2)

DAST (1.9 mmol, 230 µl) was added drop wise to a solution of 1-(4-butylpiperidin-1-yl)-3-chloropropan-2-ol (101IS93) (0.31 g, 1.28 mmol) in $CH_2Cl_2$ (5 mL). After 2 h the reaction was quenched by the addition water (5 mL) and the organic phase was extracted with $CH_2Cl_2$ (2×15 mL) and the combined organic phase was dried ($Na_2SO_4$), filtered, concentrated under reduced pressure and the residue was purified by flash chromatography ($SiO_2$; heptane/EtOAc 60:40) to yield the title compound as an oil (0.025 g, 9%); $^1$H NMR (CDCl$_3$) δ 4.79 (dm, J=48 Hz, 1H), 3.78-3.60 (m, 2H), 2.92-2.83 (m, 2H), 2.72-2.56 (m, 2H), 2.15-2.00 (m, 2H), 1.69-1.58 (m, 2H), 1.35-1.16 (m, 9H), 0.88 (t, J=6.8 Hz); $^{13}$C NMR (CDCl$_3$) δ 91.1 (d, J=111 Hz), 59.9 (d, J=22 Hz), 55.2, 54.9, 44.9 (d, J=25 Hz), 36.4, 35.6, 32.7, 32.6, 29.2, 23.1, 14.3.

General Procedure 1 (GP1)

To a flask or vial was charged 2-aminophenol (1.0 equiv) disolved in DMF (0.1 g/mL) and 2-Chloroacetyl chloride (1.1 equiv) was added. The reaction was stirred in rt for 12-20 hours and $K_2CO_3$ (2.1 equiv) was added. The reaction was stirred in rt for another 12-20 hours then evaporated to dryness, redisolved in water (10 mL) and extracted using EtOAc (3×20 mL). The combined organic phases concentrated to a crude that was used directly or purified by CC (Heptane: EtOAc).

4H-Pyrido[4,3-b][1,4]thiazin-3-one (81MF939a)

3-Amino-4-thiopyridine (0.10 g, 0.79 mmol) and 2-Chloroacetyl chloride (0.098 g, 0.87 mmol) and $K_2CO_3$ (0.23 g, 1.66 mmol) were mixed according to GP1 to give the title compound as a crude (81MF939a) (0.087 g)

8-Fluoro-4H-benzo[1,4]oxazin-3-one (95MF45)

2-Amino-6-flourophenol (95MF2085) (0.256 g, 2.0 mmol), 2-chloroacetyl chloride (0.25 g, 2.2 mmol) and $K_2CO_3$ (0.583 g, 4.2 mmol) were mixed according to GP1 to give the title compound as a crude (95MF45) (0.29 g)

7-Fluoro-4H-benzo[1,4]oxazin-3-one (111MF12)

2-Amino-5-flourophenol (111MF10) (10.3 g, 81 mmol), 2-chloroacetyl chloride (10.1 g, 89 mmol) and $K_2CO_3$ (23.5 g, 170 mmol) were mixed according to GP1. CC ($SiO_2$; Heptane/EtOAc 4:1-4) to give the title compound (111MF12) (12.6 g, 93%); $^1$H NMR (DMSO) δ 10.68 (s, 1H), 6.83-6.91 (m, 2H), 6.75-6.80 (m, 1H), 4.57 (s, 2H); $^{13}$C NMR (DMSO) δ 164.2, 157.8 (d, J=238.6 Hz), 144.0 (d, J=12.4 Hz), 123.9 (d, J=2.7 Hz), 116.3 (d, J=9.6 Hz), 108.6 (d, J=22.7 Hz), 104.0 (d, J=26.5 Hz), 66.7.

7,8-Difluoro-4H-benzo[1,4]oxazin-3-one (81MF2082A)

6-Amino-2,3-diflourophenol (81KK30a) (0.113 g, 0.78 mmol), 2-chloroacetyl chloride (0.10 g, 0.89 mmol) and $K_2CO_3$ (0.226 g, 1.6 mmol) were mixed according to GP1 to give the title compound as a crude (81MF2082A) (0.12 g)

6-Bromo-8-fluoro-4H-benzo[1,4]oxazin-3-one (95MF44)

2-Amino-4-bromo-6-flourophenol (95MF2084) (0.078 g, 0.38 mmol), 2-chloroacetyl chloride (0.048 g, 0.42 mmol) and $K_2CO_3$ (0.11 g, 0.79 mmol) were mixed according to GP1 to give the title compound as a crude (95MF44) (0.091 g)

8-Isopropyl-4H-benzo[1,4]oxazin-3-one (95MF83)

Crude 2-Amino-6-isopropylphenol (95MF80(2240)) (0.16 g, 1.1 mmol), 2-chloroacetyl chloride (0.14 g, 1.2 mmol) and K$_2$CO$_3$ (0.32 g, 2.3 mmol) were mixed according to GP1 to give the title compound as a crude (95MF83) (0.115 g).

6,8-Dichloro-7-methyl-4H-benzo[1,4]oxazin-3-one (81MF2225)

6-Amino-2.4 dichloro-3-metylphenol (1.9 g, 10 mmol), 2-chloroacetyl chloride (1.2 g, 11 mmol) and K$_2$CO$_3$ (3.0 g, 22 mmol) were mixed according to GP1 to give the title compound as a crude (80MF2225) (2.33 g).

6,8-Dichloro-7-ethyl-4H-benzo[1,4]oxazin-3-one (95MF46)

6-Amino-2.4-dichloro-3-etylphenol (95MF2226) (0.293 g, 1.5 mmol), 2-chloroacetyl chloride (0.19 g, 1.7 mmol) and K$_2$CO$_3$ (0.44 g, 3.2 mmol) were mixed according to GP1 to give the title compound as a crude (95MF46) (0.34 g).

7-fluoro-6-methyl-3,4-dihydro-1H-quinolin-2-one (97KK40)

3-Fluoro-4-methylaniline (1.247 g, 9.96 mmol), 3-chloropropionyl chloride (1.269 g, 9.99 mmol), and K$_2$CO$_3$ (1.450 g, 10.5 mmol) in MeCN (10 mL) were stirred at 40° C. for 3 h. The reaction mixture was quenched with 4M HCl and the product extracted into CH$_2$Cl$_2$. The combined organic layers were dried over Na$_2$SO$_4$, filtered, and concentrated. The residue (1.168 g) was heated to 145° C. and small portions of AlCl$_3$ (3.538 g, 26.5 mmol) were added over a period of 30 min. The reaction mixture was then cooled and 4M HCl added under stirring followed by extraction of the product into CH$_2$Cl$_2$. The combined organic layers were dried over Na$_2$SO$_4$, filtered, and concentrated. The residue was purified by flash CC (SiO$_2$; CH$_2$Cl$_2$/MeOH 40:1) to give the title compound (97KK40) (0.201 g, total yield 11%). $^1$H NMR (CDCl$_3$) δ 8.15 (br s, 1H), 6.94 (d, J=7.8 Hz, 1H), 6.47 (d, J=10.0 Hz, 1H), 2.91-2.87 (m, 2H), 2.62-2.60 (m, 2H), 2.19 (d, J=1.8 Hz, CH$_3$).

6-Fluoro-1H-quinolin-2-one (97KK38)

DDQ (0.38 g, 1.7 mmol) was added to a solution of 6-fluoro-3,4-dihydro-1H-quinolin-2-one (0.18 g, 1.1 mmol) in dioxane (25 mL) and the resulting solution was refluxed for 16 h. The mixture was concentrated, and sat aqueous Na$_2$CO$_3$ (25 mL) was added followed by extraction into an organic mixture (MeOH:CH$_2$Cl$_2$; 1:10, 3×50 mL). The combined organic phase was dried (Na$_2$SO$_4$), filtered, concentrated under reduced pressure and purified by flash CC (SiO$_2$; CH$_2$Cl$_2$/MeOH 20:1) to give the title compound (0.056 g, 31%). $^1$H NMR (DMSO-D$_6$) δ 11.8 (brs, 1H), 7.85 (d, J=9.4 Hz), 7.50 (dd, J=2.8, 9.2 Hz), 7.43-7.37 (m, 1H), 7.37-7.25 (m, 1H), 6.54 (d, J=9.4 Hz).

7-Fluoro-1H-quinolin-2-one, (97KK34)

DDQ (0.42 g, 1.9 mmol) was added to a solution of 7-fluoro-3,4-dihydro-1H-quinolin-2-one (0.20 g 1.2 mmol) in dioxane (25 mL) and the resulting mixture was refluxed under an Argon atmosphere for 16 h. The mixture was concentrated under reduced pressure and sat aqueous Na$_2$CO$_3$ solution (25 mL) was added, and this was extracted with an organic mixture (MeOH/CH$_2$Cl$_2$ 1:10, 3×50 mL). The combined organic phase was dried (Na$_2$SO$_4$), filtered, concentrated under reduced pressure and purified by combi flash LC (SiO$_2$; CH$_2$Cl$_2$/MeOH 10:1) to give the title compound (0.037 g, 18%). $^1$H NMR (DMSO-D$_6$) δ 11.8 (s, 1H), 7.88 (d, J=9.6 Hz, 1H), 7.74-7.65 (m, 1H), 7.05-6.95 (m, 2H), 6.43, (d, J=9.6 Hz); $^{13}$C NMR (CDMSO-D$_6$) δ 163.0 (d, J=247 Hz), 161.9, 140.4 (d, J=13 Hz), 130.4 (d, J=11 Hz), 120.9, 116.1, 109.8 (d, J=23), 101.0 (d, J=25 Hz).

6-Fluoro-7-methyl-3,4-dihydro-1H-quinolin-2-one (10LH75-1) and 6-Fluoro-5-methyl-3,4-dihydro-1H-quinolin-2-one (107LH75-2)

3-Chloro-N-(4-fluoro-3-methyl-phenyl)-propionamide (3.8 g, 30 mmol), 3-chloropropionyl chloride (2.9 mL, 30 mmol) and K$_2$CO$_3$ (5.0 g, 36 mmol) were added to CH$_3$CN (50 mL) and the mixture was stirred for 44 h at rt. Thereafter, the reaction was diluted with EtOAc (50 mL) and washed with water (20 mL), HCl (20 mL, 4N) and brine (20 mL). The organic phase was dried with Na$_2$SO$_4$, filtered and concentrated under reduced pressure. The residue (5.9 g) was heated to 135° C. and small portions of AlCl$_3$ (11 g, 82 mmol) were added during 30 min, the reaction was then cooled to 50° C. and HCl (4N 20, mL) was added and the resulting mixture was stirred for 15 min. The mixture was extracted with EtOAc (50 mL) and the organic phase was washed with water (20 mL). The resulting organic phase was dried (Na$_2$SO$_4$), filtered concentrated under reduced pressure and purified by prep HPLC to yield 6-fluoro-7-methyl-3,4-dihydro-1H-quinolin-2-one (0.76 g, 14%) and 6-fluoro-5-methyl-3,4-dihydro-1H-quinolin-2-one (0.190 g, 4%). 6-Fluoro-7-methyl-3,4-dihydro-1H-quinolin-2-one (107LH75-1). $^1$H NMR (CDCl$_3$) δ 8.86 (brs, 8.86, 1H), 6.81 (d, J=9.2 Hz, 1H), 6.62 (d, J=6.8 Hz, 1H), 2.91 (brt, J=7.6 Hz, 3H), 2.94-2.87 (m, 2H), 2.20 (d, J=2.0 Hz). 6-Fluoro-5-methyl-3,4-dihydro-1H-quinolin-2-one (107LH75-2). $^1$H NMR (CDCl$_3$) δ 8.78 (brs, 1H), 6.85 (t, J=8.8 Hz, 1H), 6.62 (dd, J=4.5, 8.8 Hz, 1H), 2.92 (brt, J=7.6 Hz, 2H), 2.64-2.58 (m, 2H), 2.20 (d, J=2.4 Hz, 3H).

(R)-4-(3-Hydroxy-2-methylpropyl]-4H-benzo[1,4]oxazin-3-one (108LM40-37)

A 25 mL flask was charged with 4H-benzo[1,4]oxazin-3-one (0.100 g, 0.670 mmol), (S)-3-bromo-2-methylpropanol (0.103 g, 0.670 mmol) and cesium carbonate (0.208 g, 0.670 mmol) in MeCN (10 mL) and stirred at 40° C. for 2 days. The reaction mixture was quenched with water (5 mL), and the product extracted into EtOAc (2×10 mL). The combined organic layers were dried (Na$_2$SO$_4$) and evaporated to give the crude title compound (108LM40-37) (0.219 g).

General Procedure 2 (GP2)

A dry 50 mL flask was charged with the appropriate heterocycle (1.1 equiv), (R)-(3-bromo-2-methyl-propoxy)-tert-butyl-dimethylsilane (95MF94) (1 equiv) and cesium carbonate (2.5 equiv) in DMF (20 mL) and stirred at 55° C. for 20 h. The reaction mixture was quenched with water (10 mL), and the product extracted into EtOEt (3×20 mL). The combined organic layers were washed with brine, dried (Na$_2$SO$_4$), evaporated and purified by flash CC (SiO$_2$; EtOAc/heptane 1:10).

(S)-[3-(tert-Butyldimethylsilanyloxy)-2-methylpropyl]-4H-benzo[1,4]oxazin-3-one (108LM24-21)

4H-Benzo[1,4]oxazin-3-one (2.47 g, 16.5 mmol), (R)-(3-bromo-2-methylpropoxy)-tert-butyldimethylsilane (95MF94) (4.01 g, 15.0 mmol) and Cs$_2$CO$_3$ (12.2 g, 37.6 mmol) in DMF (20 mL) were reacted according to GP2 to give the title compound (108LM24-21) (3.92 g, 78%). $^1$H NMR (CDCl$_3$) δ 7.15-7.11 (m, 1H), 6.99-6.91 (m, 3H), 4.60-4.50 (m, 2H), 3.98 (dd, J=8.3 Hz, J=12.4 Hz, 1H), 3.81 (dd, J=5.5 Hz, J=12.4 Hz, 1H), 3.51 (dd, J=4.1 Hz, J=9.7 Hz, 1H), 3.40 (dd, J=6.9 Hz, J=9.7 Hz, 1H), 2.12-2.02 (m, 1H), 0.90-0.82 (m, 12H), 0.02 (s, 6H).

(S)-4-[3-(tert-Butyldimethylsilanyloxy)-2-methylpropyl]-4H-benzo[1,4]thiazin-3-one (108LM25-22)

4H-Benzo[1,4]thiazin-3-one (2.75 g, 16.7 mmol), (R)-(3-bromo-2-methylpropoxy)-tert-butyldimethylsilane (95MF94) (4.04 g, 15.1 mmol) and cesium carbonate (12.3 g, 37.9 mmol) in DMF (20 mL) were reacted according to GP2 to give the title compound (108LM25-22) (3.74 g, 70%). $^1$H NMR (CDCl$_3$) δ 7.35 (d, J=7.6 Hz, 1H), 7.28-7.18 (m, 2H), 6.99 (t, J=7.6 Hz, 1H), 4.13 (dd, J=8.9 Hz, J=13.3 Hz, 1H), 3.95 (dd, J=5.9 Hz, J=13.3 Hz, 1H), 3.52-3.40 (m, 2H), 3.37 (s, CH$_2$), 1.96-2.07 (m, 1H), 0.92-0.83 (m, 12H), 0.02 (s, 6H).

General Procedure 3 (GP3)

A 50 mL flask was charged with the appropriate heterocycle (1 equiv) and tetrabutylammonium fluoride (TBAF) (1.3 equiv) in THF (30 mL) and stirred at rt for 20 h. The reaction mixture was concentrated to syrup and dissolved in EtOAc (30 mL). The mixture was washed with brine (2×20 mL). The combined organic layers were dried (Na$_2$SO$_4$), evaporated and purified by flash CC (SiO$_2$; EtOAc/heptane 7:3).

(S)-4-(3-Hydroxy-2-methylpropyl)-4H-benzo[1,4]oxazin-3-one (108LM26-23)

The compound (S)-4-[3-(tert-Butyldimethylsilanyloxy)-2-methylpropyl]-4H-benzo[1,4]oxazin-3-one (108LM24-21) (3.92 g, 11.7 mmol) and TBAF (4.78 g, 15.2 mmol) in THF (30 mL) were reacted according to GP3 to give the title compound (108LM26-23) (2.52 g, 98%). $^1$H NMR (CDCl$_3$) δ 7.05-6.95 (m, 4H), 4.63 (s, CH$_2$), 4.23 (dd, J=10.3 Hz, J=13.9 Hz, 1H), 3.56 (dd, J=4.8 Hz, J=13.9 Hz, 1H), 3.52-3.49 (m, 1H), 3.46-3.38 (m, 1H), 2.92-2.85 (m, 1H), 2.09-1.97 (m, 1H), 1.06 (d, J=7.3 Hz, CH$_3$).

(S)-4-[3-(tert-Butyldimethylsilanyloxy)-2-methylpropyl]-4H-benzo[1,4]thiazin-3-one The compound (108LM25-22) (3.69 g, 10.5 mmol) and TBAF (4.30 g, 13.6 mmol) in THF (30 mL) were reacted according to GP3. Purified by flash CC (SiO$_2$; EtOAc/heptane 7:3) to give the title compound (108LM34-31) (2.36 g, 95%). $^1$H NMR (CDCl$_3$) δ 7.38 (d, J=7.9 Hz, 1H), 7.28-7.18 (m, 2H), 7.03 (t, J=7.0 Hz, 1H), 4.32 (dd, J=9.0 Hz, J=15.2 Hz, 1H), 3.70 (dd, J=5.5 Hz, J=15.2 Hz, 1H), 3.52 (dd, J=3.4 Hz, J=11.7 Hz, 1H), 3.34-3.42 (m, 3H), 2.82 (bs, OH), 1.92-1.83 (m, 1H), 0.98 (d, J=6.9 Hz, CH$_3$).

General Procedure 4 (GP4)

A 50 mL flask was charged with the appropriate heterocycle (1 equiv), triphenylphosphine (2 equiv) and imidazole (2.5 equiv) in CHCl$_3$ (30 mL). When all of the material was dissolved iodine (3 equiv) was added while stirring. Stirring was continued at rt for 20 h. The reaction mixture was washed with sat. aqueous sodium thiosulfate (30 mL), dried (Na$_2$SO$_4$), evaporated and purified by flash CC (SiO$_2$; EtOAc/heptane 3:1).

(S)-4-(3-Iodo-2-methylpropyl)-4H-benzo[1,4]oxazin-3-one (108LM27-24)

The compound (S)-4-(3-Hydroxy-2-methylpropyl)-4H-benzo[1,4]oxazin-3-one (108LM26-23) (2.52 g, 11.4 mmol), triphenylphosphine (6.12 g, 23.3 mmol), imidazole (1.98 g, 29.1 mmol) and iodine (8.88 g, 35.0 mmol) in CHCl$_3$ (30 mL) were reacted according to GP4 to give the title compound (108LM27-24) (3.02 g, 80%). $^1$H NMR (CDCl$_3$) δ 7.07-7.00 (m, 4H), 4.65-4.55 (m, 2H), 3.94 (dd, J=1.7 Hz, J=6.7 Hz, CH$_2$), 3.23-3.14 (m, 2H), 2.18-2.07 (m, 1H), 1.05 (d, J=6.1 Hz, CH$_3$).

(R)-4-(3-Iodo-2-methylpropyl)-4H-benzo[1,4]oxazin-3-one (108LM46-43)

Crude (R)-4-(3-hydroxy-2-methylpropyl)-4H-benzo[1,4]oxazin-3-one (108LM40-37) (1.040 g), triphenylphosphine (0.99 g, 3.77 mmol), imidazole (0.32 g, 4.71 mmol) and iodine (1.43 g, 5.65 mmol) in CHCl$_3$ (30 mL) were reacted according to GP4 to give the crude title compound (108LM46-43) (0.312 g).

(S)-4-(3-Iodo-2-methylpropyl)-4H-benzo[1,4]thiazin-3-one (108LM37-34)

The compound (S)-4-(3-Hydroxy-2-methylpropyl)-4H-benzo[1,4]thiazin-3-one (108LM34-31) (2.33 g, 9.82 mmol), triphenylphosphine (5.15 g, 19.7 mmol), imidazole (1.67 g, 24.6 mmol) and iodine (7.48 g, 29.5 mmol) in CHCl$_3$ (30 mL) were reacted according to GP4 to give the title compound (108LM37-34) (2.57 g, 75%). $^1$H NMR (CDCl$_3$) δ 7.37 (d, J=7.8 Hz, 1H), 7.24 (t, J=7.8 Hz, 1H), 7.16 (d, J=7.8 Hz, 1H), 7.02 (t, J=7.8 Hz, 1H), 4.02 (d, J=6.8 Hz, CH$_2$), 3.37 (s, CH$_2$), 3.15-3.05 (m, CH$_2$), 1.95 (m, 1H), 0.97 (d, J=6.2 Hz, CH$_3$).

General Procedure 5 (GP5)

A 4 or 7 mL vial was charged with 4H-benzo[1,4]oxazin-3-one (1.0 equiv), Cs$_2$CO$_3$ (1.5 equiv) and 3-chloro-1-iodopropane (1.1 equiv) in 3 mL dry MeCN and shaken at rt for 66-72 h. The reaction mixture was diluted with 10 mL H$_2$O and extracted into CH$_2$Cl$_2$ or EtOAc (3×30 mL). The combined organic layers were dried over MgSO$_4$ or filtered through a PTFE Whatman filter and concentrated. The residue was purified by CC (Heptane/EtOAc) or used without further purification in the next step.

6-Bromo-4-(3-chloropropyl)-8-fluoro-4H-benzo[1,4]oxazin-3-one (95MF50(2084))

6-Bromo-8-fluoro-4H-benzo[1,4]oxazin-3-one (95MF44) (0.091 g, 0.37 mmol), Cs$_2$CO$_3$ (0.180 g, 0.55 mmol) and 3-chloro-1-iodopropane (0.083 g, 0.41 mmol) were mixed according to GP5. CC (SiO$_2$; Heptane/EtOAc 9:1-4) gave the title compound (95MF50(2084)) (0.086 g, 72%). $^1$H NMR (CDCl$_3$) δ 7.02-6.96 (m, 1H), 6.85 (d, J=5.2 Hz, 1H), 4.65 (s, 2H), 4.04-4.11 (m, 2H), 3.62 (t, J=6.2 Hz, 2H), 2.10-2.18 (m, 2H); $^{13}$C NMR (CDCl$_3$) δ 163.8, 151.7 (d, J=250.9 Hz), 133.1 (d, J=14.6 Hz), 131.5 (d, J=3.8 Hz), 115.1 (d, J=21.5 Hz), 114.2 (d, J=10.0 Hz), 113.4 (d, J=3.4 Hz), 67.6, 42.2, 39.5, 30.0.

4-(3-Chloropropyl)-8-fluoro-4H-benzo[1,4]oxazin-3-one (95MF51(2085))

8-Fluoro-4H-benzo[1,4]oxazin-3-one (95MF45) (0.290 g, 1.74 mmol), Cs$_2$CO$_3$ (0.848 g, 2.6 mmol) and 3-chloro-1- iodopropane (0.390 g, 1.91 mmol) were mixed according to GP5. CC (SiO$_2$; Heptane/EtOAc 9:1-4) gave the title compound (95MF51(2082)) (0.254 g, 60%). $^1$H NMR (CDCl$_3$) δ 7.01-6.95 (m, 1H), 6.88-6.82 (m, 2H), 4.66 (s, 2H), 4.13-4.08 (m, 2H), 3.63 (t, J=6.0 Hz, 2H), 2.19-2-12 (m, 2H); $^{13}$C NMR (CDCl$_3$) δ 164.2, 152.1 (d, J=246.8 Hz), 133.9 (d, J=15.0 Hz), 130.6 (d, J=3.1 Hz), 122.6 (d, J=8.1 Hz), 111.8 (d, J=18.4 Hz), 110.1 (d, J=3.4 Hz), 67.8, 42.4, 39.5, 30.1.

6,8-Dichloro-4-(3-chloropropyl)-7-ethyl-4H-benzo[1,4]oxazin-3-one ((95MF52(2226))

6,8-Dichloro-7-ethyl-4H-benzo[1,4]oxazin-3-one (95MF46) (0.342 g, 1.39 mmol), Cs$_2$CO$_3$ (0.678 g, 2.08 mmol) and 3-chloro-1-iodopropane (0.313 g, 1.52 mmol) were mixed according to GP5. CC (SiO$_2$; Heptane/EtOAc 9:1-4) gave the title compound (95MF52(2226)) (0.301 g, 67%). $^1$H NMR (CDCl$_3$) δ 7.01 (s, 1H), 4.68 (s, 2H), 4.06 (t, J=7.2 Hz, 2H), 3.62 (t, J=6.0 Hz, 2H), 2.91 (q, J=7.6 Hz, 2H), 2.10-2.18 (m, 2H), 1.16 (t, J=7.6 Hz, 3H); $^{13}$C NMR (CDCl$_3$) δ 163.8, 140.6, 135.8, 127.9, 127.7, 123.6, 113.8, 67.9, 42.2, 39.3, 30.0, 24.7, 12.7.

4-(3-Chloropropyl)-8-isopropyl-4H-benzo[1,4]oxazin-3-one (95MF98)

8-Isopropyl-4H-benzo[1,4]oxazin-3-one (95MF83) (0.115 g, 0.60 mmol), Cs$_2$CO$_3$ (0.293 g, 0.90 mmol) and 3-chloro-1-iodopropane (0.135 g, 0.66 mmol) were mixed according to GP5. CC (SiO$_2$; Heptane/EtOAc 9:1-4) gave the title compound (95MF98) (0.112 g, 70%). $^1$H NMR (CDCl$_3$) δ 7.03-6.95 (m, 2H), 6.93-6.90 (m, 1H), 4.57 (s, 2H), 4.09 (m, 2H), 3.62 (t, J=6.2 Hz, 2H), 3.33-3.25 (m, 1H), 2.20-2.13 (m, 2H), 1.22 (d, J=7.2 Hz, 6H); $^{13}$CNMR(CDCl$_3$) δ 164.9, 142.8, 137.8, 128.5, 122.8, 121.4, 112.5, 67.7, 42.5, 39.3, 30.3, 27.2, 22.7.

4-(3-Chloropropyl)-6-fluoro-4H-benzo[1,4]oxazin-3-one (8173MF55b)

6-Fluoro-4H-benzo[1,4]oxazin-3-one (8173MF55b) (0.090 g, 0.54 mmol), Cs$_2$CO$_3$ (0.263 g, 0.81 mmol) and 3-chloro-1-iodopropane (0.121 g, 0.59 mmol) were mixed according to GP5. CC (SiO$_2$; Heptane/EtOAc 10:1-5) gave the title compound (8173MF55b) (0.102 g, 78%). $^1$HNMR (CDCl$_3$) δ 6.95-6.91 (m, 1H), 6.82-6.78 (m, 1H), 6.72-6.67 (m, 1H), 4.57 (s, 1H), 4.05 (t, J=7.2 Hz, 2H), 3.62 (t, J=6.2 Hz, 2H), 2.19-2.11 (m, 2H); $^{13}$CNMR(CDCl$_3$) δ 164.6, 158.6 (d, J=240.7 Hz), 141.5 (d, J=2.3 Hz), 129.6 (d, J=10.5 Hz), 118.0 (d, J=9.3 Hz), 110.0 (d, J=23.1 Hz), 102.7 (d, J=28.8 Hz), 67.8, 42.3, 39.3, 30.0.

4-(3-Chloropropyl)-7,8-difluoro-4H-benzo[1,4]oxazin-3-one (81MF2082b)

7,8-Difluoro-4H-benzo[1,4]oxazin-3-one (81MF2082a) (0.119 g, 0.64 mmol), Cs$_2$CO$_3$ (0.314 g, 0.96 mmol) and 3-chloro-1-iodopropane (0.144 g, 0.70 mmol) were mixed according to GP5 giving the crude title compound (0.156 g); $^1$H NMR (CDCl$_3$) δ 6.89-6.82 (m, 1H), 6.78-6.74 (m, 1H), 4.68 (s, 2H), 4.08 (t, J=7.2 Hz, 2H), 3.62 (t, J=6.4 Hz, 2H), 2.18-2.10 (m, 2H); $^{13}$CNMR (CDCl$_3$) δ 163.5, 147.7 (q, J=245.6 Hz, J=10.4 Hz), 141.0 (q, J=249.4 Hz, J=15.7 Hz), 135.5, 126.2, 109.9 (d, J=18.4 Hz), 108.6 (q, J=7.6 Hz, J=4.2 Hz), 67.8, 42.3, 39.4, 30.0.

4-(3-Chloropropyl)-6-methoxy-4H-benzo[1,4]oxazin-3-one (81MF2249b)

6-Methoxy-4H-benzo[1,4]oxazin-3-one (81MF2249a) (0.212 g, 1.18 mmol), Cs$_2$CO$_3$ (0.578 g, 1.77 mmol) and 3-chloro-1-iodopropane (0.265 g, 1.3 mmol) were mixed according to GP5. CC (SiO$_2$; Heptane/EtOAc 10:1-2) gave the title compound (81MF2249b) (0.127 g, 42%). $^1$H NMR (CDCl$_3$) δ 6.88 (d, J=8.8 Hz, 1H), 6.62 (d, J=2.8 Hz, 1H), 6.50 (dd, J=2.8 Hz, J=8.8 Hz, 1H), 4.50 (s, 2H), 4.05-4.01 (m, 2H), 3.76 (s, 3H), 3.59 (t, J=6.2 Hz, 2H), 2.16-2.09 (m, 2H); $^{13}$C NMR (CDCl$_3$) δ 164.8, 155.5, 139.3, 129.2, 117.4, 107.8, 101.9, 67.8, 55.8, 42.4, 38.9, 30.0.

4-(3-Chloropropyl)-7-fluoro-4H-benzo[1,4]oxazin-3-one (81MF763b)

7-Fluoro-4H-benzo[1,4]oxazin-3-one (81MF763) (0.263 g, 1.57 mmol), Cs$_2$CO$_3$ (0.769 g, 2.36 mmol) and 3-chloro-1-iodopropane (0.354 g, 1.73 mmol) were mixed according to GP5 giving the crude title compound (0.40 g); $^1$H NMR (CDCl$_3$) δ 7-01-6.91 (m, 1H), 6.79-6.73 (m, 2H), 4.60 (s, 2H), 4.08 (t, J=7.2 Hz, 2H), 3.62 (t, J=6.4 Hz, 2H), 2.18-2.11 (m, 2H).

4-(3-Chloropropyl)-4H-pyrido[4,3-b][1,4]thiazin-3-one (81MF939b)

4H-pyrido[4,3-b][1,4]thiazin-3-one (81MF939a) (0.087 g, 0.52 mmol), Cs$_2$CO$_3$ (0.256 g, 0.78 mmol) and 3-chloro-1-iodopropane (0.116 g, 0.57 mmol) were mixed according to GP5 giving the crude title compound (0.139 g). $^1$H NMR (CDCl$_3$) δ 8.43 (s, 1H), 8.17 (d, J=5.2 Hz, 1H), 7.25 (d, J=5.2 Hz, 1H), 4.20-4.15 (m, 2H), 3.55 (t, J=6.2 Hz, 2H), 3.41 (s, 2H), 2.17-2.10 (m, 2H).

General Procedure 6 (GP6)

A 100 mL flask was charged with 4H-benzo[1,4]oxazin-3-one (1.0 equiv), Cs$_2$CO$_3$ (1.5 equiv) and 3-chloro-1-iodopropane (1.1 equiv) in 50 mL dry MeCN and stirred at rt for 72 h. The reaction mixture was evaporated to dryness and diluted with 100 mL H$_2$O and extracted into EtOAc (3×100 mL). The combined organic layers were dried over MgSO$_4$, filtrated, evaporated to dryness and purified by CC (Heptane/EtOAc).

6,8-Dichloro-4-(3-chloropropyl)-7-methyl-4H-benzo[1,4]oxazin-3-one (81MF2225b)

6,8-Dichloro-7-methyl-4H-benzo[1,4]oxazin-3-one (81MF2225a) (2.33 g, 10.0 mmol), Cs$_2$CO$_3$ (4.88 g, 15.0 mmol) and 3-chloro-1-iodopropane (2.25 g, 11.0 mmol) were mixed according to GP6. CC (SiO$_2$; Heptane/EtOAc 10:1-5) gave the title compound (81MF2225b) (2.44 g, 79%). $^1$H NMR (CDCl$_3$) δ 7.02 (s, 1H), 4.67 (s, 2H), 4.06 (t, J=7.2 Hz, 2H), 3.62 (t, J=6.2, 2H), 2.43 (s, 3H), 2.18-2.10 (m, 2H); $^{13}$C NMR (CDCl$_3$) δ 163.7, 140.5, 130.3, 128.3, 127.6, 124.1, 113.5, 67.9, 42.2, 39.3, 30.0, 17.2.

4-(3-Chloropropyl)-6,8-dimethyl-4H-benzo[1,4]oxazin-3-one (81MF2237b)

6,8-Dimethyl-4H-benzo[1,4]oxazin-3-one (81MF2237a) (1.70 g, 9.60 mmol), Cs$_2$CO$_3$ (4.69 g, 14.4 mmol) and 3-chloro-1-iodopropane (2.15 g, 10.6 mmol) were mixed according to GP6. CC (SiO$_2$; Heptane/EtOAc 10:1-5) gave the title compound (81MF2237b) (0.96 g, 39%). $^1$H NMR (CDCl₃) δ 6.72-6.69 (m, 2H), 4.56 (s, 2H), 4.07 (t, 2H), 3.62 (t, J=6.4 Hz, 2H), 2.30 (s, 3H), 2.20 (s, 3H), 2.19-2.12 (m, 2H); ¹³C NMR (CDCl₃) δ 164.9, 141.5, 131.9, 128.0, 126.7, 126.4, 113.1, 67.8, 42.5, 39.0, 30.3, 21.2, 15.5.

6-tert-Butyl-4-(3-chloropropyl)-4H-benzo[1,4]oxazin-3-one (81MF2248b)

6-tert-Butyl-4H-benzo[1,4]oxazin-3-one (81MF2248a) (2.07 g, 10.0 mmol), Cs₂CO₃ (4.88 g, 15.0 mmol) and 3-chloro-1-iodopropane (2.25 g, 11.0 mmol) were mixed according to GP6. CC (SiO₂; Heptane/EtOAc 10:1-5) to give the title compound (81MF2248b) (1.39 g, 49%). ¹H NMR (CDCl₃) δ 7.12 (d, J=2.0 Hz, 1H), 7.03 (dd, J=8.4 Hz, J=2.0 1H), 6.92 (d, J=8.4 Hz, 1H), 4.54 (s, 2H), 4.14 (t, J=7.2 Hz, 2H), 3.65 (t, J=6.0 Hz, 2H), 2.21-2.14 (m, 2H), 1.32 (s, 9H); ¹³C NMR (CDCl₃) δ 164.8, 146.4, 143.1, 127.9, 120.9, 116.7, 112.2, 67.8, 42.6, 38.9, 34.8, 31.6, 30.2.

6-Chloro-4-(3-chloropropyl)-7-nitro-4H-benzo[1,4]oxazin-3-one (81MF2253b)

Crude 6-Chloro-7-nitro-4H-benzo[1,4]oxazin-3-one (81MF2253a) (2.60 g, 10.0 mmol), Cs₂CO₃ (4.88 g, 15.0 mmol) and 3-chloro-1-iodopropane (2.25 g, 11.0 mmol) were mixed according to GP6. CC (SiO₂; Heptane/EtOAc 10:1-5) gave the title compound (81MF2253b) 1.23 g, 36%). ¹H NMR (CDCl₃) δ 7.66 (s, 1H), 7.20 (s, 1H), 4.70 (s, 2H), 4.12 (t, J=Hz, 2H), 3.67-3.59 (m, 2H), 2.21-2.13 (m, 2H); ¹³C NMR (CDCl₃) δ 163.6, 143.3, 133.2, 122.4, 117.2, 115.2, 67.4, 42.1, 39.6, 29.8.

7-Chloro-4-(3-chloropropyl)-4H-benzo[1,4]oxazin-3-one (81MF2271 b)

7-Chloro-4H-benzo[1,4]oxazin-3-one (81MF2271a) (1.74 g, 9.47 mmol), Cs₂CO₃ (4.63 g, 14.2 mmol) and 3-chloro-1-iodopropane (2.13 g, 10.4 mmol) were mixed according to GP6. CC (SiO₂; Heptane/EtOAc 10:1-5) gave the title compound (81MF2271b) (1.95 g, 79%). ¹H NMR (CDCl₃) δ 7.03-6.96 (m, 3H), 4.59 (s, 2H), 4.07 (t, J=7.2 Hz, 2H), 3.61 (t, J=6.4 Hz, 2H), 2.17-2.10 (m, 2H); ¹³C NMR (CDCl₃) δ 164.0, 146.0, 129.1, 127.3, 123.0, 117.8, 115.5, 67.7, 42.4, 39.2, 30.0.

4-(3-Chloropropyl)-5-methyl-4H-benzo[1,4]oxazin-3-one (81MF941b)

5-Methyl-4H-benzo[1,4]oxazin-3-one (81MF941a) (1.514 g, 9.28 mmol), Cs₂CO₃ (4.53 g, 13.9 mmol) and 3-chloro-1-iodopropane (2.09 g, 10.21 mmol) were mixed according to GP6. CC (SiO₂; Heptane/EtOAc 10:1-5) gave the title compound (81MF941b) (1.07 g, 48%). ¹H NMR (CDCl₃) δ 6.99-6.87 (m, 3H), 4.42 (s, 2H), 4.17 (t, J=7.2 Hz, 2H), 3.45 (t, J=6.4 Hz, 2H), 2,41 (s, 3H), 2.04-1.97 (m, 2H); ¹³C NMR (CDCl₃) δ 168.3, 149.9, 129.1, 128.7, 126.9, 125.1, 115.0, 69.4, 42.2, 42.1, 30.6, 20.9.

4-(3-Chloropropyl)-7-methyl-4H-benzo[1,4]oxazin-3-one (81MF2246b)

7-Methyl-4H-benzo[1,4]oxazin-3-one (81MF2246a) (1.42 g, 8.7 mmol), Cs₂CO₃ (4.24 g, 13.0 mmol) and 3-chloro-1-iodopropane (1.95 g, 9.5 mmol) were mixed according to GP6. CC (SiO₂; Heptane/EtOAc 10:1-5) gave the title compound (81MF2246b) (1.64 g, 79%). ¹H NMR (CDCl₃) δ 6.98-6.81 (m, 3H), 4.59 (s, 2H), 4.06-4.03 (m, 2H), 3.63-3.60 (m, 2H), 2.26 (s, 2H), 2.20-2.15 (m, 2H); ¹³C NMR (CDCl₃) δ 164.8, 145.8, 134.3, 123.9, 118.1, 114.9, 68.0, 42.8, 39.4, 30.5, 21.0

(R,S)-6-Methyl-4-oxiranylmethyl-4H-benzo[1,4]oxazin-3-one (101IS84F1)

A dry 7 mL vial was charged with 6-methyl-4H-benzo[1,4]oxazin-3-one (160 mg, 1.0 mmol), epichlorohydrin (0.147 g, 1.6 mmol), Cs₂CO₃ (0.820 g, 2.5 mmol) and dry DMF (1 mL), the mixture was then shaken at 60° C. for 36 h. The mixture was diluted with ether (20 mL) washed with water and brine (10 mL), dried, filtered and concentrated under reduced pressure to give an oil. Purification with flash CC (SiO₂, CH₂Cl₂: acetone/MeOH 95:3:2) gave the title compound (0.127 g, 39%). ¹H NMR (CDCl₃) δ 7.01 (d, J=1.2 Hz, 1H), 6.84 (d, J=8.4 Hz), 6.80 (dm, J=8.4 Hz), 4.58 (ABq J=15.2, 21.2 Hz, 2H), 4.50 (dd, J=3.2, 15.2 Hz, 1H), 3.66 (dd, J=6, 15.2 Hz), 3.23 (m, 1H), 2.86 (dd, J=4, 4.4 Hz, 1H), 2.69 (dd, J=2.8, 4.8 Hz, 1H), 2.33 (s, 3H); ¹³C NMR (CDCl₃) δ 156.2, 143.3, 132.9, 129.0, 124.0, 116.9, 116.6, 68.0, 50.2, 25.8, 44.0, 21.3.

General Procedure 7 (GP7)

To a dry 100 mL flask was charged 4H-benzo[1,4]oxazin-3-one (1.0 equiv), (3-bromo-2-methyl-propoxy)-tert-butyldimethylsilane (1.0 equiv), Cs₂CO₃ (2.5 equiv) dissolved in dry DMF (40 mL) and stirred under an inert atmosphere at 50° C. for 20-28 hours. To the reaction was added water (100 mL) and extraction using diethyl ether (3×150 mL). The combined organic layers were washed with brine (100 mL), dried over Na₂SO₄, and concentrated followed by purification by CC (Heptane/EtOAc)

(S)-4-[3-(tert-Butyldimethylsilanyloxy)-2-methylpropyl]-6-fluoro-4H-benzo[1,4]oxazin-3-one (111MF01)

6-Fluoro-4H-benzo[1,4]oxazin-3-one (95MF88) (2.54 g, 15.2 mmol), (R)-3-bromo-2-methylpropoxy-tert-butyldimethylsilane (4.07 g, 15.2 mmol) and Cs₂CO₃ (12.38 g, 38 mmol) were mixed according to GP7. CC (SiO₂; Heptane/EtOAc 9:1) gave the title compound (111MF01) (4.09 g, 76%). ¹H NMR (CDCl₃) δ 6.93-6.87 (m, 1H), 6.92-6.88 (m, 1H), 6.68-6.63 (m, 1H), 4.56 (m, 2H), 4.01 (m, 1H), 3.78 (m, 1H), 3.58 (m, 1H), 3.45 (m, 1H), 2.11 (m, 1H), 0.92 (s, 12H), 0.06 (d, J=0.8 Hz, 6H); ¹³C NMR (CDCl₃) δ 164.8, 158.5 (d, J=239.9 Hz), 141.6 (d, J=2.7 Hz), 130.1 (d, J=10.7 Hz), 117.6 (d, J=9.3 Hz), 109.6 (d, J=23.1 Hz), 103.6 (d, J=28.8 Hz), 67.8, 65.9, 44.2, 34.5, 26.0, 18.4, 14.9, −5.4, −5.4.

(S)-4-[3-(tert-Butyldimethylsilanyloxy)-2-methylpropyl]-7-fluoro-4H-benzo[1,4]oxazin-3-one (111MF14)

7-Fluoro-4H-benzo[1,4]oxazin-3-one (111MF12) (2.52 g, 15.1 mmol), (S)-3-bromo-2-methylpropoxy-tert-butyldimethylsilane (4.03 g, 15.1 mmol) and Cs₂CO₃ (12.3 g, 38 mmol) were mixed according to GP7. CC (SiO₂; Heptane/EtOAc 9:1) gave the title compound (111MF14) (3.79 g, 71%). ¹H NMR (CDCl₃) δ 7.12 (dd, J=5.2 Hz, J=8.8 Hz, 1H), 6.67-6.34 (m, 2H), 4.60 (q, J=14.8 Hz, J=25.4 Hz, 2H), 4.03 (dd, J=8.4 Hz, J=14.0 Hz, 1H), 3.82 (dd, J=5.6 Hz, J=14.0 Hz, 1H), 3.57 (dd, J=4.8 Hz, J=10.0 Hz, 1H), 3.45 (dd, J=7.0 Hz, J=9.8 Hz, 1H), 2.15-2.05 (m, 1H), 0.93-0.89 (m, 12H), 0.06 (s, 6H); ¹³C NMR (CDCl₃) δ 164.1, 158.9 (d, J=243.7 Hz), 146.4 (d, J=11.6 Hz), 125.3 (d, J=3.0 Hz), 116.4 (d, J=9.6

(S)-4-[3-(tert-Butyldimethylsilanyloxy)-2-methyl-propyl]-6-methoxy-4H-benzo[1,4]oxazin-3-one (111MF32)

6-Methoxy-4H-benzo[1,4]oxazin-3-one (111MF24) (2.7 g, 15.1 mmol), (S)-3-bromo-2-methylpropoxy-tert-butyldimethylsilane (4.03 g, 15.1 mmol) and $Cs_2CO_3$ (12.3 g, 38 mmol) were mixed according to GP7. CC ($SiO_2$; Heptane/EtOAc 9:1) to give the title compound (111MF32) (4.03 g, 80%). $^1$H NMR ($CDCl_3$) δ 6.89 (d, J=8.8 Hz, 1H), 6.71 (d, J=2.8 Hz, 1H), 6.50 (d, J=2.8 Hz, J=8.6 Hz, 1H), 4.53 (q, J=14.8 Hz, J=29.2 Hz, 2H), 3.98 (dd, J=8.8 Hz, J=14.0 Hz, 1H), 3.85 (dd, J=5.8 Hz, J=14.2 Hz, 1H), 3.77 (s, 3H), 3.57 (dd, J=9.2 Hz, J=10.0 Hz, 1H), 3.47 (dd, J=7.2 Hz, J=10.0 Hz, 1H), 2.20-2.12 (m, 1H), 0.91 (s, 12H), 0.05 (d, J=1.2 Hz, 6H); $^{13}$C NMR ($CDCl_3$) δ 165.3, 155.6, 139.7, 129.8, 117.2, 107.4, 103.3, 68.0, 66.2, 55.9, 43.9, 34.3, 26.1, 18.5, 14.7, −5.3, −5.4.

General Procedure 8 (GP8)

To a 100 mL flask was charged 4-[3-(tert-Butyldimethylsilanyloxy)-2-methylpropyl]-4H-benzo[1,4]oxazin-3-one (1.0 equiv) and Tetrabutylammonium flouride monohydrate (1.3 equiv) and dissolved in 40 mL dry THF. The reaction was stirred in rt under an inert atmosphere for 20-24 hours. The reaction mixture was concentrated and purified by CC (Heptane/EtOAc).

(S)-6-Fluoro-4-(3-hydroxy-2-methylpropyl)-4H-benzo[1,4]oxazin-3-one (111MF03)

The compound (S)-4-[3-(tert-Butyldimethylsilanyloxy)-2-methylpropyl]-6-fluoro-4H-benzo[1,4]oxazin-3-one (111MF01) (4.09 g, 11.6 mmol) and tetrabutylammonium flouride monohydrate (4.30 g, 15.4 mmol) were mixed according to GP8. CC ($SiO_2$; Heptane/EtOAc 4:1-4) gave the title compound (111MF03) (2.63 g, 95%). $^1$H NMR ($CDCl_3$) δ 6.92 (dd, J=5.2 Hz, J=8.8 Hz, 1H), 6.80 (dd, J=2.8 Hz, J=10.0 Hz, 1H), 6.71-6.66 (m, 1H), 4.59 (d, J=0.8 Hz, 2H), 4.17-4.11 (m, 1H), 3.58-3.40 (m, 3H), 2.79 (s, 1H), 2.08-1.96 (m, 1H) 1.04 (d, J=7.2 Hz, 3H); $^{13}$C NMR ($CDCl_3$) δ 165.3, 158.4 (d, J=238.44 Hz), 141.5 (d, J=2.7 Hz), 129.5 (d, J=10.4 Hz), 117.9 (d, J=9.3 Hz), 110.2 (d, J=23.1 Hz), 103.1 (d, J=28.4 Hz), 67.5, 63.85, 43.8, 34.0, 14.9.

(S)-7-Fluoro-4-(3-hydroxy-2-methylpropyl)-4H-benzo[1,4]oxazin-3-one (111MF18)

The compound (S)-4-[3-(tert-Butyldimethylsilanyloxy)-2-methy-propyl]-7-fluoro-4H-benzo[1,4]oxazin-3-one (111MF14) (3.79 g, 10.7 mmol) and tetrabutylammonium flouride monohydrate (3.99 g, 14.3 mmol) were mixed according to GP8. CC ($SiO_2$; Heptane/EtOAc 4:1-4) gave the title compound (111MF18) (2.57 g, 100%). $^1$H NMR ($CDCl_3$) δ 6.99-6.95 (m, 1H), 7.77-7.72 (m, 2H), 4.63 (m, 2H), 4.23-4.16 (m, 1H), 3.58-3.40 (m, 3H), 2.86 (s, 1H), 2.05-1.97 (m, 1H), 1.04 (d, J=6.8 Hz, 3H); $^{13}$C NMR ($CDCl_3$) 164.6, 159.2 (d, J=244.5 Hz), 146.4 (d, J=11.6 Hz), 124.9 (d, J=3.1 Hz), 115.9 (d, J=9.6 Hz), 109.4 (d, J=22.7 Hz), 105.3 (d, J=26.1 Hz), 67.5, 63.8, 43.8, 34.0, 15.0.

(S)-4-(3-Hydroxy-2-methylpropyl)-6-methoxy-4H-benzo[1,4]oxazin-3-one (111MF34)

The compound (S)-4-[3-(tert-Butyldimethylsilanyloxy)-2-methylpropyl]-6-methoxy-4H-benzo[1,4]oxazin-3-one (111MF32) (4.03 g, 12.0 mmol) and tetrabutylammonium flouride monohydrate (4.46 g, 16.0 mmol) were mixed according to GP8. CC ($SiO_2$; Heptane/EtOAc 4:1-4) gave the title compound (111MF34) (2.70 g, 100%). $^1$H NMR ($CDCl_3$) δ 6.91 (d, J=8.8 Hz, 1H), 6.63 (d, J=2.8 Hz, 1H), 6.54 (dd, J=2.8 Hz, J=8.8 Hz, 1H), 4.57 (s, 2H), 4.19 (dd, J=9.4 Hz, J=14.6 Hz, 1H), 3.78 (s, 3H), 3.56-3.39 (m, 3H), 2.84 (s, 1H), 2.09-1.99 (m, 1H), 1.05 (d, J=7.2 Hz, 3H); $^{13}$C NMR ($CDCl_3$) 165.8, 155.5, 139.5, 129.4, 117.4, 107.7, 103.0, 67.7, 63.8, 56.0, 43.6, 34.1, 15.0.

General Procedure 9 (GP9)

A 250 mL flask was charged with 4-(3-hydroxy-2-methylpropyl)-4H-benzo[1,4]oxazin-3-one (1.0 equiv) dissolved in $CHCl_3$ (100 mL). Then triphenylphosphine (2.2 equiv) and imidazole (2.4 equiv) was added. To the solution was added I2 (2.8 equiv) and the reaction was stirred in rt for 15-18 hours. The reaction mixture was quenched with $Na_2S_2O_3$ (aqueous, sat) (100 mL). The phases were separated and the water phase washed with $CH_2Cl_2$ (150 mL). The combined organic layers were dried over $Na_2SO_4$, concentrated and purified by CC (Heptane/EtOAc).

(S)-6-Fluoro-4-(3-iodo-2-methylpropyl)-4H-benzo[1,4]oxazin-3-one (111MF04)

The compound (S)-6-Fluoro-4-(3-hydroxy-2-methyl-propyl)-4H-benzo[1,4]oxazin-3-one (111MF03) (2.63 g, 11.0 mmol), triphenylphosphine (6.35 g, 24.2 mmol), imidazole (1.8 g, 26.4 mmol) and I2 (7.81 g, 30.8 mmol) were mixed according to GP9. CC ($SiO_2$; Heptane/EtOAc 9:1-4) gave the title compound (111MF04) (3.86 g, 100%). $^1$H NMR ($CDCl_3$) δ 6.97-6.93 (m, 1H), 6.82-6.78 (m, 1H), 6.73-6.68 (m, 1H), 4.63-4.53 (m, 2H), 3.90 (d, J=6.8 Hz, 2H), 3.20-3.16 (m, 2H), 2.15-2.04 (m, 1H), 1.06 (d, J=6.4 Hz, 3H); $^{13}$C NMR ($CDCl_3$) δ 165.0, 158.5 (d, J=240.2 Hz), 141.7 (d, J=2.3 Hz), 129.6 (d, J=10.4 Hz), 118.1 (d, J=9.2 Hz), 110.1 (d, J=23.4 Hz), 103.1 (d, J=28.7 Hz), 67.8, 46.3, 33.5, 18.9, 11.6.

(S)-7-Fluoro-4-(3-iodo-2-methylpropyl)-4H-benzo[1,4]oxazin-3-one (111MF20)

The compound (S)-7-Fluoro-4-(3-hydroxy-2-methylpropyl)-4H-benzo[1,4]oxazin-3-one (111MF18) (2.57 g, 11.0 mmol), triphenylphosphine (6.61 g, 23.7 mmol), imidazole (1.76 g, 25.8 mmol) and I2 (7.64 g, 30.1 mmol) were mixed according to GP9. CC ($SiO_2$; Heptane/EtOAc 9:1-4) gave the title compound (111MF20) (3.31 g, 89%). $^1$H NMR ($CDCl_3$) δ 7.00-6.96 (m, 1H), 6.78-6.74 (m, 2H), 4.65-4.56 (m, 2H), 3.92 (d, J=7.6 Hz, 2H), 3.21-3.13 (m, 2H), 2.13-2.03 (m, 1H), 1.04 (d, J=6.4 Hz, 3H); $^{13}$C NMR ($CDCl_3$) δ 164.3, 159.0 (d, J=244.4 Hz), 146.6 (d, J=12.0 Hz), 125.0 (d, J=3.0 Hz), 115.9 (d, J=9.7 Hz), 109.4 (d, J=22.5 Hz), 105.5 (d, J=26.0 Hz), 67.8, 46.3, 33.6, 18.9, 11.8.

(S)-4-(3-Iodo-2-methylpropyl)-6-methoxy-4H-benzo[1,4]oxazin-3-one (111MF36)

The compound (S)-4-(3-Hydroxy-2-methylpropyl)-6-methoxy-4H-benzo[1,4]oxazin-3-one (111MF34) (2.70 g, 12.0 mmol), triphenylphosphine (6.92 g, 26.4 mmol), Imidazole (1.96 g, 28.8 mmol) and I2 (8.53 g, 33.6 mmol) were mixed according to GP9. CC ($SiO_2$; Heptane/EtOAc 9:1-4) gave the title compound (111MF36) (3.54 g, 82%). $^1$H NMR ($CDCl_3$) δ 6.92 (d, J=8.4 Hz, 1H), 6.63 (d, J=2.8 Hz, 1H), 6.53 (dd, J=2.8 Hz, J=8.8 Hz, 1H), 4.54 (q, J=14.8 Hz, J=23.6 Hz, 2H), 3.92 (d, J=7.4 Hz, 2H), 3.80 (s, 3H), 3.18 (dd, J=1.0 Hz, J=6 Hz, 2H), 2.17-2.08 (m, 1H), 1.05 (d, J=6.8 Hz, 3H); $^{13}$C NMR ($CDCl_3$) δ 165.4, 155.6, 139.6, 129.4, 117.7, 108.0, 102.5, 68.0, 56.1, 46.1, 33.6, 18.9, 12.0.

(S)-4-[3-(tert-Butyldimethylsilanyloxy)-2-methylpropyl]-6-methyl-4H-benzo[1,4]oxazin-3-one (101IS60-1)

A dry 50 mL r-flask was charged with 6-Methyl-4H-benzo[1,4]oxazin-3-one (0.59 g, 3.6 mmol), (R)-(3-bromo-2-methylpropoxy)-tert-butyldimethylsilane (1.0 g, 3.6 mmol), $Cs_2CO_3$ (2.9 g, 8.9 mmol) and 10 mL of dry DMF. The mixture was stirred at 50° C. overnight (15 h) and dissolved in ether (50 mL) washed with water (20 mL) and the water phase was extracted with ether (20 mL). The combined organic phases were then washed with brine, dried ($Na_2SO_4$), filtered, concentrated under reduced pressure and the resulting oil was purified by flash chromatography ($SiO_2$; Heptane/EtOAc 85:15) to yield the title compound as an oil (1.1 g, 88%). $^1$H NMR (CDCl$_3$) δ 6.87 (d, J=1.6 Hz, 1H), 6.81 (d, J=8.0 Hz, 1H), 6.72 (dm, J=8.0 Hz, 1H), 4.5 (bars, 2H), 3.93 (dd, J=8.8, 14.0 Hz, 1H), 3.81 (dd, J=5.6, 14.0 Hz, 1H), 3.53 (dd, J=4.8, 10.2 Hz, 1H), 3.41 (dd J=7.2, 10.2 Hz, 1H), 2.25 (s, 3H), 2.18 (m, 1H), 0.87 (s, 9H), 0.83 (d, J=6.8 Hz, 3H), 0.01 (s, 6H); $^{13}$C NMR (CDCl$_3$) δ 170.5, 148.9, 137.8, 129.6, 122.2, 121.6, 73.3, 71.6, 49.0, 39.7, 31.5, 26.6, 23.8, 20.1, 0.0.

(S)-4-(3-Hydroxy-2-methylpropyl)-6-methyl-4H-benzo[1,4]oxazin-3-one (101IS60-2)

The compound (S)-4-[3-(tert-butyldimethylsilanyloxy)-2-methylpropyl]-6-methyl-4H-benzo[1,4]oxazin-3-one (101IS60-1) (1.0 g, 2.9 mmol) was dissolved in dry THF (12 mL) and TBAF (1.2 g, 3.8 mmol) was added. The reaction was stirred at rt overnight and the solution was concentrated under reduced pressure, the remaining oil was diluted with EtOAc (60 mL) and washed with brine (3×30 mL), dried ($Na_2SO_4$) filtered and concentrated under reduced pressure. The remaining oil was purified by flash chromatography ($SiO_2$; Heptane/EtOAc 30:70) to yield an oil which crystallized upon standing (0.69 g, 76%). $^1$H NMR (CDCl$_3$) δ 6.88 (d, J=8.4 Hz, 1H), 6.83-6.78 (m, 2H), 4.59 (brs 2H), 4.22 (dd J=10.0, 14.4 Hz), 3.57-3.38 (m, 3H), 2.9 (vbrs, 1H), 2.33 (s, 3H), 2.04 (m, 1H), 1.08 (d, J=7.2 Hz); $^{13}$C NMR (CDCl$_3$) δ 165.7, 143.4, 132.3, 124.9, 117.1, 115.9, 67.6, 63.7, 43.5, 34.2, 21.3, 15.1.

(S)-4-(3-Iodo-2-methylpropyl)-6-methyl-4H-benzo[1,4]oxazin-3-one (101IS70)

A dry 50 mL r-flask was charged with (S)-4-(3-hydroxy-2-methylpropyl)-6-methyl-4H-benzo[1,4]oxazin-3-one (1.0 g, 4.2 mmol), PPh$_3$ (2.2 g, 8.5 mmol), imidazole (0.58 g, 8.5 mmol) and dissolved with CH$_2$Cl$_2$ (25 mL). Iodine (2.2 g, 8.4 mmol) was then added in small portions over 4 h period. After the last addition the reaction was poured onto SiO$_2$ and filtered. Concentration under reduced pressure yielded the crude title compound (1.5 g), which was used without further purification.

1-(3-Chloropropyl)-3,4-dihydro-1H-quinolin-2-one (85LM31)

A 50 mL flask was charged with 3,4-dihydro-1H-quinolin-2-one (2.00 g, 13.6 mmol) and sodium hydride (60% in oil, 0.712 g, 16.3 mmol) in DMF (50 mL, dry) and stirred at 0° C. for 1 h, followed by addition of 1-chloro-3-iodo-propane (2.77 g, 13.6 mmol) and stirring at rt for 20 h. The reaction mixture was quenched with water (10 mL), and the product was extracted into EtOEt (3×25 mL). The combined organic layers were dried ($Na_2SO_4$), evaporated and purified by flash CC ($SiO_2$; EtOAc/heptane 1:4) to give the crude title compound (85LM31) (2.25 g). $^1$H NMR (CDCl$_3$) δ 7.29-7.22 (m, 1H), 7.17 (d, J=7.4 Hz, 1H), 7.08-6.98 (m, 2H), 4.10 (t, J=7.3 Hz, CH$_2$), 3.62 (t, J=5.9 Hz, CH$_2$), 2.88 (t, J=7.3 Hz, CH$_2$), 2.63 (t, J=7.3 Hz, CH$_2$), 2.19-2.10 (m, 2H); $^{13}$C NMR (CDCl$_3$) δ 170.5, 140.0, 128.2, 127.8, 126.3, 123.2, 115.0, 43.3, 40.2, 32.2, 30.5, 26.0.

1-(3-Chloropropyl)-6-fluoro-3,4-dihydro-1H-quinolin-2-one (92LH79)

A reaction flask was charged with 6-fluoro-3,4-dihydro-1H-quinolin-2-one (0.180 g, 1.09 mmol) in dry DMF (2 mL) under Argon. NaH (60% in oil, 0.048 g, 1.20 mmol) was added and the mixture was stirred at rt for 0.5 h. Then 1-bromo-3-chloropropane (0.180 g, 1.14 mmol) was added followed by stirring at rt for 20 h. The reaction mixture was quenched with water, and the product extracted into EtOAc. The combined organic layers were dried over $Na_2SO_4$, filtered, and concentrated. The product was purified by flash CC ($SiO_2$; DCM) to give the title compound (92LH79) (0.193 g, 73%). $^1$H NMR (CDCl$_3$) δ 7.02-6.88 (m, 3H), 4.09-4.05 (m, 2H), 3.61 (t, J=6.3 Hz, CH$_2$), 2.87 (t, J=6.7 Hz, CH$_2$), 2.65-2.61 (m, 2H), 2.16-2.09 (m, 2H); $^{13}$C NMR (CDCl$_3$) δ 169.8, 158.4 (J=242.9 Hz), 135.7 (J=2.7 Hz), 128.5 (J=7.7 Hz), 115.7 (J=8.1 Hz), 115.1 (J=22.7), 113.8 (J=22.3 Hz), 42.6, 40.3, 31.5, 30.1, 25.5.

(R,S)-1-(3-Chloro-2-methylpropyl)-6-fluoro-3,4-dihydro-1H-quinolin-2-one (107LH68)

A reaction flask was charged with 6-fluoro-3,4-dihydro-1H-quinolin-2-one (0.496 g, 3.0 mmol) in dry DMF (3 mL) under Argon. NaH (60% in oil, 0.132 g, 3.3 mmol) was added and the mixture was stirred at rt for 45 min. Then (R,S)-1-bromo-3-chloro-2-methylpropane (0.513 g, 3.0 mmol) was added followed by stirring at rt for 20 h. The reaction mixture was quenched with water, and the product extracted into EtOAc. The combined organic layers were dried over $Na_2SO_4$, filtered, and concentrated. The crude product was purified by flash CC ($SiO_2$; EtOAc/n-heptane 1:1) to give the crude title compound (107LH68) (0.308 g).

1-(3-Chloropropyl)-6-methyl-3,4-dihydro-1H-quinolin-2-one (107LH14)

A reaction flask was charged with 6-methyl-3,4-dihydro-1H-quinolin-2-one (107LH05) (0.300 g, 1.26 mmol) in dry DMF (5 mL) under Argon. NaH (60% in oil, 0.055 g, 1.38 mmol) was added and the mixture was stirred at rt for 1 h. Then 1-bromo-3-chloropropane (0.198 g, 1.24 mmol) was added followed by stirring at rt for 20 h. The reaction mixture was quenched with water, and the product extracted into EtOAc. The combined organic layers were dried over $Na_2SO_4$, filtered, and concentrated. The crude product was purified by flash CC ($SiO_2$; DCM) to give the crude title compound (107LH14) (0.257 g).

1-(3-Chloropropyl)-7-fluoro-6-methyl-3,4-dihydro-1H-quinolin-2-one (112KK01)

A reaction flask was charged with 7-fluoro-6-methyl-3,4-dihydro-1H-quinolin-2-one (97KK40) (0.102 g, 0.57 mmol) in dry DMF (5 mL) under an argon atmosphere. Washed NaH (0.015 g, 0.63 mmol) was added and the mixture was stirred at rt for 1 h. Then 1-chloro-3-iodopropane (0.104 g, 0.51 mmol) dissolved in DMF (1 mL) was added followed by stirring at rt for 20 h. The reaction mixture was quenched with water, and the product extracted into Et$_2$O. The combined organic layers were washed with aqueous 4% MgSO$_4$, dried over Na$_2$SO$_4$, filtered, and concentrated. The product was purified by flash CC (SiO$_2$; DCM/n-heptane 2:1, DCM, MeOH/DCM 1:10) to give the title compound (112KK01) (0.050 g, 38%). $^1$H NMR (CDCl$_3$) δ 6.95-6.93 (m, 1H), 6.73 (d, J=11.5 Hz, 1H), 4.03-4.00 (m, 2H), 3.59 (t, J=6.5 Hz, CH$_2$), 2.83-2.79 (m, 2H), 2.62-2.58 (m, 2H), 2.20 (d, J=1.8 Hz, CH$_3$), 2.13-2.07 (m, 2H).

1-(3-Chloropropyl)-6,7-difluoro-3,4-dihydro-1H-quinolin-2-one (112KK03)

A reaction flask was charged with 6,7-difluoro-3,4-dihydro-1H-quinolin-2-one (97KK47) (0.181 g, 0.99 mmol) in dry DMF (5 mL) under an argon atmosphere. Washed NaH (0.026 g, 1.08 mmol) was added and the mixture was stirred at rt for 0.5 h. Then 3-chloro-1-iodopropane (0.205 g, 1.00 mmol) dissolved in DMF (1 mL) was added followed by stirring at rt for 20 h. The reaction mixture was quenched with water, and the product extracted into Et$_2$O. The combined organic layers were washed with aqueous 4% MgSO$_4$, dried over Na$_2$SO$_4$, filtered, and concentrated. The product was purified by flash CC (SiO$_2$; DCM) to give the title compound (112KK03) (0.122 g, 47%). $^1$H NMR (CD$_3$OD) δ 6.99-6.86 (m, 2H), 4.03-3.99 (m, 2H), 3.60 (t, J=6.1, CH$_2$), 2.84-2.81 (m, 2H), 2.63-2.59 (m, 2H), 2.13-2.06 (m, 2H).

1-(3-Chloropropyl)-5-methyl-3,4-dihydro-1H-quinolin-2-one and 1-(3-chloropropyl)-7-methyl-3,4-dihydro-1H-quinolin-2-one Neat 2-chloro-N-m-tolylacetamide (92LH85) (1.7 g, 8.5 mmol) was heated to 135° C. and AlCl$_3$ (3.4 mg, 26 mmol) was added under an Argon atmosphere, in small portions, during 30 min. The reaction was allowed cool to 60° C. and then HCl (10 mL, 4 M) was added. The mixture was extracted with EtOAc (2×30 mL) and the combined organic phase was dried over Na$_2$SO$_4$, filtered and concentrated under reduced pressure. The residue was purified by flash chromatography (SiO$_2$; CH$_2$Cl$_2$/MeOH 9:1) to yield The compound 7-Methyl-3,4-dihydro-1H-quinolin-2-one and 5-Methyl-3,4-dihydro-1H-quinolin-2-one (1.1 g). This mixture was dissolved in dry DMF (8 mL) and NaH (60% in oil, 310 mg, 7.7 mmol) was added and the solution was stirred under a N$_2$ atmosphere at rt for 45 min. Thereafter, 1-bromo-3-chloropropan was added and the reaction was stirred overnight at rt. The reaction mixture was diluted with EtOAc (50 mL) and washed with water (10 mL). The organic phase was dried over Na$_2$SO$_4$ filtered, concentrated under reduced pressure and the residue was purified by prep RP-HPLC to yield 1-(3-chloropropyl)-5-methyl-3,4-dihydro-1H-quinolin-2-one (0.057 g, 3%) and 1-(3-chloropropyl)-7-methyl-3,4-dihydro-1H-quinolin-2-one (0.12 g, 6%). 1-(3-Chloropropyl)-5-methyl-3,4-dihydro-1H-quinolin-2-one, (107LH27-11.7). Retention time=11.7 min. $^1$H NMR (CD$_3$OD) δ 7.12 (vbrt, 7.7 Hz, 1H), 6.98 (d, J=8.0 Hz, 1H), 6.90 (d, J=7.2 Hz, 1H), 4.09-4.02 (m, 2H), 3.59 (t, J=6.4 Hz, 2H), 2.85-2.78 (m, 2H), 2.58-2.50 (m, 2H), 2.27 (s, 3H), 2.10-2.01 (m, 2H); $^{13}$C NMR (CD$_3$OD) δ 171.5, 139.2, 135.9, 126.9, 125.4, 125.3, 113.1, 42.2, 40.1, 31.1, 30.3, 21.2, 18.5. 1-(3-Chloropropyl)-7-methyl-3,4-dihydro-1H-quinolin-2-one, (107LH27-13.1). Retention time=13.1 min. $^1$H NMR (CD$_3$OD) δ 7.02 (brd, J=7.6 Hz, 1H), 6.94 (brs, 1H), 6.81 (brd, J=7.6 Hz, 1H), 4.03 (brt, J=7.2 Hz, 2H), 3.58 (t, J=6.2 Hz, 2H), 2.78 (t, J=7.4 Hz, 2H), 2.51 (t, J=7.4 Hz), 2.30 (s, 3H), 2.09-2.00 (m, 2H); $^{13}$C NMR (CD$_3$OD) δ 171.6, 139.0, 137.4, 127.8, 123.9, 115.7, 42.3, 39.8, 31.7, 30.3, 24.6, 20.4.

(S)-1-[3-(t-Butyldimethylsilanyl)-2-methylpropyl]-3,4-dihydro-1H-quinolin-2-one (122LH13)

A reaction flask was charged with 3,4-dihydro-1H-quinolin-2-one (1.60 g, 10.9 mmol) in dry DMF (30 mL) under Argon. NaH (60% in oil, 0.480 g, 12.0 mmol) was added and the mixture was stirred at rt for 1 h. Then (R)-(3-bromo-2-methylpropoxy)-t-butyldimethylsilane (3.0 g, 10.9 mmol) was added followed by stirring at rt for 4 days. The reaction mixture was quenched with water, and the product extracted into EtOAc. The combined organic layers were dried over Na$_2$SO$_4$, filtered, and concentrated. The product was purified by flash CC (SiO$_2$; DCM) to give the title compounds (122LH13) (2.685 g, 74%).

(S)-1-(3-Hydroxy-2-methylpropyl)-3,4-dihydro-1H-quinolin-2-one (122LH16)

A reaction flask was charged with (S)-1-[3-(t-Butyldimethylsilanyl)-2-methylpropyl]-3,4-dihydro-1H-quinolin-2-one (122LH13) (2.685 g, 8.05 mmol) and tetrabutylammonium fluoride (2.70 g, 10.3 mmol) in dry THF (20 mL) and stirred at rt for 20 h under an Argon atmosphere. The reaction mixture was concentrated, and the product purified by flash CC (SiO$_2$; n-heptane/EtOAc 1:1) to give the title compound (122) (1.54 g, 87%).

(S)-1-(3-Iodo-2-methylpropyl)-3,4-dihydro-1H-quinolin-2-one (122LH18)

A reaction flask was charged with (S)-1-(3-Hydroxy-2-methylpropyl)-3,4-dihydro-1H-quinolin-2-one (122LH16) (1.54 g, 7.0 mmol) dissolved in 50 mL DCM. PPh$_3$ (4.04 g, 15.4 mmol) and imidazole (1.14 g, 16.7 mmol) were added followed by stirring at rt for 15 min. The mixture was cooled with an ice-bath followed by addition of 12 (5.00 g, 19.7 mmol). The reaction mixture was slowly warmed to rt and stirred over night. The reaction mixture was washed with a Na$_2$S$_2$O$_3$ solution, dried over Na$_2$SO$_4$, and concentrated. The product was purified by flash CC (SiO$_2$; n-heptane/EtOAc 1:1) to give the title compound (122LH18) (2.140 g, 93%).

1-(3-Chloropropyl)-1H-quinolin-2-one (107LH80)

A 7 mL vial was charged with 1H-quinolin-2-one (0.62 g, 4.2 mmol), 4 mL dry DMF and NaH (60% in oil, 0.200 g, 5.1 mmol). The mixture was stirred under a N$_2$ atmosphere at rt for 45 min, and thereafter 1-bromo-3-chloropropane (0.42 mL, 4.2 mmol) was added and the reaction was stirred at rt overnight. The reaction was diluted with EtOAc (50 mL) and washed with water (15 mL). The water phase was extracted with EtOAc (25 mL) and the combined organic phase was dried (Na$_2$SO$_4$), filtered, concentrated under reduced pressure and the residue was purified by flash chromatography (SiO$_2$; CH$_2$Cl$_2$) to yield the title compound (0.38 g, 41%), containing 15% of 1-(3-bromopropyl)-1H-quinolin-2-one. $^1$H NMR (CD$_3$OD) δ 7.90 (d, J=9.4 Hz, 1H), 7.73-7.57 (m, 3H), 7.34-7.28 (m, 1H), 6.66 (d, J=9.4 Hz), 4.46 (t, J=7.4 Hz, 2H), 3.71 (t, J=6.4 Hz, 2H), 2.21-2.02 (m, 2H); $^{13}$C NMR (CD$_3$OD) δ 163.2, 140.7, 138.8, 131.3, 129.3, 122.8, 121.4, 120.2, 114.4, 42.18, 40.2, 30.5.

1-(3-Chloropropyl)-5-metyl-1H-quinolin-2-one, (107LH39)

A microwave vial was charged with 1-(3-chloropropyl)-5-methyl-3,4-dihydro-1H-quinolin-2-one (0.081 g, 0.34 mmol), DDQ (0.116 g, 0.51 mmol), dioxane (2 mL) and sealed. After microwave irradiation, 175° C., 10 min, the reaction was diluted with EtOAc (50 mL), washed with sat aqueous NaHCO$_3$ (2×15 mL) and the organic phase was dried (Na$_2$SO$_4$), filtered, concentrated under reduced pressure and the residue was purified with prep RP-HPLC to yield the crude title compound (0.053 g), which was used without further purification. HPLC-MS (ammonium acetate) [M+H]$^+$=236.2.

1-(3-Chloropropyl)-7-methyl-1H-quinolin-2-one (107LH40)

A microwave vial was charged with 1-(3-chloropropyl)-7-methyl-3,4-dihydro-1H-quinolin-2-one (0.21 g, 0.88 mmol), DDQ (0.30 g, 1.3 mmol), dioxane (4 mL) and sealed. After microwave irradiation, 175° C., 10 min, the reaction was diluted with EtOAc (50 mL), washed with sat aqueous NaHCO$_3$ (2×15 mL) and the organic phase was dried over Na$_2$SO$_4$, filtered, and concentrated under reduced pressure. The residue was purified with prep RP-HPLC to yield the crude title compound (0.130 g), which was used without further purification. HPLC-MS (ammonium acetate) [M+H]$^+$=236.2.

(S)-1-[3-(tert-Butyldimethylsilanyloxy)-2-methyl-propyl]-1H-quinolin-2-one (107LH43)

1H-Quinolin-2-one (1.9 g, 13 mmol) and NaH (60% in oil, 0.58 g, 15 mmol) were added to dry DMF (30 mL) and the reaction was stirred under a N$_2$ atmosphere at rt for 45 min. Thereafter, (R)-(3-bromo-2-methylpropyltert-butyldimethylsilane (3.7 g, 13 mmol) was added and the reaction was stirred for 72 h at 50° C. The reaction was poured onto water and extracted with EtOAc (2×50 mL) and the combined organic phase was dried, filtered and concentrated under reduced pressure. The residue was purified by flash chromatography (SiO$_2$; CH$_2$Cl$_2$) to yield the title compound (2.10 g, 6.4 mmol, 48%). $^1$H NMR (CDCl$_3$) δ 7.60-7.53 (m, 2H), 7.49-7.40 (m, 2H), 7.12 (dt, J=0.9, 7.6 Hz, 1H), 6.62 (d, J=9.6 Hz, 1H), 4.39 (dd, J=8.4, 14.0 Hz, 1H), 4.15 (dd, J=5.4, 14.0 Hz), 3.54 (dd, J=4.4, 10.2 Hz, 1H), 3.45 (dd, J=7.6, 10.2 Hz), 2.27-2.12 (m, 1H), 0.88 (s, 12H), 0.01 (s, 6H); $^{13}$C NMR (CDCl$_3$) δ 168.2, 145.2, 144.5, 135.8, 134.3, 127.3, 127.2, 126.4, 120.5, 71.7, 50.4, 40.9, 31.4, 23.8, 20.4, 0.0.

(S)-1-(3-Hydroxy-2-methylpropyl)-1H-quinolin-2-one (107LH62)

TBAF (1.2 g, 4.6 mmol) and (S)-1-[3-(tert-butyldimethylsilanyloxy)-2-methylpropyl]-1H-quinolin-2-one (0.31 g, 0.93 mmol) were dissolved in THF (5 mL) and stirred under an Argon atmosphere at rt overnight. The mixture was concentrated under reduced pressure and dissolved in EtOAc (30 mL). The solution was washed with water (15 mL), dried over Na$_2$SO$_4$, and concentrated under reduced pressure. The residue thereof was filtered through silica to give the crude title compound (0.19 g), which was used without further purification.

(S)-1-(3-Iodo-2-methylpropyl)-1H-quinolin-2-one (107LH64)

Imidazole (0.14 g, 2.1 mmol), crude (S)-1-(3-hydroxy-2-methyl-propyl)-1H-quinolin-2-one (0.19 g, 0.87 mmol) and PPh$_3$ (0.50 g, 1.9 mmol) were dissolved in CH$_2$Cl$_2$ (5 mL) and the solution was cooled to 0° C., thereafter 12 (0.61 g, 2.4 mmol) was added and the reaction reached rt overnight. The reaction diluted with CH$_2$Cl$_2$ (25 mL) and washed with sat aqueous Na$_2$SO$_4$ (2×25 mL) and the organic phase was dried over Na$_2$SO$_4$, filtered, concentrated under reduced pressure to yield the crude product that was used without further purification. HPLC-MS (ammonium acetate) [M+H]$^+$=328.1.

General Procedure 10 (GP10)

A 4 mL vial was charged with the appropriate heterocycle (1 equiv) and the appropriate piperidine (1.2 or 2 equiv) in dry MeCN (½ mL) and shaken. The reaction mixture was quenched with water (1 mL), and the product extracted into EtOAc (2×1 mL). The combined organic layers were purified by cation exchange CC and by flash CC.

(R)-4-[3-(4-Butylpiperidin-1-yl)-2-methylpropyl]-4H-benzo[1,4]thiazin-3-one (108LM43-40)

The compound (S)-4-(3-Iodo-2-methyl-propyl)-4H-benzo[1,4]thiazin-3-one (108LM37-34) (0.105 g, 0.304 mmol) and 4-butyl-piperidine (0.052 g, 0.369 mmol) in MeCN (½ mL) were reacted according to GP10 shaking at 60° C. for 3 days. Purified by cation exchange CC and flash CC (SiO$_2$; MeOH/DCM 1:20) to give the title compound (108LM43-40) (0.082 g, 75%). $^1$H NMR (CDCl$_3$) δ 7.34 (d, J=9.1 Hz, 1H), 7.25-7.17 (m, 2H), 7.02-6.95 (m, 1H), 4.15-3.99 (m, 2H), 3.35 (s, CH$_2$), 2.83 (bd, J=10.4 Hz, 1H), 2.68 (bd, J=10.4 Hz, 1H), 2.20-2.05 (m, 2H), 2.00-1.85 (m, 2H), 1.82-1.73 (m, 1H), 1.67-1.55 (m, 2H), 1.30-1.14 (m, 9H), 0.88 (t, J=7.2, CH$_3$), 0.82 (d, J=6.5 Hz, CH$_3$); $^{13}$C NMR (CDCl$_3$) δ 166.0, 139.2, 128.8, 127.1, 124.8, 123.5, 118.9, 63.8, 55.5, 54.4, 47.7, 36.6, 36.1, 32.9, 32.8, 32.1, 29.4, 29.3, 23.2, 16.7, 14.4; HPLC-MS (ammonium acetate) [M+H]$^+$=361.3.

(R)-4-[2-Methyl-3-(4-propoxypiperidin-1-yl)propyl]-4H-benzo[1,4]thiazin-3-one (108LM49-46)

The compound (S)-4-(3-Iodo-2-methyl-propyl)-4H-benzo[1,4]thiazin-3-one (108LM37-34) (0.433 g, 1.25 mmol) and 4-propoxypiperidine (79KS66) (0.225 g, 1.55 mmol) in MeCN (½ mL) were reacted according to GP10 shaking at 60° C. for 4 days. Purified by cation exchange CC and flash CC (SiO$_2$; MeOH/DCM 1:20) to give the title compound (108LM49-46) (0.220 g, 49%). $^1$H NMR (CDCl$_3$) δ 7.37 (d, J=8.1 Hz, 1H), 7.25-7.20 (m, 2H), 7.05-6.97 (m, 1H), 4.18-4.00 (m, 2H), 3.42-3.35 (m, 4H), 3.30-3.20 (m, 1H), 2.80-2.70 (m, 1H), 2.65-2.55 (m, 1H), 2.20-2.05 (m, 3H), 2.00-1.82 (m, 4H), 1.62-1.50 (m, 4H), 0.92 (t, J=7.4, CH$_3$), 0.82 (d, J=6.8 Hz, CH$_3$); $^{13}$C NMR (CDCl$_3$) δ 166.1, 139.2, 128.8, 127.1, 124.9, 123.5, 118.8, 75.5, 69.8, 63.3, 52.7, 51.9, 47.6, 32.1, 32.0, 29.6, 23.5, 16.6, 10.9; HPLC-MS (ammonium acetate) [M+H]$^+$=363.3.

(R)-4-[3-(4-Butylidene-piperidin-1-yl)-2-methylpropyl]-4H-benzo[1,4]thiazin-3-one (108LM50-47)

The compound (S)-4-(3-Iodo-2-methyl-propyl)-4H-benzo[1,4]thiazin-3-one (108LM37-34) (0.432 g, 1.25 mmol) and 4-butylidenepiperidine (111MF05) (0.208 g, 1.49 mmol) in MeCN (12 mL) were reacted according to GP10 shaking at 60° C. for 4 days. Purified by cation exchange CC and flash CC (SiO$_2$; MeOH/DCM 1:20) to give the title compound (108LM50-47) (0.267 g, 60%). $^1$H NMR (CDCl$_3$) δ 7.35 (d, J=7.5 Hz, 1H), 7.26-7.18 (m, 2H), 6.98 (t, J=7.5 Hz, 1H), 5.10 (t, J=7.4 Hz, CH), 4.17-4.03 (m, 2H), 3.36 (s, CH$_2$), 2.43-2.33 (m, 2H), 2.30-2.08 (m, 8H), 2.00-1.90 (m, 3H), 1.28-1.38 (m, 2H), 0.90-0.80 (m, 6H); $^{13}$C NMR (CDCl$_3$) δ 166.0, 139.2, 136.4, 128.8, 127.1, 124.8, 123.5, 122.7, 118.8, 63.4, 56.4, 55.6, 47.7, 36.4, 32.1, 29.5, 29.4, 28.6, 23.4, 16.7, 14.0; HPLC-MS (ammonium acetate) [M+H]$^+$=359.3.

(R)-4-[3-(3-Butyl-8-aza-bicyclo[3.2.1]oct-8-yl)-2-methyl-propyl]-4H-benzo[1.4]thiazin-3-one (108LM51-48)

The compound (S)-4-(3-Iodo-2-methyl-propyl)-4H-benzo[1,4]thiazin-3-one (108LM37-34) (0.093 g, 0.269 mmol) and 3-butyl-8-aza-bicyclo[3.2.1]octane (104KS29) (0.054 g, 0.323 mmol) in MeCN (½ mL) were reacted according to GP10 shaking at 40° C. for 5 days. Purified by cation exchange CC and flash CC (SiO$_2$; MeOH/DCM 1:10) to give the title compound (108LM51-48) (0.042 g, 40%). $^1$H NMR (CDCl$_3$) δ 7.38 (d, J=7.8 Hz, 1H), 7.33 (d, J=8.1 Hz, 1H), 7.22 (t, J=7.9 Hz, 1H), 7.00 (t, J=8.0 Hz, 1H), 4.18-4.10 (m, 2H), 3.38 (s, CH$_2$), 3.15-3.00 (m, 2H), 2.30-2.22 (m, 1H), 2.20-2.10 (m, 1H), 1.90-1.75 (m, 3H), 1.60-1.40 (m, 5H), 1.40-1.15 (m, 8H), 0.90-0.82 (m, 6H); $^{13}$C NMR (CDCl$_3$) δ 166.1, 139.2, 128.7, 127.2, 124.7, 123.5, 119.1, 61.4, 60.1, 57.3, 47.6, 38.3, 36.9, 32.1, 31.2, 29.9, 29.4, 28.2, 27.2, 26.5, 23.1, 16.7, 14.3; HPLC-MS (ammonium acetate) [M+H]$^+$=387.3.

(R)-4-[2-Methyl-3-(3-pentyl-8-aza-bicyclo[3.2.1]oct-8-yl)propyl]-4H-benzo[1,4]thiazin-3-one (108LM52-49)

The compound (S)-4-(3-Iodo-2-methylpropyl]-4H-benzo[1,4]thiazin-3-one (108LM37-34) (0.080 g, 0.231 mmol) and 3-pentyl-8-azabicyclo[3.2.1]octane (104KS32-2) (0.050 g, 0.276 mmol) in MeCN (12 mL) were reacted according to GP10 shaking at 40° C. for 5 days. Purified by cation exchange CC and flash CC (SiO$_2$; MeOH/DCM 1:50+1% Et$_3$N) to give the title compound (108LM52-49) (0.045 g, 49%). $^1$H NMR (CDCl$_3$) δ 7.36 (d, J=7.6 Hz, 1H), 7.32 (d, J=7.7 Hz, 1H), 7.22 (t, J=7.6 Hz, 1H), 7.00 (t, J=7.6 Hz, 1H), 4.16 (d, J=7.3 Hz, CH$_2$), 3.34 (s, CH$_2$), 3.10-2.95 (m, 2H), 2.25-2.17 (m, 1H), 2.15-2.03 (m, 3H), 1.94-1.75 (m, 3H), 1.70-1.60 (m, 1H), 1.60-1.50 (m, 2H), 1.40-1.15 (m, 10H), 0.90-0.80 (m, 6H); $^{13}$C NMR (CDCl$_3$) δ 166.1, 139.2, 128.7, 127.1, 124.7, 123.4, 119.1, 60.5, 59.0, 57.4, 47.5, 38.4, 36.4, 32.2, 32.1, 31.4, 29.9, 28.5, 28.4, 27.9, 27.2, 22.9, 16.7, 14.3; HPLC-MS (ammonium acetate) [M+H]$^+$=401.3.

General Procedure 11 (GP11)

A 100 mL flask was charged with 4-(3-chloropropyl)-4H-benzo[1,4]oxazin-3-one (1.0 equiv), K$_2$CO$_3$ (2.0 equiv), NaI (2.0 equiv) and 4-Butylpiperidine (1.05 equiv) in 25 mL dry MeCN and stirred at rt for 168 h under N$_2$ atmosphere. The reaction mixture was evaporated to dryness and diluted with 100 mL H$_2$O and extracted into EtOAc (3×120 mL). The combined organic layers were dried over MgSO$_4$, evaporated to dryness, and purified by CC (Heptane:EtOAc or CH$_2$Cl$_2$: MeOH).

4-[3-(4-Butylpiperidin-1-yl)propyl]-6,8-dichloro-7-methyl-4H-benzo[1,4]oxazin-3-one (81MF2225F)

6,8-Dichloro-4-(3-chloropropyl)-7-methyl-4H-benzo[1, 4]oxazin-3-one (81MF2225b), (2.44 g, 7.92 mmol), K$_2$CO$_3$ (2.19 g, 15.84 mmol), NaI (2.37 g, 15.84 mmol) and 4-butylpiperidine (1.172 g, 8.3 mmol) were mixed according to GP11. CC (SiO$_2$; Heptane/EtOAc 10:1-4) gave the title compound (81MF2225F) (1.55 g, 47%). $^1$H NMR (CDCl$_3$) δ 7.11 (s, 1H), 4.65 (s, 2H), 3.93 (t, 2H), 2.86, (d, 2H), 2.41 (s, 3H), 2.41 (s, 3H), 2.33 (t, 2H), 1.92-1.77 (m, 4H), 1.65 (d, 2H), 1.31-1.19 (m, 9H), 0.88 (t, 3H); $^{13}$C NMR (CDCl$_3$) δ 163.5, 140.5, 129.9, 128.1, 123.7, 114.0, 67.9, 55.8, 54.4, 40.1, 36.4, 36.0, 32.6, 29.2, 24.8, 23.1, 17.2, 14.2.

To the pure compound (0.235 g, 0.50 mmol) dissolved in diethyl ether (4 mL) was added oxalic acid (0.047 g, 0.52 mmol) in diethyl ether (2 mL). The formed crystals filtered and washed with diethyl ether to give the title compound as oxalic salt (0.24 g, 94%); HPLC-MS (ammonium acetate) [M+H]$^+$=413.2

4-[3-(4-Butyl-piperidin-1-yl)propyl]-6,8-dimethyl-4H-benzo[1,4]oxazin-3-one (81MF2237F)

4-(3-Chloropropyl)-6,8-dimethyl-4H-benzo[1,4]oxazin-3-one (81MF2237b) (0.96 g, 3.78 mmol), K$_2$CO$_3$ (1.05 g, 7.57 mmol), NaI (1.14 g, 7.57 mmol) and 4-butylpiperidine (0.56 g, 3.97 mmol) were mixed according to GP11. CC (SiO$_2$; Heptane/EtOAc 10:1-4) gave the title compound (81MF2237F) (0.98 g, 72%). $^1$H NMR (CDCl$_3$) δ 6.71 (s, 1H), 6.65 (s, 1H), 4.52 (s, 2H), 3.93 (t, J=7.2, 2H), 2.87 (d, J=11.2, 2H), 2.36 (t, J=7.2 Hz, 2H), 2.27 (s, 3H), 2.18 (s, 3H), 1.81-1.89 (m, 4H), 1.65 (d, J=9.6 Hz, 2H), 1.28-1.17 (m, 9H), 0.87 (t, J=6-8 Hz, 3H); $^{13}$C NMR (CDCl$_3$) δ 164.6, 141.4, 131.6, 128.3, 126.3, 126.1, 113.4, 67.8, 56.1, 54.3, 39.8, 36.4, 35.9, 32.7, 29.1, 25.0, 23.0, 21.1, 15.5, 14.2.

To the pure compound (0.193 g, 0.54 mmol) dissolved in diethyl ether (4 mL) was added oxalic acid (0.051 g, 0.57 mmol) in diethyl ether (2 mL). The formed crystals filtered and washed with diethyl ether to give the title compound as oxalic salt (0.22 g, 91%); HPLC-MS (ammonium acetate) [M+H]$^+$=359.3

6-tert-Butyl-4-[3-(4-butyl-piperidin-1-yl)propyl]-4H-benzo[1,4]oxazin-3-one (81MF2248F)

6-tert-Butyl-4-(3-chloropropyl)-4H-benzo[1,4]oxazin-3-one (81MF2248b) (1.39 g, 4.93 mmol), K$_2$CO$_3$ (1.36 g, 9.85 mmol), NaI (1.48 g, 9.85 mmol) and 4-butylpiperidine (0.73 g, 5.17 mmol) were mixed according to GP11. CC (SiO$_2$; Heptane/EtOAc 10:1-4) gave the title compound (81MF2248F) (1.66 g, 87%). $^1$H NMR (CDCl$_3$) δ 7.01-6.98 (m, 2H), 6.91-6.88 (m, 1H), 4.55 (s, 2H), 3.99 (t, J=7.2 Hz, 2H), 2.89 (d, J=6.4 Hz, 2H), 2.42 (t, J=6.8 Hz, 2H), 1.92-1.82 (m, 4H), 1.65 (d, J=9.6 Hz 2H), 1.31 (s, 9H), 1.29-1.17 (m, 9H), 0.88 (t, J=6.8 Hz, 3H); $^{13}$C NMR (CDCl$_3$) δ 164.6, 146.1, 143.3, 128.1, 120.6, 116.6, 112.2, 67.9, 56.5, 54.4, 39.8, 36.4, 35.9, 34.7, 32.6, 31.6, 29.2, 24.8, 23.1, 14.2.

To the pure compound (0.178 g, 0.46 mmol) dissolved in diethyl ether (4 mL) was added oxalic acid (0.044 g, 0.49 mmol) in diethyl ether (2 mL). The formed crystals filtered and washed with diethyl ether to give the title compound as oxalic salt (0.19 g, 87%); HPLC-MS (ammonium acetate) [M+H]$^+$=387.4

4-[3-(4-Butylpiperidin-1-yl)propyl]-5-methyl-4H-benzo[1,4]oxazin-3-one (81MF941x)

4-(3-Chloropropyl)-5-methyl-4H-benzo[1,4]oxazin-3-one (81MF941b) (1.08 g, 4.48 mmol), K$_2$CO$_3$ (1.24 g, 8.95 mmol), NaI (1.34 g, 8.95 mmol) and 4-butylpiperidine (0.66 g, 4.70 mmol) were mixed according to GP11. CC (SiO$_2$; Heptane/EtOAc 10:1-4) gave the title compound (81MF941x) (0.814 g, 53%). $^1$H NMR (CDCl$_3$) δ 6.97-6.83 (m, 3H), 4.41 (s, 2H), 4.07 (t, J=7.2 Hz, 2H), 2.67 (d, J=10.8 Hz, 2H), 2.39 (s, 3H), 2.18 (t, J=7.2 Hz, 2H), 1.76 (t, J=10.8 Hz, 2H), 1.69-1.62 (m, 2H), 1.58 (d, J=10.0 Hz, 2H), 1.30-

1.06 (m, 9H), 0.87 (t, J=6.8 Hz, 3H); $^{13}$C NMR (CDCl$_3$) δ 168.3, 150.0, 129.2, 128.9, 126.8, 124.8, 114.8, 69.5, 55.7, 54.2, 42.6, 36.4, 35.9, 32.6, 29.2, 25.3, 23.0, 20.9, 14.2.

To the pure compound (0.177 g, 0.52 mmol) dissolved in diethyl ether (4 mL) was added oxalic acid (0.047 g, 0.49 mmol) in diethyl ether (2 mL). The formed crystals were filtered and washed with diethyl ether to give the title compound as oxalic salt (0.21 g, 92%); HPLC-MS (ammonium acetate) [M+H]$^+$=345.1

4-[3-(4-Butylpiperidin-1-yl)propyl]-7-methyl-4H-benzo[1,4]oxazin-3-one (81MF2246F)

4-(3-Chloropropyl)-7-methyl-4H-benzo[1,4]oxazin-3-one (81MF2246b) (1.64 g, 6.84 mmol), K$_2$CO$_3$ (1.89 g, 13.68 mmol), NaI (2.05 g, 13.68 mmol) and 4-butylpiperidine (1.02 g, 7.18 mmol) were mixed according to GP11. CC (SiO$_2$; Heptane/EtOAc 10:1-4) gave the title compound (81MF2246F) (1.85 g, 79%). $^1$H NMR (CDCl$_3$) δ 6.97 (d, J=8.0 Hz, 1H), 6.82-6.78 (m, 2H), 4.54 (s, 2H), 3.94 (t, J=7.2 Hz, 2H), 2.86 (d, J=10.8 Hz, 2H), 2.37 (t, J=7.0 Hz, 2H), 2.28 (s, 3H), 1.92-1.79 (m, 4H), 1.66 (d, J=9.2 Hz, 2H), 1.31-1.18 (m, 9H), 0.88 (t, J=7.2 Hz, 3H) $^{13}$C NMR (CDCl$_3$) δ 164.2, 145.3, 133.9, 126.3, 123.3, 117.7, 115.0, 67.8, 56.0, 54.3, 39.7, 36.5, 36.0, 32.7, 29.2, 24.9, 23.1, 20.8, 14.2.

To the pure compound (0.156 g, 0.45 mmol) dissolved in diethyl ether (4 mL) was added oxalic acid (0.042 g, 0.47 mmol) in diethyl ether (2 mL). The formed crystals were filtered and washed with diethyl ether to give the title compound as oxalic salt (0.192 g, 97%); HPLC-MS (ammonium acetate) [M+H]$^+$=345.1

4-[3-(4-Butylpiperidin-1-yl)propyl]-6-chloro-7-nitro-4H-benzo[1,4]oxazin-3-one (81MF2253x)

6-Chloro-4-(3-chloropropyl)-7-nitro-4H-benzo[1,4]oxazin-3-one (81MF2253b) (1.23 g, 4.05 mmol), K$_2$CO$_3$ (1.12 g, 8.09 mmol), NaI (1.21 g, 8.09 mmol) and 4-butylpiperidine (0.60 g, 4.24 mmol) were mixed according to GP11. CC (SiO$_2$; Heptane/EtOAc 10:1-4) gave the title compound (81MF2253x) (0.698 g, 42%). $^1$H NMR (CDCl$_3$) δ 7.61 (s, 1H), 7.36 (s, 1H), 4.66, (s, 2H), 3.99 (t, J=6.8 Hz, 2H), 2.85 (d, J=11.2 Hz, 2H), 2.34 (t, J=6.4 Hz, 2H), 1.94-1.80 (m, 4H), 1.67 (d, J=10.0 Hz, 2H), 1.31-1.20 (m, 9H), 0.88 (t, J=6.4 Hz, 3H); $^{13}$C NMR (CDCl$_3$) δ 163.4, 143.4, 141.9, 133.9, 122.1, 117.7, 114.8, 67.5, 55.5, 54.4, 40.5, 36.4, 36.0, 32.6, 29.2, 24.6, 23.0, 14.2.

To the pure compound (0.128 g, 0.31 mmol) dissolved in diethyl ether (4 mL) was added oxalic acid (0.029 g, 0.33 mmol) in diethyl ether (2 mL). The formed crystals were filtered and washed with diethyl ether to give the title compound as oxalic salt (0.125 g, 80%); HPLC-MS (ammonium acetate) [M+H]$^+$=410.1

4-[3-(4-Butylpiperidin-1-yl)propyl]-7-chloro-4H-benzo[1,4]oxazin-3-one (81MF2271x)

7-Chloro-4-(3-chloropropyl)-4H-benzo[1,4]oxazin-3-one (81MF2271b) (1.953 g, 7.49 mmol), K$_2$CO$_3$ (2.07 g, 14.9 mmol), NaI (2.24 g, 14.9 mmol) and 4-butylpiperidine (1.11 g, 7.86 mmol) were mixed according to GP11. CC (SiO$_2$; Heptane/EtOAc 10:1-4) gave the title compound (81MF2271x) (2.46 g, 90%). $^1$H NMR (CDCl$_3$) δ 7.08-6.96 (m, 3H), 4.57 (s, 2H), 3.95 (t, J=7.2 Hz, 2H), 2.85 (d, J=10.8 Hz, 2H), 2.35 (t, J=7.2 Hz, 2H), 1.93-1.78 (m, 4H), 1.66 (d, J=9.2 Hz, 2H), 1.31-1.18 (m, 9H), 0.88 (t, J=6.4 Hz, 3H); $^{13}$C NMR (CDCl$_3$) δ 163.7, 146.0, 128.7, 127.7, 122.7, 117.6, 116.1, 67.7, 55.9, 54.3, 39.9, 36.5, 36.0, 32.7, 29.2, 24.8, 23.1, 14.2.

To the pure compound (0.171 g, 0.47 mmol) dissolved in diethyl ether (4 mL) was added oxalic acid (0.043 g, 0.49 mmol) in diethyl ether (2 mL). The formed crystals were filtered and washed with diethyl ether to give the title compound as oxalic salt (0.206 g, 97%); HPLC-MS (ammonium acetate) [M+H]$^+$=365.1

General Procedure 12 (GP12)

A 4 mL vial was charged with 4-(3-chloropropyl)-4H-benzo[1,4]oxazin-3-one (1.0 equiv), K$_2$CO$_3$ (2.0 equiv), NaI (2.0 equiv) and amine (1.05 equiv) in 3 mL dry MeCN and shaken at 60° C. for 100 h. The reaction mixture was evaporated to dryness, diluted with 4 mL H$_2$O, extracted into CH$_2$Cl$_2$ (3×10 mL), and filtered through a PTFF Whatman filter. The combined organic layers were evaporated to dryness and purified by CC (Heptane/EtOAc or CH$_2$Cl$_2$/MeOH) or Prep TLC (Heptane/EtOAc or CH$_2$Cl$_2$/MeOH).

4-[3-(4-Butylpiperidin-1-yl)propyl]-6-fluoro-4H-benzo[1,4]oxazin-3-one (8173MF55F)

4-(3-Chloropropyl)-6-fluoro-4H-benzo[1,4]oxazin-3-one (8173MF55b) (0.102 g, 0.42 mmol), K$_2$CO$_3$ (0.12 g, 0.84 mmol), NaI (0.13 g, 0.84 mmol) and 4-butylpiperidine (0.06 g, 0.44 mmol) were mixed according to GP12. CC (SiO$_2$; Heptane/EtOAc 10:1-4) gave the title compound (8183MF55F) (0.12 g, 80%). $^1$H NMR (CDCl$_3$) 6.6.96 (dd, J=10.4 Hz, J=2.8 Hz, 1H), 6.87 (dd, J=9.6 Hz, J=5.2 Hz, 1H), 6.66-6.12 (m, 1H), 4.51 (s, 2H), 3.91 (t, J=7.2 Hz, 2H), 2.84 (d, J=11.2 Hz, 2H), 2.32 (t, J=7.2 Hz, 2H), 1.91-1.77 (m, 4H), 1.64 (d, J=9.6 Hz, 2H), 1.29-1.16 (m, 9H), 0.86 (t, J=6.8 Hz, 3H); $^{13}$C NMR (CDCl$_3$) δ 164.2, 158.5 (d, J=239.5 Hz), 141.4 (d, J=2.7 Hz), 130.0 (d, J=10.4 Hz), 117.5 (J=9.3 Hz), 109.5 (d, J=23.5 Hz), 103.2 (d, J=28.8 Hz), 67.7, 55.7, 54.3, 40.0, 36.4, 35.9, 32.6, 29.1, 24.7, 23.0, 14.2.

To the pure compound (0.12 g, 0.34 mmol) dissolved in diethyl ether (4 mL) was added oxalic acid (0.032 g, 0.37 mmol) in diethyl ether (2 mL). The formed crystals were filtered and washed with diethyl ether to give the title compound as oxalic salt (0.128 g, 87%). HPLC-MS (ammonium acetate) [M+H]$^+$=349.2.

4-[3-(4-Butylpiperidin-1-yl)propyl]-7,8-difluoro-4H-benzo[1,4]oxazin-3-one (81MF2082x)

4-(3-Chloropropyl)-7,8-difluoro-4H-benzo[1,4]oxazin-3-one (81MF2082b) (0.16 g, 0.60 mmol), K$_2$CO$_3$ (0.17 g, 11.9 mmol), NaI (0.18 g, 11.9 mmol) and 4-butylpiperidine (0.09 g, 0.63 mmol) were mixed according to GP12. CC (SiO$_2$; Heptane/EtOAc 10:1-4) gave the title compound (81MF2082x) (0.14 g, 65%). $^1$H NMR (CDCl$_3$) δ 6.88-6.76 (m, 2H) 4.66 (s, 2H), 3.96 (t, J=7.2 Hz, 2H), 2.84 (d, J=11.2, 2H), 2.34 (t, J=6.8 Hz, 2H), 1.91-1.78 (m, 4H), 1.67 (d J=9.6 Hz, 2H), 1.30-1.15 (m, 9H); $^{13C}$ NMR (CDCl$_3$) δ 163.1, 147.4 (q, J=245.0 Hz, J=10.6 Hz), 140.1 (q, J=248.7 Hz, J=15.7 Hz), 135.4 (d, J=12.0 Hz), 126.5, 109.5 (d, J=18.4 Hz), 109.0 (q, J=7.6 Hz, J=3.8 Hz), 67.8, 55.8, 52.3, 40.1, 36.4, 35.9, 32.7, 29.1, 24.8, 23.0, 14.2.

To the pure compound (0.14 g, 0.39 mmol) dissolved in diethyl ether (4 mL) was added oxalic acid (0.042 g, 0.46 mmol) in diethyl ether (2 mL). The formed crystals were filtered and washed with diethyl ether to give the title compound as oxalic salt (0.16 g, 89%). HPLC-MS (ammonium acetate) [M+H]$^+$=367.3.

4-[3-(4-Butylpiperidin-1-yl)propyl]-4H-pyrido[4,3-b][1,4]thiazin-3-one (81MF939)

4-(3-Chloropropyl)-4H-pyrido[4,3-b][1,4]thiazin-3-one (81MF939b) (0.14 g, 0.57 mmol), K$_2$CO$_3$ (0.16 g, 11.4 mmol), NaI (0.18 g, 11.4 mmol) and 4-butylpiperidine (0.09 g, 0.60 mmol) were mixed according to GP12. CC (SiO$_2$; Heptane/EtOAc 10:1-4) gave the title compound (81MF939) (0.064 g, 32%). $^1$H NMR (CDCl$_3$) δ 8.48 (s, 1H), 8.17 (d, J=5.2 Hz, 1H), 7.25 (d, J=4.8 Hz, 1H), 4.06-4.12 (m, 2H), 3.41 (s, 2H), 2.82 (d, J=11.2 Hz, 2H), 2.33 (t, J=6.8 Hz, 2H), 1.83-1.89 (m, 4H), 1.64 (d, J=9.2 Hz, 2H), 1.16-1.29 (m, 9H), 0.87 (t, J=6.8 Hz, 3H); $^{13}$C NMR (CDCl$_3$) δ 163.91, 143.84, 138.92, 136.20, 134.04, 122.31, 55.80, 54.32, 43.29, 36.43, 35.99, 32.68, 30.78, 29.19, 25.20, 23.05, 14.24.

To the pure compound (0.064 g, 0.18 mmol) dissolved in diethyl ether (4 mL) was added oxalic acid (0.020 g, 0.22 mmol) in diethyl ether (2 mL). The formed crystals were filtered and washed with diethyl ether to give the title compound as oxalic salt (0.16 g, 89%); HPLC-MS (ammonium acetate) [M+H]$^+$=348.2

4-[3-(4-Propoxypiperidin-1-yl)propyl]-4H-benzo[1,4]thiazin-3-one (81MF07KS)

4-(3-Chloropropyl)-4H-benzo[1,4]thiazin-3-one (81MF07) (0.18 g, 0.74 mmol), K$_2$CO$_3$ (0.20 g, 14.8 mmol), NaI (0.22 g, 14.8 mmol) and 4-propoxypiperidine (0.12 g, 0.81 mmol) were mixed according to GP12. CC (SiO$_2$; Heptane/EtOAc 4:1-4) gave the title compound (81MF07KS) (0.205 g, 79%). $^1$H NMR (CDCl$_3$) δ 7.33 (d, J=7.6 Hz, 2H), 7.21 (d, J=3.2 Hz, 2H), 7.00-6.96 (m, 1H), 4.03 (t, J=7.2 Hz, 2H), 3.38-3.34 (m, 4H), 3.26-3.21 (m, 1H), 2.69 (t, J=5.6 Hz, 2H), 2.33 (t, J=7.2 Hz, 2H), 2.04 (t, J=9.8 Hz, 2H), 1.86-1.76 (m, 4H), 1.58-1.51 (m, 4H), 0.90 (t, J=7.2 Hz, 3H); $^{13}$C NMR (CDCl$_3$) δ 165.2, 139.7, 128.5, 127.2, 124.1, 123.4, 118.1, 75.2, 69.7, 55.4, 51.5, 43.2, 31.8, 31.7, 25.3, 23.4, 10.8.

To the pure compound (0.205 g, 0.58 mmol) dissolved in diethyl ether (4 mL) was added oxalic acid (0.058 g, 0.64 mmol) in diethyl ether (2 mL). The formed crystals were filtered and washed with diethyl ether to give the title compound as oxalic salt (0.192 g, 74%). HPLC-MS (ammonium acetate) [M+H]$^+$=349.2.

4-[3-(4-Propoxypiperidin-1-yl)propyl]-4H-benzo[1,4]oxazin-3-one (81(81MF08KS)

4-(3-Chloropropyl)-4H-benzo[1,4]oxazin-3-one (81MF08) (0.13 g, 0.58 mmol), K$_2$CO$_3$ (0.16 g, 1.15 mmol), NaI (0.17 g, 1.15 mmol) and 4-propoxypiperidine (0.089 g, 0.60 mmol) were mixed according to GP12. CC (SiO$_2$; Heptane/EtOAc 4:1-4) gave the title compound (81(81MF08KS)) (0.147 g, 76%). $^1$H NMR (CDCl$_3$) δ.7.11-7.08 (m, 1H), 7.01-6.94 (m, 3H), 4.55 (s, 2H), 3.96 (t, J=7.2 Hz, 2H), 3.37 (t, J=6.8 Hz, 2H), 3.28-3.21 (m, 1H), 2.74-2.69 (m, 2H), 2.36 (t, J=7.2 Hz, 2H), 2.10-2.03 (m, 2H), 1.90-1.77 (m, 4H), 1.61-1.51 (m, 4H), 0.90 (t, J=7.2 Hz, 3H); $^{13}$C NMR (CDCl$_3$) δ 164.3, 145.4, 128.7, 123.8, 122.8, 117.1, 115.1, 75.1, 69.6, 67.7, 55.5, 51.5, 39.6, 31.6, 24.9, 23.4, 10.7.

To the pure compound (0.147 g, 0.44 mmol) dissolved in diethyl ether (4 mL) was added oxalic acid (0.048 g, 0.53 mmol) in diethyl ether (2 mL). The formed crystals were filtered and washed with diethyl ether to give the title compound as oxalic salt (0.160 g, 86%). HPLC-MS (ammonium acetate) [M+H]$^+$=333.3.

4-[3-(4-Butylpiperidin-1-yl)propyl]-7-fluoro-4H-benzo[1,4]oxazin-3-one (81MF763)

4-(3-Chloropropyl)-7-fluoro-4H-benzo[1,4]oxazin-3-one (81MF763b) (0.40 g, 1.6 mmol), K$_2$CO$_3$ (0.44 g, 3.2 mmol), NaI (0.48 g, 3.2 mmol) and 4-butylpiperidine (0.24 g, 1.70 mmol) were mixed according to GP12. CC (SiO$_2$; Heptane/EtOAc 4:1-4) gave the title compound (81MF763) (0.26 g, 46%). $^1$H NMR (CDCl$_3$) δ 7.09-7.04 (m, 1H), 6.74-6.69 (m, 2H), 4.58 (s, 2H), 3.95 (t, J=7.2 Hz, 2H), 2.84 (d, J=11.2 Hz, 2H), 3.45 (t, J=6.8 Hz, 2H), 1.91-1.78 (m, 4H), 1.66 (d, J=9.2 Hz, 2H), 1.29-1.16 (m, 9H), 0.88 (t, 7.2 Hz, 3H); $^{13}$C NMR (CDCl$_3$) δ 163.6, 158.9 (d, J=243.7 Hz), 146.3 (d, J=11.5 Hz), 125.2 (d, J=3.0 Hz), 115.9 (d, J=9.7 Hz), 109.1 (d, J=22.8 Hz), 105.1 (d, J=26.1 Hz), 67.8, 55.9, 54.3, 39.9, 36.5, 36.0, 32.7, 29.2, 24.8, 23.1, 14.2.

To the pure compound (0.26 g, 0.74 mmol) dissolved in diethyl ether (4 mL) was added oxalic acid (0.073 g, 0.818 mmol) in diethyl ether (2 mL). The formed crystals were filtered and washed with diethyl ether to give the title compound as oxalic salt (0.26 g, 78%) HPLC-MS (ammonium acetate) [M+H]$^+$=349.3.

4-[3-(4-Butylidenepiperidin-1-yl)propyl]-4H-benzo[1,4]thiazin-3-one (81MF26)

4-(3-Chloropropyl)-4H-benzo[1,4]thiazin-3-one (81MF07) (0.073 g, 0.30 mmol), K$_2$CO$_3$ (0.12 g, 0.90 mmol), NaI (0.090 g, 0.6 mmol) and 4-butylidenepiperidine (0.050 g, 0.28 mmol) were mixed according to GP12. Prep TLC (SiO$_2$; CH$_2$Cl$_2$/MeOH 10:1) gave the title compound (81MF26) (0.034 g, 33%). $^1$H NMR (CDCl$_3$) δ 7.34-7.31 (m, 1H), 7.23-7.20 (m, 1H), 7.00-6.95 (m, 1H), 5.10 (t, J=7.2 Hz, 1H), 4.04 (t, J=7.2 Hz, 2H), 3.34 (s, 2H), 2.37-2.32 (m, 6H), 2.23-2.14 (m, 2H), 1.96-1.90 (m, 2H), 1.86-1.78 (m, 2H), 1.37-1.27 (m, 2H), 0.86 (t, J=7.2 Hz, 3H); $^{13}$C NMR (CDCl$_3$) δ 165.1, 139.6, 136.0, 128.5, 127.2, 124.1, 123.4, 122.7, 118.1, 55.6, 55.4, 54.8, 43.2, 36.1, 31.7, 29.2, 28.3, 25.2, 23.2, 13.8.

To the pure compound (0.034 g, 0.10 mmol) dissolved in diethyl ether (4 mL) was added oxalic acid (0.010 g, 0.10 mmol) in diethyl ether (2 mL). The formed crystals were filtered and washed with diethyl ether to give the title compound as oxalic salt (0.030 g, 69%); HPLC-MS (ammonium acetate) [M+H]$^+$=345.2

4-[3-(4-Butylidenepiperidin-1-yl)propyl]-4H-benzo[1,4]oxazin-3-one (81MF25)

4-(3-Chloropropyl)-4H-benzo[1,4]oxazin-3-one (81MF08) (0.068 g, 0.30 mmol), K$_2$CO$_3$ (0.12 g, 0.90 mmol), NaI (0.090 g, 0.60 mmol) and 4-butylidenepiperidine (0.050 g, 0.28 mmol) were mixed according to GP12. Prep TLC (SiO$_2$; CH$_2$Cl$_2$/MeOH 10:1) gave the title compound (81MF25) (0.070 g, 71%). $^1$H NMR (CDCl$_3$) δ 7.12 (d, J=6.8 Hz, 1H), 7.03-6.95 (m, 3H), 5.12 (J=7.4 Hz, 1H), 4.56 (s, 1H), 3.99 (t, J=7.6 Hz, 2H), 2.41-2.36 (m, 6H), 2.26-2.17 (m, 2H), 1.98-1.81 (m, 4H), 1.38-1.28 (m, 2H), 0.87 (t, J=7.2 Hz, 3H); $^{13}$C NMR (CDCl$_3$) δ 164.3, 145.5, 136.0, 128.7, 123.8, 122.8, 122.8, 117.1, 115.2, 67.7, 55.7, 55.6, 54.9, 39.7, 36.1, 29.2, 28.4, 24.8, 23.2, 13.8.

To the pure compound (0.070 g, 0.21 mmol) dissolved in diethyl ether (4 mL) was added oxalic acid (0.020 g, 0.22 mmol) in diethyl ether (2 mL). The formed crystals were filtered and washed with diethyl ether to give the title compound as oxalic salt (0.087 g, 97%) HPLC-MS (ammonium acetate) [M+H]$^+$=329.3.

4-[3-(3-Butylidene-8-aza-bicyclo[3.2.1]oct-8-yl)-propyl]-4H-benzo[1,4]oxazin-3-one (81MF24)

4-(3-Chloropropyl)-4H-benzo[1,4]oxazin-3-one (81MF08) (0.030 g, 0.13 mmol), $K_2CO_3$ (0.037 g, 0.26 mmol), NaI (0.040 g, 0.27 mmol) and 3-butylidene-8-azabicyclo[3.2.1]octane (0.029 g, 0.17 mmol) were mixed according to GP12. Prep TLC ($SiO_2$; $CH_2Cl_2$/MeOH 10:1) gave the title compound (81MF24) (0.019 g, 41%). $^1$H NMR ($CDCl_3$) δ 7.22-7.19 (m, 1H), 7.05-6.96 (m, 3H), 5.24 (t, J=7.2 Hz, 1H), 5.08 (s, 2H), 4.06 (t, J=6.4 Hz, 2H), 2.61 (t, J=6.8 Hz, 2H), 2.30 (s, 2H), 2.03-1.83 (m, 7H), 1.58-1.43 (m, 2H), 1.39-1.22 (m, 3H), 0.89 (m, 3H); $^{13}$C NMR ($CDCl_3$) δ 164.5, 145.5, 131.4, 128.7, 127.9, 124.0, 123.0, 117.1, 115.5, 67.8, 60.4, 60.2, 48.8, 41.0, 39.6, 33.7, 29.5, 26.8, 26.4, 25.8, 23.2, 13.9.

To the pure compound (0.019 g, 0.05 mmol) dissolved in diethyl ether (2 mL) was added oxalic acid (0.005 g, 0.006 mmol) in diethyl ether (1 mL). The formed crystals were filtered and washed with diethyl ether to give the title compound as oxalic salt (0.012 g, 50%); HPLC-MS (ammonium acetate) [M+H]$^+$=355.3

4-[3-(4-Butylpiperidin-1-yl)propyl]-6-methoxy-4H-benzo[1,4]oxazin-3-one (81MF2249)

4-(3-Chloropropyl)-6-methoxy-4H-benzo[1,4]oxazin-3-one (81MF2249b) (0.127 g, 0.50 mmol), $K_2CO_3$ (0.137 g, 1.0 mmol), NaI (0.149 g, 1.0 mmol) and 4-butylpiperidine (0.075 g, 0.52 mmol) were mixed according to GP12. CC ($SiO_2$; Heptane/EtOAc 4:1-4) gave the title compound (81MF2249) (0.14 g, 85%). $^1$H NMR ($CDCl_3$) 8.6.88 (d, J=8.8 Hz, 1H), 6.67 (d, J=2.4 Hz, 1H), 6.49 (dd, J=8.8 Hz, J=2.4 Hz, 1H), 4.51 (s, 2H), 3.93 (t, 7.2 Hz, 2H), 3.77 (s, 3H), 2.86 (d, J=10.8 Hz, 2H), 2.36 (t, J=7.2 Hz, 2H), 1.90-1.80 (m, 4H), 1.64 (d J=8.8 Hz, 2H), 1.29-1.17 (m, 9H), 0.88 (t, J=6.2 Hz, 3H); $^{13}$C NMR ($CDCl_3$) δ 168.8, 155.6, 139.6, 129.7, 117.2, 107.2, 102.9, 68.0, 56.1, 56.0, 54.4, 39.9, 36.5, 35.9, 32.6, 29.2, 24.9, 23.0, 14.2.

To the pure compound (0.14 g, 0.37 mmol) dissolved in diethyl ether (4 mL) was added oxalic acid (0.037 g, 0.41 mmol) in diethyl ether (2 mL). The formed crystals were filtered and washed with diethyl ether to give the title compound as oxalic salt (0.15 g, 90%). HPLC-MS (ammonium acetate) [M+H]$^+$=361.3.

General Procedure 13 (GP13)

A 7 mL vial was charged with 4-(3-chloropropyl)-4H-benzo[1,4]oxazin-3-one (1.0 equiv), $K_2CO_3$ (2.0 equiv), NaI (2.0 equiv) and 4-Butylpiperidine (1.05 equiv) in 5 mL dry MeCN and shaken at 60° C. for 48 h. The reaction mixture was evaporated to dryness, diluted with 10 mL $H_2O$, extracted into $CH_2Cl_2$ (3×13 mL), and filtered through a PTFF Whatman filter. The combined organic layers were evaporated to dryness and purified by CC (Heptane/EtOAc or $CH_2Cl_2$/MeOH) or prep TLC (Heptane/EtOAc or $CH_2Cl_2$/MeOH).

4-[3-(4-Butylpiperidin-1-yl)propyl]-6,8-dichloro-7-ethyl-4H-benzo[1,4]oxazin-3-one (95MF60)

6,8-Dichloro-4-(3-chloro-propyl)-7-ethyl-4H-benzo[1,4]oxazin-3-one ((95MF52(2226)) (0.30 g, 0.93 mmol), $K_2CO_3$ (0.26 g, 1.86 mmol), NaI (0.28 g, 1.86 mmol) and 4-butylpiperidine (0.14 g, 0.98 mmol) were mixed according to GP13. CC ($SiO_2$; $CH_2Cl_2$/MeOH 10:0.2-4) gave the title compound (95MF60) (0.24 g, 59%). $^1$H NMR ($CDCl_3$) δ 7.10 (s, 1H), 4.65 (s, 2H), 3.93 (t, J=6.8 Hz, 2H), 2.95-2.81 (m, 4H), 2.33 (t, J=6.8 Hz, 2H), 1.90-1.78 (m, 4H), 1.66 (d, J=10.0 Hz, 2H) 1.30-1.13 (m, 12H), 0.88 (s, 3H); $^{13}$C NMR ($CDCl_3$) δ 163.5, 140.6, 135.3, 128.2, 127.7, 123.2, 114.3, 67.9, 55.8, 54.4, 40.1, 36.4, 36.0, 32.7, 29.2, 24.8, 24.6, 23.1, 14.2, 12.7; HPLC-MS (ammonium acetate) [M+H]$^+$=427.2.

4-[3-(4-Butylpiperidin-1-yl)propyl]-8-fluoro-4H-benzo[1,4]oxazin-3-one (95MF59)

4-(3-Chloropropyl)-8-fluoro-4H-benzo[1,4]oxazin-3-one (95MF51(2085)) (0.25 g, 1.04 mmol), $K_2CO_3$ (0.29 g, 2.1 mmol), NaI (0.31 g, 2.1 mmol) and 4-butylpiperidine (0.15 g, 1.1 mmol) were mixed according to GP13. CC ($SiO_2$; $CH_2Cl_2$/MeOH 10:0.2-4) gave the title compound (95MF59) (0.29 g, 80%). $^1$H NMR ($CDCl_3$) δ 6.92-6.84 (m, 2H), 6.79-6.74 (m, 1H), 4.59 (s, 2H), 3.93 (t, J=7.4 Hz, 2H), 2.81 (d, J=10.8 Hz, 2H), 2.31 (t, J=7.0 Hz, 2H), 1.87-1.75 (m, 4H), 1.62 (d, J=9.2 Hz, 2H), 1.27-1.12 (m, 9H), 0.84 (t, J=6.8 Hz, 3H); $^{13}$C NMR ($CDCl_3$) δ 163.7, 151.8 (d, J=246.0 Hz), 133.8 (d, J=14.6 Hz), 130.7 (d, J=3.5 Hz), 122.1 (d, J=8.0 Hz), 111.2 (d, J=18.4 Hz), 110.4 (d, J=3.4 Hz), 67.6, 55.8, 54.2, 40.0, 36.4, 35.8, 32.6, 29.0, 24.8, 22.9, 14.1.

To the pure compound (0.29 g, 0.83 mmol) dissolved in diethyl ether (4 mL) was added oxalic acid (0.078 g, 0.86 mmol) in diethyl ether (2 mL). The formed crystals were filtered and washed with diethyl ether to give the title compound as oxalic salt (0.31 g, 85%). HPLC-MS (ammonium acetate) [M+H]$^+$=349.3.

6-Bromo-4-[3-(4-butylpiperidin-1-yl)propyl]-8-fluoro-4H-benzo[1,4]oxazin-3-one (95MF58)

6-Bromo-4-(3-chloropropyl)-8-fluoro-4H-benzo[1,4]oxazin-3-one (95MF50(2084)) (0.086 g, 0.27 mmol), $K_2CO_3$ (0.074 g, 0.53 mmol), NaI (0.080 g, 0.53 mmol) and 4-butylpiperidine (0.039 g, 0.28 mmol) were mixed according to GP13. CC ($SiO_2$; $CH_2Cl_2$/MeOH 10:0.2-4) gave the title compound (95MF58) (0.040 g, 35%). $^1$H NMR ($CDCl_3$) δ 6.92-6.84 (m, 2H), 6.79-6.74 (m, 1H), 4.59 (s, 2H), 3.93 (t, J=7.4 Hz, 2H), 2.81 (d, J=10.8 Hz, 2H), 2.31 (t, J=7.0 Hz, 2H), 1.87-1.75 (m, 4H), 1.62 (d, J=9.2 Hz, 2H), 1.27-1.12 (m, 9H), 0.84 (t, J=6.8 Hz, 3H); $^{13}$C NMR ($CDCl_3$) δ 163.7, 151.8 (d, J=246.0 Hz), 133.8 (d, J=14.6 Hz), 130.7 (d, J=3.5 Hz), 122.1 (d, J=8.0 Hz), 111.2 (d, J=18.4 Hz), 110.4 (d, J=3.4 Hz), 67.6, 55.8, 54.2, 40.0, 36.4, 35.8, 32.6, 29.0, 24.8, 22.9, 14.1.

To the pure compound (0.040 g, 0.09 mmol) dissolved in diethyl ether (4 mL) was added oxalic acid (0.009 g, 0.098 mmol) in diethyl ether (2 mL). The formed crystals were filtered and washed with diethyl ether to give the title compound as oxalic salt (0.040 g, 82%). HPLC-MS (ammonium acetate) [M+H]$^+$=427.2.

4-[3-(4-Butylpiperidin-1-yl)propyl]-8-isopropyl-4H-benzo[1,4]oxazin-3-one (111MF02)

4-(3-Chloropropyl)-8-isopropyl-4H-benzo[1,4]oxazin-3-one (95MF98) (0.112 g, 0.42 mmol), $K_2CO_3$ (0.115 g, 0.84 mmol), NaI (0.125 g, 0.84 mmol) and 4-butylpiperidine (0.062 g, 0.44 mmol) were mixed according to GP13. Prep TLC ($SiO_2$; $CH_2Cl_2$/MeOH 10:1) gave the title compound (111MF02) (0.06 g, 39%). $^1$H NMR ($CDCl_3$) δ 6.99-6.91 (m, 3H), 4.55 (s, 2H), 3.96 (t, J=7.4 Hz, 2H), 3.27 (m, 1H), 2.89 (d, J=11.2 Hz, 2H), 2.40 (t, J=7.2 Hz, 2H), 1.93-1.83 (m, 4H), 1.66 (d, J=9.6 Hz, 2H), 1.27-1.20 (m, 15H), 0.88 (t, J=6.8 Hz, 3H); $^{13}$C NMR ($CDCl_3$) δ 164.7, 142.9, 137.5, 128.7, 122.6, 121.1, 112.9, 67.7, 56.0, 54.2, 39.9, 36.4, 35.9, 32.5, 29.1, 27.2, 24.9, 23.0, 22.7, 14.2.

To the pure compound (0.06 g, 0.16 mmol) dissolved in diethyl ether (4 mL) was added oxalic acid (0.016 g, 0.18 mmol) in diethyl ether (2 mL). The formed crystals were filtered and washed with diethyl ether to give the title compound as oxalic salt (0.07 g, 88%). HPLC-MS (ammonium acetate) [M+H]$^+$=373.3.

(R,S)-4-[3-(4-Butylpiperidin-1-yl)-2-hydroxy-propyl]-6-methyl-4H benzo[1,4]oxazin-3-one (101IS86)

A dry 4 mL vial was charged with (R,S)-6-methyl-4-oxiranylmethyl-4H-benzo[1,4]oxazin-3-one (0.090 g, 0.41 mmol), 4-butylpiperidine (0.090 g, 0.60 mmol), K$_2$CO$_3$ (0.097 g, 0.70 mmol) and dry THF (2 mL). The mixture was shaken at 40° C. for 74 h and was thereafter concentrated under reduced pressure and the residue was diluted with EtOAc (20 mL) and washed with water (10 mL), brine, dried over Na$_2$SO$_4$. Filtration, concentration under reduced pressure and purification of the residue with flash chromatography (SiO$_2$; CH$_2$Cl$_2$/acetone/MeOH 85:10:5) gave the title product as an oil (0.080 g, 54%). $^1$H NMR (CD$_3$OD) δ 7.12 (s, 1H), 6.85 (d, J=8.2 Hz, 1H), 6.81 (brd, J=8.2 Hz, 1H), 4.53 (ABq, 14.8, 18.0 Hz, 2H), 4.12-4.02 (m, 2H), 3.95-3.85 (m, 1H), 3.05-2.98 (m, 1H), 2,92-2.84 (m, 1H), 2.48-2,40 (m, 2H), 2.31 (s, 3H), 2.10-1.98 (m, 2H), 1.71-1.62, (m, 2H), 1.35-1.15 (m, 9H), 0.90 (t, J=6.8 Hz). $^{13}$C NMR (CD$_3$OD) δ 166.0, 143.7, 132.4, 128.8, 124.4, 116.5, 116.4, 67.5, 65.9, 62.8, 54.6, 54.5, 46.1, 36.3, 35.6, 32.2 (br), 29.0, 22.8, 20.0, 13.3.

The product was dissolved in diethyl ether and oxalic acid (1.1 equiv) dissolved in diethyl ether was added. The formed crystals were filtered and washed with acetone to give the title compound as oxalic salt (0.033 g). HPLC-MS (ammonium acetate) [M+H]$^+$=361.3.

(R,S)-4-[3-(4-Butylpiperidin-1-yl)-2-hydroxypropynyl]-4H-benzo[1,4]oxazin-3-one (101IS85)

Epichlorohydrin (0.48 g, 5.2 mmol), Cs$_2$CO$_3$ (2.3 g, 7.0 mmol), 4H-benzo[1,4]oxazin-3-one (0.52 g, 3.5 mmol) were stirred with dry DMF (7 mL) for 22 h. Thereafter the mixture was diluted with ether (50 mL) and washed with water (10 mL) and brine (10 mL). The organic phase was dried over Na$_2$SO$_4$, filtered, concentrated under reduced pressure and the residue was purified by flash chromatography (SiO$_2$; CH$_2$Cl$_2$/acetone/MeOH 95:3:2). The resulting oil (0.50 g, 2.5 mmol) was dissolved in THF, 4-butylpiperidine (0.43 g, 3.0 mmol) and K$_2$CO$_3$ (0.83 g, 6.0 mmol) were added and the reaction was shaken at 40° C. for 72 h. The reaction was thereafter concentrated under reduced pressure, and the residue was purified by flash CC (SiO$_2$; CH$_2$Cl$_2$/acetone/MeOH 85:10:5) to give the title compound (0.43 g, 1,2 mmol, 35%). $^1$H NMR (CD$_3$OD) δ 7.32 (brd, J=7.2 Hz, 1H), 7.06-6.94 (m, 3H), 4.58 (ABq, J=14.8, 17.6 Hz, 2H), 4.13-4.03 (m, 2H), 3.91 (dd, J=8.8, 15.2 Hz), 3.97 (brd, J=10.7 Hz, 1H), 2.87 (brd, J=10.1 Hz), 2.43 (d, J=6 Hz, 2H), 2.09-1.96 (m, 2H), 1.69-1.60 (m, 2H), 1.34-1.16 (m, 9H), 0.90 (t, J=6.8 Hz); $^{13}$C NMR (CD$_3$OD) δ 165.8, 145.8, 129.2, 124.0, 122.6, 116.7, 116.2, 67.4, 65.9, 54.7, 54.5, 46.2, 36.3, 35.6, 32.2 (br), 29.0, 22.8, 13.3.

The product was dissolved in diethyl ether and oxalic acid (1.1 equiv) dissolved in diethyl ether was added. The formed crystals were filtered and washed with acetone to give the title compound as oxalic salt (0.037 g). HPLC-MS (ammonium acetate) [M+H]$^+$=347.3.

(−)-4-[3-(4-Butylpiperidin-1-yl)-2-hydroxypropyl]-4H-benzo[1,4]oxazin-3-one (101IS95)

Following the method outlined above for (R/S)-4-[3-(4-butylpiperidin-1-yl)-2-hydroxypropyl]-4H-benzo[1,4]oxazin-3-one using (R)-(−)-epichlorohydrine (97% ee), (instead of racemic epichlorohydrin, gave the title compound. The optical purity was determined by HPLC analysis (Chiralpak AD, 250×4.6, 5 μm; hexane/i-PrOH/diethylamine 95:4.7: 0.3, 0.5 mL/min) to be 96.3% ee. ([α]$_D^{20}$=−6, c=0.5, EtOH). $^1$H NMR, $^{13}$C NMR and HPLC-MS spectral data were identical to those of the racemic compound.

(R,S)-4-[3-(4-Butylpiperidin)-2-methoxypropyl]-4H-benzo[1,4]oxazin-3-one (101IS91)

A dry 4 mL vial was charged with NaH (6.5 mg, 0.15 mmol) and then a solution of (R,S)-4-[3-(4-Butylpiperidin-1-yl)-2-hydroxypropyl]-4H-benzo[1,4]oxazin-3-one (101IS85) (0.043 g, 0.12 mmol) in dry THF (1 mL) was added and the mixture was allowed to stir at rt for 2 h. Thereafter, neat MeI (7.5 μl, 0.12 mmol) was added and after another 2 h at rt the reaction mixture was quenched with water (2 mL) and extracted with EtOAc (3×10 mL). The organic phase was dried over Na$_2$SO$_4$, filtered, concentrated under reduced pressure and the residue was purified by flash chromatography (SiO$_2$; CH$_2$Cl$_2$/acetone/MeOH 90:6:4) to yield the title compound as an oil (5.1 mg, 12%). $^1$H NMR (CD$_3$OD) δ 7.25 (dm, J=7.2 Hz, 1H), 7.00-6.88 (m, 3H), 4.49 (ABq, J=15.2, 18.8 Hz, 2H), 4.06-3.94 (m, 2H), 3.69-3.61 (m, 1H), 3.25 (s, 3H), 2.94-2.82 (m, 2H), 2.54-2.36 (m, 2H), 2.10-1.94 (m, 2H), 1.64-1.55 (m, 2H), 1.25-1.05 (m, 9H), 0.81 (t, J=6.8 Hz); $^{13}$C NMR (CD$_3$OD) δ 165.9, 146.0, 129.1, 124.2, 122.7, 116.8, 116.1, 76.0, 67.5, 60.2, 57.2, 54.6, 54.5, 43.7, 36.2, 35.3, 31.8, 28.9, 22.8, 13.2; HPLC-MS (ammonium acetate) [M+H]$^+$=361.3.

(R,S)-4-[2-Hydroxy-3-(3-pentylbicyclo[3.2.1]oct-8-yl)-propyl]-4H-benzo[1,4]oxazin-3-one (123IS03)

Epichlorohydrin (0.48 g, 5.2 mmol), Cs$_2$CO$_3$ (2.3 g, 7.0 mmol), 4H-benzo[1,4]oxazin-3-one (0.52 g, 3.5 mmol) were stirred with dry DMF (7 mL) for 22 h. Thereafter the mixture was diluted with ether (50 mL) washed with water (10 mL) and then brine (10 mL). The organic phase was dried over Na$_2$SO$_4$, filtered, concentrated under reduced pressure and the residue was purified by flash CC (SiO$_2$; CH$_2$Cl$_2$/acetone/MeOH 95:3:2). Of the resulting oil (0.060 g, 0.29 mmol) was dissolved in DMF (1.5 mL), 3-pentyl-8-azabicyclo[3.2.1]octane (0.060 g, 0.33 mmol) and Cs$_2$CO$_3$ (0.30 g, 0.81 mmol) were added and the mixture was shaken at 65° C. for 72 h. The mixture was then poured into ether (25 mL) washed with water (10 mL) and the water phase was extracted with ether (20 mL). The combined organic phase was washed with brine (10 mL), dried over Na$_2$SO$_4$, filtered, concentrated under reduced pressure and the residue was purified by cation exchange CC, followed by flash CC (SiO$_2$; CH$_2$Cl$_2$:acetone:MeOH 85/10/5) to yield the title compound (0.060 g, 33% (from 4H-benzo[1,4]oxazin-3-one)). $^1$H NMR (CDCl$_3$) δ 7.42 (dm, J=7.2 Hz, 1H), 7.05-6.94 (m, 3H), 4.60 (ABq, J=14.8, 16.8 Hz, 2H), 4.15 (dd, J=3.2, 14.0 Hz, 1H), 3.86-3.78 (m, 3H), 3.14 (m, 2H), 2.54 (dd, J=4.8, 12.5 Hz, 1H), 2.22 (dd, J=9.2, 12.4 Hz), 2.16-1.98 (m, 2H), 1.98-1.83 (m, 2H), 1.72-1.55 (m, 3H), 1.43-1.34 (m, 2H), 1.42-1.15 (m, 8H), 0.87 (t, J=7.2 Hz). $^{13}$C NMR (CDCl$_3$) δ 165.3, 145.5, 129.7, 124.2, 122.9, 117.0, 116.6, 67.9, 67.4, 60.9, 58.6, 56.7, 46.7, 38.3, 36.7, 36.5, 28.5, 28.3, 28.2, 27.1, 22.9, 14.3. HPLC-MS (ammonium acetate) [M+H]$^+$=387.3.

4-[2-(4-Butylpiperidin-1-ylmethyl)allyl]-4H-benzo[1,4]oxazin-3-one (123IS02)

3-Chloro-2-chloromethyl-1-propene (0.20 g, 1.5 mmol), 4H-benzo[1,4]oxazin-3-one (0.15 g, 1.0 mmol) and $Cs_2CO_3$ (0.65 g, 2.0 mmol) were mixed with 1 mL DMF and were shaken at 65° C. for 5 h. The mixture was diluted with ether (20 mL) and washed with water (20 mL) and the water phase was extracted with ether (20 mL). The combined organic phase was washed with brine (10 mL), dried over $Na_2SO_4$, filtered concentrated under reduced pressure and the residue was purified by flash CC ($SiO_2$; heptane/EtOAc 70:30). This product (0.080 g, 0.34 mmol) was dissolved in DMF (1 mL), thereafter 4-butylpiperidine (0.053 g, 0.37 mmol) and $Cs_2CO_3$ (0.23 g, 0.71 mmol) were added and the mixture was shaken at 65° C. for 24 h. The mixture was then poured into ether (25 mL) washed with water (10 mL) and the water phase was extracted with ether (20 mL). The combined organic phase was washed with brine (10 mL), dried over $Na_2SO_4$, filtered, concentrated under reduced pressure and the residue was purified by cation exchange CC, followed by flash CC ($SiO_2$; EtOAc/MeOH/$NH_4OH$ (25% $NH_3$ in water) 97.5:2:0.5), to yield the title compound (0.075 g, 21%). $^1$H NMR ($CDCl_3$) δ 7.05-2.92 (m, 4H), 5.01 (brs, 1H), 4.82 (brs, 2H), 4.64 (brs 2H), 4.57 (brs, 2H), 2.94 (brs, 2H), 2.86 (brd, J=10.4 Hz, 2H), 1,93-1.82 (m, 2H), 1.71-1.62 (m, 2H), 1.34-1.15 (m, 9H), 0.89 (t, J=6.2 Hz, 3H); $^{13}$C NMR ($CDCl_3$) δ 1.64.5, 145.4, 129.2, 123.9, 122.8, 116.9, 113.2, 67.9, 63.2, 54.4, 44.8, 36.6, 36.0, 32.8, 29.3, 23.1, 14.3; HPLC-MS (ammonium acetate) $[M+H]^+$=343.3.

(R,S)-4-[3-(4-Butylpiperidin-1-yl)-2-fluoropropyl]-4H-benzo[1,4]oxazin-3-one (101IS96)

A 4 mL vial was charged with (R,S)-4-butyl-1-(3-chloro-2-fluoropropyl)piperidine (0.020 g, 85 μmol) and 4H-benzo[1,4]oxazin-3-one (0.023 g 0.16 mmol) and $CH_3CN$ (1 mL). The mixture was stirred at 60° C. for 70 h and the mixture was diluted with MeOH and filtered through a small silica pad onto a cationic-exchange CC. Concentration under reduced pressure yielded an oil that was purified by flash chromatography ($SiO_2$; heptane:EtOAc 50/50;) to yield the title compound as an oil (0.011 g, 38%). $^1$H NMR ($CD_3OD$) δ 7.28-7.24 (m, 1H), 7.07-6.96 (m, 3H), 5.05 (dm, J=50.4 Hz), (ABq, J=15.2, 20.o Hz), 4.29-4.12 (m, 2H), 3.00-2.92 (m, 2H), 2.78-2.60 (m, 2H), 2.14-2.05 (m, 2H), 1.73-1.63 (m, 2H), 1.35-1.16 (m, 10H), 0.90 (t, J=6.8 Hz, 3H). $^{13}$C NMR ($CD_3OD$) δ 165.8, 145.8, 129.0, 124.2, 122.7, 116.8, 117.0, 116.8, 89.5 (d, J=174 Hz), 67.4, 60.1 (d, J=21 Hz), 54.5, 43.8 (d, J=23 Hz), 36.2, 35.4, 32.0, 31.9, 28.9, 22.8, 13.2.

The product was dissolved in diethyl ether and oxalic acid (1.1 equiv) dissolved in diethyl ether was added. The formed crystals were filtered and washed with acetone to give the title compound as oxalic salt (0.037 g). HPLC-MS (ammonium acetate) $[M+H]^+$=349.3.

(S)-4-[3-(4-Butyl-piperidin-1-yl)-2-methyl-propyl]-4H-benzo[1,4]oxazin-3-one (108LM53-50)

A 4 ml vial was charged with crude (R)-4-(3-iodo-2-methyl-propyl]-4H-benzo[1,4]oxazin-3-one (108LM46-43) (0.312 g) and 4-butyl-piperidine (0.210 g, 1.49 mmol) in dry MeCN (½ ml) and shaken at 60° C. for 3 days. The reaction mixture was quenched with water (1 ml), and the product extracted into EtOAc (2×1 ml). The combined organic layers were added a cation exchange column. The column was washed with MeOH (2 column volumes) then the product was eluded of the column using 8% ammonium hydroxide in MeOH (2 column volumes). The product was purified by flash CC ($SiO_2$; MeOH/DCM 1:20) to give the title compound (108LM53-50) (0.193 g, 17%-3 steps). $^1$H NMR ($CDCl_3$) δ 7.18 (d, J=7.8 Hz, 1H), 7.03-6.96 (m, 3H), 4.58 (ABq, J=14.3 Hz, J=33.9 Hz, $CH_2$), 4.05-3.90 (m, 2H), 2.88 (bd, J=10.4 Hz, 1H), 2.71 (bd, J=10.4 Hz, 1H), 2.25-2.01 (m, 3H), 2.00-1.92 (m, 1H), 1.83-1.75 (m, 1H), 1.68-1.56 (m, 2H), 1.33-1.12 (m, 9H), 0.95-0.85 (m, 6H); $^{13}$C NMR ($CDCl_3$) δ 164.9, 145.7, 128.9, 123.8, 122.7, 117.2, 115.8, 67.8, 64.2, 55.8, 54.4, 45.4, 36.6, 36.1, 33.0, 32.8, 29.3, 23.2, 17.1, 14.4; HPLC-MS (ammonium acetate) $[M+H]^+$=345.3.

(R)-4-[3-(4-Butylpiperidin-1-yl)-2-methylpropyl]-4H-benzo[1,4]oxazin-3-one (108LM22-20)

The compound (S)-4-(3-Iodo-2-methyl-propyl]-4H-benzo[1,4]oxazin-3-one (108LM27-24) (0.063 g, 0.19 mmol) and 4-butyl-piperidine (0.053 g, 0.38 mmol) in MeCN (12 mL) were reacted according to GP10 shaking at 50° C. for 1 day and at 70° C. for 2 days. Purified by cation exchange CC and flash CC ($SiO_2$; MeOH/DCM 1:50) to give the title compound (108LM22-20) (0.051 g, 79%). $^1$H NMR ($CDCl_3$) δ 7.18-7.15 (m, 1H), 7.02-6.96 (m, 3H), 4.60 (ABq, J=15.0 Hz, J=31.3 Hz, $CH_2$), 3.99 (dd, J=8.1 Hz, 13.8 Hz, 1H), 3.92 (dd, J=5.0 Hz, 13.8 Hz, 1H), 2.88 (bd, J=10.0 Hz, 1H), 2.72 (bd, J=10.0 Hz, 1H), 2.26-2.02 (m, 3H), 2.00-1.92 (m, 1H), 1.85-1.75 (m, 1H), 1.70-1.59 (m, 2H), 1.32-1.14 (m, 9H), 0.92-0.85 (m, 6H); HPLC-MS (ammonium acetate) $[M+H]^+$=345.3.

General Procedure 14 (GP14)

A 4 mL vial was charged with the appropriate heterocycle (1 equiv) and the appropriate piperidine (1.1 equiv) and shaken at 60° C. for 2 days. $Et_3N$ (12 mL) was added and shaking was continued for 1 day. The reaction mixture was quenched with water (1 mL), and $Et_2O$ (1 mL) and sodium hydroxide (until pH 10) were added. The product was extracted into $Et_2O$ (2×1 mL). The combined organic layers were dried over $Na_2SO_4$, and concentrated. The product was purified by cation exchange CC followed by flash CC ($Si_2O$; MeOH/DCM 1:50).

(R)-4-[2-Methyl-3-(4-propoxypiperidin-1-yl)propyl]-4H-benzo[1,4]oxazin-3-one (108LM32-29)

The compound (S)-4-(3-Iodo-2-methyl-propyl]-4H-benzo[1,4]oxazin-3-one (108LM27-24) (0.202 g, 0.61 mmol) and 4-propoxy-piperidine (79KS66) (0.097 g, 0.67 mmol) in MeCN (½ mL) were reacted according to GP14 to give the title compound (108LM32-29) (0.136 g, 65%). $^1$H NMR ($CDCl_3$) δ 7.15 (bd, J=7.3 Hz, 1H), 7.03-6.95 (m, 3H), 4.60 (ABq, J=13.9 Hz, J=31.6 Hz, $CH_2$), 4.05-3.90 (m, 2H), 3.48 (t, J=7.0 Hz, $CH_2$), 3.28-3.20 (m, 1H), 2.79 (bs, 1H), 2.63 (bs, 1H), 2.27-2.11 (m, 3H), 2.10-1.93 (m, 2H), 1.92-1.83 (m, 2H), 1.63-1.52 (m, 4H), 0.94-0.86 (m, 6H); $^{13}$C NMR ($CDCl_3$) δ 164.5, 145.4, 128.5, 123.4, 122.3, 116.9, 115.2, 75.0, 69.4, 67.4, 63.2, 52.5, 51.5, 45.0, 31.6, 31.5, 29.1, 23.1, 16.6, 10.5; HPLC-MS (ammonium acetate) $[M+H]^+$=347.3.

(R)-4-[3-(4-Butylidenepiperidin-1-yl)-2-methylpropyl]-4H-benzo[1,4]oxazin-3-one (108LM33-30)

The compound (S)-4-(3-Iodo-2-methyl-propyl]-4H-benzo[1,4]oxazin-3-one (108LM27-24) (0.441 g, 1.33 mmol) and 4-butylidenepiperidine (111MF05) (0.204 g, 1.47 mmol) in MeCN (12 mL) were reacted according to GP14 to give the title compound (108LM33-30) (0.293 g, 64%). $^1$H NMR (CDCl$_3$) δ 7.19 (bd, J=7.0 Hz, 1H), 7.04-6.97 (m, 3H), 5.13 (t, J=7.9 Hz, CH), 4.60 (ABq, J=14.1 Hz, J=16.2 Hz, CH$_2$), 4.00 (d, J=7.0 Hz, CH$_2$), 2.50-2.38 (m, 2H), 2.35-2.05 (m, 9H), 1.95 (dt, J=7.0 Hz, CH$_2$), 1.50-1.40 (m, 2H), 0.94-0.86 (m, 6H); $^{13}$C NMR (CDCl$_3$) δ 165.0, 145.8, 136.3, 128.9, 123.8, 122.8, 122.7, 117.3, 115.7, 67.9, 63.7, 56.5, 55.7, 45.5, 36.4, 29.4, 28.6, 23.4, 17.1, 13.9; HPLC-MS (ammonium acetate) [M+H]$^+$=343.3.

General Procedure 15 (GP15)

A 7 mL vial was charged with the appropriate heterocycle (1 equiv) and the appropriate piperidine (1.1 equiv) in Et$_3$N (½ mL) and shaken at 60° C. for 4 days. The reaction mixture was quenched with water (1 mL), and Et$_2$O (1 mL) and sodium hydroxide (until pH 10) were added. The product was extracted into Et$_2$O (10×1 mL) and EtOAc (10×1 mL). The combined organic layers were dried (Na$_2$SO$_4$), and concentrated. The product was purified by cation exchange CC followed by flash CC (Si$_2$O; MeOH/DCM 1:20).

(R)-4-[3-(3-Butyl-8-aza-bicyclo[3.2.1]oct-8-yl)-2-methylpropyl]-4H-benzo[1,4]oxazin-3-one (108LM38-35)

The compound (S)-4-(3-Iodo-2-methylpropyl]-4H-benzo[1,4]oxazin-3-one (108LM27-24) (0.092 g, 0.28 mmol) and 3-butyl-8-aza-bicyclo[3.2.1]octane (104KS29) (0.051 g, 0.31 mmol) in Et$_3$N (½ mL) were reacted according to GP15 to give the title compound (108LM38-35) (0.068 g, 64%). $^1$H NMR (CDCl$_3$) δ 7.32 (d, J=6.7 Hz, 1H), 7.03-6.95 (m, 3H), 4.60 (ABq, J=7.2 Hz, J=10.8 Hz, CH$_2$), 4.12-4.00 (m, 2H), 3.16 (bs, 1H), 3.07 (bs, 1H), 2.33 (dd, J=6.1 Hz, J=2.1 Hz, 1H), 2.12 (t, J=4.7 Hz, 1H), 2.01-1.78 (m, 2H), 1.58-1.40 (m, 5H), 1.38-1.13 (m, 9H), 0.92-0.84 (m, 6H); $^{13}$C NMR (CDCl$_3$) δ 164.9, 145.7, 128.9, 123.7, 122.7, 117.1, 116.2, 67.9, 61.8, 60.0, 58.1, 45.4, 38.7, 38.6, 37.1, 31.6, 29.4, 28.2, 27.4, 26.5, 23.1, 17.1, 14.3; HPLC-MS (ammonium acetate) [M+H]$^+$=371.3.

(R)-4-[2-Methyl-3-(3-pentyl-8-azabicyclo[3.2.1]oct-8-yl)propyl]-4H-benzo[1,4]oxazin-3-one (108LM39-36)

The compound (S)-4-(3-Iodo-2-methylpropyl]-4H-benzo[1,4]oxazin-3-one (108LM27-24) (0.083 g, 0.25 mmol) and 3-pentyl-8-aza-bicyclo[3.2.1]octane (104KS32-2) (0.051 g, 0.28 mmol) in Et$_3$N (½ mL) were reacted according to GP15 to give the title compound (108LM39-36) (0.061 g, 63%). $^1$H NMR (CDCl$_3$) δ 7.33-7.29 (m, 1H), 7.03-6.96 (m, 3H), 4.60 (ABq, J=14.8 Hz, J=37.1 Hz, CH$_2$), 4.14-4.00 (m, 2H), 3.13 (bs, 1H), 3.05 (bs, 1H), 2.63-2.50 (m, 1H), 2.17-2.03 (m, 3H), 2.00-1.80 (m, 3H), 1.72-1.53 (m, 3H), 1.42-1.15 (m, 10H), 0.93-0.85 (m, 6H); $^{13}$C NMR (CDCl$_3$) δ 165.0, 145.7, 128.9, 123.7, 122.6, 117.1, 116.1, 67.9, 60.9, 58.9, 58.2, 45.3, 38.4, 37.0, 36.8, 32.2, 31.7, 28.5, 28.3, 27.2, 22.9, 17.1, 14.3; HPLC-MS (ammonium acetate) [M+H]$^+$=385.3.

General Procedure 16 (GP16)

A 7 mL vial charged with 4-(3-iodo-2-methylpropyl)-4H-benzo[1,4]oxazin-3-one (1.0 equiv) and amine (1.0 equiv) was shaken at 60° C. for 20 hours. The reaction mixture was added Et$_3$N (2.5 equiv) and shaken at 60° C. for 60-80 hours. The reaction mixture was concentrated, dissolved in 1 M NaOH (10 mL), extracted into CH$_2$Cl$_2$ (3×15 mL), and dried through a PTFF Whatman filter. The combined organic layers were concentrated and purified by cation exchange CC and CC (Heptane/EtOAc) or Prep HPLC.

(R)-6-Fluoro-4-[2-methyl-3-(4-propoxy-piperidin-1-yl)propyl]-4H-benzo[1,4]oxazin-3-one (108LM30-27)

The compound (S)-6-Fluoro-4-(3-iodo-2-methyl-propyl)-4H-benzo[1,4]oxazin-3-one (111MF04) (0.400 g, 1.15 mmol) and 4-propoxy-piperidine (79KS66) (0.332 g, 2.29 mmol) in MeCN (12 mL) were reacted according to GP10 shaking at 60° C. for 3 days and at 70° C. for 1 day. Purified by cation exchange CC and flash CC (SiO$_2$; MeOH/DCM 1:50-1:20) to give the title compound (108LM30-27) (0.263 g, 63%). $^1$H NMR (CDCl$_3$) δ 6.96 (dd, J=9.7 Hz, J=2.9 Hz, 1H), 6.91 (dd, J=8.9 Hz, J=4.9 Hz, 1H), 6.66 (dt, J=8.9 Hz, J=2.9 Hz, 1H), 4.56 (ABq, J=15.5 Hz, J=31.7 Hz, CH$_2$), 3.95 (dd, J=13.5 Hz, J=8.1 Hz, 1H), 3.88 (dd, J=13.5 Hz, J=4.7 Hz, 1H), 3.38 (t, J=6.7 Hz, CH$_2$), 3.32-3.23 (m, 1H), 2.79 (bs, 1H), 2.62 (bs, 1H), 2.26-2.12 (m, 3H), 2.19-1.95 (m, 2H), 1.94-1.84 (m, 2H), 1.66-1.53 (m, 4H), 0.95-0.85 (m, 6H); $^{13}$C NMR (CDCl$_3$) δ 164.9, 158.5 (d, J=952.8 Hz, 1H), 141.7 (d, J=9.2 Hz, 1H), 130.0 (d, J=42.4 Hz, 1H), 117.7 (d, J=38.4 Hz, 1H), 109.6 (d, J=93.2 Hz, 1H), 103.4 (d, J=114.4 Hz, 1H), 75.2, 69.8, 67.9, 63.7, 52.8, 52.0, 45.7, 31.8, 31.6, 29.5, 23.5, 17.1, 10.9; HPLC-MS (ammonium acetate) [M+H]$^+$=365.3.

(R)-4-[3-(4-Butylidenepiperidin-1-yl)-2-methylpropyl]-6-fluoro-4H-benzo[1,4]oxazin-3-one (111MF06)

The compound (S)-6-Fluoro-4-(3-iodo-2-methyl-propyl)-4H-benzo[1,4]oxazin-3-one (111MF04)_(0.718 g, 2.06 mmol) and 4-Butylidenepiperidine (0.301 g, 2.16 mmol) were mixed according to GP16. CC (SiO$_2$; Heptane/EtOAc 4:1-4) gave the title compound (111MF06) (0.40 g, 54%). $^1$HNMR(CDCl$_3$) δ 7.01 (dd, J=3.0 Hz, J=10.2 Hz, 1H), 6.90 (dd, J=5.4 Hz, J=8.6 Hz, 1H), 6.89-6.63 (m, 1H), 5.12 (t, J=7.4 Hz, 1H), 4.63-4.51 (m, 2H), 4.02-3.89 (m, 1H), 2.51-2.44 (m, 2H), 2.32-2.23 (m, 5H), 2.21-2.15 (m, 5H), 2.11-2.03 (m, 1H), 1.98-1.93 (m, 2H), 1.39-1.29 (m, 2H), 0.91-0.86 (m, 6H); $^{13}$C NMR (CDCl$_3$) δ 164.8, 158.5 (d, J=239.4 Hz), 141.6 (d, J=2.7 Hz), 136.2, 130.0 (d, J=10.8 Hz), 122.7, 117.6 (d, J=9.3 Hz), 109.5 (d, J=23.1 Hz), 103.4 (d, J=29.1 Hz), 67.8, 63.7, 56.6, 55.8, 45.7, 36.2, 29.4, 29.3, 28.4, 23.3, 17.0, 13.9.

To the pure compound (0.38 g, 1.0 mmol) dissolved in diethyl ether (4 mL) was added oxalic acid (0.104 g, 1.15 mmol) in diethyl ether (2 mL). The formed crystals filtered and washed with diethyl ether to give the title compound as oxalic salt (0.44 g, 92%); HPLC-MS (ammonium acetate) [M+H]$^+$=361.4

(R)-4-[3-(4-Butylpiperidin-1-yl)-2-methylpropyl]-6-fluoro-4H-benzo[1,4]oxazin-3-one The compound (S)-6-Fluoro-4-(3-iodo-2-methyl-propyl)-4H-benzo[1,4]oxazin-3-one (111MF04)_(0.873 g, 2.50 mmol) and 4-Butylpiperidine (0.371 g, 2.63 mmol) were mixed according to GP16. CC (SiO$_2$; Heptane/EtOAc 4:1-4) gave the title compound (111MF08) (0.53 g, 58%). $^1$H NMR (CDCl$_3$) δ 7.01 (d, J=10.0 Hz, 1H), 6.92-6.88 (m, 1H), 6.68-6.64 (m, 1H), 5.57 (q, J=32.4 Hz, J=15.2 Hz, 2H), 4.02-3.83 (m, 2H), 2.92-2.70 (m, 2H), 2.23-2.10 (m, 2H), 2.04-1.97 (m, 2H), 1.81 (t, J=10.8 Hz, 1H), 1.72-1.61 (m, 2H), 1.36-1.19 (m, 9H), 0.90-0.88 (m, 6H); $^{13}$C NMR (CDCl$_3$) δ 164.8, 158.5 (d, J=239.4 Hz), 141.6 (d, J=2.3 Hz), 130.0 (d, J=10.4 Hz), 117.6 (d, J=9.6 Hz), 109.4 (d, J=23.1 Hz), 103.5 (d, J=29.3 Hz), 67.8, 64.1, 56.0, 54.3, 45.7, 36.5, 36.0, 33.0, 32.5, 29.5, 29.2, 23.1, 17.1, 14.3.

To the pure compound (0.53 g, 1.5 mmol) dissolved in diethyl ether (4 mL) was oxalic acid (0.104 g, 1.15 mmol) in diethyl ether (2 mL). The formed crystals filtered and washed with diethyl ether to give the title compound as oxalic salt (0.614 g, 93%); HPLC-MS (ammonium acetate) [M+H]$^+$=363.3.

(R)-4-[3-(3-Butyl-8-azabicyclo[3.2.1]oct-8-yl)-2-methylpropyl]-6-fluoro-4H-benzo[1,4]oxazin-3-one (111MF26)

The compound (S)-6-Fluoro-4-(3-iodo-2-methyl-propyl)-4H-benzo[1,4]oxazin-3-one (111MF04) (0.219 g, 0.6 mmol) and 3-butyl-8-azabicyclo[3.2.1]octane (0.10 g, 0.6 mmol) were mixed according to GP16. CC (SiO$_2$; Heptane/EtOAc (4:1-4) gave the title compound (111MF26) (0.16 g, 58%). $^1$H NMR (CDCl$_3$) δ 7.16 (dd, J=2.8 Hz, J=10.0 Hz, 1H), 6.90 (dd, J=5.0 Hz, J=9.0 Hz, 1H), 6.69-6.63 (m, 1H), 4.58 (q, J=14.8 Hz, J=38.0 Hz, 2H), 4.10-3.93 (m, 2H), 3.16-3.06 (m, 2H), 2.33 (dd, J=4.0 Hz, J=12.8 Hz, 1H), 2.05 (t, J=11.6 Hz, 1H), 1.94-1.82 (m, 2H), 1.58-1.43 (m, 6H), 1.39-1.32 (m, 2H), 1.31-1.15 (m, 6H), 0.90-0.87 (m, 6H); $^{13}$C NMR (CDCl$_3$) δ 164.9, 158.5 (d, J=239.4 Hz), 141.6 (d, J=2.7 Hz), 130.0 (d, J=10.4 Hz), 117.5 (d, J=9.3 Hz), 109.4 (d, J=23.5 Hz), 103.9 (d, J=28.9 Hz), 67.8, 61.9, 60.1, 58.2, 45.6, 38.6, 38.5, 36.9, 31.8, 29.4, 28.2, 27.4, 26.5, 23.1, 17.1, 14.3.

To the pure compound (0.16 g, 0.41 mmol) dissolved in diethyl ether (4 mL) was added oxalic acid (0.039 g, 0.43 mmol) in diethyl ether (2 mL). The formed crystals filtered and washed with diethyl ether to give the title compound as oxalic salt (0.173 g, 88%); HPLC-MS (ammonium acetate) [M+H]$^+$=389.3

(R)-6-Fluoro-4-[2-methyl-3-(3-pentyl-8-azabicyclo[3.2.1]oct-8-yl)-propyl]-4H-benzo[1,4]oxazin-3-one (111MF27)

The compound (S)-6-Fluoro-4-(3-iodo-2-methylpropyl)-4H-benzo[1,4]oxazin-3-one (111MF04) (0.208 g, 0.6 mmol) and 3-Pentyl-8-azabicyclo[3.2.1]octane (0.10 g, 0.56 mmol) were mixed according to GP16. CC (SiO$_2$; Heptane/EtOAc 4:1-4) gave the title compound (111MF27) (0.16 g, 58%). $^1$H NMR (CDCl$_3$) δ 7.13 (dd, J=2.8 Hz, J=10.0 Hz, 1H), 6.90 (dd, J=5.2 Hz, J=8.8 Hz, 1H), 6.68-6.63 (m, 1H), 4.57 (q, J=14.8 Hz, J=40.0 Hz, 1H), 4.11-3.94 (m, 2H), 3.14-3.04 (m, 2H), 2.30 (dd, J=4.0 Hz, J=12.8 Hz, 1H), 2.20-2.09 (m, 2H), 2.06-2.00 (m, 1H), 1.95-1.82 (m, 3H), 1.71-1.52 (m, 3H), 1.40-1.34 (m, 2H), 1.32-1.19 (m, 8H), 0.89-0.85 (m, 6H); $^{13}$C NMR (CDCl$_3$) δ 164.9, 158.5 (d, J=239.4 Hz), 141.6 (d, J=2.6 Hz), 130.0 (d, J=10.8 Hz), 117.5 (d, J=9.3 Hz), 109.4 (d, J=23.4 Hz), 103.8 (d, J=28.9 Hz), 67.8, 61.0, 59.0, 58.2, 45.5, 38.4, 36.6, 36.5, 32.8, 31.8, 28.4, 28.4, 28.2, 27.2, 22.8, 7.0, 14.2.

To the pure compound (0.16 g, 0.41 mmol) dissolved in diethyl ether (4 mL) was added oxalic acid (0.039 g, 0.43 mmol) in diethyl ether (2 mL). The formed crystals filtered and washed with diethyl ether to give the title compound as oxalic salt (0.198 g, 97%); HPLC-MS (ammonium acetate) [M+H]$^+$=403.3

(R)-4-[3-(4-Butylpiperidin-1-yl)-2-methylpropyl]-7-Fluoro-4H-benzo[1,4]oxazin-3-one (112KK04)

A microwave vial was charged with (S)-7-fluoro-4-(3-Iodo-2-methylpropyl)-4H-benzo[1,4]oxazin-3-one (111MF20) (0.274 g, 0.78 mmol) and 4-butylpiperidine (0.226 g, 1.60 mmol) in MeCN (4 mL) and sealed. After microwave irradiation, 100° C., 60 min, the reaction mixture was purified by cation exchange CC followed by flash CC (SiO$_2$; CH$_2$Cl$_2$/MeOH 50:1) to give the title compound (112KK04) (0.180 g, 63%). $^1$H NMR (CD$_3$OD) δ 7.24-7.21 (m, 1H), 6.81-6.76 (m, 2H), 4.60 (ABq, J=17.4 Hz, J=15.1 Hz, CH$_2$), 3.98 (dd, J=14.3 Hz, J=5.9 Hz, 1H), 3.87 (dd, J=14.3 Hz, J=7.6 Hz, 1H), 2.86 (d, J=11.0 Hz, 1H), 2.73 (d, J=9.8 Hz, 1H), 2.28-2.23 (m, 1H), 2.16-2.08 (m, 2H), 1.93-1.81 (m, 2H), 1.79-1.62 (m 2H), 1.32-1.13 (m, 9H), 0.93-0.88 (m, 2 CH$_3$); $^{13}$C NMR (CD$_3$OD) δ 166.1, 160.3 (d, J=242.3 Hz), 148.1 (d, J=11.9 Hz), 126.4 (d, J=2.9 Hz), 117.8 (d, J=9.4 Hz), 109.9 (d, J=22.9 Hz), 105.7 (d, J=26.1 Hz), 68.6, 65.1, 56.3, 55.4, 46.6, 37.5, 37.0, 33.6, 33.4, 30.1, 29.9, 24.0, 17.2, 14.4.

The product was dissolved in MeOH/Et$_2$O and oxalic acid dissolved in Et$_2$O was added. The formed crystals were filtered and washed with acetone to give the title compound as oxalic salt (0.176 g). HPLC-MS (ammonium acetate) [M+H]$^+$=363.29.

(R)-7-Fluoro-4-[2-methyl-3-(4-propoxypiperidin-1-yl)propyl]-4H-benzo[1,4]oxazin-3-one (111MF28)

The compound (S)-7-Fluoro-4-(3-iodo-2-methylpropyl)-4H-benzo[1,4]oxazin-3-one (111MF20) (0.501 g, 1.43 mmol) and 4-propyloxypiperidine (0.205 g, 1.43 mmol) were mixed according to GP16. CC (SiO$_2$; Heptane/EtOAc 4:1-4) gave the title compound (111MF28) (0.375 g, 71%). $^1$H NMR (CDCl$_3$) δ 7.12-7.08 (m, 1H), 6.74-6.69 (m, 2H), 4.59 (q, J=15.0 Hz, J=31.0 Hz, 2H), 4.01-3.88 (m, 2H), 3.39 (t, J=6.8 Hz, 2H), 3.29-3.22 (m, 1H), 2.77 (t, J=6.3 Hz, 1H), 2.63 (t, J=5.6 Hz, 1H), 2-26-2.12 (m, 3H), 2.04-1.96 (m, 2H), 1.88-1.84 (m, 2H), 1.62-1.50 (m, 4H), 0.93-0.87 (m, 6H); $^{13}$C NMR (CDCl$_3$) δ 164.2, 158.9 (d, J=241.9 Hz), 146.5 (d, J=12.1 Hz), 125.2 (d, J=3.0 Hz), 116.1 (d, J=9.6 Hz), 109.0 (d, J=22.3 Hz), 105.2 (d, J=25.8 Hz), 75.2, 69.8, 67.8, 63.5, 52.8, 51.8, 45.5, 31.9, 31.8, 29.4, 23.5, 17.0, 10.8.

To the pure compound (0.375 g, 1.03 mmol) dissolved in diethyl ether (4 mL) was added oxalic acid (0.097 g, 1.08 mmol) in diethyl ether (2 mL). The formed crystals filtered and washed with diethyl ether to give the title compound as oxalic salt (0.41 g, 88%); HPLC-MS (ammonium acetate) [M+H]$^+$=365.3.

(R)-4-[3-(4-Butylidenepiperidin-1-yl)-2-methylpropyl]-7-fluoro-4H-benzo[1,4]oxazin-3-one (111MF29)

The compound (S)-7-Fluoro-4-(3-iodo-2-methylpropyl)-4H-benzo[1,4]oxazin-3-one (111MF20)_(0.515 g, 1.47 mmol) and 4-butylidenepiperidine (0.205 g, 1.47 mmol) were mixed according to GP16. CC (SiO$_2$; Heptane/EtOAc 4:1-4) gave the title compound (111MF29) (0.393 g, 73%). $^1$H NMR (CDCl$_3$) δ 7.17-7.12 (m, 1H), 6.74-6.69 (m, 2H), 5.15-5.11 (t, J=7.2 Hz, 1H), 4.61 (q, J=15.2 Hz, 2H), 4.04-3.92 (m, 2H), 2.48-2.40 (m, 2H), 2.32-2.13 (m, 9H), 1.96 (q, J=7.2 Hz, 2H), 1.38-1.30 (m, 2H), 0.91-0.86 (m, 6H); $^{13}$C NMR (CDCl$_3$) δ 164.1, 158.9 (d, J=243.4 Hz), 146.5 (d, J=11.9 Hz), 136.1, 125.2 (d, J=3.0 Hz), 128.9, 116.2 (d, J=22.7 Hz), 109.0 (d, J=22.7 Hz), 105.2 (d, J=26.2 Hz), 67.8, 63.7, 56.5, 55.7, 54.6, 36.3, 29.3, 28.5, 23.3, 17.1, 13.9.

To the pure compound (0.393 g, 1.09 mmol) dissolved in diethyl ether (4 mL) was added oxalic acid (0.103 g, 1.14 mmol) in diethyl ether (2 mL). The formed crystals filtered and washed with diethyl ether to give the title compound as oxalic salt (0.46 g, 94%); HPLC-MS (ammonium acetate) [M+H]$^+$=361.3.

(R)-4-[3-(3-Butyl-8-azabicyclo[3.2.1]oct-8-yl)-2-methylpropyl]-7-fluoro-4H-benzo[1,4]oxazin-3-one (112KK05)

A microwave vial was charged with (S)-7-fluoro-4-(3-Iodo-2-methylpropyl)-4H-benzo[1,4]oxazin-3-one (111MF20) (0.047 g, 0.13 mmol) and 3-butyl-8-azabicyclo [3,2,1]octane (0.039 g, 0.23 mmol) in MeCN (2 mL) and sealed. After microwave irradiation, 100° C., 60 min, the reaction mixture was purified by cation exchange CC followed by flash CC (SiO$_2$; CH$_2$Cl$_2$/MeOH 50:1) to give the title compound (112KK05) (0.017 g, 33%). $^1$H NMR (CD$_3$OD) δ 7.34-7.30 (m, 1H), 6.80-6.75 (m, 2H), 4.61 (ABq, J=18.8 Hz, J=15.1 Hz, CH$_2$), 4.04 (dd, J=14.3 Hz, J=5.9 Hz, 1H), 3.93 (dd, J=14.3 Hz, J=8.2 Hz, 1H), 3.18-3.10 (m, 2H), 2.36-2.23 (m, 2H), 2.03-1.85 (m, 3H), 1.62-1.45 (m, 5H), 1.36-1.14 (m, 8H), 0.92-0.87 (m, 2 CH$_2$); $^{13}$C NMR (CD$_3$OD) δ 166.2, 160.4 (d, J=242.3 Hz), 148.1 (d, J=11.9 Hz), 126.3 (d, J=2.9 Hz), 118.1 (d, J=9.7 Hz), 109.8 (d, J=22.9 Hz), 105.7 (d, J=26.5 Hz), 68.6, 62.5, 61.2, 58.3, 46.4, 39.0, 37.9, 32.1, 30.2, 29.0, 27.8, 27.2, 23.9, 17.2, 14.4.

The product was dissolved in MeOH/Et$_2$O and oxalic acid dissolved in Et$_2$O was added. The formed crystals were filtered and washed with acetone to give the title compound as oxalic salt (0.016 g). HPLC-MS (ammonium acetate) [M+H]$^+$=389.34.

(R)-7-Fluoro-4-[2-methyl-3-(3-pentyl-8-azabicyclo[3.2.1]oct-8-yl)-propyl]-4H-benzo[1,4]oxazin-3-one (111MF30)

The compound (S)-7-Fluoro-4-(3-iodo-2-methylpropyl)-4H-benzo[1,4]oxazin-3-one (111MF20) (0.208 g, 0.59 mmol) and 3-Pentyl-8-azabicyclo[3.2.1]octane (0.106 g, 0.58 mmol) were mixed according to GP16. CC (SiO$_2$; Heptane/EtOAc 4:1-4) and prep HPLC gave the title compound (111MF30) (0.070 g, 29%). $^1$H NMR (CDCl$_3$) δ 7.23-7.19 (m, 1H), 6.66-6.60 (m, 2H), 4.60-4.46 (m, 2H), 4.05-3.99 (m, 1H), 3.95-3.90 (m, 1H), 3.06-3.03 (m, 1H), 2.99-2.96 (m, 1H), 2.24-2.19 (m, 1H), 2.07-1.94 (m, 3H), 1.90-1.73 (m, 3H), 1.60-1.45 (m, 3H), 1.33-1.25 (m, 2H), 1.24-1.12 (m, 8H), 0.83-0.78 (m, 6H); $^{13}$C NMR (CDCl$_3$) δ 164.1, 158.8 (d, J=243.3 Hz), 146.4 (d, J=11.5 Hz), 125.1 (d, J=3.1 Hz), 116.6 (d, J=9.3 Hz), 108.9 (d, J=22.8 Hz), 105.0 (d, J=25.7 Hz), 67.7, 60.9, 58.8, 58.1, 45.4, 38.3, 36.8, 36.6, 32.1, 31.6, 28.5, 28.4, 28.1, 27.0, 22.8, 17.0, 14.2.

To the pure compound (0.070 g, 0.17 mmol) dissolved in diethyl ether (1 mL) was added oxalic acid (0.016 g, 0.18 mmol) in diethyl ether (1 mL). The formed crystals filtered and washed with diethyl ether to give the title compound as oxalic salt (0.082 g, 96%); HPLC-MS (ammonium acetate) [M+H]$^+$=402.56

(R)-4-[3-(4-Butylpiperidin-1-yl)-2-methyl-propyl]-6-methoxy-4H-benzo[1,4]oxazin-3-one (111MF38)

The compound (S)-4-(3-Iodo-2-methylpropyl)-6-methoxy-4H-benzo[1,4]oxazin-3-one (111MF36) (0.636 g, 1.77 mmol) and 4-butylpiperidine (0.226 g, 1.6 mmol) were mixed according to GP16. CC (SiO$_2$; Heptane/EtOAc 4:1-4) and prep HPLC gave the title compound (111MF38) (0.245 g, 27%). $^1$H NMR (CDCl$_3$) δ 6.89 (d, J=8.8 Hz, 1H), 6.72 (d, J=2.4 Hz, 1H), 6.50 (dd, J=2.8, J=8.8 Hz, 1H), 4.54 (q, J=32.4, J=14.8, 2H), 3.94-3.90 (m, 2H), 3.77 (s, 3H), 2.90 (d, J=11.2 Hz, 1H), 2.72 (d, J=10.8 Hz, 1H), 2.25-2.10 (m, 3H), 1.93 (t, J=11.2 Hz, 1H), 1.80 (t, J=11.2 Hz, 1H), 1.61 (d, J=10.8 Hz, 2H), 1.31-1.19 (m, 9H), 0.90-0.86 (m, 6H); $^{13}$C NMR (CDCl$_3$) δ 165.3, 155.5, 139.7, 129.8, 117.2, 107.1, 103.3, 68.0, 64.2, 55.9, 55.7, 54.5, 45.5, 36.5, 36.0, 32.9, 32.5, 29.2, 29.2, 23.1, 16.9, 14.3.

To the pure compound (0.245 g, 0.65 mmol) dissolved in diethyl ether (2 mL) was added oxalic acid (0.062 g, 0.68 mmol) in diethyl ether (2 mL). The formed crystals filtered and washed with diethyl ether to give the title compound as oxalic salt (0.229 g, 75%) HPLC-MS (ammonium acetate) [M+H]$^+$=375.3.

(R)-4-[3-(4-Butylidenepiperidin-1-yl)-2-methylpropyl]-6-methoxy-4H-benzo[1,4]oxazin-3-one (111MF39)

The compound (S)-4-(3-Iodo-2-methylpropyl)-6-methoxy-4H-benzo[1,4]oxazin-3-one (111MF36) (0.612 g, 1.69 mmol) and 4-butylidenepiperidine (0.212 g, 1.5 mmol) were mixed according to GP16. CC (SiO$_2$; Heptane/EtOAc 4:1-4) gave the title compound (111MF39) (0.489 g, 77%). $^1$H NMR (CDCl$_3$) δ 6.90 (d, J=8.4 Hz, 1H), 6.73 (d, J=2.8 Hz, 1H), 6.50 (dd, J=8.4 Hz, J=2.8 Hz, 1H), 5.11 (t, J=7.6 Hz, 1H), 4.54 (q, J=14.4 Hz, 2H), 3.97-3.94 (d, J=6.8 Hz, 2H), 3.78 (s, 3H), 2.48-2.41 (m, 2H), 2.33-2.23 (m, 5H), 2.20-2.13 (m, 4H), 1.96 (q, J=7.4 Hz, 2H), 1.40-1.29 (m, 2H), 0.91-0.86 (m, 6H); $^{13}$C NMR (CDCl$_3$) δ 165.3, 155.5, 139.8, 136.5, 129.8, 122.5, 117.2, 107.0, 103.4, 68.1, 63.8, 56.5, 56.0, 55.7, 45.5, 36.2, 29.3, 29.2, 28.4, 23.3, 16.9, 13.9; HPLC-MS; (ammonium acetate) [M+H]$^+$=373.3.

(R)-4-[3-(3-Butyl-8-azabicyclo[3.2.1]oct-8-yl)-2-methylpropyl]-6-methoxy-4H-benzo[1,4]oxazin-3-one (111MF40)

The compound (S)-4-(3-Iodo-2-methylpropyl)-6-methoxy-4H-benzo[1,4]oxazin-3-one (111MF36) (0.239 g, 0.66 mmol) and 3-Butyl-8-azabicyclo[3.2.1]octane (0.100 g, 0.60 mmol) were mixed according to GP16. CC (SiO$_2$; Heptane/EtOAc 4:1-4) gave the title compound (111MF40) (0.163 g, 61%). $^1$H NMR (CDCl$_3$) δ 6.88 (d, J=8.8 Hz, 1H), 6.85 (d, J=2.8 Hz, 1H), 6.49 (dd, J=8.8 Hz, J=2.8 Hz, 1H), 4.61-4.47 (m, 2H), 4.01-3.99 (m, 2H), 3.77 (s, 3H), 3.17-3.04 (m, 2H), 2.35-2.29 (m, 1H), 2.14-1.79 (m, 3H), 1.57-1.13 (m, 6H), 0.88 (m, 3H); $^{13}$C NMR (CDCl$_3$) δ 165.4, 155.6, 139.8, 129.8, 117.1, 107.0, 103.8, 68.0, 61.6, 60.2, 58.1, 56.0, 45.4, 38.5, 38.4, 36.9, 31.6, 29.4, 28.2, 27.3, 26.5, 23.9, 14.3; HPLC-MS (ammonium acetate) [M+H]$^+$=401.3.

(R)-6-Methoxy-4-[2-methyl-3-(3-pentyl-8-aza-bicyclo[3.2.1]oct-8-yl)propyl]-4H-benzo[1,4]oxazin-3-one (111MF41)

The compound (S)-4-(3-Iodo-2-methylpropyl)-6-methoxy-4H-benzo[1,4]oxazin-3-one (111MF36) (0.226 g, 0.63 mmol) and 3-pentyl-8-azabicyclo[3.2.1]octane (0.101 g, 0.56 mmol) were mixed according to GP16. CC (SiO$_2$; heptane/EtOAc 4:1-4) and prep HPLC gave the title compound (111MF41) (0.101 g, 39%). $^1$H NMR (CDCl$_3$) δ 6.89 (d, J=8.8 Hz, 1H), 6.81 (d, J=2.8 Hz, 1H), 6.49 (dd, J=8.8 Hz, J=2.8 Hz, 1H), 4.60-4.46 (m, 2H), 4.01 (d, J=6.8 Hz, 2H), 3.77 (s, 3H), 3.15-3.02 (m, 2H), 2.32-2.26 (m, 1H), 2.20-1.79 (m; 7H), 1.68-1.51 (m, 3H), 1.42-1.16 (m, 10H), 0.89-0.85 (m, 6H); $^{13}$C NMR (CDCl$_3$) δ 168.4, 155.6, 139.8, 129.8, 117.0, 106.9, 103.8, 68.0, 60.6, 59.1, 58.1, 56.0, 45.3, 39.4, 36.6, 36.4, 32.2, 31.5, 28.4, 28.4, 28.0, 27.3, 22.8, 16.8, 14.2; HPLC-MS (ammonium acetate) [M+H]$^+$=415.3.

(R)-6-Methoxy-4-[2-methyl-3-(4-propoxypiperidin-1-yl)propyl]-4H-benzo[1,4]oxazin-3-one (111MF42)

The compound (S)-4-(3-Iodo-2-methylpropyl)-6-methoxy-4H-benzo[1,4]oxazin-3-one (111MF36) (0.556 g, 1.5 mmol) and 4-propyloxypiperidine (0.20 g, 1.4 mmol) were mixed according to GP16. CC (SiO$_2$; Heptane/EtOAc 4:1-4) gave the title compound (111MF42) (0.30 g, 53%). $^1$H NMR (CDCl$_3$) δ 6.89 (d, J=8.8 Hz, 1H), 6.85 (d, 2.8 Hz, 1H), 6.49 (dd, J=8.8 Hz, J=2.8 Hz, 1H), 4.53 (q, J=14.6 Hz, 2H), 3.93 (d, J=6.6 Hz, 2H), 3.77 (s, 3H), 3.38 (t, J=6.8 Hz, 2H), 3.29-3.22 (m, 1H), 2.80-2.77 (t, 6.4 Hz, 1H), 2.65-2.61 (t, J=6.0 Hz, 1H), 2.29-2.00 (m, 5H), 1.88-1.84 (m, 2H), 1.65-1.53 (m, 4H), 0.94-0.87 (m, 6H); $^{13}$C NMR (CDCl$_3$) δ 165.4, 155.5, 139.8, 129.8, 117.2, 107.1, 103.3, 75.1, 69.7, 68.0, 63.7, 56.0, 52.5, 51.9, 45.4, 31.6, 31.5, 29.2, 23.5, 16.9, 10.8; HPLC-MS (ammonium acetate) [M+H]$^+$=377.3.

General Procedure 17 (GP17)

A 7 mL vial was charged with the crude 4-(3-iodo-2-methylpropyl)-6-methyl-4H-benzo[1,4]oxazin-3-one (1 equiv), Et$_3$N (0.5 mL) and the secondary amine (1.2-1.5 equiv). This mixture was shaken at 60° C. for 72 h and thereafter diluted with MeOH (10 mL) and concentrated with basic Al$_2$O$_3$ (2 g) and purified by flash chromatography.

(R)-6-Methyl-4-[2-methyl-3-(4-propoxypiperidin-1-yl)-propyl]-4H-benzo[1,4]oxazin-3-one (101IS69)

Crude (S)-4-(3-iodo-2-methylpropyl)-6-methyl-4H-benzo[1,4]oxazin-3-one (0.23 g), 4-propyloxypiperidine (0.12 g, 0.81 mmol) and Et$_3$N (0.5 mL) were reacted according to GP17. Flash CC (SiO$_2$; CH$_2$Cl$_2$/acetone/MeOH 90:5:5) gave the title compound (0.20 g, 83%). $^1$H NMR (CD$_3$OD) δ 6.97 (brs, 1H), 6.79 (d, J=8.0 Hz, 1H), 6.75 (dm, J=8.0 Hz, 1H), 4.47 (brs, 2H), 3.97 (dd, J=6.4, 14.4 Hz, 1H), 8.82 (dd, J=7.2, 14.4 Hz, 1H), 3.44 (brs, 1H), 3.33 (t, J=6.8 Hz, 2H), 3.10-2.90 (m, 2H), 2.90-2.6 (m, 3H), 2.29 (m, 1H), 2.24 (s, 3H), 1.98-1.86 (m, 2H), 1.78-1.64 (m, 2H), 1.47 (tq, J=14.4, 7.2 Hz, 2H), 0.92 (d, J=6.4 Hz), 0.83 (t, J=7.2 Hz); $^{13}$C NMR (CD$_3$OD) δ 166.4, 143.8, 132.8, 128.3, 124.7, 116.7, 116.1, 69.9, 67.4, 61.5, 50.7, 50.5, 44.1, 28.9, 28.6, 23.0, 20.0 15.6, 9.8.

The product was dissolved in diethyl ether and oxalic acid (1.1 equiv) dissolved in diethyl ether was added. The formed crystals were filtered and washed with acetone to give the title compound as oxalic salt (0.204 g). HPLC-MS (ammonium acetate) [M+H]$^+$=361.3.

(R)-4-[3-(4-Butylidenepiperidin-1-yl)-2-methylpropyl]-6-methyl-4H-benzo[1,4]oxazin-3-one (101IS71-A)

Crude (S)-4-(3-iodo-2-methylpropyl)-6-methyl-4H-benzo[1,4]oxazin-3-one (0.34 g), Et$_3$N (0.5 mL) and 4-butylidenepiperidine (0.17 g, 1.2 mmol) were reacted according to GP17. Flash CC (SiO$_2$; CH$_2$Cl$_2$/acetone/MeOH 90:7:3) gave the title compound (0.22 g, 58%). $^1$H NMR (CD$_3$OD) δ 7.01 (s, 1H), 6.86 (d, J=8.0 Hz, 1H), 6.82 (dm, J=8.0 Hz, 1H), 5.12 (t, J=7.2 Hz, 1H), 4.52 (ABq, J=14.8, 20.8 Hz, 2H), 4.03 (dd, J=5.6, 14.4 Hz, 1H), 3.91 (dd, J=8.0, 14.4 Hz, 1H), 2.48-2.34 (m, 2H), 2.33-2.11 (m, 8H), 2.31 (s, 3H), 1.96 (q, J=7.2 Hz, 2H), 1.34 (m, 2H), 0.91-0.86 (m, 6H); $^{13}$C NMR (CD$_3$OD) δ 165.9, 143.9, 136.0, 132.4, 128.3, 124.3, 122.4, 116.6, 116.2, 67.4, 63.6, 56.3, 55.4, 45.0, 28.92, 28.85, 28.0, 23.0, 20.0, 15.9, 12.8.

The product was dissolved in diethyl ether and oxalic acid (1.1 equiv) dissolved in diethyl ether was added. The formed crystals were filtered and washed with acetone to give the title compound as oxalic salt (0.236 g). HPLC-MS (ammonium acetate) [M+H]$^+$=367.3.

(R)-4-[3-(4-Butylpiperidin-1-yl)-2-methylpropyl]-6-methyl-4H-benzo[1,4]oxazin-3-one (101IS71-D)

Crude (S)-4-(3-iodo-2-methylpropyl)-6-methyl-4H-benzo[1,4]oxazin-3-one (0.30 g), Et$_3$N (0.5 mL) and 4-butylpiperidine (0.15 g, 1.0 mmol) were reacted according to GP17. Flash CC (SiO$_2$; CH$_2$Cl$_2$/acetone/MeOH 90:7:3) gave the title compound (0.26 g, 84%). $^1$H NMR (CD$_3$OD) δ 7.00 (s, 1H), 6.86 (d, J=8.0 Hz, 1H), 6.81 (dm, J=8.0 Hz, 1H), 4.52 (ABq, J=14.4, 20.8 Hz, 2H), 3.99 (dd, J=6.0, 14.4 Hz, 1H), 3.90 (dd, J=8.4, 14.4 Hz, 1H), 2.97 (brd, J=11.2 Hz, 1H), 2.82 (brd, J=8.4 Hz, 1H), 2.39-2.10 (m, 2H), 2.31 (s, 3H), 2.07-1.88 (m, 2H), 1.73-1.62 (m, 2H), 1.35-1.18 (m, 9H), 0.94-0.08 (m, 6H); $^{13}$C NMR (CD$_3$OD) δ 166.0, 143.8, 132.4, 128.3, 124.3, 116.6, 116.2, 67.4, 63.6, 55.0, 54.2, 44.8, 36.2, 35.6, 32.1 (br), 28.9, 28.8, 22.8, 20.0, 15.9, 13.2.

The product was dissolved in diethyl ether and oxalic acid (1.1 equiv) dissolved in diethyl ether was added. The formed crystals were filtered and washed with acetone to give the title compound as oxalic salt (0.253 g). HPLC-MS (ammonium acetate) [M+H]$^+$=359.3.

(R)-4-[3-(3-Butyl-8-azabicyclo[3.2.1]oct-8-yl)-2-methylpropyl]-6-methyl-4H-benzo[1,4]oxazin-3-one (101IS71-B3)

Crude (S)-4-(3-iodo-2-methylpropyl)-6-methyl-4H-benzo[1,4]oxazin-3-one (0.19 g, 0.54 mmol), Et$_3$N (0.5 mL) and 3-butyl-8-azabicyclo[3.2.1]octane (0.10 g, 0.61 mmol) were reacted according to GP17. Flash CC (SiO$_2$; CH$_2$Cl$_2$/i-PrOH 92:8) gave the title compound (0.13 g, 62%). $^1$H NMR (CD$_3$OD) δ 7.05 (s, 1H), 6.86 (d, J=8.4 Hz, 1H), 6.81 (dm, J=8.4 Hz, 1H), 4.52 (ABq J=14.8, 24.8 Hz, 2H), 4.05 (dd, J=5.6, 14.0 Hz, 1H), 3.94 (dd, J=8.8, 14.0 Hz, 1H), 3.05-3.16 (m, 2H), 2.35-2.14 (m, 2H), 2.31 (s, 3H), 2.05-1.78 (m, 3H), 1.63-1.40 (m, 5H), 1.36-1.12 (m, 5H), 0.99 (d, J=6.4 Hz, 3H), 0.90 (t, J=6.8 Hz, 3H); $^{13}$C NMR (CD$_3$OD) δ 167.4, 144.9, 133.7, 129.2, 125.6, 117.7, 117.3, 68.5, 63.2 (br), 62.5(br), 56.0(Br), 43.3, 37.8 (br), 31.3, 30.5, 30.0, 28.3, 26.7, 26.4, 23.7, 21.0, 16.8, 14.2.

The product was dissolved in diethyl ether and oxalic acid (1.1 equiv) dissolved in diethyl ether was added. The formed crystals were filtered and washed with acetone to give the title compound as oxalic salt (0.104 g). HPLC-MS (ammonium acetate) [M+H]$^+$=349.3.

(R)-4-[3-(3-Pentyl-8-azabicyclo[3.2.1]oct-8-yl)-2-methylpropyl]-6-methyl-4H-benzo[1,4]oxazin-3-one (101IS71-C3)

Crude (S)-4-(3-Iodo-2-methylpropyl)-6-methyl-4H-benzo[1,4]oxazin-3-one (0.15 g), Et$_3$N (0.5 mL) and 3-pentyl-8-azabicyclo[3.2.1]octane (95 mg, 5.2 mmol) were reacted according to GP17. Flash CC (SiO$_2$; CH$_2$Cl$_2$/I-PrOH 92:8) gave the title compound (0.12 g, 68%). $^1$H NMR (CD$_3$OD) δ 7.06 (s, 1H), 6.86 (d, J=8.0 Hz, 1H), 6.81 (brd, J=8.0 Hz, 1H), 4.52 (ABq, J=14.8, 27.2 Hz, 2H), 4.06 (dd, J=5.6, 14.2 Hz, 1H), 4.96 (dd, J=8.8, 14.2 Hz, 1H), 3.16-3.02 (m, 2H), 2.34-2.07 (m, 7H), 2.31(s, 3H), 2.04-1.81 (m, 3H), 1.70-1.55 (m, 3H), 1.46-1.21 (m, 10H), 0.92-0.85 (m, 6H); $^{13}$C NMR (CD$_3$OD) δ 167.2, 145.1, 133.6, 129.4, 125.5, 117.7, 117.5, 68.7, 61.6, 60.2, 58.6, 46.1, 39.6, 37.2, 36.9, 33.1, 32.4, 29.6, 29.5, 28.5, 27.8, 23.7, 21.18, 17.0, 14.4.

The product was dissolved in diethyl ether and oxalic acid (1.1 equiv) dissolved in diethyl ether was added. The formed crystals were filtered and washed with acetone to give the title compound as oxalic salt (0.128 g). HPLC-MS (ammonium acetate) [M+H]$^+$=399.3.

1-[3-(4-Propoxypiperidin-1-yl)propyl]-3,4-dihydro-1H-quinolin-2-one (85LM32)

A 4 mL vial was charged with crude 1-(3-chloro-propyl)-3,4-dihydro-1H-quinolin-2-one (85LM31) (0.200 g), 4-propoxy-piperidine (79KS-66) (0.130 g, 0.897 mmol), potassium carbonate (0.247 g, 1.79 mmol) and sodium iodide (0.269 g, 1.79 mmol) in MeCN (2 mL) and shaken at 50° C. for 20 h. The reaction mixture was quenched with water (1 mL), and the product was extracted into EtOAc (3×1 mL). The combined organic layers were dried over Na$_2$SO$_4$, evaporated and purified by flash CC (SiO$_2$; MeOH/DCM 0:1-3:7) to give the title compound (85LM32) (0.012 g, total yield 3%). $^1$H NMR (CDCl$_3$) δ 7.25 (t, J=7.4 Hz, 1H), 7.18-7.08 (m, 2H), 6.98 (t, J=7.4 Hz, 1H), 3.98 (t, J=7.6 Hz, CH$_2$), 3.38 (t, J=6.8 Hz, CH$_2$), 3.35-3.25 (m, 1H), 2.87 (t, J=7.6 Hz, CH$_2$), 2.80-2.70 (m, 2H), 2.65-2.60 (m, 2H), 2.45-2.35 (m, 2H), 2.20-2.10 (m, 2H), 1.95-1.80 (m, 4H), 1.65-1.50 (m, 4H), 0.95 (t, J=7.6 Hz, CH$_3$); $^{13}$C NMR (CDCl$_3$) δ 170.2, 140.0, 128.2, 127.5, 126.6, 122.8, 115.3, 70.0, 56.0, 51.8, 40.5, 32.0, 31.5, 25.8, 25.2, 22.8, 10.7; HPLC-MS (ammonium acetate) [M+H]$^+$=331.3.

1-[3-(4-Butylpiperidin-1-yl)propyl]-6-fluoro-3,4-dihydro-1H-quinolin-2-one (92LH81)

A 4 mL vial was charged with 1-(3-chloropropyl)-6-fluoro-3,4-dihydro-1H-quinolin-2-one (92LH79) (0.090 g, 0.37 mmol), 4-butylpiperidine (0.078 g, 0.55 mmol), KI (0.091 g, 0.55 mmol), and K$_2$CO$_3$ (0.076 g, 0.55 mmol) in MeCN and shaken at 50° for 20 h. The reaction mixture was quenched with water, and the product extracted into EtOAc. The combined organic layers were dried over Na$_2$SO$_4$, filtered, and concentrated. The product was purified by flash CC (SiO$_2$; EtOAc) to give the title compound (92LH81) (0.090 g, 70%). $^1$H NMR (CD$_3$OD) δ 7.19-7.15 (m, 1H), 6.99-6.97 (m, 2H), 3.97 (t, J=6.4 Hz, CH$_2$), 2.90-2.87 (m, 4H), 2.59 (t, J=7.6 Hz, CH$_2$), 2.38 (t, J=7.6 Hz, CH$_2$); 1.96-1.78 (m, 4H), 1.67 (d, J=9.6 Hz, 2H), 1.29-1.22 (m, 9H), 0.90-0.88 (m, 3H); $^{13}$C NMR (CD$_3$OD) δ 172.1, 160.0 (d, J=241.8 Hz), 136.7 (d, J=2.3 Hz), 130.6 (d, J=7.7 Hz), 117.8 (d, J=8.1 Hz), 115.9 (d, J=23.1 Hz), 114.6 (d, J=22.7 Hz), 57.0, 55.0, 41.6, 37.4, 36.9, 33.1, 32.4, 30.1, 26.2, 25.5, 23.9, 14.4; HPLC-MS (ammonium acetate) [M+H]$^+$=347.33.

6-Fluoro-1-[3-(4-propoxypiperidin-1-yl)propyl]-3,4-dihydro-1H-quinolin-2-one (107LH70)

A 4 mL vial was charged with 1-(3-chloropropyl)-6-fluoro-3,4-dihydro-1H-quinolin-2-one (92LH79) (0.242 g, 1.00 mmol), 4-propoxypiperidine (0.143 g, 1.00 mmol), KI (0.250 g, 1.50 mmol), and K$_2$CO$_3$ (0.207 g, 1.50 mmol) in MeCN (2 mL) and shaken at 40° for 20 h. The reaction mixture was quenched with water, and the product extracted into EtOAc. The combined organic layers were dried over Na$_2$SO$_4$, filtered, and concentrated. The product was purified by flash CC (SiO$_2$; EtOAc, MeOH/EtOAc 1:4) to give the title compound (107LH70) (0.165 g, 47%). $^1$H NMR (CD$_3$OD) δ 7.19-7.15 (m, 1H), 7.01-6.97 (m, 2H), 3.96 (t, J=7.4 Hz, CH$_2$), 3.40 (t, J=6.6 Hz, CH$_2$), 3.35-3.30 (m, 3H), 2.88 (t, J=6.8 Hz, 2H), 2.76 (m, 2H), 2.60-2.57 (m, 2H), 2.43-2.39 (m, 2H), 2.22-2.17 (m, 2H), 1.90-1.78 (m, 4H), 1.61-1.50 (m, 4H), 0.91 (t, J=7.4 Hz, CH$_3$); $^{13}$C NMR (CD$_3$OD) δ 172.2, 160.0 (d, J=242.2 Hz), 136.7 (d, J=2.3 Hz), 130.6 (d, J=7.7 Hz), 117.8 (d, J=8.5 Hz), 115.9 (d, J=23.1 Hz), 114.64 (d, J=22.3 Hz), 75.6, 70.7, 56.5, 52.0, 41.6, 32.4, 31.8, 26.1, 25.5, 24.2, 11.0; HPLC-MS (ammonium acetate) [M+H$^+$]=349.30.

(R,S)-1-[3-(4-Butylpiperidin-1-yl)-2-methyl]propyl]-6-fluoro-3,4-dihydro-1H-quinolin-2-one (107LH71-1)

A 4 mL vial was charged with crude (R,S)-1-(3-chloro-2-methylpropyl)-6-fluoro-3,4-dihydro-1H-quinolin-2-one (107LH68) (0.154 g), 4-butylpiperidine (0.141 g, 1.0 mmol), KI (0.250 g, 1.5 mmol), and K$_2$CO$_3$ (0.207 g, 1.5 mmol) in DMF (2 mL) and shaken at 100° for 20 h. The reaction mixture was quenched with water, and the product extracted into EtOAc. The combined organic layers were dried over Na$_2$SO$_4$, filtered, and concentrated. The crude product was purified by cation exchange CC and flash CC (SiO$_2$; EtOAc) to give the title compound (107LH77-1) (0.069 g, total yield 13%). $^1$H NMR (CD$_3$OD) δ 7.22-7.18 (m, 1H), 7.00-6.93 (m, 1H), 3.94 (d, J=6.8 Hz, 2H), 2.91-2.86 (m, 3H), 2.74 (d, J=10.2 Hz, 1H), 2.62-2.58 (m, 2H), 2.24-2.02 (m, 3), 1.90-1.81 (m, 2H), 1.66-1.61 (m, 2H), 1.30-1.19 (m, 9H), 0.89 (t, J=6.6 Hz, CH$_3$), 0.86 (d, J=6.7 Hz, CH$_3$); $^{13}$C NMR(CD$_3$OD) δ 172.7, 160.0 (d, J=241.8 Hz), 136.7 (d, J=2.7 Hz), 130.9 (d, J=8.1 Hz), 118.4 (d, J=8.1 Hz), 115.9 (d, J=23.5 Hz), 114.4 (d, J=22.7 Hz), 65.0, 56.1, 55.6, 46.9, 37.5, 37.0, 33.5, 33.4, 32.6, 30.1, 30.1, 26.2, 24.0, 17.2, 14.4.

The product was dissolved in acetone and oxalic acid dissolved in acetone was added. The formed crystals were filtered and washed with acetone to give the title compound as oxalic salt (0.076 g). HPLC-MS (ammonium acetate) [M+H]$^+$=361.32.

(R,S)-6-Fluoro-1-[3-(4-propoxypiperidin-1-yl)-2-methylpropyl]-3,4-dihydro-1H-quinolin-2-one (107LH71-2)

A 4 mL vial was charged with crude (R,S)-1-(3-chloro-2-methylpropyl)-6-fluoro-3,4-dihydro-1H-quinolin-2-one (107LH68) (0.154 g), 4-propoxypiperidine (0.143 g, 1.0 mmol), KI (0.250 g, 1.5 mmol), and K$_2$CO$_3$ (0.207 g, 1.5 mmol) in DMF (2 mL) and shaken at 100° for 20 h. The reaction mixture was quenched with water, and the product extracted into EtOAc. The combined organic layers were dried over Na$_2$SO$_4$, filtered, and concentrated. The crude product was purified by cation exchange CC and flash CC (SiO$_2$; EtOAc) to give the title compound (107LH77-2) (0.053 g, total yield 10%). $^1$H NMR (CD$_3$OD) δ 7.23-7.19 (m, 1H), 7.00-6.95 (m, 1H), 3.95 (d, J=7.0 Hz, 2H), 3.41 (t, J=6.6 Hz, CH$_2$), 3.31-3.27 (m, 1H), 2.90 (t, J=6.6 Hz, 2H), 2.74-2.71 (m, 1H), 2.64-2.58 (m, 3H), 2.26-2.00 (m, 5H), 1.89-1.85 (m, 2H), 1.60-1.49 (m, 4H), 0.91 (t, J=7.4 Hz, CH$_3$), 0.86 (d, J=6.7 Hz, CH$_3$); $^{13}$C NMR (CD$_3$OD) δ 172.7, 160.0 (d, J=242.2 Hz), 136.7 (d, J=2.7 Hz), 130.9 (d, J=7.7 Hz), 118.3 (d, J=8.1 Hz), 115.9 (d, J=23.1 Hz), 114.5 (d, J=22.7 Hz), 76.4, 70.7, 64.4, 53.2, 52.8, 46.9, 32.5, 32.4, 32.3, 30.3, 26.17, 26.15, 24.2, 17.1, 11.0.

The product was dissolved in acetone and oxalic acid dissolved in acetone was added. The formed crystals were filtered and washed with acetone to give the title compound as oxalic salt (0.048 g). HPLC-MS (ammonium acetate) [M+H]$^+$=363.30.

1-[3-(4-Butylpiperidin-1-yl)propyl]-6-chloro-3,4-dihydro-1H-quinolin-2-one (107LH36)

A reaction flask was charged with 6-chloro-3,4-dihydro-1H-quinolin-2-one (107LH30) (0.100 g, 0.55 mmol) in dry DMF (2 mL) under Argon. NaH (60% in oil, 0.024 g, 0.60 mmol) was added and the mixture was stirred at rt for 0.5 h. Then 1-bromo-3-chloropropane (0.087 g, 0.55 mmol) was added followed by stirring at 30° for 20 h. The reaction mixture was quenched with water, and the product extracted into EtOAc. The combined organic layers were dried over $Na_2SO_4$, filtered, and concentrated. The crude material was dissolved in MeCN (3 mL) followed by addition of 4-butylpiperidine (0.078 g, 0.055 mmol), KI (0.166 g, 1.00 mmol), and $K_2CO_3$ (0.138 g, 1.00 mmol) and shaken at 50° for 2 days. The reaction mixture was quenched with water, and the product extracted into EtOAc. The combined organic layers were dried over $Na_2SO_4$, filtered, and concentrated. The product was purified by prep RP-HPLC to give the title compound (107LH36) (0.047 g, 24%). $^1H$ NMR $(CD_3OD)^-\delta$ 7.25-7.13 (m, 3H), 3.96 (t, J=7.2 Hz, $CH_2$), 2.95-2.86 (m, 4H), 2.61-2.57 (m, 2H), 2.45-2.41 (m, 2H), 2.04-1.98 (m, 2H), 1.87-1.79 (m, 2H), 1.28-1.18 (m, 9H), 0.90 (t, J=7.0 Hz, $CH_3$); $^{13}C$ NMR $(CD_3OD)$ δ 172.3, 139.2, 130.2, 129.3, 128.9, 128.4, 117.8, 56.8, 54.9, 41.4, 37.2, 36.6, 32.9, 32.4, 30.0, 26.0, 25.3, 23.9, 14.4; HPLC-MS (ammonium acetate) $[M+H^+]$=363.28.

1-[3-(4-Butylpiperidin-1-yl)propyl]-6-methyl-3,4-dihydro-1H-quinolin-2-one (107LH18-1)

A 4 mL vial was charged with crude 1-(3-chloropropyl)-6-methyl-3,4-dihydro-1H-quinolin-2-one (107LH14) (0.128 g), 4-butylpiperidine (0.076 g, 0.54 mmol), KI (0.166 g, 1.00 mmol), and $K_2CO_3$ (0.138 g, 1.00 mmol) in MeCN (2 mL) and shaken at 50° for 20 h. The reaction mixture was quenched with water, and the product extracted into EtOAc. The combined organic layers were dried over $Na_2SO_4$, filtered, and concentrated. The product was purified by flash CC ($SiO_2$; EtOAc, MeOH/EtOAc 1:4) to give the title compound (107LH18-1) (0.088 g, total yield 41%). $^1H$ NMR $(CD_3OD)$ δ 7.07-7.01 (m, 3H), 3.94 (t, J=7.4 Hz, $CH_2$), 2.90-2.80 (m, 4H), 2.57-2.53 (m, 2H), 2.39-2.33 (m, 2H), 2.27 (s, 3H, $CH_3$), 1.95-1.90 (m, 2H), 1.85-1.79 (m, 2H), 1.66 (d, J=9.8 Hz, 2H), 1.30-1.17 (m, 9H), 0.89 (t, J=6.8 Hz, $CH_3$); $^{13}C$ NMR $(CD_3OD)$ δ 172.4, 137.9, 134.1, 129.8, 129.0, 128.0, 116.3, 57.1, 55.0, 41.3, 37.4, 36.8, 33.1, 32.8, 30.1, 26.2, 25.5, 23.9, 20.7, 14.4; HPLC-MS (ammonium acetate) $[M+H^+]$=343.33.

6-Methyl-1-[3-(4-propoxypiperidin-1-yl)propyl]-3,4-dihydro-1H-quinolin-2-one (107LH18-2)

A 4 mL vial was charged with 1-(3-Chloropropyl)-6-methyl-3,4-dihydro-1H-quinolin-2-one (107LH14) (0.128 g), 4-propoxypiperidine (0.079 g, 0.54 mmol), KI (0.166 g, 1.0 mmol), and $K_2CO_3$ (0.138 g, 1.0 mmol) in MeCN (2 mL) and shaken at 50° for 20 h. The reaction mixture was quenched with water, and the product extracted into EtOAc. The combined organic layers were dried over $Na_2SO_4$, filtered, and concentrated. The product was purified by flash CC ($SiO_2$; EtOAc, MeOH/EtOAc 1:4) to give the title compound (107LH18-2) (0.108 g, total yield 50%). $^1H$ NMR $(CD_3OD)$ δ 7.05-7.00 (m, 3H), 3.95 (t, J=7.2, $CH_2$), 3.41-3.30 (m, 3H), 2.84-2.76 (m, 4H), 2.57-2.53 (m, 2H), 2.47-2.43 (m, 2H), 2.27 (s, 3H, $CH_3$), 2.27-2.22 (m, 2H), 1.90-1.81 (m, 4H), 1.63-1.52 (m, 4H), 0.91 (t, J=7.4 Hz, $CH_3$); $^{13}C$ NMR $(CD_3OD)$ δ 172.4, 137.8, 134.0, 129.8, 129.0, 128.0, 116.2, 75.3, 70.7, 56.5, 51.9, 41.2, 32.8, 31.7, 26.2, 25.5, 24.3, 20.7, 11.0; HPLC-MS (ammonium acetate) $[M+H^+]$=345.30.

1-[3-(4-Butylpiperidin-1-yl)propyl]-7-fluoro-3,4-dihydro-1H-quinolin-2-one (107LH21)

A reaction flask was charged with 7-fluoro-3,4-dihydro-1H-quinolin-2-one (97LH36) (0.080 g, 0.48 mmol) in dry DMF (2 mL) under Argon. NaH (60% in oil, 0.021 g, 0.53 mmol) was added and the mixture was stirred at rt for 0.5 h. Then 1-bromo-3-chloropropane (0.075 g, 0.48 mmol) was added followed by stirring at rt for 20 h. The reaction mixture was quenched with water, and the product extracted into EtOAc. The combined organic layers were dried over $Na_2SO_4$, filtered, and concentrated. The crude material was dissolved in MeCN (3 mL) followed by addition of 4-butylpiperidine (0.071 g, 0.50 mmol), KI (0.166 g, 1.00 mmol), and $K_2CO_3$ (0.138 g, 1.00 mmol) and shaken at 50° for 4 days. The reaction mixture was quenched with water, and the product extracted into EtOAc. The combined organic layers were dried over $Na_2SO_4$, filtered, and concentrated. The product was purified by flash CC ($SiO_2$; EtOAc) to give the title compound (107LH21) (0.062 g, 37%). $^1H$ NMR $(CD_3OD)$ δ 7.20-7.17 (m, 1H), 7.01-6.98 (m, 1H), 6.76-6.72 (m, 1H), 3.95 (t, J=7.4 Hz, $CH_2$), 2.93-2.84 (m, 4H), 2.61-2.57 (m, 2H), 2.42-2.38 (m, 2H), 2.00-1.94 (m, 2H), 1.84-1.80 (m, 2H), 1.68 (d, J=10.0 Hz, 2H), 1.30-1.22 (m, 9H), 0.89 (t, J=6.8 Hz, $CH_3$); HPLC-MS (ammonium acetate) $[M+H^+]$=347.31.

1-[3-(4-Butylpiperidin-1-yl)propyl]-5-methyl-3,4-dihydro-1H-quinolin-2-one (107LH28)

A 4 mL vial was charged with 1-(3-chloropropyl)-5-methyl-3,4-dihydro-1H-quinolin-2-one (107LH27-11,3) (0.057 g, 0.24 mmol), 4-butylpiperidine (0.042 g, 0.30 mmol), KI (0.083 g, 0.50 mmol), and $K_2CO_3$ (0.069 g, 0.50 mmol) in MeCN and shaken at 50°. The reaction mixture was quenched with water, and the product extracted into EtOAc. The combined organic layers were dried over $Na_2SO_4$, filtered, and concentrated. The product was purified by flash CC ($SiO_2$; EtOAc, MeOH/EtOAc 1:4) to give the title compound (107LH28) (0.060 g, 74%). $^1H$ NMR $(CD_3OD)$ δ 7.15 (t, J=8.0 Hz, 1H); 7.03 (d, J=8.2 Hz, 1H), 6.92 (d, J=7.4 Hz), 4.00 (t, J=7.2 Hz, $CH_2$), 3.10 (d, J=12.1 Hz, 2H), 2.87-2.83 (m, 2H), 2.66-2.62 (m, 2H) 2.59-2.55 (m, 2H), 2.31-2.25 (m, 2H), 2.29 (s, $CH_3$), 1.93-1.87 (m, 2H), 1.76 (d, J=11.7 Hz, 2H), 1.31-1.24 (m, 9H), 0.90 (t, J=6.8 Hz, $CH_3$); $^{13}C$ NMR $(CD_3OD)$ δ 172.7, 140.2, 137.0, 128.1, 126.6, 126.5, 114.5, 56.5, 54.6, 41.2, 37.0, 36.0, 32.2, 32.2, 30.0, 25.0, 23.9, 22.4, 19.7, 14.4; HPLC-MS (ammonium acetate) $[M+H^+]$=343.36.

1-[3-(4-Butylpiperidin-1-yl)propyl]-7-methyl-3,4-dihydro-1H-quinolin-2-one (107LH29)

A 4 mL vial was charged with 1-(3-chloropropyl)-7-methyl-3,4-dihydro-1H-quinolin-2-one (107LH27-13,1) (0.117 g, 0.49 mmol), 4-butylpiperidine (0.071 g, 0.50 mmol), KI (0.166 g, 1.00 mmol), and $K_2CO_3$ (0.138 g, 1.00 mmol) in MeCN and shaken at 50°. The reaction mixture was quenched with water, and the product extracted into EtOAc. The combined organic layers were dried over $Na_2SO_4$, filtered, and concentrated. The product was purified by flash CC ($SiO_2$; EtOAc, MeOH/EtOAc 1:4) to give the title compound (107LH28) (0.060 g, 74%). $^1H$ NMR δ 7.06 (d, J=7.4 Hz, 1H), 6.97 (s, 1H), 6.84 (d, J=7.6 Hz, 1H), 3.97 (t, J=7.4 Hz, $CH_2$), 2.91 (d, J=11.2 Hz, 2H), 2.82 (t, J=6.8 Hz, $CH_2$), 2.57-2.54 (m, 2H), 2.41-2.37 (m, 2H), 2.33 (s, $CH_3$), 1.98-1.92 (m, 2H), 1.87-1.79 (m, 2H), 1.68 (d, J=9.6 Hz, 2H), 1.30-1.17 (m, 9H), 0.89 (t, J=6.8 Hz, $CH_3$); $^{13}C$ NMR (CD₃OD) δ 172.7, 140.1, 138.5, 128.9, 125.1, 124.9, 117.0, 57.0, 55.0, 41.3, 37.3, 36.8, 33.1, 30.1, 25.8, 25.6, 23.9, 21.6, 14.4; HPLC-MS (ammonium acetate) [M+H]⁺=343.37.

1-[3-(4-Butylpiperidin-1-yl)propyl]-7-fluoro-6-methyl-3,4-dihydro-1H-quinolin-2-one (112KK06)

A 4 mL vial was charged with 1-(3-chloropropyl)-7-fluoro-6-methyl-3,4-dihydro-1H-quinolin-2-one (112KK01) (0.047 g, 0.18 mmol), 4-butylpiperidine (0.039 g, 0.28 mmol), NaI (0.100 g, 0.67 mmol), and K₂CO₃ (0.075 g, 0.54 mmol) in MeCN (2 mL) and shaken at 50° for 20 h. The reaction mixture was quenched with water, and the product extracted into EtOAc. The combined organic layers were purified by cation exchange CC followed by purification by flash CC (SiO₂; MeOH/DCM 1:10) to give the title compound (112KK06) (0.022 g, 34%). ¹H NMR (CD₃OD) δ 7.05 (d, J=8.4 Hz, 1H), 6.93 (d, J=11.7 Hz, 1H), 3.93 (t, J=7.2 Hz, CH₂), 2.93 (d, J=11.1 Hz, 2H), 2.83 (t, J=6.9 Hz, CH₂), 2.60-2.56 (m, 2H), 2.44-2.40 (m, 2H), 2.19 (D, J=1.8 Hz, CH₃) 2.03-1.98 (m, 2H), 1.86-1.79 (m, 2H), 1.69 (d, J=11.0 Hz, 2H), 1.31-1.19 (m, 9H), 0.89 (t, J=6.6 Hz, CH₃); ¹³C NMR (CD₃OD) δ 172.4, 161.7 (d, J=241.0 Hz), 139.5 (d, J=10.0 Hz), 131.7 (d, J=6.1 Hz), 123.5 (d, J=3.6 Hz), 119.9 (d, J=17.4 Hz), 104.0 (d, J=28.1 Hz), 56.8, 55.0, 41.5, 37.3, 36.7, 33.0, 32.8, 30.1, 25.5, 25.3, 23.9, 14.4, 13.7.

The product was dissolved in MeOH/Et₂O and oxalic acid dissolved in Et₂O was added. The formed crystals were filtered and washed with acetone to give the title compound as oxalic salt (0.018 g). HPLC-MS (ammonium acetate) [M+H]⁺=361.35.

1-[3-(4-Butylpiperidin-1-yl)propyl]-6,7-difluoro-3,4-dihydro-1H-quinolin-2-one (112KK07)

A 4 mL vial was charged with 1-(3-chloropropyl)-6,7-difluoro-3,4-dihydro-1H-quinolin-2-one (112KK03) (0.123 g, 0.47 mmol), 4-butylpiperidine (0.074 g, 0.52 mmol), NaI (0.100 g, 0.67 mmol), and K₂CO₃ (0.075 g, 0.54 mmol) in MeCN (2 mL) and shaken at 50° for 20 h. The reaction mixture was quenched with water, and the product extracted into EtOAc. The combined organic layers were purified by cation exchange CC followed by purification by flash CC (SiO₂; MeOH/DCM 1:10) to give the title compound (112KK07) (0.097 g, 57%). ¹H NMR (CD₃OD) δ 7.20-7.09 (m, 2H), 3.91 (t, J=7.2 Hz, CH₂), 2.90-2.82 (m, 4H), 2.59-2.55 (m, 2H), 2.38-2.34 (m, 2H), 1.97-1.91 (m, 2H), 1.82-1.75 (m, 2H), 1.66 (d, J=9.8 Hz, 2H), 1.28-1.16 (m, 9H), 0.87 (t, J=6.7 Hz, CH₃); ¹³C NMR (CD₃OD) δ 172.1, 150.4 (q, J=243.2 Hz, J=13.2 Hz), 146.9 (q, J=243.2 Hz, J=12.6 Hz), 137.3 (q, J=8.1 Hz, J=2.9 Hz), 124.9 (q, J=5.8 Hz, J=3.9 Hz), 117.6 (d, J=18.7 Hz), 106.4 (d, J=22.6 Hz), 56.8, 55.0, 41.8, 37.4, 36.8, 33.1, 32.4, 30.1, 25.5, 25.3, 23.9, 14.4.

The product was dissolved in MeOH/Et₂O and oxalic acid dissolved in Et₂O was added. The formed crystals were filtered and washed with acetone to give the title compound as oxalic salt (0.046 g). HPLC-MS (ammonium acetate) [M+H]⁺=365.32.

6,7-Difluoro-1-[3-(4-propoxypiperidin-1-yl)propyl]-3,4-dihydro-1H-quinolin-2-one (122LH7)

A 4 mL vial was charged with 1-(3-chloropropyl)-6,7-difluoro-3,4-dihydro-1H-quinolin-2-one (112KK03) (0.286 g, 1.1 mmol), 4-propoxypiperidine (0.160 g, 1.1 mmol), KI (0.250 g, 1.5 mmol), and K₂CO₃ (0.207 g, 1.54 mmol) in MeCN (2.5 mL) and shaken at 40° for 2 days. The reaction mixture was quenched with water, and the product extracted into EtOAc. The combined organic layers were dried over Na₂SO₄, filtered, and concentrated. The crude product was purified by cation exchange CC followed by flash CC (SiO₂; EtOAc) and then prep RP-HPLC to give the title compound (122LH07) (0.165 g, 41%). ¹H NMR (CD₃OD) δ 7.22-7.11 (m, 2H), 3.94 (t, J=7.2 Hz, CH₂), 3.42-3.35 (m, 3H), 2.89-2.83 (m, 4H), 2.62-2.51 (m, 4H), 2.40-2.36 (m, 2H), 1.95-1.82 (m, 4H), 1.69-1.51 (m, 4H), 0.91 (t, J=7.2 Hz, CH₃); ¹³C NMR (CD₃OD) δ 172.0, 150.3 (q, J=243.3 Hz, J=13.5 Hz), 146.9 (q, J=243.3 Hz, J=12.7 Hz), 137.3 (q, J=8.1 Hz, J=2.7 Hz), 124.9 (q, J=5.8 Hz, J=3.8 Hz), 117.6 (d, J=18.8 Hz), 106.3 (d, J=22.7 Hz), 74.8, 70.7, 56.1, 51.7, 41.5, 32.3, 31.4, 25.5, 25.1, 24.3, 11.0.

The product was dissolved in acetone and oxalic acid dissolved in acetone was added. The formed crystals were filtered and washed with acetone to give the title compound as oxalic salt (0.154 g). HPLC-MS (ammonium acetate) [M+H]⁺=367.25.

(R,S)-1-[3-(4-Butylpiperidin-1-yl)-2-methylpropyl]-6,7-difluoro-3,4-dihydro-1H-quinolin-2-one (122LH11-1)

A reaction flask was charged with 6,7-difluoro-3,4-dihydro-1H-quinolin-2-one (97KK47) (0.183 g, 1.0 mmol) in dry DMF (1 mL) under Argon. NaH (60% in oil, 0.050 g, 1.3 mmol) was added and the mixture was stirred at rt for 0.5 h. Then (R,S)-1-bromo-3-chloro-2-methylpropane (0.172 g, 1.0 mmol) was added followed by stirring at rt for 20 h. The reaction mixture was quenched with water, and the product extracted into EtOAc. The combined organic layers were dried over Na₂SO₄, filtered, and concentrated. After purification by flash CC (SiO₂; EtOAc/n-heptane 1:1), the crude product was solvated in DMF (0.5 mL) and added 4-butylpiperidine 0.085 g, 0.6 mmol), NaI (0.113 g, 0.075 mmol), and K₂CO₃ (0.104 g, 0.075 mmol) followed by stirring at 50° for 3 days. The reaction mixture was quenched with water, and the product extracted into EtOAc. The combined organic layers were dried over Na₂SO₄, filtered, and concentrated. The crude product was purified by cation exchange CC and prep RP-HPLC to give the title compound (122LH11-1). ¹H NMR (CD₃OD) δ 7.25-7.20 (m, 1H), 7.16-7.12 (m, 1H), 3.97 (dd, J=14.3 Hz, J=8.4 Hz, 1H), 3.85 (dd, J=14.5 Hz, J=5.1 Hz, 1H), 2.94-2.85 (m, 3H), 2.78 (d, J=9.4 Hz, 1H), 2.66-2.57 (m, 2H), 2.27-2.13 (m, 2H), 2.03-1.85 (m, 3H), 1.67-1.65 (m, 2H), 1.31-1.22 (m, 9H), 0.90 (t, J=6.6 Hz, CH₃), 0.87 (d, J=6.7 Hz, CH₃).

The crude product was dissolved in acetone and oxalic acid dissolved in acetone was added. The formed crystals were filtered and washed with acetone to give the title compound as oxalic salt (0.025 g, 7%). HPLC-MS (ammonium acetate) [M+H]⁺=379.27.

(R,S)-6,7-Difluoro-1-[3-(4-propoxypiperidin-1-yl)-2-methylpropyl]-3,4-dihydro-1H-quinolin-2-one (122LH11-2)

A reaction flask was charged with 6,7-difluoro-3,4-dihydro-1H-quinolin-2-one (97KK47) (0.183 g, 1.0 mmol) in dry DMF (1 mL) under Argon. NaH (60% in oil, 0.050 g, 1.3 mmol) was added and the mixture was stirred at rt for 0.5 h. Then (R,S)-1-bromo-3-chloro-2-methylpropane (0.172 g, 1.0 mmol) was added followed by stirring at rt for 20 h. The reaction mixture was quenched with water, and the product extracted into EtOAc. The combined organic layers were dried over Na₂SO₄, filtered, and concentrated. After purification by flash CC (SiO$_2$; EtOAc/n-heptane 1:1), the crude product was solvated in DMF (0.5 mL) and added 4-butylpiperidine 0.085 g, 0.6 mmol), NaI (0.113 g, 0.075 mmol), and K$_2$CO$_3$ (0.104 g, 0.075 mmol) followed by stirring at 50° for 3 days. The reaction mixture was quenched with water, and the product extracted into EtOAc. The combined organic layers were dried over Na$_2$SO$_4$, filtered, and concentrated. The crude product was purified by cation exchange CC and prep RP-HPLC to give the crude title compound (122LH11-2). $^1$H NMR (CD$_3$OD) δ 7.24-7.12 (m, 2H), 3.97 (dd, J=14.5 Hz, J=8.6 Hz, 1H), 3.87 (dd, J=14.3 Hz, J=5.1 Hz, 1H), 3.41 (t, J=6.7 Hz, CH$_2$), 3.35-3.28 (m, 1H), 2.89-2.85 (m, 2H), 2.78-2.75 (m, 1H), 2.66-2.59 (m, 3H), 2.26-2.21 (m, 1H), 2.17-2.11 (m, 2H), 2.07-1.97 (m, 2H), 1.90-1.86 (m, 2H), 1.61-1.51 (m, 4H), 0.92 (t, J=7.4 Hz, CH$_3$), 9.86 (d, J=6.6 Hz, CH$_3$); $^{13}$C NMR (CD$_3$OD) δ 172.5, 150.3 (q, J=242.9 Hz, J=13.1 Hz), 146.8 (q, J=243.3 Hz, J=13.1 Hz), 137.3 (q, J=8.1 Hz, J=2.7 Hz), 125.1 (q, J=5.8 Hz, J=3.8 Hz), 117.6 (d, J=18.8 Hz), 106.7 (d, J=22.7 Hz), 76.3, 70.9, 64.5, 53.4, 52.8, 47.1, 32.5, 32.4, 30.5, 25.5, 24.3, 17.2, 11.0.

The crude product was dissolved in acetone and oxalic acid dissolved in acetone was added. The formed crystals were filtered and washed with acetone to give the title compound as oxalic salt (0.030 g, 8%). HPLC-MS (ammonium acetate) [M+H]$^+$=381.27.

1-[3-(4-Butylpiperidin-1-yl)propyl]-6-fluoro-7-methyl-3,4-dihydro-1H-quinolin-2-one (107LH93-1)

A reaction flask was charged with 6-fluoro-7-methyl-3,4-dihydro-1H-quinolin-2-one (0.150 g, 0.84 mmol) in dry DMF (1 mL) under N$_2$. NaH (60% in oil, 0.038 g, 0.92 mmol) was added and stirred at rt for 30 min. Then 3-chloro-1-iodopropane (0.131 g, 0.84 mmol) was added followed by stirring at r.t for 20 h. The reaction mixture was quenched with water and the product extracted into EtOAc. The combined organic layers were dried over Na$_2$SO$_4$, filtered, and concentrated. The crude material was dissolved in MeCN (2 mL) followed by addition of 4-butylpiperidine (0.085 g, 0.6 mmol), NaI (0.150 g, 1.0 mmol), and K$_2$CO$_3$ (0.138 g, 1.0 mmol) and shaken at 50° C. for 20 h. The reaction mixture was quenched with water and the product extracted into EtOAc. The combined organic layers were dried over Na$_2$SO$_4$, filtered, and concentrated. The residue was purified by cation exchange CC followed by flash CC (SiO$_2$; EtOAc) to give the title compound (107LH93-1) (0.166 g, total yield 55%). $^1$H NMR (CH$_3$OD) δ 7.00 (d, J=6.4 Hz, 1H), 6.88 (d, J=9.2 Hz, 1H), 3.98-3.91 (m, 2H), 2.93-2.86 (m, 2H), 2.85-2.78 (m, 2H), 2.58-2.52 (m, 2H), 2.40-2.43 (m, 2H), 2.25 (d, J=2.0 Hz, 3H), 1.98-1.76 (m, 4H), 1.70-1.62 (m, 2H), 1.35-1.22 (m, 9H), 0.88 (t, J=7.0 Hz, 3H); $^{13}$C NMR (CH$_3$OD) δ 171.1, 157.2 (d, J=241 Hz), 135.1 (d, J=3 Hz), 126.5 (d, J=8 Hz), 123.2 (d, J=18 Hz), 118.1 (d, J=5 Hz), 114.3 (d, J=24 Hz), 55.8, 43.9, 40.4, 36.2, 35.7, 32.0, 31.5, 29.0, 24.6, 24.3, 22.8, 13.4 (br).

The product was dissolved in acetone and oxalic acid (1.1 equiv) dissolved in acetone was added. The formed crystals were filtered and washed with acetone to give the title compound as oxalic salt (0.172 g). HPLC-MS (ammonium acetate) [M+H]$^+$=363.4.

6-Fluoro-7-methyl-1-[3-(4-propoxypiperidin-1-yl) propyl]-3,4-dihydro-1H-quinolin-2-one (107LH93-2)

A reaction flask was charged with 6-fluoro-7-methyl-3,4-dihydro-1H-quinolin-2-one (0.150 g, 0.84 mmol) in dry DMF (1 mL) under N$_2$. NaH (60% in oil, 0.038 g, 0.92 mmol) was added and stirred at rt for 30 min. Then 3-chloro-1-iodopropane (0.131 g, 0.84 mmol) was added followed by stirring at r.t for 20 h. The reaction mixture was quenched with water and the product extracted into EtOAc. The combined organic layers were dried over Na$_2$SO$_4$, filtered, and concentrated. The crude material was dissolved in MeCN (2 mL) followed by addition of 4-propoxypiperidine (0.086 g, 0.6 mmol), NaI (0.150 g, 1.0 mmol), and K$_2$CO$_3$ (0.138 g, 1.0 mmol) and shaken at 50° C. for 20 h. The reaction mixture was quenched with water and the product extracted into EtOAc. The combined organic layers were dried over Na$_2$SO$_4$, filtered, and concentrated. The residue was purified by cation exchange CC followed by flash CC (SiO$_2$; EtOAc) to give the title compound (107LH93-2) (0.171 g, total yield 56%). $^1$H NMR (CH$_3$OD) δ 7.00 (d, J=6.4 Hz, 1H), 6.87 (d, J=9.2 Hz, 1H), 3.94 (brt, J=7.2 Hz, 2H), 3.39 (t, J=6.6 Hz, 2H), 3.35-3.26 (m, 1H), 2.85-2.70 (m, 4H), 2.58-2.51 (m, 2H), 2.39 (brt, 7.4 Hz, 2H), 2.24 (d, J=1.6 Hz, 3H), 2.21-2.12 (m, 2H), 1.92-1.75 (m, 4H), 1.62-1.48 (m, 4H), 0.91 (t, J=7.4 Hz); $^{13}$C NMR (CH$_3$OD) δ 171.0, 157.1 (d, J=241), 135.2 (d, J=3 Hz), 126.5 (d, J=8 Hz), 123.2 (d, J=18 Hz), 118.1 (d, J=5 Hz), 114.3 (d, J=24 Hz), 74.6, 69.5, 55.4, 51.0, 40.4, 31.5, 30.9, 24.7, 24.5, 23.2, 13.5 (br), 10.0.

The product was dissolved in acetone and oxalic acid (1.1 equiv) dissolved in acetone was added. The formed crystals were filtered and washed with acetone to give the title compound as oxalic salt (0.172 g). HPLC-MS (ammonium acetate) [M+H]$^+$=364.3.

(R,S)-1-[3-(4-Butylpiperidin-1-yl)-2-methylpropyl]-6-fluoro-7-methyl-3,4-dihydro-1H-quinolin-2-one (107LH94-1)

A reaction flask was charged with 6-fluoro-7-methyl-3,4-dihydro-1H-quinolin-2-one (0.150 g, 0.84 mmol) in dry DMF (1 mL) under N$_2$. NaH (60% in oil, 0.038 g, 0.92 mmol) was added and stirred at rt for 30 min. Then (R,S)-1-bromo-3-chloro-2-methylpropane (0.144 g, 0.84 mmol) was added followed by stirring at r.t for 20 h. The reaction mixture was quenched with water and the product extracted into EtOAc. The combined organic layers were dried over Na$_2$SO$_4$, filtered, and concentrated. The crude material was dissolved in dry DMF (2 mL) followed by addition of 4-butylpiperidine (0.085 g, 0.6 mmol), NaI (0.150 g, 1.0 mmol), and K$_2$CO$_3$ (0.138 g, 1.0 mmol) and shaken at 100° C. for 20 h. The reaction mixture was quenched with water and the product extracted into EtOAc. The combined organic layers were dried over Na$_2$SO$_4$, filtered, and concentrated. The residue was purified by cation-exchange CC followed by flash CC (SiO$_2$; EtOAc) to give the title compound (107LH94-1) (0.045 g, total yield 14%). $^1$H NMR (CH$_3$OD) δ 7.01 (d, J=6.4 Hz, 1H), 6.90 (d, J=9.2 Hz), 4.03-3.88 (m, 2H), 2.90 (brd, J=10.8 Hz, 2H), 2.83 (brt, J=7.0 Hz, 2H), 2.75 (brd, J=10.2 Hz), 2.64-2.50 (m, 2H), 2.26-1.98 (m, 6H), 1.93-1.78 (m, 2H), 1.68-1.58 (m, 2H), 1.35-1.14 8 (m, 9H), 0.89 (t, J=6.8 Hz, 3H), 0.84 (d, J=6.8 Hz, 3H); $^{13}$C NMR (CH$_3$OD) δ 171.6, 156.1 (d, J=241 Hz), 135.1 (d, J=3 Hz), 126.9 (d, J =8 Hz), 123.0, (d, J=19 Hz), 118.6 (d, J=5 Hz), 114.3 (d, J=24 Hz), 63.9, 55.1, 54.4, 45.5, 36.3, 35.9, 32.4 (br), 31.6, 29.0, 28.8, 24.6, 22.8, 16.0, 13.5 (br).

The product was dissolved in acetone and oxalic acid (1.1 equiv) dissolved in acetone was added. The formed crystals were filtered and washed with acetone to give the title compound as oxalic salt (0.037 g). HPLC-MS (ammonium acetate) [M+H]$^+$=375.3.

(R,S)-6-Fluoro-7-methyl-1-[2-methyl-3-(4-propoxypiperidin-1-yl)-propyl]-3,4-dihydro-1H-quinolin-2-one (107LH94-2)

A reaction flask was charged with 6-fluoro-7-methyl-3,4-dihydro-1H-quinolin-2-one (0.150 g, 0.84 mmol) in dry DMF (1 mL) under $N_2$. NaH (60% in oil, 0.038 g, 0.92 mmol) was added and stirred at rt for 30 min. Then (R,S)-1-bromo-3-chloro-2-methylpropane (0.144 g, 0.84 mmol) was added followed by stirring at r.t for 20 h. The reaction mixture was quenched with water and the product extracted into EtOAc. The combined organic layers were dried over $Na_2SO_4$, filtered, and concentrated. The crude material was dissolved in dry DMF (2 mL) followed by addition of 4-propoxypiperidine (0.086 g, 0.6 mmol), NaI (0.150 g, 1.0 mmol), and $K_2CO_3$ (0.138 g, 1.0 mmol) and shaken at 100° C. for 20 h. The reaction mixture was quenched with water and the product extracted into EtOAc. The combined organic layers were dried over $Na_2SO_4$, filtered, and concentrated. The residue was purified by cation-exchange CC followed by flash CC ($SiO_2$; EtOAc) to give the title compound (107LH94-2) (0.033 g, total yield 10%). $^1H$ NMR ($CH_3OD$) δ 7.02 (d, J=6.8 Hz, 1H), 6.91 (d, J=9.6 Hz, 1H), 3.95 (d, J=7.2 Hz, 2H), 3.41 (t, J=6.6 Hz, 2H), 3.33-3.25 (m, 1H), 2.84 (brt, J=7.4 Hz), 2.79-2.71 (m, 1H), 2.67-2.51 (m, 3H), 2.28-1.98 (m, 8H), 1.92-1.83 (m, 2H), 1.60-1.48 (m, 4H), 0.91 (t, J=7.6 Hz, 3H), 0.85 (d, J=6.4 Hz, 3H); $^{13}C$ NMR ($CH_3OD$) δ 171.7, 157.2 (d, J=241 Hz), 135.1 (d, J=3 Hz), 126.9 (d, J=8 Hz), 123.1 (d, J=18 Hz), 114.3 (d, J=24 Hz), 75.2, 69.5, 52.1, 51.7, 45.5, 31.6, 31.3, 29.0, 24.6, 23.1, 15.9, 13.5, 13.3, 9.8.

The product was dissolved in acetone and oxalic acid (1.1 equiv) dissolved in acetone was added. The formed crystals were filtered and washed with acetone to give the title compound as oxalic salt (0.036 g). HPLC-MS (ammonium acetate) $[M+H]^+$=377.3.

1-[3-(4-Butyl-piperidin-1-yl)propyl]-6-fluoro-5-methyl-3,4-dihydro-1H-quinolin-2-one (107LH95-1)

A reaction flask was charged with 6-fluoro-5-methyl-3,4-dihydro-1H-quinolin-2-one (0.090 g, 0.50 mmol) in dry DMF (0.5 mL) under $N_2$. NaH (60% in oil, 0.023 g, 0.55 mmol) was added and stirred at rt for 30 min. Then 3-chloro-1-iodopropane (0.079 g, 0.50 mmol) was added followed by stirring at r.t for 20 h. The reaction mixture was quenched with water and the product extracted into EtOAc. The combined organic layers were dried over $Na_2SO_4$, filtered, and concentrated. The crude material was dissolved in MeCN (2 mL) followed by addition of 4-butylpiperidine (0.085 g, 0.6 mmol), NaI (0.150 g, 1.0 mmol), and $K_2CO_3$ (0.138 g, 1.0 mmol) and shaken at 50° C. for 20 h. The reaction mixture was quenched with water and the product extracted into EtOAc. The combined organic layers were dried over $Na_2SO_4$, filtered, and concentrated. The residue was purified by cation-exchange CC followed by flash CC ($SiO_2$; EtOAc) to give the title compound (107LH95-1) (0.059 g, total yield 33%). $^1H$ NMR ($CH_3OD$) δ 7.02 (dd, J=4.8, 9.2 Hz, 1H), 6.98-6.92 (m, 1H), 3.95 (brt, J=7.4 Hz, 2H), 2.92-2.82 (m, 4H), 2.59-2.52 (m, 2H), 2.39-2.32 (m, 2H), 2.00 (d, J=1.6 Hz, 3H), 1.97-1.75 (m, 4H), 1.66 (brd, 10.8 Hz, 2H), 1.35-1.12 (m, 9H), 0.89 (t, J=6.4 Hz); $^{13}C$ NMR ($CH_3OD$) δ 170.9, 157.6 (d, J=240 Hz), 135.4 (d, J=3 Hz), 128.1 (d, J=4 Hz), 122.7 (d, J=18 Hz), 114.2 (d, J=8 Hz), 112.9, (d, J=25 Hz), 55.9, 53.9, 40.6, 36.2, 35.7, 31.9, 30.9, 28.9, 24.4, 22.8, 21.4 (br), 13.2, 9.7 (br).

The product was dissolved in acetone and oxalic acid (1.1 equiv) dissolved in acetone was added. The formed crystals were filtered and washed with acetone to give the title compound as oxalic salt (0.058 g). HPLC-MS (ammonium acetate) $[M+H]^+$=361.3.

6-Fluoro-5-methyl-1-[3-(4-propoxypiperidin-1-yl) propyl]-3,4-dihydro-1H-quinolin-2-one (107LH95-2)

A reaction flask was charged with 6-fluoro-5-methyl-3,4-dihydro-1H-quinolin-2-one (0.090 g, 0.50 mmol) in dry DMF (0.5 mL) under $N_2$. NaH (60% in oil, 0.023 g, 0.55 mmol) was added and stirred at rt for 30 min. Then 3-chloro-1-iodopropane (0.079 g, 0.50 mmol) was added followed by stirring at r.t for 20 h. The reaction mixture was quenched with water and the product extracted into EtOAc. The combined organic layers were dried over $Na_2SO_4$, filtered, and concentrated. The crude material was dissolved in MeCN (2 mL) followed by addition of 4-propoxypiperidine (0.086 g, 0.6 mmol), NaI (0.150 g, 1.0 mmol), and $K_2CO_3$ (0.138 g, 1.0 mmol) and shaken at 50° C. for 20 h. The reaction mixture was quenched with water and the product extracted into EtOAc. The combined organic layers were dried over $Na_2SO_4$, filtered, and concentrated. The residue was purified by cation-exchange CC followed by flash CC ($SiO_2$; EtOAc) to give the title compound (107LH95-2) (0.074 g, total yield 41%). $^1H$ NMR ($CH_3OD$) δ 7.03 (dd, J=4.8, 9.2 Hz, 1H), 6.99-6.92 (m, 1H), 3.98 (brt, J=7.4 Hz, 2H), 3.46-3.38 (m, 3H), 2.95-2.84 (m, 4H), 2.64-2.42 (m, 6H), 2.20 (d, J=2.0 Hz, 3H), 1.98-1.83 (m, 4H), 1.72-1.30 (m, 4H), 0.92 (t, J=7.4 Hz, 3H); $^{13}C$ NMR ($CH_3OD$) δ 171.1, 157.7 (d, J=240 Hz), 135.4 (d, J=3 Hz), 128.1 (d, J=4 Hz), 122.8 (d, J=18 Hz), 114.1, (d, J=9 Hz), 113.0 (d, J=25 Hz), 73.1, 69.7, 55.0, 50.3, 40.3, 30.8, 29.9, 23.9, 23.1, 22.7, 21.4, 9.8 (br).

The product was dissolved in acetone and oxalic acid (1.1 equiv) dissolved in acetone was added. The formed crystals were filtered and washed with acetone to give the title compound as oxalic salt (0.067 g). HPLC-MS (ammonium acetate) $[M+H]^+$=363.3.

(R)-1-[3-(4-Butylpiperidin-1-yl)-2-methylpropyl]-3,4-dihydro-1H-quinolin-2-one (107LH47-A)

A 4 mL vial was charged with (S)-1-(3-iodo-2-methylpropyl)-3,4-dihydro-1H-quinolin-2-one (122LH18) (0.329 g, 1.0 mmol) and 4-butylpiperidine (0.283 g, 2.0 mmol) in MeCN (2 mL) and shaken at 60° for 20 h. The reaction mixture was concentrated, and the product purified by flash CC ($SiO_2$; EtOAc, EtOAc/MeOH 4:1) to give the title compound (107LH47-A) (0.186 g, 54%). $^1H$ NMR ($CD_3OD$) δ 7.26-7.19 (M, 3H), 7.04-7.00 (m, 1H), 2.93-2.88 (m, 3H), 2.77 (d, J=10.4 Hz, 2H), 2.62-2.58 (m, 2H), 2.29-2.06 (m, 3H), 1.93-1.86 (m, 2H), 1.68-1.62 (m, 2H), 1.31-1.22 (m, 9H), 0.91-0.86 (m, 2 $CH_3$); $^{13}C$ NMR ($CD_3OD$) δ 173.2, 140.3, 129.1, 128.5, 128.4, 124.4, 166.9, 64.9, 56.0, 55.6, 37.5, 36.9, 33.4, 33.3, 32.9, 30.1, 30.1, 26.2, 24.0, 17.2, 14.4.

The product was dissolved in acetone and oxalic acid dissolved in acetone was added. The formed crystals were filtered and washed with acetone to give the title compound as oxalic salt (0.222 g). HPLC-MS (ammonium acetate) $[M+H]^+$=343.33.

(R)-1-[2-Methyl-3-(4-propoxypiperidin-1-yl)propyl]-3,4-dihydro-1H-quinolin-2-one (107LH48)

A 4 mL vial was charged with (S)-1-(3-iodo-2-methylpropyl)-3,4-dihydro-1H-quinolin-2-one (122LH18) (0.493 g, 1.5 mmol) and 4-propoxypiperidine (0.430 g, 3.0 mmol) in MeCN (2 mL) and shaken at 60° for 20 h. The reaction mixture was quenched with water, basified with ammonium hydroxide, and the product extracted into EtOAc. The combined organic layers were dried over Na$_2$SO$_4$, filtered, and concentrated. The product was purified by flash CC (SiO$_2$; EtOAc, EtOAc/MeOH 4:1) to give the title compound (107LH48) (0.197 g, 38%). $^1$H NMR (CD$_3$OD) δ 7.26-7.19 (m, 3H), 7.03-6.98 (m, 1H), 3.96 (d, J=7.0 Hz, 2H), 3.40 (t, J=6.7 Hz, 2H), 2.90-2.86 (m, 2H), 2.74-2.71 (m, 1H), 2.65-2.54 (m, 3H), 2.26-1.99 (m, 6H), 1.87-1.84 (m, 2H), 1.59-1.49 (m, 4H), 0.91 (t, J=7.4 Hz, CH$_3$), 0.85 (d, J=6.6 Hz, CH$_3$); $^{13}$C NMR (CD$_3$OD) δ 173.0, 140.3, 129.1, 128.4, 128.4, 124.3, 116.8, 76.3, 70.7, 64.5, 53.2, 52.8, 32.9, 32.4, 32.4, 30.3, 26.2, 24.3, 17.1, 11.0.

The product was dissolved in acetone and oxalic acid dissolved in acetone was added. The formed crystals were filtered and washed with acetone to give the title compound as oxalic salt (0.189 g). HPLC-MS (ammonium acetate) [M+H]$^+$=345.31.

(R)-1-[3-(4-Butylidenepiperidin-1-yl)-2-methylpropyl]-3,4-dihydro-1H-quinolin-2-one (107LH53)

A 4 mL vial was charged with (S)-1-(3-iodo-2-methylpropyl)-3,4-dihydro-1H-quinolin-2-one (122LH18) (0.169 g, 0.51 mmol) and 4-butylidenepiperidine (0.200 g, 1.4 mmol) in MeCN (2 mL) and shaken at 40° for 20 h. The reaction mixture was quenched with water, basified with ammonium hydroxide, and the product extracted into EtOAc. The combined organic layers were dried over Na$_2$SO$_4$, filtered, and concentrated. The product was purified by flash CC (SiO$_2$; n-heptane/EtOAc 4:1) to give the title compound (107LH53) (0.116 g, 67%). $^1$H NMR (CD$_3$OD) δ 7.23-7.18 (m, 3H), 7.02-6.98 (m, 1H), 5.11 (t, J=7.4 Hz, 1H), 3.98 (d, J=6.8 Hz, 2H), 2.89-2.85 (m, 2H), 2.61-2.56 (m, 2H), 2.40-2.35 (m, 2H), 3.32-2.04 (m, 11H), 1.98-1.92 (m, 2H), 1.36-1.29 (m, 2H), 0.90-0.85 (m, 2 CH$_3$); $^{13}$C NMR (CD$_3$OD) δ 173.0, 140.3, 137.1, 129.1, 128.4, 128.4, 124.3, 123.7, 116.9, 64.6, 57.4, 56.6, 46.5, 37.0, 32.9, 30.2, 30.1, 29.1, 26.3, 24.2, 17.2, 14.1.

The product was dissolved in acetone and oxalic acid dissolved in acetone was added. The formed crystals were filtered and washed with acetone to give the title compound as oxalic salt (0.130 g). HPLC-MS (ammonium acetate) [M+H]$^+$=341.33.

(R)-1-[3-(3-Butyl-8-azabicyclo[3.2.1]oct-8-yl)-2-methylpropyl]-3,4-dihydro-1H-quinolin-2-one (107LH54)

A 4 mL vial was charged with (S)-1-(3-iodo-2-methylpropyl)-3,4-dihydro-1H-quinolin-2-one (122LH18) (0.185 g, 0.56 mmol) and 3-butyl-8-azabicyclo[3.2.1]octane (0.100 g, 0.60 mmol) in MeCN (0.5 mL) and shaken at 40° for 20 h. The reaction mixture was quenched with water, basified with ammonium hydroxide, and the product extracted into EtOAc. The combined organic layers were dried over Na$_2$SO$_4$, filtered, and concentrated. The product was purified by flash CC (SiO$_2$; n-heptane/EtOAc 4:1) to give the title compound (107LH54) (0.063 g, 30%). $^1$H NMR (CD$_3$OD) δ 7.29-7.19 (m, 3H), 7.03-6.99 (m, 1H), 4.03-4.00 (m, 2H), 3.14-3.13 (m, 1H), 3.07-3.05 (m, 1H), 2.90-2.86 (m, 2H), 2.62-2.57 (m, 2H), 2.26-2.19 (m, 2H), 1.97-1.82 (m, 3), 1.58-1.42 (m, 5H), 1.34-1.15 (m, 8H), 0.90-0.87 (m, 6H); $^{13}$C NMR (CD$_3$OD) δ 173.1, 140.3, 129.1, 128.4, 128.3, 124.3, 117.2, 62.2, 61.2, 58.2, 46.5, 39.0, 38.0, 32.9, 32.1, 30.3, 29.1, 27.8, 27.3, 26.3, 24.0, 17.1, 14.5.

The product was dissolved in acetone and oxalic acid dissolved in acetone was added. The formed crystals were filtered and washed with acetone to give the title compound as oxalic salt (0.064 g). HPLC-MS (ammonium acetate) [M+H]$^+$=369.34.

(R)-1-[2-Methyl-3-(3-pentyl-8-azabicyclo[3.2.1]oct-8-yl)propyl]-3,4-dihydro-1H-quinolin-2-one (107LH55)

A 4 mL vial was charged with (S)-1-(3-iodo-2-methylpropyl)-3,4-dihydro-1H-quinolin-2-one (122LH18) (0.185 g, 0.56 mmol) and 3-pentyl-8-azabicyclo[3.2.1]octane (0.112 g, 0.62 mmol) in MeCN (0.5 mL) and shaken at 40° for 20 h. The reaction mixture was quenched with water, basified with ammonium hydroxide, and the product extracted into EtOAc. The combined organic layers were dried over Na$_2$SO$_4$, filtered, and concentrated. The product was purified by flash CC (SiO$_2$; n-heptane/EtOAc 4:1) to give the title compound (107LH55) (0.075 g, 35%). $^1$H NMR (CD$_3$OD) δ 7.28-7.18 (m, 3H), 7.01 (t, J=7.2 Hz, 1H), 4.03 (d, J=7.0 Hz, 2H), 3.11-3.04 (m, 2H), 2.90-2.85 (m, 2), 2.64-2.56 (m 2H), 2.28-2.11 (m, 4H), 1.97-1.84 (m, 3H), 1.66-1.54 (m, 3H), 1.42-1.21 (m, 10H), 0.90-0.85 (m, 2 CH$_3$); $^{13}$C NMR (CD$_3$OD) δ 173.1, 140.3, 129.1, 128.4, 128.3, 124.3, 117.1, 61.4, 60.2, 58.3, 46.4, 39.5, 37.1, 37.0, 33.1, 32.9, 32.2, 29.5, 29.4, 28.5, 27.9, 26.3, 23.7, 17.1, 14.4.

The product was dissolved in acetone and oxalic acid dissolved in acetone was added. The formed crystals were filtered and washed with acetone to give the title compound as oxalic salt (0.054 g). HPLC-MS (ammonium acetate) [M+H]$^+$=383.35.

1-[3-(4-Butylpiperidin-1-yl)propyl]-1H-quinolin-2-one (092LH70-A)

A 7 mL vial was charged with 1-(3-chloropropyl)-1H-quinolin-2-one (0.450 g, 2.0 mmol), K$_2$CO$_3$ (0.34 g, 2.5 mmol), KI (0.42 g, 2.5 mmol), 4-butylpiperidine (0.30 g, 2.1 mmol) and dry CH$_3$CN (3 mL). The mixture was shaken at 50° C. for 60 h and thereafter diluted with EtOAc (50 mL) and washed with water (50 mL). The water phase was extracted with EtOAc (2×50 mL). The combined organic phase was dried over Na$_2$SO$_4$, filtered, and concentrated under reduced pressure. The residue was purified by flash CC (SiO$_2$; EtOAc/MeOH 4:1) followed by prep RP-HPLC to give the title compound (0.32 g, 49%). $^1$H NMR (CD$_3$OD) δ 7.88 (d, J=9.6 Hz), 7.68 (brd, J=8.0 Hz), 7.65-7.61 (m, 2H), 7.33-7.25 (m, 1H), 6.64 (d, 9.6 Hz), 4.39-4.32 (m, 2H), 2.95-2.86 (m, 2H), 2.50-2.43 (m, 2H), 2.01-1.86 (m, 4H), 1.71-1.62 (m, 2H), 1.35-1.12 (m, 9H), 0.89 (t, J=6.6 Hz); $^{13}$C NMR (CD$_3$OD) δ 163.1, 140.4, 139.0, 131.1, 129.2, 122.6, 121.4, 120.3, 114.7, 55.8, 53.9, 40.6, 36.2, 35.7, 32.0, 28.9, 24.7, 22.8, 13.2.

The product was dissolved in acetone and oxalic acid (1.1 equiv) dissolved in acetone was added. The formed crystals were filtered and washed with acetone to give the title compound as oxalic salt (0.356 g). HPLC-MS (ammonium acetate) [M+H]$^+$=327.3.

1-[3-(4-Propoxypiperidin-1-yl)propyl]-1H-quinolin-2-one, (092LH69)

A 4 mL vial was charged with 1-(3-chloropropyl)-1H-quinolin-2-one (0.069 g, 0.31 mmol), K$_2$CO$_3$ (0.069 g, 0.50 mmol), KI (0.083 g, 0.50 mmol), 4-propoxypiperidine (0.050 g, 0.35 mmol) and dry CH$_3$CN (2 mL). The mixture was shaken at 50° C. for 24 h and thereafter diluted with water (25 mL) and EtOAc (25 mL). The phases were separated and the water phase was extracted with EtOAc (2×50 mL). The combined organic phase was then dried over Na$_2$SO$_4$, filtered, and concentrated under reduced pressure. The residue was purified by flash CC (SiO$_2$; EtOAc/MeOH 4:1) followed by prep RP-HPLC to give the title compound (0.060 g, 59%). $^1$H NMR (CD$_3$OD) δ 7.85 (d, J=9.4 Hz, 1H), 7.65 (brd, J=7.2 Hz, 1H), 7.63 (m, 2H), 7.29-7.22 (m, 1H), 6.62, (d, J=9.4 Hz), 4.36-4.29 (m, 1H), 3.38 (t, J=6.6 Hz, 2H), 3.34-3.24 (m, 1H), 2.78-2.69 (m, 2H), 2.48-2.41 (m, 2H), 2.18-2.09 (m, 2H), 1.94-1.82 (m, 4H), 1.59-1.47 (m, 4H), 0.90 (t, J=7.4 Hz); $^{13}$C NMR (CD$_3$OD) δ 162.0, 140.3, 139.0, 131.1, 129.2, 122.6, 121.4, 120.3, 114.7, 74.7, 69.5, 55.4, 51.0, 40.6, 31.0, 24.9, 32.1, 9.9; HPLC-MS (ammonium acetate) [M+H]$^+$=329.3.

1-[3-(4-Butylpiperidin-1-yl)propyl]-6-fluoro-1H-quinolin-2-one (107LH22)

A 4 mL vial was charged with 6-fluoro-1H-quinolin-2-one (00.56 g, 0.34 mmol), dry DMF (2 mL) and NaH (60% in oil, 0.015 g, 0.34 mmol). The mixture was stirred at rt for 1 h under a N$_2$ atmosphere, and thereafter 1-bromo-3-chloropropane (34 μl, 0.34 mmol) was added and the mixture was then shaken at rt for 20 h. The reaction was diluted with diethyl ether (25 mL) and washed with water (15 mL). The organic phase was washed with water (15 mL) and brine (15 mL), dried over Na$_2$SO$_4$, and concentrated under reduced pressure. The oily residue was diluted with CH$_3$CN (2 mL) and KI (0.083 g, 0.50 mmol), K$_2$CO$_3$ (0.069 g, 0.50 mmol) and 4-butylpiperidine (0.048 g, 0.34 mmol) was added. The mixture was shaken at 50° C. for 72 h and then diluted with EtOAc (25 mL) and washed with water (15 mL). The water phase was extracted (2×25 mL) and the combined organic phase was dried over Na$_2$SO$_4$, and concentrated under reduced pressure. The residue was purified by cation-exchange CC followed by flash CC (SiO$_2$; EtOAc/MeOH 4:1) to yield the title compound (0.034 g, 29%). $^1$H NMR (CD$_3$OD) δ 7.90 (d, J=9.2 Hz, 1H), 7.69 (dd, J=4.0, 8.8 Hz, 1H), 7.50-7.41 (m, 2H), 6.72 (d, J=8.8 Hz, 1H), 4.41 (t, J=6.8 Hz, 2H), 3.02-2.95 (m, 2H), 2.65-2.60 (m, 2H), 2.19-2.08 (m, 2H), 1.91-1.82 (m, 4H), 1.53-1.21 (m, 9H), 0.90 (t, J=7.0 Hz); $^{13}$C NMR (CD$_3$OD) δ 169.9, 158.4 (d, J=242 Hz), 139.8 (d, J=3 Hz), 134.4 (d, J=2 Hz), 122.5 (d, J=9 Hz), 121.6, 119.9 (d, J=24 Hz), 116.8 (d, J=8 Hz), 113.9 (d=23 Hz), 54.4, 53.0, 40.1, 34.5, 34.1, 30.1, 28.7, 23.3, 22.6, 13.2; HPLC-MS (ammonium acetate) [M+H]$^+$=345.3.

1-[3-(4-Butylpiperidin-1-yl)propyl]-6-methyl-1H-quinolin-2-one (107LH32-A)

A 4 mL vial was charged with 6-methyl-1H-quinolin-2-one (0.110 g, 0.71 mmol), dry DMF (2 mL) and NaH (60% in oil, 0.031 g, 0.78 mmol). The mixture was shaken under a N$_2$ atmosphere for 1 h, and thereafter 1-bromo-3-chloropropane (70 μl, 0.71 mmol) was added. The reaction was shaken at rt for 20 h and then poured into diethyl ether (25 mL) and washed with water (15 mL). The ether phase was washed with water (15 mL) and brine (15 mL). The organic phase was dried over Na$_2$SO$_4$, and concentrated under reduced pressure. The residue was diluted with CH$_3$CN (2 mL) and KI (0.160 g, 1.0 mmol), K$_2$CO$_3$ (0.140 g, 1.0 mmol) and 4-butylpiperidine (0.100 g, 0.71 mmol) was added. The mixture was shaken at 50° C. for 72 h and then poured onto The compound EtOAc (25 mL) and water (15 mL). The water phase was extracted (2×25 mL) and the combined organic phase was dried over Na$_2$SO$_4$, and concentrated under reduced pressure. The residue was purified by flash CC (SiO$_2$; EtOAc/MeOH 4:1) followed by prep RP-HPLC to give the title compound (0.058 g, 23%). $^1$H NMR (CD$_3$OD) δ 7.78 (d, J=9.2 Hz, 1H), 7.52-7.40 (m, 3H), 6.60 (d, J=9.2 Hz, 1H), 4.3 (t, J=7.6 Hz, 2H), 2.92-2.2.85 (m, 2H), 2.50-2.39 (m, 2H), 2.39 (s, 3H), 1.99-1.84 (m, 4H), 1.69-1.61 (m, 2H), 1.35-1.11 (m, 9H), 0.88 (t, J=6.8 Hz); $^{13}$C NMR (CD$_3$OD) δ 162.9, 140.1, 137.0, 132.5, 132.3, 128.8, 121.4, 120.2, 114.6, 55.8, 53.9, 40.6, 36.2, 35.7, 32.0, 28.9, 24.8, 22.8, 19.4, 13.3; HPLC-MS (ammonium acetate) [M+H]$^+$=341.3.

1-[3-(4-Butylpiperidin-1-yl)propyl]-7-fluoro-1H-quinolin-2-one (107LH33-A)

A 4 mL vial was charged with 7-fluoro-1H-quinolin-2-one (0.032 g, 0.19 mmol), NaH (60% in oil, 8.7 mg, 0.21 mmol) and dry DMF (2.5 mL). The mixture was shaken at rt for 1 h and then 1-bromo-3-chloropropane (20 μl, 0.19 mmol) was added and the reaction was shaken overnight shaken at rt overnight. The mixture was then diluted with ether (25 mL) and washed water (15 mL), the ether phase was washed with water (15 mL) and brine (15 mL). The organic phase was dried over Na$_2$SO$_4$, and concentrated under reduced pressure. The oily residue was diluted with CH$_3$CN (2 mL) and to the resulting solution was added: KI (0.050 g, 0.30 mmol), K$_2$CO$_3$ (0.041 g, 0.30 mmol) and 4-butylpiperidine (0.028 g, 0.20 mmol). The mixture was shaken at 50° C. for 72 h and then poured onto The compound EtOAc (25 mL) and water (15 mL). The water phase was extracted (2×25 mL) and the combined organic phase was dried over Na$_2$SO$_4$, and concentrated under reduced pressure. The residue was purified by flash CC (SiO$_2$; EtOAc/MeOH 4:1) followed by prep RP-HPLC to give the title compound (7.0 mg, 11%). $^1$H NMR (CD$_3$OD) δ 7.89 (d, J=9.6 Hz, 1H), 7.73 (dd, J=6.2, 8.6 Hz, 1H), 7.47 (dd, J=2.4, 11.6 Hz, 1H), 7.08 (dt, J=2.4, 8.6 Hz, 1H), 6.60 (d J=9.6 Hz, 1H), 4.33 (t, J=7.6 Hz, 2H), 2.98-2.00 (m, 2H), 2.50-2.42 (m, 2H), 2.05-1.86 (m, 4H), 1.55-1.64 (m, 2H), 1.36-1.15 (m, 9H), 0.90 (t, J=6.8 Hz); $^{13}$C NMR (CD$_3$OD) δ 164.7 (d, J=248), 163.2, 140.9 (br), 139.9, 131.4 (d, J=10 Hz), 119.3 (d, J=3 Hz), 118.1 (br), 110.6 (d, J=23 Hz), 101.6 (d, J=28 Hz), 55.5, 53.9, 41.0, 36.8, 35.6, 31.9, 28.9, 24.5, 22.7, 13.2; HPLC-MS (ammonium acetate) [M+H]$^+$=345.3

1-[3-(4-Butylpiperidin-1-yl)propyl]-6-methoxy-1H-quinolin-2-one (107LH37-A)

A 4 mL vial was charged with 6-methoxy-1H-quinolin-2-one (0.032 g, 0.18 mmol) dry DMF (2 mL) and NaH (60% in oil, 8 mg, 0.20 mmol), thereafter the mixture was stirred at 45° C. for 45 min under a N$_2$ atmosphere, followed by the addition of 1-bromo-3-chloropropane (18 μl, 0.18 mmol) and the mixture was shaken at 30° C. overnight. The reaction was then diluted with ether (25 mL) and washed with water (15 mL) and brine (15 mL), dried over Na$_2$SO$_4$, and concentrated under reduced pressure. The oily residue was diluted with CH$_3$CN (3 mL) and KI (0.080 g, 0.50 mmol), K$_2$CO$_3$ (0.070 g, 0.50 mmol) and 4-butylpiperidine (0.028 g, 0.20 mmol) were added. The mixture was shaken at 50° C. for 48 h and then diluted with EtOAc (25 mL) and washed with water (15 mL). The water phase was extracted (2×25 mL) and the combined organic phase was dried over Na$_2$SO$_4$, and concentrated under reduced pressure. The residue was purified by prep RP-HPLC to give the title compound (0.028 g, 44%). $^1$H NMR (CD$_3$OD) δ 7.85 (d, J=9.6 Hz, 1H), 7.56 (d, J=9.2 Hz, 1H), 7.26 (dd, J=2.8, 9.6 Hz, 1H), 7.19 (d J=2.8 Hz, 1H), 6.65 (d, J=9.6 Hz, 1H), 4.34 (t, J=7.2 Hz, 2H), 3.85 (s, 3H), 3.07-2.98 (m, 2H), 2.64-2.58 (m, 2H), 2.19-2.10 (m, 2H), 2.04-1.94 (m, 2H), 1.76-1.66 (m, 2H), 1.35-0.96 (m, 9H), 0.89 (t, J=6.8 Hz); $^{13}$C NMR (CD$_3$OD) δ 162.7, 155.5, 140.1, 133.3, 122.3, 120.6, 120.1, 116.1, 110.5, 55.3, 55.0, 53.6, 40.5, 36.0, 35.2, 31.4, 28.8 24.4, 22.7, 13.2; HPLC-MS (ammonium acetate) [M+H]$^+$=357.3.

1-[3-(4-Butylpiperidin-1-yl)propyl]-6-chloro-1H-quinolin-2-one (107LH38-A)

A 4 mL vial was charged with 6-chloro-1H-quinolin-2-one (107LH35) (0.085 g, 0.47 mmol), dry DMF (3 mL) and NaH (60% in oil, 0.023 g, 0.56 mmol) and the mixture was stirred at rt for 45 min under a N$_2$ atmosphere. Thereafter, 1-bromo-3-chloropropane (18 µl, 0.18 mmol) was added and the mixture was shaken at rt overnight, the reaction diluted with ether (25 mL) and washed with water (15 mL). The ether phase was washed with brine (15 mL), dried over Na$_2$SO$_4$, concentrated under reduced pressure. The oily residue was diluted with dry CH$_3$CN (2 mL) and KI (0.170 g, 1.0 mmol), K$_2$CO$_3$ (0.140 g, 1.0 mmol) and 4-butylpiperidine (0.071 g, 0.50 mmol) were added. The mixture was shaken at 50° C. for 24 h and then diluted with EtOAc (25 mL) and washed with water (15 mL). The water phase was extracted (2×25 mL) and the combined organic phases were dried over Na$_2$SO$_4$, and concentrated under reduced pressure. The residue was purified by prep RP-HPLC to give the title compound (32 mg, 89 mmol, 19%). $^1$H NMR (CD$_3$OD) δ 7.80 (d, J=9.2 Hz, 1H), 7.66 (brs, 1H), 7.60-7.51 (m, 2H), 6.65 (d, J=9.6 Hz, 1H), 5.30 (t, J=7.6 Hz, 2H), 3.09-2.95 (m, 2H), 2.68-2.57 (m, 2H), 2.24-2.06 (m 2H), 2.00-1.90 (m, 2H), 1.75-1.64 (m, 2H), 1.32-1.12 (m, 9H), 0.84 (t, 6.4 Hz, 3H); $^{13}$C NMR (CD$_3$OD) δ 162.6, 139.2, 137.4, 130.8, 128.0, 127.8, 122.4, 121.5, 116.3, 55.0, 53.3, 40.3, 35.7, 34.8, 31.0, 28.6, 23.9, 22.5, 13.0; HPLC-MS (ammonium acetate) [M+H]$^+$=361.3.

1-[3-(4-Butylpiperidin-1-yl)propyl]-5-methyl-1H-quinolin-2-one (107LH45)

A 4 mL vial was charged with 1-(3-chloropropyl)-5-metyl-1H-quinolin-2-one (0.053 g, 0.23 mmol), KI (0.083 g, 0.5 mmol), K$_2$CO$_3$ (0.069 g, 0.50 mmol) and 4-butylpiperidine (50 µl, 0.30 mmol) in CH$_3$CN (2 mL). The mixture was shaken at 50° C. for 72 h and then diluted with EtOAc (25 mL) and washed with water (15 mL). The water phase was extracted (2×25 mL) and the combined organic phases were dried over Na$_2$SO$_4$, and concentrated under reduced pressure. The residue was purified by flash CC (SiO$_2$; EtOAc/MeOH 1:4) to give the title compound (0.058 g, 74%). $^1$H NMR (CD$_3$OD) δ 8.13 (d, J=9.8 Hz, 1H), 7.56-7.46 (m, 2H), 7.15 (brd, 6.8 Hz, 2H), 6.67 (d, J=9.8 Hz, 1H), 4.38 (t, J=7.2 Hz, 2H), 3.10-3.03 (m, 2H), 2.68-2.61 (m, 2H), 2.57 (s, 3H), 2.25-2.15 (m, 2H), 2.04-1.95 (m, 2H), 1.78-1.69 (m, 2H), 1.36-1.16 (m, 9H), 0.89 (t, J=7.0 Hz, 3H); $^{13}$C NMR (CD$_3$OD) δ 162.3, 138.7, 136.6, 136.2, 130.4, 123.6, 119.4, 118.9, 112.4, 54.7, 52.9, 39.9, 35.3, 34.5, 30.7, 28.2, 23.7, 22.1, 17.3, 12.6; HPLC-MS (ammonium acetate) [M+H]$^+$=341.3.

1-[3-(4-Butyl-piperidin-1-yl)propyl]-7-methyl-1H-quinolin-2-one (107LH46-A)

A 4 mL vial was charged with 1-(3-chloro-propyl)-7-methyl-1H-quinolin-2-one 107LH40 (0.130 g, 0.56 mmol), KI (0.170 g, 1.0 mmol), K$_2$CO$_3$ (0.140 g, 1.0 mmol) and 4-butylpiperidine (100 µl, 0.60 mmol) in CH$_3$CN (2 mL). The mixture was shaken at 50° C. for 72 h and then poured onto The compound EtOAc (25 mL) and water (15 mL). The water phase was extracted (2×25 mL) and the combined organic phases were dried over Na$_2$SO$_4$, and concentrated under reduced pressure. The residue was purified by flash CC (SiO$_2$; EtOAc/MeOH 1:4) to give the title compound (0.017 g, 6%). $^1$H NMR (CD$_3$OD) δ 7.84 (d, J=9.4 Hz), 7.56 (d, J=8.0 Hz, 1H), 7.43 (brs, 1H), 7.14 (brd, J=8 Hz, 1H), 6.58 (d, J=9.4 Hz), 4.36 (d, J=7.2 Hz, 2H), 3.02-2.95 (m, 2H), 2.57-2.48 (m, 2H), 2.51 (s, 3H), 2.09-1.91 (m, 4H), 1.75-1.65 (m, 2H9, 1.36-1.16 (m, 9H), 0.89 (t, J=6.8 Hz, 3H); $^{13}$C NMR (CD$_3$OD) δ 163.3, 142.2, 140.3, 139.1, 129.1, 124.1, 119.3, 119.0, 114.7, 55.6, 53.8, 40.4, 36.1, 35.5, 31.8, 28.9, 24.6, 22.7, 21.1, 13.2; HPLC-MS (ammonium acetate) [M+H]$^+$=341.3.

(R)-1-[3-(4-Butylpiperidin-1-yl)-2-methylpropyl]-1H-quinolin-2-one (107LH52)

A 4 mL vial was charged with crude (S)-1-(3-iodo-2-methyl-propyl)-1H-quinolin-2-one (0.66 g), 4-butylpiperidine (0.43 g, 3.0 mmol) and dry CH$_3$CN (1 mL). The mixture was shaken at 50° C. for 72 h and then poured onto The compound EtOAc (50 mL) and water (25 mL). The water phase was extracted (2×25 mL) and the combined organic phases were dried over Na$_2$SO$_4$, and concentrated under reduced pressure. The residue was purified by flash CC (SiO$_2$; EtOAc/MeOH 1:4) and then cation-exchange CC producing the title compound (0.300 g, 44%). $^1$H NMR (CD$_3$OD) δ 7.88 (d, J=9.2 Hz, 1H), 7.73-7.66 (m, 2H), 7.61 (t, J=8.0 Hz, 1H), 7.29 (t, J=7.4 Hz, 1H), 6.65 (d, J=9.2 Hz, 1H), 4.42-4.26 (m, 2H), 2.90 (brd, J=11.4 Hz, 1H), 2.74 (brd, J=11.4 Hz, 1H), 2.40-2.16 (m, 3H), 1.94-1.78 (m, 2H), 1.64-1.54 (m, 2H), 1.35-1.00 (m, 9H), 0.96-0.85 (m, 6H); $^{13}$C NMR (CD$_3$OD) δ 163.7, 140.2, 139.5, 130.8, 129.1, 122.5, 121.4, 120.4, 115.3, 64.0, 55.1, 54.2, 46.8, 36.3, 35.8, 32.4, 32.3, 29.8, 28.9, 22.8, 16.1, 13.2.

The product was dissolved in acetone and tartric acid (1.1 equiv) dissolved in acetone was added. The formed crystals were filtered and washed with acetone to give the title compound as oxalic salt (0.277 g). HPLC-MS (ammonium acetate) [M+H]$^+$=341.3.

(R)-1-[2-Methyl-3-(4-propoxypiperidin-1-yl)-propyl-1H-quinolin-2-one (107LH65)

A 4 mL vial was charged with crude (S)-1-(3-iodo-2-methylpropyl)-1H-quinolin-2-one (0.190 g), 4-propyloxypiperidine (0.137 g, 0.96 mmol) and dry CH$_3$CN (2.5 mL). The mixture was shaken at 50° C. for 24 h and then purified by cation-exchange CC followed by flash CC (SiO$_2$; EtOAc/MeOH 1:4) to give the title compound (0.051 g, 17%). $^1$H NMR (CD$_3$OD) δ 7.85 (d, J=9.6 Hz), 7.70-7.63 (m, 2H), 7.60 (brt, J=7.8 Hz, 1H), 7.26 (brt, 7.6 Hz), 6.63 (d, J=9.6 Hz, 1H), 4.39-4.23 (m, 2H), 3.37 (t, J=6.6 Hz), 3.28-3.18 (m, 1H), 2.77-2.69 (m, 1H), 2.64-2.58 (m, 1H), 2.35 (dd, J=8.4, 12.0 Hz), 2.51-2.21 (m, 1H), 2.18 (dd, J=4.8, 12.0 Hz), 2.13-2.04 (m, 1H), 2.00-1.92 (m, 1H), 1.84-1.75 (m, 2H), 1.58-1.32 (m, 4H), 0.95-0.85 (m, 6H); $^{13}$C NMR (CD$_3$OD) δ 163.7, 140.2, 139.5, 130.8, 129.2, 12.5, 121.4, 120.4, 115.2, 75.3, 69.5, 63.6, 52.3, 51.5, 46.8, 31.4, 31.3, 30.0, 23.1, 16.1, 9.8.

The product was dissolved in acetone and oxalic acid (1.1 equiv) dissolved in acetone was added. The formed crystals were filtered and washed with acetone to give the title compound as oxalic salt (0.032 g). HPLC-MS (ammonium acetate) [M+H]$^+$=343.3.

1-[3-(4-Allyloxypiperidin-1-yl)propyl]-1H-quinolin-2-one (107LH85)

A 4 mL vial was charged with 1-(3-chloropropyl)-1H-quinolin-2-one (0.130 g, 0.6 mmol), NaI (0.225 g, 1.5 mmol), K$_2$CO$_3$ (0.210 g, 1.5 mmol), 4-allyloxypiperidine (0.085 g, 0.60 mmol) and dry CH$_3$CN (1 mL). The mixture was shaken at 40° C. for 72 h and then poured onto The compound EtOAc (25 mL) and water (15 mL). The water phase was extracted (2×25 mL) and the combined organic phases were dried over Na$_2$SO$_4$, and concentrated under reduced pressure. The residue was purified by flash CC (SiO$_2$; EtOAc/MeOH 4:1) followed by cation-exchange CC to yield the title compound (0.140 g, 70%). $^1$H NMR (CD$_3$OD) δ 7.81 (d, J=9.6 Hz, 1H), 7.64-7.55 (m, 3H), 7.27-7.21 (m, 1H), 6.61 (d, J=9.6 Hz, 1H), 5.93-5.82 (m, 1H), 5.27-5.20 (m, 1H), 5.13-5.07 (m, 1H), 4.33-4.26 (m, 2H), 3.40-3.28 (m, 2H), 2.76-2.67 (m, 2H), 2.47-2.39 (m, 2H), 2.18-2.08 (m, 1H), 1.93-1.80 (m, 4H), 1.61-1.50 (m, 2H); $^{13}$C NMR (CD$_3$OD) δ 162.9, 140.3, 139.0, 135.5, 131.1, 129.2, 122.6, 121.3, 120.4, 115.5, 114.7, 74.2, 68.7, 55.3, 51.0, 40.6, 30.9, 24.9.

The product was dissolved in acetone and oxalic acid (1.1 equiv) dissolved in acetone was added. The formed crystals were filtered and washed with acetone to give the title compound as oxalic salt (0.140 g). HPLC-MS (ammonium acetate) [M+H]$^+$=327.3.

General Procedure 18 (GP18)

A 7 mL vial was charged with heterocycle (1 equiv), (R,S)-1-bromo-3-chloro-2-methylpropane (1.2 equiv), and Cs$_2$CO$_3$ (2 equiv) in MeCN (4 mL) and stirred at 50 for 20 h. The reaction mixture was added water, and the product extracted into EtOAc. The combined organic layers were filtered through a PTFF filter and concentrated. The product was used for the next reaction step without further purification.

(R,S)-4-(3-Chloro-2-methylpropyl)-6-methyl-4H-benzo[1,4]oxazin-3-one (112KK19-a)

6-Methyl-4H-benzo[1,4]oxazin-3-one (0.512 g, 3.14 mmol), (R,S)-1-bromo-3-chloro-2-methylpropane (0.646 g, 3.77 mmol), and Cs$_2$CO$_3$ (2.036 g, 6.25 mmol) in MeCN (4 mL) were reacted and worked up according to GP18 to give the crude title compound (112KK19-a) (0.692 g).

(R,S)-4-(3-Chloro-2-methylpropyl)-6-fluoro-4H-benzo[1,4]oxazin-3-one (112KK19-b)

6-Fluoro-4H-benzo[1,4]oxazin-3-one (0.502 g, 3.00 mmol), (R,S)-1-bromo-3-chloro-2-methylpropane (0.617 g, 3.60 mmol), and Cs$_2$CO$_3$ (1.983 g, 6.09 mmol) in MeCN (4 mL) were reacted and worked up according to GP18 to give the crude title compound (112KK19-b) (0.768 g).

(R,S)-4-(3-Chloro-2-methylpropyl)-7-fluoro-4H-benzo[1,4]oxazin-3-one (112KK19-c)

7-Fluoro-4H-benzo[1,4]oxazin-3-one (0.498 g, 2.98 mmol), (R,S)-1-bromo-3-chloro-2-methylpropane (0.613 g, 3.58 mmol), and Cs$_2$CO$_3$ (1.985 g, 6.09 mmol) in MeCN (4 mL) were reacted and worked up according to GP18 to give the crude title compound (112KK19-c) (0.694 g).

(R,S)-3-(3-Chloro-2-methylpropyl)-3H-benzothiazol-2-one (112KK19-d)

Benzothiazol-2-ol (0.476 g, 3.15 mmol), (R,S)-1-bromo-3-chloro-2-methylpropane (0.648 g, 3.78 mmol), and Cs$_2$CO$_3$ (2.024 g, 6.21 mmol) in MeCN (4 mL) were reacted and worked up according to GP18 to give the crude title compound (112KK19-d) (0.804 g).

General Procedure 19 (GP19)

A 7 mL vial was charged with heterocycle (1 equiv), (R,S)-1-bromo-3-chloro-2-methylpropane (1 equiv), and Cs$_2$CO$_3$ (1.5 equiv) in MeCN (3 mL) and stirred at 50° for 20 h. The reaction mixture was added water and the product extracted into EtOAc. The combined org. layers were dried over Na$_2$SO$_4$, filtered, and concentrated. The product was purified by flash CC (SiO$_2$; EtOAc/n-heptane 1:1).

(R,S)-4-(3-Chloro-2-methylpropyl)-4H-benzo[1,4]oxazin-3-one (107LH61-1)

4H-benzo[1,4]oxazin-2-one (0.447 g, 3.0 mmol), (R,S)-1-bromo-3-chloro-2-methylpropane (0.514-g, 3.0 mmol), and Cs$_2$CO$_3$ (1.466 g, 4.5 mmol) in MeCN (3 mL) were reacted and purified according to GP19 to give the crude title compound (107LH61-1) (0.595 g).

(R,S)-4-(3-Chloro-2-methylpropyl)-4H-benzo[1,4]thiazin-3-one (107LH61-2)

4H-Benzo[1,4]thiazin-3-one (0.496 g, 3.0 mmol), (R,S)-1-bromo-3-chloro-2-methylpropane (0.514 g, 3.0 mmol), and Cs$_2$CO$_3$ (1.466 g, 4.5 mmol) in MeCN (3 mL) were reacted and purified according to GP19 to give the crude title compound (107LH61-2) (0.593 g).

(R,S)-4-(3-Chloro-2-methylpropyl)-6-methoxy-4H-benzo[1,4]oxazin-3-one (107LH69)

6-Methoxy-4H-benzo[1,4]oxazin-3-one (111MF24) (0.538 g, 3.0 mmol), (R,S)-1-bromo-3-chloro-2-methylpropane (0.514 g, 3.0 mmol), and Cs$_2$CO$_3$ (1.466 g, 4.5 mmol) in MeCN (3 mL) were reacted and purified according to GP19 to give the crude title compound (107LH69) (0.658 g).

(R,S)-1-(3-Chloro-2-methylpropyl)-3,4-dihydro-1H-quinolin-2-one (107LH63)

A reaction flask was charged with 3,4-dihydro-1H-quinolin-2-one (1.00 g, 6.8 mmol) in dry DMF (10 mL). NaH 60% (0.300 g, 7.5 mmol) was added and the mixture was stirred at rt for 1 h under an Argon atmosphere. Then (R,S)-1-bromo-3-chlor-2-methylpropane (1.165 g, 6.8 mmol) was added followed by stirring at rt for 20 h. The crude product was concentrated and purified by flash CC (SiO$_2$; EtOAc/n-heptane 1:1) to give the crude title compound (107LH63) (0.753 g)

General Procedure 20 (GP20)

A 4 mL vial was charged with crude heterocycle, amine, NaI (0.100 g, 0.67 mmol), and K$_2$CO$_3$ (0.075 g, 0.54 mmol) in DMF and stirred at 100° for 5 days. The reaction mixture was added water and the product extracted into EtOAc. The crude product was purified by cation exchange CC and then prep. RP-HPLC to give the title compound.

(R,S)-4-[3-(4-Butylpiperidin-1-yl)-2-methylpropyl]-6-methyl-4H-benzo[1,4]oxazin-3-one (112KK20-a1)

Crude (R,S)-4-(3-chloro-2-methylpropyl)-6-methyl-4H-benzo[1,4]oxazin-3-one (112KK19-a) (0.046 g), 4-butylpiperidine (0.050 g, 0.35 mmol), NaI (0.100 g, 0.67 mmol), and K$_2$CO$_3$ (0.075 g, 0.54 mmol) in DMF (1.4 mL) were reacted and purified according to GP20 to give the title compound (112KK20-a1) (0.007 g). HPLC-MS (ammonium acetate) [M+H]$^+$=359.32.

(R,S)-4-[2-Methyl-3-(4-propoxypiperidin-1-yl)propyl]-6-methyl-4H-benzo[1.4]oxazin-3-one (112KK20-a2)

Crude (R,S)-4-(3-chloro-2-methylpropyl)-6-methyl-4H-benzo[1.4]oxazin-3-one (112KK19-a) (0.046 g), 4-propoxypiperidine (0.050 g, 0.35 mmol), NaI (0.100 g, 0.67 mmol), and $K_2CO_3$ (0.075 g, 0.54 mmol) in DMF (1.4 mL) were reacted and purified according to GP20 to give the title compound (112KK20-a2) (0.010 g). HPLC-MS (ammonium acetate) $[M+H]^+$=361.29.

(R,S)-4-[3-(4-Butylidenepiperidin-1-yl)-2-methylpropyl]-6-methyl-4H-benzo[1.4]oxazin-3-one (112KK20-a3)

Crude (R,S)-4-(3-chloro-2-methylpropyl)-6-methyl-4H-benzo[1.4]oxazin-3-one (112KK19-a) (0.046 g), 4-butylidenepiperidine (0.053 g, 0.38 mmol), NaI (0.100 g, 0.67 mmol), and $K_2CO_3$ (0.075 g, 0.54 mmol) in DMF (1.4 mL) were reacted and purified according to GP20 to give the title compound (112KK20-a3) (0.008 g). HPLC-MS ammonium acetate) $[M+H]^+$=357.30.

(R,S)-4-[3-(3-Butyl-8-azabicyclo[3.2.1]oct-8-yl)-2-methylpropyl]-6-methyl-4H-benzo[1.4]oxazin-3-one (112KK20-a4)

Crude (R,S)-4-(3-chloro-2-methylpropyl)-6-methyl-4H-benzo[1.4]oxazin-3-one (112KK19-a) (0.023 g), 3-butyl-8-azabicyclo[3.2.1]octane (0.025 g, 0.15 mmol), NaI (0.100 g, 0.67 mol), and $K_2CO_3$ (0.075 g, 0.54 mmol) in DMF (1.2 mL) were reacted and purified according to GP20 to give the title compound (112KK20-a4) (0.007 g). HPLC-MS (ammonium acetate) $[M+H]^+$=385.32.

(R,S)-4-[2-Methyl-3-(3-pentyl-8-azabicyclo[3.2.1]oct-8-yl)propyl]-6-methyl-4H-benzo[1.4]oxazin-3-one (112KK20-a5)

Crude (R,S)-4-(3-chloro-2-methylpropyl)-6-methyl-4H-benzo[1.4]oxazin-3-one (112KK19-a) (0.023 g), 3-pentyl-8-azabicyclo[3.2.1]octane (0.024 g, 0.13 mmol), NaI (0.100 g, 0.67 mol), and $K_2CO_3$ (0.075 g, 0.54 mmol) in DMF (1.2 mL) were reacted and purified according to GP20 to give the title compound (112KK20-a5) (0.002 g). HPLC-MS (ammonium acetate) $[M+H]^+$=399.35.

(R,S)-4-[3-(4-Butylpiperidin-1-yl)-2-methylpropyl]-6-fluoro-4H-benzo[1.4]oxazin-3-one (112KK20-b1)

Crude (R,S)-4-(3-chloro-2-methylpropyl)-6-fluoro-4H-benzo[1.4]oxazin-3-one (112KK19-b) (0.051 g), 4-butylpiperidine (0.050 g, 0.35 mmol), NaI (0.100 g, 0.67 mmol), and $K_2CO_3$ (0.075 g, 0.54 mmol) in DMF (1.4 mL) were reacted and purified according to GP20 to give the title compound (112KK20-b1) (0.011 g). HPLC-MS (ammonium acetate) $[M+H]^+$=363.28.

(R,S)-6-Fluoro-4-[2-methyl-3-(4-propoxypiperidin-1-yl)propyl]-4H-benzo[1.4]oxazin-3-one (112KK20-b2)

Crude (R,S)-4-(3-chloro-2-methylpropyl)-6-fluoro-4H-benzo[1.4]oxazin-3-one (112KK19-b) (0.051 g), 4-propoxypiperidine (0.050 g, 0.35 mmol), NaI (0.100 g, 0.67 mmol), and $K_2CO_3$ (0.075 g, 0.54 mmol) in DMF (1.4 mL) were reacted and purified according to GP20 to give the title compound (112KK20-b2) (0.010 g). HPLC-MS (ammonium acetate) $[M+H]^+$=365.26.

(R,S)-4-[3-(4-Butylidenepiperidin-1-yl)-2-methylpropyl]-6-fluoro-4H-benzo[1.4]oxazin-3-one (112KK20-b3)

Crude (R,S)-4-(3-chloro-2-methylpropyl)-6-fluoro-4H-benzo[1.4]oxazin-3-one (112KK19-b) (0.051 g), 4-butylidenepiperidine (0.053 g, 0.38 mmol), NaI (0.100 g, 0.67 mmol), and $K_2CO_3$ (0.075 g, 0.54 mmol) in DMF (1.4 mL) were reacted and purified according to GP20 to give the title compound (112KK20-b3) (0.011 g). HPLC-MS (ammonium acetate) $[M+H]^+$=361.27.

(R,S)-4-[3-(3-Butyl-8-azabicyclo[3.2.1]oct-8-yl)-2-methylpropyl]-6-fluoro-4H-benzo[1.4]oxazin-3-one (112KK20-4)

Crude (R,S)-4-(3-chloro-2-methylpropyl)-6-fluoro-4H-benzo[1.4]oxazin-3-one (112KK19-b) (0.026 g), 3-butyl-8-azabicyclo[3.2.1]octane (0.025 g, 0.15 mmol), NaI (0.100 g, 0.67 mmol), and $K_2CO_3$ (0.075 g, 0.54 mmol) in DMF (1.2 mL) were reacted and purified according to GP20 to give the title compound (112KK20-W) (0.009 g). HPLC-MS (ammonium acetate) $[M+H]^+$=389.30.

(R,S)-6-Fluoro-4-[2-methyl-3-(3-pentyl-8-azabicyclo[3.2.1]oct-8-yl)propyl]-4H-benzo[1.4]oxazin-3-one (112KK20-b5)

Crude (R,S)-4-(3-chloro-2-methylpropyl)-6-fluoro-4H-benzo[1.4]oxazin-3-one (112KK19-b) (0.026 g), 3-pentyl-8-azabicyclo[3.2.1]octane (0.024 g, 0.13 mmol), NaI (0.100 g, 0.67 mmol), and $K_2CO_3$ (0.075 g, 0.54 mmol) in DMF (1.2 mL) were reacted and purified according to GP20 to give the title compound (112KK20-b5) (0.009 g). HPLC-MS (ammonium acetate) $[M+H]^+$=403.31.

(R,S)-4-[3-(4-Butylpiperidin-1-yl)-2-methylpropyl]-7-fluoro-4H-benzo[1.4]oxazin-3-one (112KK20-c1)

Crude (R,S)-4-(3-chloro-2-methylpropyl)-7-fluoro-4H-benzo[1.4]oxazin-3-one (112KK19-c) (0.046 g), 4-butylpiperidine (0.050 g, 0.35 mmol), NaI (0.100 g, 0.67 mmol), and $K_2CO_3$ (0.075 g, 0.54 mmol) in DMF (1.4 mL) were reacted and purified according to GP20 to give the title compound (112KK20-c1) (0.002 g). HPLC-MS (ammonium acetate) $[M+H]^+$=363.29.

(R,S)-7-Fluoro-4-[2-methyl-3-(4-propoxypiperidin-1-yl)propyl]-4H-benzo[1.4]oxazin-3-one (112KK20-c2)

Crude (R,S)-4-(3-chloro-2-methylpropyl)-7-fluoro-4H-benzo[1.4]oxazin-3-one (112KK19-c) (0.046 g), 4-propoxypiperidine (0.050 g, 0.35 mmol), NaI (0.100 g, 0.67 mmol), and $K_2CO_3$ (0.075 g, 0.54 mmol) in DMF (1.4 mL) were reacted and purified according to GP20 to give the title compound (112KK20-c2) (0.002 g). HPLC-MS (ammonium acetate) $[M+H]^+$=365.28.

(R,S)-4-[3-(4-Butylidenepiperidin-1-yl)-2-methylpropyl]-7-fluoro-4H-benzo[1.4]oxazin-3-one (112KK20-c3)

Crude (R,S)-4-(3-chloro-2-methylpropyl)-7-fluoro-4H-benzo[1.4]oxazin-3-one (112KK19-c) (0.046 g), 4-butylidenepiperidine (0.053 g, 0.38 mmol), NaI (0.100 g, 0.67 mmol), and K₂CO₃ (0.075 g, 0.54 mmol) in DMF (1.4 mL) were reacted and purified according to GP20 to give the title compound (112KK20-c3) (0.008 g). HPLC-MS (ammonium acetate) [M+H]⁺=361.29.

(R,S)-4-[3-(3-Butyl-8-azabicyclo[3.2.1]oct-8-yl)-2-methylpropyl]-7-fluoro-4H-benzo[1,4]oxazin-3-one (112KK20-c4)

Crude (R,S)-4-(3-chloro-2-methylpropyl)-7-fluoro-4H-benzo[1,4]oxazin-3-one (112KK19-c) (0.023 g), 3-butyl-8-azabicyclo[3.2.1]octane (0.025 g, 0.15 mmol), NaI (0.100 g, 0.67 mmol), and K₂CO₃ (0.075 g, 0.54 mmol) in DMF (1.2 mL) were reacted and purified according to GP20 to give the title compound (112KK20-c4) (0.004 g). HPLC-MS (ammonium acetate) [M+H]⁺=389.31.

(R,S)-7-Fluoro-4-[2-methyl-3-(3-pentyl-8-azabicyclo[3.2.1]oct-8-yl)propyl]-4H-benzo[1,4]oxazin-3-one (112KK20-c5)

Crude (R,S)-4-(3-chloro-2-methylpropyl)-7-fluoro-4H-benzo[1,4]oxazin-3-one (112KK19-c) (0.023 g), 3-pentyl-8-azabicyclo[3.2.1]octane (0.024 g, 0.13 mmol), NaI (0.100 g, 0.67 mmol), and K₂CO₃ (0.075 g, 0.54 mmol) in DMF (1.2 mL) were reacted and purified according to GP20 to give the title compound (112KK20-c5) (0.002 g). HPLC-MS (ammonium acetate) [M+H]⁺=403.32.

(R,S)-3-[3-(4-Butylpiperidin-1-yl)-2-methylpropyl]-3H-benzothiazol-2-one (112KK20-d1)

Crude (R,S)-3-(3-chloro-2-methylpropyl)-3H-benzothiazol-2-one (112KK19-d) (0.054 g), 4-butylpiperidine (0.050 g, 0.35 mmol), NaI (0.100 g, 0.67 mmol), and K₂CO₃ (0.075 g, 0.54 mmol) in DMF (1.4 mL) were reacted and purified according to GP20 to give the title compound (112KK20-d1) (0.012 g). HPLC-MS (ammonium acetate) [M+H]⁺=347.28.

(R,S)-4-[2-Methyl-3-(4-propoxypiperidin-1-yl)propyl]-3H-benzothiazol-2-one (112KK20-d2)

Crude (R,S)-3-(3-chloro-2-methylpropyl)-3H-benzothiazol-2-one (112KK19-d) (0.054 g), 4-propoxypiperidine (0.050 g, 0.35 mmol), NaI (0.100 g, 0.67 mmol), and K₂CO₃ (0.075 g, 0.54 mmol) in DMF (1.4 mL) were reacted and purified according to GP20 to give the title compound (112KK20-d2) (0.011 g). HPLC-MS (ammonium acetate) [M+H]⁺=349.25.

(R,S)-4-[3-(4-Butylidenepiperidin-1-yl)-2-methylpropyl]-3H-benzothiazol-2-one (112KK20-d3)

Crude (R,S)-3-(3-chloro-2-methylpropyl)-3H-benzothiazol-2-one (112KK19-d) (0.054 g), 4-butylidenepiperidine (0.053 g, 0.38 mmol), NaI (0.100 g, 0.67 mmol), and K₂CO₃ (0.075 g, 0.54 mmol) in DMF (1.4 mL) were reacted and purified according to GP20 to give the title compound (112KK20-d3) (0.011 g). HPLC-MS (ammonium acetate) [M+H]⁺=345.27.

(R,S)-3-[3-(3-Butyl-8-azabicyclo[3.2.1]oct-8-yl)-2-methylpropyl]-3H-benzothiazol-2-one (112KK20-d4)

Crude (R,S)-3-(3-chloro-2-methylpropyl)-3H-benzothiazol-2-one (112KK19-d) (0.027 g), 3-butyl-8-azabicyclo[3.2.1]octane (0.025 g, 0.15 mmol), NaI (0.100 g, 0.67 mmol), and K₂CO₃ (0.075 g, 0.54 mmol) in DMF (1.2 mL) were reacted and purified according to GP20 to give the title compound (112KK20-d4) (0.011 g). HPLC-MS (ammonium acetate) [M+H]⁺=373.30.

(R,S)-3-[2-Methyl-3-(3-pentyl-8-azabicyclo[3.2.1]oct-8-yl)propyl]-3H-benzothiazol-2-one (112KK20-d5)

Crude (R,S)-3-(3-chloro-2-methylpropyly)-3H-benzothiazol-2-one (112KK19-d) (0.027 g), 3-pentyl-8-azabicyclo[3.2.1]octane (0.024 g, 0.13 mmol), NaI (0.100 g, 0.67 mmol), and K₂CO₃ (0.075 g, 0.54 mmol) in DMF (1.2 mL) were reacted and purified according to GP20 to give the title compound (112KK20-d5) (0.011 g). HPLC-MS (ammonium acetate) [M+H]⁺=387.30.

(R,S)-4-[3-(4-Butylpiperidin-1-yl)-2-methylpropyl]-4H-benzo[1,4]oxazin-3-one (107LH74-a1)

Crude (R,S)-4-(3-chloro-2-methylpropyl)-4H-benzo[1,4]oxazin-3-one (107LH61-1) (0.149 g), 4-butylpiperidine (0.042 g, 0.30 mmol), NaI (0.100 g, 0.67 mmol), and K₂CO₃ (0.075 g, 0.54 mmol) in DMF (1 mL) were reacted and purified according to GP20 to give the title compound (107LH74-a1) (0.092 g). HPLC-MS (ammonium acetate) [M+H]⁺=345.30.

(R,S)-4-[2-Methyl-3-(4-propoxypiperidin-1-yl)propyl]-4H-benzo[1,4]oxazin-3-one (107LH74-a2)

Crude (R,S)-4-(3-chloro-2-methylpropyl)-4H-benzo[1,4]oxazin-3-one (107LH61-1) (0.149 g), 4-propoxypiperidine (0.043 g, 0.30 mmol), NaI (0.100 g, 0.67 mmol), and K₂CO₃ (0.075 g, 0.54 mmol) in DMF (1 mL) were reacted and purified according to GP20 to give the title compound (107LH74-a2) (0.077 g). HPLC-MS (ammonium acetate) [M+H]⁺=347.30.

(R,S)-4-[3-(4-Butylidenepiperidin-1-yl)-2-methylpropyl]-4H-benzo[1,4]oxazin-3-one (107LH74-a3)

Crude (R,S)-4-(3-chloro-2-methylpropyl)-4H-benzo[1,4]oxazin-3-one (107LH61-1) (0.149 g), 4-butylidenepiperidine (0.042 g, 0.30 mmol), NaI (0.100 g, 0.67 mmol), and K₂CO₃ (0.075 g, 0.54 mmol) in DMF (1 mL) were reacted and purified according to GP20 to give the title compound (107LH74-a3) (0.083 g). HPLC-MS (ammonium acetate) [M+H]⁺=343.30.

(R,S)-4-[3-(3-Butyl-8-azabicyclo[3.2.1]oct-8-yl)-2-methylpropyl]-4H-benzo[1,4]oxazin-3-one (107LH74-a4)

Crude (R,S)-4-(3-chloro-2-methylpropyl)-4H-benzo[1,4]oxazin-3-one (107LH61-1) (0.074 g), 3-butyl-8-azabicyclo[3.2.1]octane (0.025 g, 0.15 mmol), NaI (0.100 g, 0.67 mmol), and K₂CO₃ (0.075 g, 0.54 mmol) in DMF (1 mL) were reacted and purified according to GP20 to give the title compound (107LH74-a4) (0.046 g). HPLC-MS (ammonium acetate) [M+H]⁺=371.33.

(R,S)-4-[2-Methyl-3-(3-pentyl-8-azabicyclo[3.2.1]oct-8-yl)propyl]-4H-benzo[1,4]oxazin-3-one (107LH74-a5)

Crude (R,S)-4-(3-chloro-2-methylpropyl)-4H-benzo[1,4]oxazin-3-one (107LH61-1) (0.074 g), 3-pentyl-8-azabicyclo[3.2.1]octane (0.027 g, 0.15 mmol), NaI (0.100 g, 0.67 mmol), and K$_2$CO$_3$ (0.075 g, 0.54 mmol) in DMF (1 mL) were reacted and purified according to GP20 to give the title compound (107LH74-a5) (0.053 g). HPLC-MS (ammonium acetate) [M+H]$^+$=385.34.

(R,S)-4-[3-(4-Butylpiperidin-1-yl)-2-methylpropyl]-4H-benzo[1,4]thiazin-3-one (107LH74-b1)

Crude (R,S)-4-(3-chloro-2-methylpropyl)-4H-benzo[1,4]thiazin-3-one (107LH61-2) (0.148 g), 4-butylpiperidine (0.042 g, 0.30 mmol), NaI (0.100 g, 0.67 mmol), and K$_2$CO$_3$ (0.075 g, 0.54 mmol) in DMF (1 mL) were reacted and purified according to GP20 to give the title compound (107LH74-b1) (0.083 g). HPLC-MS (ammonium acetate) [M+H]$^+$361.29.

(R,S)-1-[2-Methyl-3-(4-propoxypiperidin-1-yl)propyl]-4H-benzo[1,4]thiazin-3-one (107LH74-b2)

Crude (R,S)-1-(3-chloro-2-methylpropyl)-4H-benzo[1,4]thiazin-3-one (107LH61-2) (0.148 g), 4-propoxypiperidine (0.043 g, 0.30 mmol), NaI (0.100 g, 0.67 mmol), and K$_2$CO$_3$ (0.075 g, 0.54 mmol) in DMF (1 mL) were reacted and purified according to GP20 to give the title compound (107LH74-b2) (0.071 g). HPLC-MS (ammonium acetate) [M+H]$^+$=363.27.

(R,S)-4-[3-(4-Butylidenepiperidin-1-yl)-2-methylpropyl]-4H-benzo[1,4]thiazin-3-one (107LH74-b3)

Crude (R,S)-4-(3-chloro-2-methylpropyl)-4H-benzo[1,4]thiazin-3-one (107LH61-2) (0.148 g), 4-butylidenepiperidine (0.042 g, 0.30 mmol), NaI (0.100 g, 0.67 mmol), and K$_2$CO$_3$ (0.075 g, 0.54 mmol) in DMF (1 mL) were reacted and purified according to GP20 to give the title compound (107LH74-b3) (0.064 g). HPLC-MS (ammonium acetate) [M+H]$^+$=359.27.

(R,S)-4-[3-(3-Butyl-8-azabicyclo[3.2.1]oct-8-yl)-2-methylpropyl]-4H-benzo[1,4]thiazin-3-one (107LH74-b4)

Crude (R,S)-4-(3-chloro-2-methylpropyl)-4H-benzo[1,4]thiazin-3-one (107LH61-2) (0.074 g), 3-butyl-8-azabicyclo[3.2.1]octane (0.025 g, 0.15 mmol), NaI (0.100 g, 0.67 mmol), and K$_2$CO$_3$ (0.075 g, 0.54 mmol) in DMF (1 mL) were reacted and purified according to GP20 to give the title compound (107LH74-b4) (0.040 g). HPLC-MS (ammonium acetate) [M+H]$^+$=387.30.

(R,S)-4-[2-Methyl-3-(3-pentyl-8-azabicyclo[3.2.1]oct-8-yl)propyl]-4H-benzo[1,4]thiazin-3-one (107LH74-b5)

Crude (R,S)-4-(3-chloro-2-methylpropyl)-4H-benzo[1,4]thiazin-3-one (107LH61-2) (0.074 g), 3-pentyl-8-azabicyclo[3.2.1]octane (0.027 g, 0.15 mmol), NaI (0.100 g, 0.67 mmol), and K$_2$CO$_3$ (0.075 g, 0.54 mmol) in DMF (1 mL) were reacted and purified according to GP20 to give the title compound (107LH74-b5) (0.040 g). HPLC-MS (ammonium acetate) [M+H]$^+$=401.30.

(R,S)-1-[3-(4-Butylpiperidin-1-yl)-2-methylpropyl]-3,4-dihydro-1H-quinolin-2-one (107LH74-c1)

Crude(R,S)-1-(3-chloro-2-methylpropyl)-3,4-dihydro-1H-quinolin-2-one (107LH63) (0.188 g), 4-butylpiperidine (0.042 g, 0.30 mmol), NaI (0.100 g, 0.67 mmol), and K$_2$CO$_3$ (0.075 g, 0.54 mmol) in DMF (1 mL) were reacted and purified according to GP20 to give the title compound (107LH74-c1) (0.047 g). HPLC-MS (ammonium acetate) [M+H]$^+$=343.32

(R,S)-1-[2-Methyl-3-(4-propoxypiperidin-1-yl)propyl]-3,4-dihydro-1H-quinolin-2-one (107LH74-c2)

Crude(R,S)-1-(3-chloro-2-methylpropyl)-3,4-dihydro-1H-quinolin-2-one (107LH63) (0.188 g), 4-propoxypiperidine (0.043 g, 0.30 mmol), NaI (0.100 g, 0.67 mmol), and K$_2$CO$_3$ (0.075 g, 0.54 mmol) in DMF (1 mL) were reacted and purified according to GP20 to give the title compound (107LH74-c2) (0.040 g). HPLC-MS (ammonium acetate) [M+H]$^+$=345.32.

(R,S)-1-[3-(4-Butylidenepiperidin-1-yl)-2-methylpropyl]-3,4-dihydro-1H-quinolin-2-one (107LH74-c3)

Crude (R,S)-1-(3-chloro-2-methylpropyl)-3,4-dihydro-1H-quinolin-2-one (107LH63) (0.188 g), 4-butylidenepiperidine (0.042 g, 0.30 mmol), NaI (0.100 g, 0.67 mmol), and K$_2$CO$_3$ (0.075 g, 0.54 mmol) in DMF (1 mL) were reacted and purified according to GP20 to give the title compound (107LH74-c3) (0.038 g). HPLC-MS (ammonium acetate) [M+H]$^+$=341.31.

(R,S)-1-[3-(3-Butyl-8-azabicyclo[3.2.1]oct-8-yl)-2-methylpropyl]-3,4-dihydro-1H-quinolin-2-one (107LH74-c4)

Crude (R,S)-1-(3-chloro-2-methylpropyl)-3,4-dihydro-1H-quinolin-2-one (107LH63) (0.094 g), 3-butyl-8-azabicyclo[3.2.1]octane (0.025 g, 0.15 mmol), NaI (0.100 g, 0.67 mmol), and K$_2$CO$_3$ (0.075 g, 0.54 mmol) in DMF (1 mL) were reacted and purified according to GP20 to give the title compound (107LH74-c4) (0.025 g). HPLC-MS (ammonium acetate) [M+H]$^+$=369.33.

(R,S)-1-[2-Methyl-3-(3-pentyl-8-azabicyclo[3.2.1]oct-8-yl)-propyl]-3,4-dihydro-1H-quinolin-2-one (107LH74-c5)

Crude (R,S)-1-(3-chloro-2-methylpropyl)-3,4-dihydro-1H-quinolin-2-one (107LH63) (0.094 g), 3-pentyl-8-azabicyclo[3.2.1]octane (0.027 g, 0.15 mmol), NaI (0.100 g, 0.67 mmol), and K$_2$CO$_3$ (0.075 g, 0.54 mmol) in DMF (1 mL) were reacted and purified according to GP20 to give the title compound (107LH74-c5) (0.023 g). HPLC-MS (ammonium acetate) [M+H]$^+$=383.34.

(R,S)-4-[3-(4-Butylpiperidin-1-yl)-2-methylpropyl]-6-methoxy-4H-benzo[1,4]oxazin-3-one (107LH74-d1)

Crude (R,S)-4-(3-chloro-2-methylpropyl)-6-methoxy-4H-benzo[1,4]oxazin-3-one (107LH69) (0.165 g), 4-butylpiperidine (0.042 g, 0.30 mmol), NaI (0.100 g, 0.67 mmol), and K$_2$CO$_3$ (0.075 g, 0.54 mmol) in DMF (1 mL) were reacted and purified according to GP20 to give the title compound (107LH74-d1) (0.094 g). HPLC-MS (ammonium acetate) [M+H]$^+$=375.31.

(R,S)-4-[2-Methyl-3-(4-propoxypiperidin-1-yl)-6-methoxy]-4H-benzo[1,4]oxazin-3-one (107LH74-d2)

Crude (R,S)-4-(3-chloro-2-methylpropyl)-6-methoxy-4H-benzo[1,4]oxazin-3-one (107LH69) (0.165 g), 4-propoxypiperidine (0.043 g, 0.30 mmol), NaI (0.100 g, 0.67 mmol), and $K_2CO_3$ (0.075 g, 0.54 mmol) in DMF (1 mL) were reacted and purified according to GP20 to give the title compound (107LH74-d2) (0.086 g). HPLC-MS (ammonium acetate) $[M+H]^+=377.29$.

(R,S)-4-[3-(4-Butylidenepiperidin-1-yl)-2-methyl-propyl]-6-methoxy-4H-benzo[1,4]oxazin-3-one (107LH74-d3)

Crude (R,S)-4-(3-chloro-2-methylpropyl)-6-methoxy-4H-benzo[1,4]oxazin-3-one (107LH69) (0.165 g), 4-butylidenepiperidine (0.042 g, 0.30 mmol), NaI (0.100 g, 0.67 mmol), and $K_2CO_3$ (0.075 g, 0.54 mmol) in DMF (1 mL) were reacted and purified according to GP20 to give the title compound (107LH74-d3) (0.086 g). HPLC-MS (ammonium acetate) $[M+H]^+=373.29$.

(R,S)-4-[3-(3-Butyl-8-azabicyclo[3.2.1]oct-8-yl)-2-methylpropyl]-6-methoxy-4H-benzo[1,4]oxazin-3-one (107LH74-d4)

Crude (R,S)-4-(3-chloro-2-methylpropyl)-6-methoxy-4H-benzo[1,4]oxazin-3-one (107LH69) (0.082 g), 3-butyl-8-azabicyclo[3.2.1]octane (0.025 g, 0.15 mmol), NaI (0.100 g, 0.67 mmol), and $K_2CO_3$ (0.075 g, 0.54 mmol) in DMF (1 mL) were reacted and purified according to GP20 to give the title compound (107LH74-d4) (0.044 g). HPLC-MS (ammonium acetate) $[M+H]^+=401.32$.

(R,S)-1-[2-Methyl-3-(3-pentyl-8-azabicyclo[3.2.1]oct-8-yl)propyl]-6-methoxy-4H-benzo[1,4]oxazin-3-one (107LH74-d5)

Crude (R,S)-4-(3-chloro-2-methylpropyl)-6-methoxy-4H-benzo[1,4]oxazin-3-one (107LH69) (0.082 g), 3-pentyl-8-azabicyclo[3.2.1]octane (0.027 g, 0.15 mmol), NaI (0.100 g, 0.67 mmol), and $K_2CO_3$ (0.075 g, 0.54 mmol) in DMF (1 mL) were reacted and purified according to GP20 to give the title compound (107LH74-d5) (0.051 g). HPLC-MS (ammonium acetate) $[M+H]^+=415.34$.

1-[3-(4-Butyl-piperidin-1-yl)-propyl]-1,2,3,4-tetrahydro-quinoline (55-LH-12-2)

A solution of n-butyllithium in hexane (1.5M, 7.3 mL, 11 mmol) was added drop wise to a solution of 1,2,3,4-tetrahydro-quinoline (1.256 mL, 10 mmol) in tetrahydrofuran (10 mL) at −78° C. under an atmosphere of argon. The reaction mixture was stirred for ½ h then 1-chloro-3-iodopropane (1.0 mL, 9.5 mmol) was added. The reaction mixture was stirred at −78° C. for ½ h then stirred for additional 16 h at room temperature. Tetrahydrofuran was evaporated off and the solid was dissolved in acetonitrile (10 mL). KI (1.83 g, 11 mmol), $K_2CO_3$ (2.76 g, 20 mmol) and 4-butylpiperidine (1.66 mL, 10 mmol) were added. The slurry was stirred at 50° C. for 48 h then water (10 mL) was added and the product was extracted with ethyl acetate (2×20 mL). The organic layer was dried ($Na_2SO_4$) and concentrated in vacuo. The product was purified by column chromatography (eluent: ethyl acetate) to give the title compound (1.11 g, 35%) Oxalate-salt was prepared from oxalic acid (1.1 eq.) in acetone. HPLC-MS: M+$1^+=315.1$ (MS(%)=95). $^1$H NMR (400 MHz, $CDCl_3$): δ=0.89 (3H, t), 1.18-1.34 (9H, m), 1.64-1.70 (2H, m), 1.79 (2H, quin.), 1.85-1.98 (4H, m), 2.36 (2H, t), 2.74 (2H, t), 2.92 (2H, broad d), 3.24-3.31 (4H, m), 6.54 (1H, ddd), 6.60 (1H, dd), 6.93 (1H, dd), 7.03 (1H, ddd). $^{13}$C NMR ($CDCl_3$): δ 14.3, 22.5, 23.1, 24.2, 28.4, 29.3, 32.7, 36.0, 36.5, 49.6, 49.8, 54.4, 56.7, 110.9, 115.5, 122.5, 127.3, 129.3, 145.6.

1-[3-(4-Butyl-piperidin-1-yl)-propyl]-2-methyl-1,2,3,4-tetrahydro-quinoline (55-LH-28-8)

2-Methyl-1,2,3,4-tetrahydroquinoline (346 mg, 2.35 mmol) was converted to the title product according to the procedure for the synthesis of 1-[3-(4-butyl-piperidin-1-yl)-propyl]-1,2,3,4-tetrahydro-quinoline. Yield: 88.6 mg, 11%. HPLC-MS: M+$1^+=329.5$ (UV/MS(%)=100/99). $^1$H NMR (400 MHz, $CDCl_3$): δ=0.89 (3H, t), 1.11 (3H, d), 1.16-1.34 (9H, m), 1.67 (2H, broad d), 1.65-2.03 (8H, m), 2.39 (2H, t), 2.57-2.66 (1H, m), 2.74-2.85 (1H, m), 2.93 (2H, broad d), 3.12-3.21 (1H, m), 3.33-3.42 (1H, m), 3.44-3.52 (1H, m), 6.45 (1H, t), 6.54 (1H, d), 6.87 (1H, d), 6.97 (1H, t). $^{13}$C NMR ($CD_3OD$): δ 13.2, 17.8, 22.8, 23.7, 24.4, 28.0, 28.9, 31.9, 35.7, 36.2, 52.7, 53.9, 54.0, 56.4, 110.8, 115.1, 121.9, 126.7, 128.7, 144.2.

1-[3-(4-Butyl-piperidin-1-yl)-propyl]-6-methyl-1,2,3,4-tetrahydro-quinoline (55-LH-44A)

6-Methyl-1,2,3,4-tetrahydroquinoline (346 mg, 2.35 mmol) was converted to the title product according to the procedure for the synthesis of 1-[3-(4-butyl-piperidin-1-yl)-propyl]-1,2,3,4-tetrahydro-quinoline. Yield: 137 mg, 18%. HPLC-MS: M+$1^+=329.5$ (UV/MS(%)=98/99). $^1$H NMR (400 MHz, $CDCl_3$): δ=0.89 (3H, t), 1.14-1.34 (9H, m), 1.68 (2H, broad d), 1.76 (2H, quin.), 1.85-1.99 (4H, m), 2.14 (3H, s), 2.34-2.39 (2H, m), 2.66 (2H, t), 2.92 (2H, broad d), 3.18-3.26 (4H, m), 6.49 (1H, d), 6.58 (1H, broad s), 6.76 (1H, broad d). $^{13}$C NMR-($CD_3OD$): δ 13.2, 19.2, 22.5, 22.8, 23.2, 28.0, 28.9, 31.9, 35.7, 36.2, 49.4, 49.6, 53.9, 56.5, 111.3, 122.7, 124.7, 127.2, 129.6, 143.2.

1-[3-(4-Butyl-piperidin-1-yl)propyl]-8-methyl-1,2,3,4-tetrahydro-quinoline (77-LH-1)

8-Methyl-1,2,3,4-tetrahydroquinoline (125 mg, 0.85 mmol), 1-chloro-3-iodopropane (82 μl, 0.77 mmol) and $Cs_2CO_3$ (415 mg, 1.27 mmol) in acetonitrile (2 mL) were shaken at 60° C. for 7 days. KI (140 mg, 0.85 mmol), $K_2CO_3$ (117 mg, 0.85 mmol) and 4-butylpiperidine (113 μl, 0.68 mmol) were added and the reaction mixture was shaken at 60° C. for 2 days. Water (5 mL) was added and the product was extracted with ethyl acetate (2×10 mL). The organic layer was dried ($Na_2SO_4$) and concentrated in vacuo. The product was purified by column chromatography (eluent: 20% methanol in ethyl acetate) to yield the title compound. Yield: 45.6 mg (20.4%). HPLC-MS: M+$1^+=329.5$ (UV/MS(%)=99/97). $^1$H NMR (400 MHz, $CDCl_3$): δ=0.89 (3H, t), 1.18-1.34 (9H, m), 1.70 (2H, broad d), 1.75-1.92 (4H, m), 1.99 (2H, broad t), 2.22 (3H, s), 2.38 (2H, dd), 2.70-2.81 (4H, m), 2.96 (2H, broad d), 3.04-3.10 (2H, m), 6.76 (1H, t), 6.80 (1H, broad d), 6.91 (1H, broad d). $^{13}$C NMR ($CD_3OD$): δ 13.2, 17.2, 18.0, 18.1, 22.8, 25.7, 27.7, 28.9, 31.9, 35.7, 36.2, 52.7, 53.9, 56.3, 121.5, 127.1, 128.7, 128.9, 131.0, 148.0.

1-[3-(4-Butyl-piperidin-1-yl)-propyl]-7-fluoro-2-methyl-1,2,3,4-tetrahydro-quinoline (77-LH-2)

7-Fluoro-2-methyl-1,2,3,4-tetrahydro-quinoline (165 mg, 1.0 mmol) was converted to the title product according to the procedure for the synthesis of 1-[3-(4-butyl-piperidin-1-yl)-propyl]-8-methyl-1,2,3,4-tetrahydro-quinoline. Yield: 43.2 mg, 16%. HPLC-MS: M+1$^+$=347.5 (UV/MS(%)=95/92). $^1$H NMR (400 MHz, CDCl$_3$): δ=0.89 (3H, t), 1.10 (3H, d), 1.18-1.36 (9H, m), 1.66-1.91 (6H, m), 2.00-2.10 (2H, m), 2.44 (2H, t), 2.62 (1H, dt), 2.74-2.85 (1H, m), 2.99 (2H, broad d), 3.16 (1H, q), 3.30-3.40 (1H, m), 3.41-3.49 (1H, m), 6.63-6.74 (1H, m), 6.63-6.74 (2H, m). $^{13}$C NMR (CD$_3$OD): δ 13.2, 17.6, 22.7, 23.7, 23.8, 24.3, 29.9, 28.9, 31.7, 35.5, 36.1, 52.6, 53.8, 56.2, 112.7 (d), 114.8 (d), 123.7, 140.8, 153.5, 155.8.

1-[3-(4-Butyl-piperidin-1-yl)-propyl]-7-trifluoromethyl-1,2,3,4-tetrahydro-quinoline (55-LH-54)

7-Trifluoromethyl-1,2,3,4-tetrahydro-quinoline (0.50 g, 2.5 mmol) was converted to the title product according to the procedure for the synthesis of 1-[3-(4-butyl-piperidin-1-yl)propyl]-1,2,3,4-tetrahydro-quinoline. Yield: 1.71 mg, 18%. HPLC-MS: M+1$^+$=347.5 (UV/MS(%)=99/91). $^1$H NMR (400 MHz, CDCl$_3$): δ=0.89 (3H, t), 1.14-1.36 (9H, m), 1.68 (2H, broad d), 1.79 (2H, quin.), 1.86-2.03 (4H, m), 2.38 (2H, dd), 2.75 (2H, dd), 2.94 (2H, broad d), 3.32 (4H, m), 6.71 (1H, d), 6.75 (1H, s), 6.99 (1H, d).

1-[3-(4-Butyl-piperidin-1-yl)propyl]-3,4-dihydro-1H-quinolin-2-one (77-LH-28-1)

A suspension of NaH in mineral oil (55-60%) (712 mg) was added to a solution of 3,4-dihydro-1H-quinolin-2-one (2.0 g, 13.6 mmol) in N,N-dimethylformamide (50 mL) at 0° C. The reaction mixture was stirred at 0° C. for 1 h. then 1-bromo-3-chloropropane (1.34 mL, 13.6 mmol) was added. The slurry was stirred for additional 16 h. at ambient temperature then water (50 mL) was added and the product was extracted with diethyl ether (2×50 mL). The organic layer was dried (Na$_2$SO$_4$) and concentrated in vacuo. The product was purified by flash-chromatography (eluent: dichloromethane) to give 1-[3-chloropropyl]-3,4-dihydro-1H-quinolin-2-one (2.41 g, 10.8 mmol). KI (2.5 g, 15 mmol), K$_2$CO$_3$ (2.1 g, 15 mmol) and 4-butylpiperidine (1.8 mL, 15 mmol) were added to a solution of 1-[3-chloropropyl]-3,4-dihydro-1H-quinolin-2-one (2.41 g, 10.8 mmol) in acetonitrile (50 mL). The reaction mixture was stirred at 60° C. for 16 h. The acetonitrile was evaporated in vacuo, water (50 mL) was added and the product was extracted with ethyl acetate (2×50 mL). The organic layer was dried (Na$_2$SO$_4$), filtered and concentrated in vacuo. Purification by flash-chromatography (eluent: ethyl acetate) gave the title product. Yield: 2.06 g, 58%. Oxalate-salt was prepared from oxalic acid (1.1 eq.) in acetone. HPLC-MS: M+1$^+$=329.5 (UV/MS(%)=100/100). $^1$H NMR (400 MHz, CD$_3$OD): δ=0.89 (3H, t), 1.12-1.36 (9H, m), 1.67 (2H, broad d), 1.83 (2H, quin.), 1.97 (2H, broad t), 2.41 (2H, t), 2.59 (2H, t), 2.84-2.96 (4H, m), 3.99 (2H, t), 7.02 (1H, broad t), 7.16 (1H, broad d), 7.20 (1H, broad d), 7.25 (1H, broad t). $^{13}$C NMR (CD$_3$OD): δ 13.2, 22.8, 24.3, 25.0, 28.9, 31.6, 31.9 (2C), 35.6, 36.2, 40.1, 53.8 (2C), 55.9, 115.2, 123.2, 127.0, 127.4, 127.9, 139.1, 171.5

1-[3-(4-Butyl-piperidin-1-yl)-propyl]-6-methoxy-3,4-dihydro-1H-quinolin-2-one (77-LH-22A)

6-Methoxy-3,4-dihydro-1H-quinolin-2-one (108 mg, 0.61 mmol), 1-chloro-3-iodopropane (64 μl, 0.6 mmol) and Cs$_2$CO$_3$ (290 mg, 0.9 mmol) in acetonitrile (2 mL) were shaken at 60° C. for 14 h then the reaction was cooled to room temperature. Water (5 mL) was added and the product was extracted with ethyl acetate (2×10 mL). The organic layer was dried (Na$_2$SO$_4$), filtered and concentrated in vacuo. The syrup was dissolved in acetonitrile (4 mL). KI (83 mg, 3.6 mmol), K$_2$CO$_3$ (100 mg, 0.6 mmol) and 4-butylpiperidine (83 μl, 0.5 mmol) were added and the reaction mixture was shaken at 60° C. for 16 h. Water (5 mL) was added and the product was extracted with ethyl acetate (2×10 mL). The organic layer was dried (Na$_2$SO$_4$) and concentrated in vacuo. The product was purified by column chromatography (eluent: 20% methanol in ethyl acetate) to yield the title compound. Yield: 24.8 mg, 11.3%. HPLC-MS: M+1$^+$=359.5 (UV/MS(%)=90/78). $^1$H NMR (400 MHz, CDCl$_3$): δ=0.89 (3H, t), 1.12-1.34 (9H, m), 1.67 (2H, broad d), 1.85 (2H, quin.), 1.93 (2H, broad t), 2.39 (2H, t), 2.59 (2H, dd), 2.83 (2H, t), 2.90 (2H, broad d), 3.76 (3H, s), 3.94 (2H, t), 6.70 (1H, d), 6.74 (1H, dd), 7.01 (1H, d). $^{13}$C NMR (CDCl$_3$): δ 14.3, 23.0, 25.0, 26.1, 29.2, 32.1, 32.5 (2C), 35.9, 36.4, 40.8, 54.3 (2C), 55.8, 56.3, 112.2, 114.2, 116.2, 128.3, 133.4, 155.4, 169.9

4-[3-(4-Butyl-piperidin-1-yl)-propyl]-6-methyl-4H-benzo[1,4]oxazin-3-one 64-(LHY-89-6)

6-Methyl-4H-benzo[1,4]oxazin-3-one (82 mg, 0.5 mmol), 1-chloro-3-iodopropane (50 μl, 0.5 mmol) and Cs$_2$CO$_3$ (163 mg, 0.5 mmol) in acetonitrile (2 mL) were shaken at 50° C. for 24 h then the reaction mixture was concentrated in vacuo. The product (4-[3-chloropropyl]-6-methyl-4H-benzo[1,4]-oxazin-3-one) was purified on an Isco CombiFlash Sq 16× (4 g silica column, eluting 0-20% ethyl acetate in heptanes) then dissolved in acetonitrile (2 mL). K$_2$CO$_3$ (85 mg, 0.5 mmol) and 4-butylpiperidine (80 μl, 0.5 mmol) were added. The reaction mixture was shaken at 60° C. for 16 h then cooled to room temperature. Dichloromethane (2 mL) and PS-isocyanate (loading 1.47 mmol/g, 100 mg) were added. The mixture was filtered after 5 h and the organic layer was loaded onto a Varian SCX ion exchange column. The column was washed with methanol (2×5 mL) then the product was eluted off the column using 10% ammonium hydroxide in methanol (6 mL). The solute was concentrated in vacuo to give the title product. Yield: 100 mg, 58%. HPLC-MS: M+1$^+$=345.5 (UV/MS(%)=99/99). $^1$H NMR (400 MHz, CDCl$_3$): δ=0.89 (3H, t), 1.15-1.30 (9H, m), 1.65 (2H, broad d), 1.81-1.89 (4H, m), 2.30 (3H, s), 2.36 (2H, t), 2.86 (2H, broad d), 3.94 (2H, dd), 4.51 (2H, s), 6.76 (1H, dd), 6.84 (1H, d), 6.86 (1H, d). $^{13}$C NMR (CDCl$_3$): δ 14.3, 21.3, 23.1, 25.1, 29.2, 32.8 (2C), 36.0, 36.5, 39.8, 54.4 (2C), 56.1, 67.9, 115.8, 116.9, 124.3, 128.6, 132.5, 143.4, 164.6.

6-Acetyl-4-[3-(4-butyl-piperidin-1-yl)propyl]-4H-benzo[1,4]oxazin-3-one (64-LHY-89-5)

6-Acetyl-4H-benzo[1,4]oxazin-3-one (96 mg, 0.5 mmol) was converted to the title product according to the procedure for the synthesis of 4-[3-(4-butyl-piperidin-1-yl)-propyl]-6-methyl-4H-benzo[1,4]-oxazin-3-one. Yield: 120 mg, 64%. HPLC-MS: M+1$^+$=373.5 (UV/MS(%)=99/100). $^1$H NMR (400 MHz, CDCl$_3$): δ=0.89 (3H, t), 1.13-1.27 (9H, m), 1.63 (2H, broad d), 1.81-1.88 (4H, m), 2.37 (2H, t), 2.55 (3H, s), 2.84 (2H, broad d), 4.02 (2H, dd), 4.65 (2H, s), 6.99 (1H, d), 7.58 (1H, dd), 7.66 (1H, d). $^{13}$C NMR (CDCl$_3$): δ 14.3, 23.1, 24.7, 26.5, 29.2, 32.7 (2C), 36.0, 36.5, 39.9, 54.4 (2C), 56.3, 67.6, 114.9, 117.0, 125.3, 128.8, 132.4, 149.5, 163.5, 196.3.

4-[3-(4-Butyl-piperidin-1-yl)-propyl]-6-methyl-3,4-dihydro-2H-benzo[1,4]oxazine (64-LHY-91-6)

A solution of borane in THF (1M, 0.5 mL, 0.5 mmol) was added to a solution of 4-[3-(4-butyl-piperidin-1-yl)-propyl]-6-methyl-4H-benzo[1,4]oxazin-3-one (50 mg, 0.15 mmol) in THF (6 mL). The reaction mixture was stirred at 40° C. for 16 h then aqueous HCl (4M, 10 mL) was added drop wise at room temperature. The reaction mixture was stirred for 16 h then concentrated in vacuo. A solution of $K_2CO_3$ (0.5 g) in water (5 mL) was added and the product was extracted with dichloromethane (2×10 mL). The organic layer was dried ($Na_2SO_4$) and concentrated in vacuo. The product was purified on an Isco CombiFlash Sq 16× (4 g silica column, eluting 0-20% ethyl acetate in heptanes+1% $Et_3N$). Yield: 29.2 mg, 56%. HPLC-MS: M+1$^+$=373.5 (UV/MS(%)=95/90). $^1$H NMR (400 MHz, $CDCl_3$): δ=0.90 (3H, t), 1.18-1.35 (9H, m), 1.68 (2H, broad d), 1.78 (2H, quin.), 1.89 (2H, broad t), 2.24 (3H, s), 2.35 (2H, t), 2.89 (2H, broad d), 3.27 (2H, t), 3.31 (2H, t), 4.19 (2H, t), 6.39 (1H, broad d), 6.52 (1H, broad s), 6.66 (1H, d). $^{13}$C NMR ($CDCl_3$): δ 14.3, 21.4, 23.1, 24.2, 29.3, 32.8 (2C), 36.1, 36.6, 47.4, 49.3, 54.5 (2C), 56.5, 64.7, 113.0, 116.2, 117.7, 131.1, 135.3, 142.0.

4-[3-(4-Butyl-piperidin-1-yl)-propyl]-6-ethyl-3,4-dihydro-2H-benzo[1,4]oxazine (64-LHY-91-5)

6-Acetyl-4-[3-(4-butyl-piperidin-1-yl)propyl]-4H-benzo[1,4]oxazin-3-one (60 mg, 0.161 mmol) was converted to the title product according to the procedure for the synthesis of 4-[3-(4-butyl-piperidin-1-yl)propyl]-6-methyl-3,4-dihydro-2H-benzo[1,4]oxazine. Yield: 22 mg, 40%. HPLC-MS: M+1$^+$=373.5 (UV/MS(%)=98/97). $^1$H NMR (400 MHz, $CDCl_3$): δ=0.89 (3H, t), 1.18-1.35 (12H, m), 1.68 (2H, broad d), 1.75 (2H, quin.), 1.89 (2H, broad t), 2.35 (2H, t), 2.53 (2H, qv), 2.89 (2H, broad d), 3.26-3.33 (4H, m), 4.20 (2H, t), 6.43 (1H, dd), 6.53 (1H, d), 6.69 (1H, d). $^{13}$C NMR ($CDCl_3$): δ 14.3, 16.2, 23.1, 24.2, 28.9, 29.3, 32.8 (2C), 36.1, 36.6, 47.4, 49.4, 54.5 (2C), 56.5, 64.7, 112.0, 116.2, 116.5, 135.3, 137.7, 142.2.

4-(3-Chloropropyl)-4H-benzo[1,4]thiazin-3-one (81MF07)

2H-1,4-benzothiazine-3(4H)-one (1.0 g, 6.05 mmol) and $Cs_2CO_3$ (2.96 g, 9.08 mmol) were dissolved in dry acetonitrile (20 mL) under nitrogen atmosphere and stirred at rt for 30 min. 3-chloro-1-iodopropane (1.37 g, 6.66 mmol) dissolved in acetonitrile (4 mL) was added via a syringe. The reaction mixture was stirred at rt for 18 hours and concentrated in vacuo. Water (150 mL) was added and the reaction mixture was extracted with ethyl acetate (3×150 mL). The combined organic phases were dried ($MgSO_4$) and concentrated in vacuo to give 1.45 g of crude. The crude product was subjected to CC[eluent:Heptane:EtOAC(4:1)] to give the pure title compound as a slightly yellow oil. Yield 1.37 g, 90.2%. Rr 0.24 [Heptane:EtOAC(4:1)], $^1$H NMR ($CDCl_3$): δ 2.14 (m, 2H), 3.38 (s, 2H), 3.36 (t, 2H), 4.17 (t, 2H), 7.03 (t, 1H), 7.18 (d, 1H), 7.26 (t, 1H), 7.37 (d, 1H). $^{13}$C NMR ($CDCl_3$): δ 30.61, 31.81, 42.48, 42.66, 117.87, 123.78, 124.29, 127.52, 127.52, 128.78, 139.40, 165.51

4-[3-(4-Butyl-piperidin-1-yl)-propyl]-4H-benzo[1,4]thiazin-3-one (81MF09)

NaI (1.24 g, 8.27 mmol), $K_2CO_3$ (1.14 g, 8.27 mmol), and 4-butylpiperidine (0.62 g, 4.34 mmol) in acetonitrile (10 mL) were stirred at rt. 4-(3-chloropropyl)-4H-benzo[1,4]thiazin-3-one (1.0 g, 4.14 mmol) in acetonitrile (15 mL) was added via a syringe. The reaction was stirred at 60° C. for 13 hours and then at 80° C. for another 25 hours under nitrogen atmosphere and concentrated in vacuo. Water (150 mL) was added and the reaction mixture was extracted with ethyl acetate (3×150 mL). The combined organic phases were dried ($Na_2SO_4$) and concentrated in vacuo to give 1.63 g of crude. The crude product was subjected to CC[eluent:EtOAC:MeOH(100:1-5%)] to give the pure title compound. Yield 1.06 g 74.2% HPLC-MS [M+H]$^+$ 347 (UV/MS(%)=100/99. $^1$H NMR ($CDCl_3$): δ 0.88 (t, 3H), 1.23 (m, 9H), 1.64 (d, 2H), 1.85 (m, 4H), 2.34 (t, 2H), 2.83 (d, 2H), 3.36 (s, 1H), 4.03 (t, 2H), 6.99 (m, 1H), 7.22 (d, 2H), 7.34 (d, 1H), $^{13}$C NMR ($CDCl_3$): δ 14.21, 23.03, 25.23, 29.15, 31.80, 32.63, 35.90, 36.44, 43.28, 54.26, 55.91, 118.18, 123.45, 124.17, 127.27, 128.56, 139.63, 165.19.

To 4-[3-(4-butyl-piperidin-1-yl)-propyl]-4H-benzo[1,4]thiazin-3-one (1.06 g, mmol) in 30 ml diethyl ether was charged oxalic acid (0.28 g, 3.1 mmol) dissolved in diethyl ether (5 mL). The formed crystals were filtered of and washed with diethyl ethyl (5×10 mL) to give 1.21 g of the oxalic salt after drying. HPLC-MS [M+H]$^+$ 347 (UV/MS(%)=100/99

4-(3-Chloropropyl)-4H-benzo[1,4]oxazin-3-one (81MF08)

2H-1,4 benzoxazine-3(4H)one (1.0 g, 6.70 mmol) and $Cs_2CO_3$ (3.28 g, 10.1 mmol) were dissolved in dry acetonitrile (20 mL) under nitrogen atmosphere and stirred at rt for 30 min. 3-chloro-1-iodopropane (1.58 g, 7.38 mmol) dissolved in acetonitrile (4 mL) was added via a syringe. The reaction mixture was stirred at rt for 18 hours and concentrated in vacuo. Water (150 mL) was added and the reaction mixture was extracted with ethyl acetate (3×150 mL). The combined organic phases were dried ($MgSO_4$) and concentrated in vacuo to give 1.65 g of crude. The crude product was subjected to CC[eluent:Heptane:EtOAC(4:1)] to give the pure title compound as a colorless oil. Yield 1.36 g, 89.2%. R$_f$=0.24 [Heptane:EtOAC(4:1)], $^1$H NMR ($CDCl_3$): δ 2.16 (m, 2H), 3.62 (t, 2H), 4.10 (t, 2H), 4.59 (s, 2H), 7.00 (m, 2H), 7.05 (m, 2H), $^{13}$C NMR ($CDCl_3$): δ 30.16, 39.04, 42.45, 67.72, 114.80, 117.38, 123.07, 124.14, 128.49, 145.47, 164.58.

4-[3-(4-Butyl-piperidin-1-yl)-propyl]-4H-benzo[1,4]oxazin-3-one (81MF10)

NaI (1.33 g, 8.87 mmol), $K_2CO_3$ (1.23 g, 8.90 mmol), and 4-butylpiperidine (0.66 g, 4.71 mmol) in acetonitrile (10 mL) were stirred at rt. 4-(3-chloropropyl)-4H-benzo[1,4]oxazin-3-one (1.0 g, 4.43 mmol) in acetonitrile (15 mL) was added via a syringe. The reaction was stirred at 60° C. for 13 hours and then at 80° C. for another 5 hours under nitrogen atmosphere and concentrated in vacuo. Water (150 mL) was added and the reaction mixture was extracted with ethyl acetate (3×150 mL). The combined organic phases were dried (Na$_2$SO$_4$) and concentrated in vacuo to give 1.58 g of crude. The crude product was subjected to CC[eluent:EtOAC: MeOH(100:1-5%)] to give the pure title compound. Yield 0.82 g 56.0% HPLC-MS [M+H]$^+$ 331 (UV/MS(%)=100/99. $^1$H NMR (CDCl$_3$): δ 0.88 (t, 3H), 1.21 (m, 6H), 1.26 (m, 3H), 1.66 (d, 2H), 1.86 (m, 4H), 2.37 (t, 2H), 2.86, (d, 2H), 3.97 (t, 2H), 4.58 (s, 2H), 6.99 (m, 3H), 7.11 (d, 1H), $^{13}$C NMR (CDCl$_3$): δ 14.22, 23.04, 24.90, 29.17, 32.68, 35.95, 36.46, 39.74, 54.31, 56.02, 67.77, 115.26, 117.15, 122.83, 123.83, 128.78, 145.50, 164.34.

To 4-[3-(4-Butyl-piperidin-1-yl)-propyl]-4H-benzo[1,4]oxazin-3-one (0.82 g, mmol) in 30 ml diethyl ether was charged oxalic acid (0.25 g, 2.8 mmol) dissolved in diethyl ether (5 mL). The formed crystals were filtered of and washed with diethyl ether (5×10 mL) to give 0.75 g of the oxalic salt after drying. HPLC-MS [M+H]$^+$ 331 (UV/MS(%)=100/99

Example 2

Pharmacological Data

Receptor Selection and Amplification (R-SAT) assays were carried out using the cloned M1-M5 receptors essentially as described in: Brauner-Osborne H, Brann MR. Pharmacology of muscarinic acetylcholine receptor subtypes (m1-m5): high throughput assays in mammalian cells. Eur J Pharmacol 1996 Jan. 4;295(1):93-102, and Spalding T A, Trotter C, Skjaerbaek N, Messier T L, Currier E A, Burstein E S, Li D, Hacksell U, Brann M R. Discovery of an ectopic activation site on the M(1) muscarinic receptor. Mol Pharmacol. 2002 June;61(6):1297-302.

What is claimed is:

1. A compound of formula I, as well as salts and isomers thereof

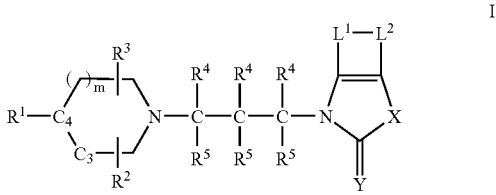

wherein

R$^1$ is a monoradical selected from the group consisting of optionally substituted C$_{1-6}$-alkyl, optionally substituted C$_{1-6}$-alkylidene, optionally substituted C$_{2-6}$-alkenyl, optionally substituted C$_{2-6}$-alkynyl, optionally substituted O—C$_{1-6}$-alkyl, optionally substituted O—C$_{2-6}$-alkenyl, optionally substituted O—C$_{2-6}$-alkynyl; optionally substituted S—C$_{1-6}$-alkyl, optionally substituted S—C$_{2-6}$-alkenyl, optionally substituted S—C$_{2-6}$-alkynyl;

m is 0, 1 or 2;

C$_3$-C$_4$ is CH$_2$—CH or CH=C, or C$_4$ is CH and C$_3$ is absent;

R$^2$ and R$^3$ are independently selected from the group consisting of hydrogen, optionally substituted C$_{1-6}$ alkyl, optionally substituted O—C$_{1-6}$ alkyl, halogen, hydroxy or selected such that R$^2$ and R$^3$ together form a ring system, wherein the ring system is formed by selecting R$^2$, R$^3$, m, and C$_3$-C$_4$ such that

| Compound Number | m1 | | m2 | | m3 | | m4 | | m5 | |
|---|---|---|---|---|---|---|---|---|---|---|
| | % Efficacy | pEC$_{50}$ | % Efficacy | pEC$_{50}$ | % Efficacy | pEC$_{50}$ | % Efficacy | pEC$_{50}$ | % Efficacy | pEC$_{50}$ |
| 55-LH-28-1 (1549) | 87 | 7.5 | 41 | 5.8 | No response | | 66 | 6.2 | No response | |
| 77-LH-1 (1606) | No response | | No response | | No response | | No response | | No response | |
| 55-LH-28-8 (1598) | 45 | 6.7 | 67 | <5.5 | No response | | 64 | <5.5 | Not tested | |
| 55-LH-12-2 | 72 | 7.3 | 35 | 6.2 | No response | | 68 | 6.0 | No response | |
| 55LH44-A | 54 | 6.5 | No response | | No response | | 28 | <5.5 | Not tested | |
| 55LH54 | 57 | 6.4 | No response | | No response | | No response | | No response | |
| 73MF01 | 90 | 7.7 | 55 | 6.3 | No response | | 65 | 6.8 | 49 | 6.2 |
| 73MF02 | 90 | 7.6 | 50 | 6.0 | No response | | 75 | 6.6 | 30 | 6.3 |
| 77LH02-1917 | 55 | 6.7 | No response | | No response | | 37 | <5.5 | No response | |
| 64LHY89-5 | 45 | 5.6 | No response | | No response | | No response | | Not tested | |
| 64LHY89-6 | 80 | 7.4 | 35 | 6.2 | No response | | 50 | 6.5 | 48 | 6.2 |
| 64LHY91-5 | 69 | 6.8 | No response | | No response | | 51 | 5.7 | 38 | 6.2 |
| 64LHY91-6 | 86 | 7.2 | 31 | 6.9 | No response | | 52 | 6.6 | No response | |
| 77LH22-A | 76 | 7.1 | No response | | No response | | No response | | 37 | <5.5 |
| 82LHY19 | 81 | 7.7 | 39 | 6.3 | No response | | 46 | 6.8 | Not tested | |
| 77LH61-A | 79 | 7.5 | 28 | <5.5 | No response | | 33 | 5.8 | 51 | <5.5 |
| 81MF24 | 96 | 7.8 | 70 | 7.0 | No response | | Not tested | | Not tested | |
| 81MF763 | 92 | 7.5 | 47 | 6.6 | No response | | 57 | 6.4 | 50 | 5.9 |
| 85LM47A | 122 | 7.9 | 74 | 6.0 | No response | | 91 | 6.1 | 35 | <5.5 |
| 85LM96-86R | 106 | 7.6 | 97 | 6.2 | 30 | 5.9 | 94 | 5.8 | 90 | 5.6 |
| 85LM96-87R | 101 | 7.7 | 116 | 5.9 | 36 | 6.0 | 140 | 6.1 | 62 | 6.0 |
| 107LH55 | 103 | 8.9 | 28 | 7.5 | No response | | 54 | 7.3 | No response | |
| 108LM39-36 | 106 | 8.8 | 37 | 8.1 | No response | | 71 | 7.7 | No response | |
| 107LH74-3D | 97 | 8.0 | No response | | Not tested | | Not tested | | Not tested | |
| 112KK20-c5 | 117 | 8.3 | No response | | No response | | Not tested | | Not tested | |
| 107LH95-1 | 103 | 7.6 | No response | | Not tested | | Not tested | | Not tested | |

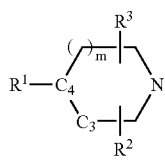

is selected from the group consisting of

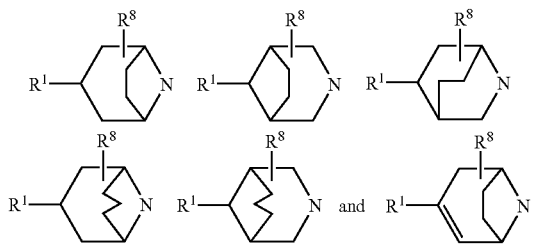

wherein R⁸ is present 0,1, or 2 times and is independently selected from the group consisting of optionally substituted $C_{1-6}$ alkyl, optionally substituted O—$C_{1-6}$ alkyl, halogen, and hydroxy;

each $R^4$ and $R^5$ is independently selected from the group consisting of hydrogen, halogen, hydroxy, optionally substituted $C_{1-6}$-alkyl, optionally substituted O—$C_{1-6}$alkyl, optionally substituted aryl-$C_{1-6}$alkyl, and optionally substituted arylheteroalkyl;

$L^1$ and $L^2$ are separately biradicals having the formula —C($R^6$)═C($R^7$);

Y is selected from the group consisting of O, S, and $H_2$;

X is —C($R^6$)($R^7$)—S—, wherein $R^6$ and $R^7$ are independently selected from the group consisting of hydrogen, halogen, hydroxy, nitro, cyano, $NR^N R^N$, $N(R^N)$—C(O)—$N(R^N)$, optionally substituted $C_{1-6}$alkyl, $C_{2-6}$-alkenyl, $C_{2-6}$-alkynyl, optionally substituted O—$C_{1-6}$-alkyl, optionally substituted O-aryl, optionally substituted O—$C_{2-6}$-alkenyl, optionally substituted O—$C_{2-6}$-alkynyl wherein $R^N$ is selected from the group consisting of hydrogen, and optionally substituted $C_{1-6}$-alkyl.

2. The compound according to claim 1, wherein $R^1$ is selected from the group consisting of optionally substituted $C_{1-6}$-alkyl, optionally substituted $C_{1-6}$-alkylidene, and optionally substituted 0—$C_{1-6}$-alkyl.

3. The compound according to claim 1, wherein $R^2$ and $R^3$ are hydrogen or $R^2$, $R^3$, $C_3$-$C_4$ and m are selected such that

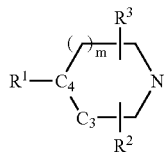

is selected from the group consisting of

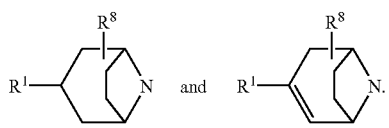

4. The compound according to claim 1, wherein $R^2$ and $R^3$ are independently selected from the group consisting of hydrogen, optionally substituted $C_{1-6}$ alkyl, optionally substituted O—$C_{1-6}$ alkyl, halogen and hydroxy.

5. The compound according to claim 1, wherein m is 1.

6. The compound according to claim 1, wherein m is 0, $C_3$ is absent, and $C_4$ is CH such that

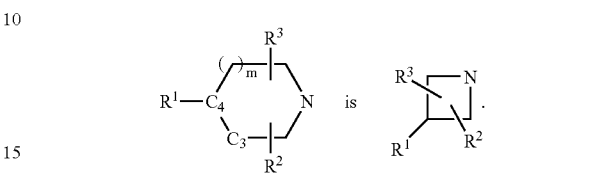

7. The compound according to claim 1, wherein Y is selected from the group consisting of O and $H_2$.

8. The compound according to claim 1, of formula Ia

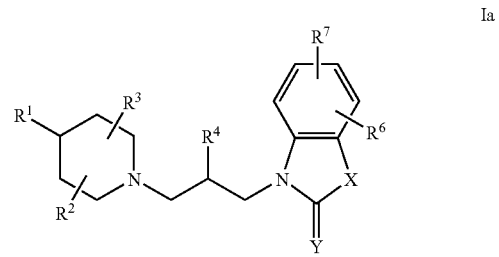

Ia wherein $R^1$ is selected from the group consisting of optionally substituted $C_{1-6}$-alkyl, optionally substituted $C_{1-6}$-alkylidene, optionally substituted $C_{2-6}$-alkenyl, optionally substituted $C_{2-6}$-alkynyl, optionally substituted O—$C_{1-6}$-alkyl, and optionally substituted O—$C_{2-6}$-alkenyl; and $R^2$, $R^3$, $R^4$, X, Y, $R^6$ and $R^7$ are as defined in claim 1.

9. The compound of claim 8, wherein the optionally substituted $C_{1-6}$-alkyl is selected from the group consisting of unsubstituted $C_{1-6}$-alkyl, and $C_{1-6}$-alkoxyalkyl, and wherein Y is selected from the group consisting of O and $H_2$, and wherein $R^4$ selected from the group consisting of hydrogen, halogen, hydroxy, optionally substituted $C_{1-6}$-alkyl, and optionally substituted O—$C_{1-6}$alkyl.

10. The compound according to claim 1 selected from the group consisting of 4-[3 -(4-Butyl-piperidin-1-yl)-propyl]-4H-benzo[1,4]thiazin-3-one; (R)-4-[3-(4-Butylpiperidin-1-yl)-2methylpropyl]-4H-benzo[1,4]thiazin-3-one; (R)-4-[2-Methyl-3-(4-propoxypiperidin-1-yl)propyl]-4H-benzo[1,4] thiazin-3-one; (R)-4-[3-(4-Butylidene-piperidin- 1-yl)-2-methyl-propyl]-4H-benzo[1,4]thiazin-3-one; (R)-4-[3-(3-Butyl-8-aza-bicyclo[3.2.1]oct-8-yl)-2-methyl-propy]-4H-benzo[1,4]thiazin-3-one; (R)-4-[2-Methyl-3-(3-pentyl-8-aza-bicyclo[3.2.1]oct-8-yl)propyl]-4H-benzo[1,4]thiazin-3one; 4-[3-(4-Propoxypiperidin-1-yl)propyl]-4H-benzo[1,4] thiazin-3-one; 4-[3-(4-Butylidenepiperidin- 1-yl)propyl]-4H-benzo[1,4]thiazin-3-one; (R,S)-4-[3(4-Butylpiperidin-1 -yl)-2-methylpropyl]-4H-benzo[1,4]thiazin-3-one; (R,S)-1-[2-Methyl-3-(4-propoxypiperidin-1-yl)propyl]-4H-benzo [1,4]thiazin-3-one; (R,S)-4-[3-(4-Butylidenepiperidin-1-yl)-2methylpropyl]-4H-benzo[1,4]thiazin-3-one; (R,S)-4-[3-(3-Butyl-8azabicyclo[3.2.1]oct-8-yl)-2methylpropyl]-4H- benzo[1,4]thiazin-3-one; and (R,S)-4-[2-Methyl-3-(3-pentyl-8-azabicyclo[3.2.1]oct-8-yl)propyl]-4H-benzo[1,4]thiazin-3-one.

11. A composition comprising
   i) one or more compounds of formula I, as defined in claim 1, and
   ii) at least one pharmaceutically acceptable excipient or carrier.

12. A method of treating a disease in a mammal, wherein modulation of the activity of a cholinergic receptor is associated with a physiologically beneficial response in said disease of said mammal,
   said method comprising administering an effective amount of a compound of formula I, as defined in claim 1, and
   wherein said disease is selected from the group consisting of Alzheimer's disease, Parkinson's disease, schizophrenia, Huntington's chorea, Friedreich's ataxia, Gilles de la Tourette's Syndrome, Down Syndrome, Pick disease, dementia, clinical depression, age-related cognitive decline, cognitive impairment, forgetfulness, confusion, memory loss, attentional deficits, deficits in visual perception, depression, pain, sleep disorders, psychosis, sudden infant death syndrome, increased intraocular pressure and glaucoma.

13. The method according to claim 12, wherein the cholinergic receptor is a muscarinic receptor.

14. The method according to claim 12, wherein the cholinergic receptor is a muscarinic $M_1$-receptor subtype.

15. The method according to claim 12, wherein the cholinergic receptor is the muscarinic $M_4$-receptor subtype.

16. The method according to claim 12, wherein the physiologically beneficial response is associated with the selective modulation of the muscarinic $M_1$-receptor subtype in relation to the muscarinic $M_2$- or $M_3$-receptor subtypes.

17. The method according to claim 12, wherein the compound is a muscarinic agonist.

18. A method of treating a disease or condition in a mammal, said disease or condition selected from the group consisting of cognitive impairment, forgetfulness, confusion, memory loss, attentional deficits, deficits in visual perception, depression, pain, sleep disorders, psychosis, increased intraocular pressure, Alzheimer's disease, Parkinson's disease, schizophrenia, Huntington's chorea, Friedreich's ataxia, Gilles de la Tourette's Syndrome, Downs Syndrome, Pick disease, dementia, clinical depression, age-related cognitive decline, attention-deficit disorder, sudden infant death syndrome, and glaucoma, comprising contacting a cholinergic receptor with an effective amount of at least one compound as defined in claim 1.

19. A method of treating or alleviating the symptoms associated with a disorder in a mammal, comprising the administration of an effective amount of at least one compound as defined in claim 1, said disorder associated with a wherein said disorder is selected from the group consisting of cognitive impairment, forgetfulness, confusion, memory loss, attentional deficits, deficits in visual perception, depression, pain, sleep disorders, psychosis, increased intraocular pressure, Alzheimer's disease, Parkinson's disease, schizophrenia, Huntington's chorea, Friederich's ataxia, Gilles de la Tourette's Syndrome, Downs Syndrome, Pick disease, dementia, clinical depression, age-related cognitive decline, attention-deficit disorder, sudden infant death syndrome, and glaucoma.

20. The method according to claim 12, wherein the physiologically beneficial response is due to modulation in terms of $M_1$ agonism; $M_1$ and $M_4$ agonism; both $M_1$ agonism and $D_2$ antagonism; or $M_1$ and $M_4$ agonism and $D_2$ antagonism.

* * * * *

UNITED STATES PATENT AND TRADEMARK OFFICE
CERTIFICATE OF CORRECTION

PATENT NO. : 7,576,078 B2  
APPLICATION NO. : 11/417865  
DATED : August 18, 2009  
INVENTOR(S) : Niels Skjaerbaek It is certified that error appears in the above-identified patent and that said Letters Patent is hereby corrected as shown below:

At column 1, line 64, please change "ACHE" to -- AChE --, therefor.

At column 14, line 31, change "-C($R^6$)($R^7$) C($R^6$)($R^7$)–N($R^N$)-," to -- –C($R^6$)($R^7$)–C($R^6$)($R^7$)–N($R^N$)–, --, therefor.

At column 14, line 32, change "–C($R^6$)($R^7$)–CH–CH–" to -- –C($R^6$)($R^7$)–CH=CH– --, and change "–CH–CH–C($R^6$)($R^7$)–" to -- –CH=CH–C($R^6$)($R^7$)– --, therefor.

At column 26, line 61, change "(S) - [3" to -- (S)-4-[3 --, therefor.

At column 31, line 29, change "J=Hz," to -- J=7.6 Hz --, therefor.

At column 31, line 30, change "143.3" to -- 143.5, --, therefor.

At column 38, line 42, change "12" to -- $I_2$ --, therefor.

At column 40, line 61, change "(12 mL)" to -- (1/2 mL) --, therefor.

At column 41, line 7, change "[1.4]" to -- [1,4] --, therefor.

At column 41, line 33, change "(12 mL)" to -- (1/2 mL) --, therefor.

At column 44, line 31, change "11H)," to -- 1H), --, therefor.

At column 44, line 32, change "11H)," to -- 1H), --, therefor.

At column 52, line 19, change "(12 mL)" to -- (1/2 mL) --, therefor.

At column 52, line 67, change "(12 mL)" to -- (1/2 mL) --, therefor.

At column 54, line 8, change "(12 mL)" to -- (1/2 mL) --, therefor.

Signed and Sealed this

Thirty-first Day of August, 2010

David J. Kappos  
*Director of the United States Patent and Trademark Office*

CERTIFICATE OF CORRECTION (continued)
U.S. Pat. No. 7,576,078 B2

At column 54, line 52, after "one" insert -- (111MF08) --, therefor.

At column 55, line 2, after "was" insert -- added --, therefor.

At column 67, line 15, change "9.86" to -- 0.86 --, therefor.

At column 74, line 34, change "111)," to -- 11), --, therefor.

At column 77, line 29, change "50" to -- 50° --, therefor.

At column 79, line 32, change "0.67 mol)," to -- 0.67 mmol), --, therefor.

At column 79, line 44, change "0.67 mol)," to -- 0.67 mmol), --, therefor.

At column 93, line 47, in Claim 2, change "0–$C_{1-6}$" to -- O–$C_{1-6}$ --, therefor.

At column 94, line 60, in Claim 10, change "3one," to -- 3-one, --, therefor.

At column 94, line 66, in Claim 10, change "2methylpropyl]" to -- 2-methylpropyl] --, therefor.

At column 94, line 67, in Claim 10, change "8azabicyclo" to -- 8-azabicyclo --, therefor.

At column 94, line 67, in Claim 10, change "2methylpropyl]" to -- 2-methylpropyl] --, therefor.